US009206438B2

(12) United States Patent
Beghyn et al.

(10) Patent No.: US 9,206,438 B2
(45) **Date of Patent: *Dec. 8, 2015**

(54) DOWN-REGULATING GENE EXPRESSION IN INSECT PESTS

(75) Inventors: Myriam Beghyn, Zulte (BE); Thierry Andre Olivier Eddy Bogaert, Kortrijk (BE); Pascale Feldmann, Gent-Mariakerke (BE); Romaan Raemaekers, De Pinte (BE)

(73) Assignee: Devgen NV (BE)

( * ) Notice: Subject to any disclaimer, the term of this patent is extended or adjusted under 35 U.S.C. 154(b) by 479 days.

This patent is subject to a terminal disclaimer.

(21) Appl. No.: 13/462,636

(22) Filed: May 2, 2012

(65) Prior Publication Data

US 2012/0322660 A1 Dec. 20, 2012
US 2013/0231246 A9 Sep. 5, 2013

Related U.S. Application Data

(63) Continuation-in-part of application No. PCT/EP2012/057332, filed on Apr. 20, 2012.

(60) Provisional application No. 61/477,371, filed on Apr. 20, 2011, provisional application No. 61/508,826, filed on Jul. 18, 2011.

(51) Int. Cl.
*C12N 15/82* (2006.01)
*C07K 14/435* (2006.01)

(52) U.S. Cl.
CPC ...... *C12N 15/8286* (2013.01); *C07K 14/43563* (2013.01); *C12N 15/8218* (2013.01)

(58) Field of Classification Search
None
See application file for complete search history.

(56) References Cited

U.S. PATENT DOCUMENTS 7,560,542 B2 * 7/2009 Andersen et al. ............ 536/23.6
2012/0297501 A1 * 11/2012 Beghyn et al. ................ 800/265

FOREIGN PATENT DOCUMENTS

WO WO 2007/074405 7/2007
WO WO 2009/091864 7/2009

OTHER PUBLICATIONS

Crowhurst et al, 2008, BMC Genomics, 9:1-26.*
Thomas et al, 2001, Plant J., 25:417-425.*
Genbank Submission; NCBI; Accession No. CB408878; Eigenheer et al.; Oct. 25, 2003.
Genbank Submission; NCBI; Accession No. DV392288; Loftus et al.; Oct. 21, 2005.

* cited by examiner

*Primary Examiner* — Medina A Ibrahim
*Assistant Examiner* — Jason Deveau Rosen
(74) *Attorney, Agent, or Firm* — Yoshimi D. Barron

(57) ABSTRACT

The present invention relates to genetic control of infestation by insect pest species, particularly prevention and/or control of pest infestation of plants, using interfering ribonucleic acid (RNA) molecules. Compositions and combinations containing the interfering RNA molecules of the invention for use in topical applications, for example in the form of insecticides.

35 Claims, 24 Drawing Sheets

Figure 1:
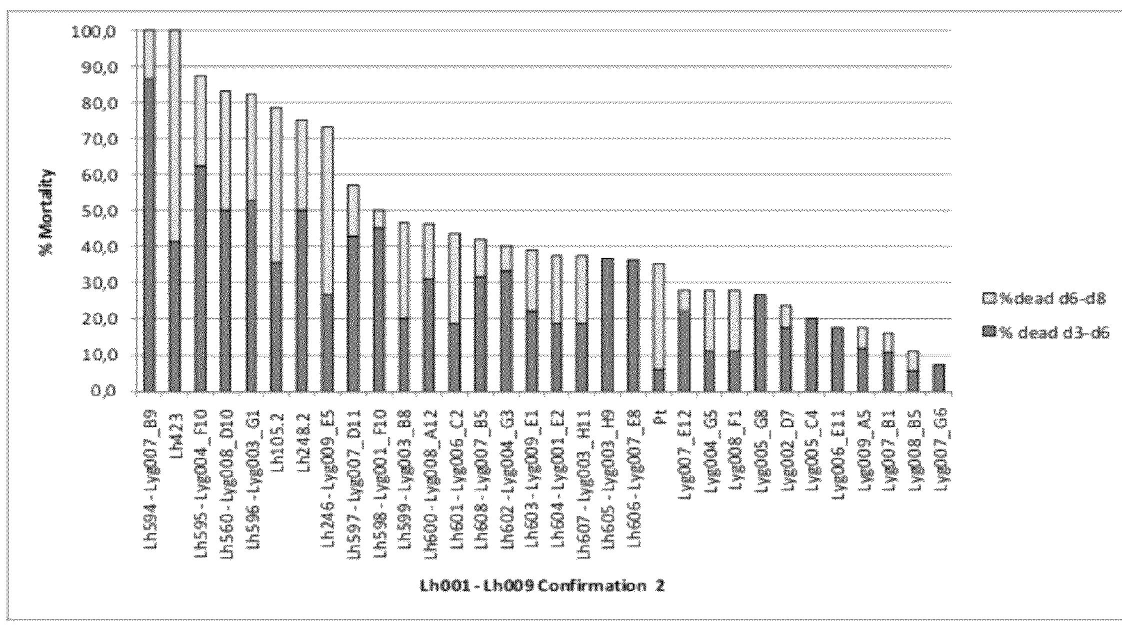

A.

B.

SEQUENCE LISTING

```
<160> NUMBER OF SEQ ID NOS: 405

<210> SEQ ID NO 1
<211> LENGTH: 1096
<212> TYPE: DNA
<213> ORGANISM: Lygus hesperus

<400> SEQUENCE: 1

gcgatctaag gcaggtggca gacagctcga tgacggcagt gggccaagca ataatggata     60

gtcattcata gcaccccagc tttactaagc tctgccgtag tgttggattg ggagcggata    120

caattcacca cagaacagct atgacatgat acgcagtccg aataccctca taaaggacta    180

gtctgcaggt ttaacgatcg cgtagcagtg tatcacgcag agtacatggg gagtgactgt    240

gtgaacctgc tgggtacatc atcacccctc tccttcttca gttatataag acacagtccc    300

taaaggacac cagcaaaaat ggcggatgat gaggcgaaga aggccaaaca ggccgaaatc    360

gagaggaagc gcgctgaagt gcgcaagagg atggaggaag cctctaaggc gaagaaagcc    420

aagaagggtt tcatgacccc ggaaaggaag aagaaactcc gactcctgct gaggaaaaaa    480

gccgctgagg aactgaagaa ggagcaggaa cgcaaagcag ctgagaggag gcgaacgatt    540

gaggagcgct gcgggcaaat tgccgacgtc gacaacgcca atgaagcaac cttgaagaaa    600
```

```
ctctgcacag actaccataa gcgaattgac gctctggaga ggagtaaaat tgacatcgaa    660

ttcgaagtgg agagacgtga ccttgagatc gccgacctca acagccaggt caacgacctc    720

cgtggtaaat tcgtcaaacc taccttgaaa aaggtttcca agtacgaaaa caaattcgcc    780

aagctccaga agaaggctgc cgagttcaac ttcagaaacc aactcaaggt cgtcaaaaag    840

aaagaattca ccctggaaga agaagacaaa gagccgaaga aatcggaaaa ggcggagtgg    900

cagaagaaat gaagggaaaa caagcacacc atctcacaaa ataaaataaa cgaaaatctt    960

tcacacgttt accaatttta taacacggtc ctcacaaatt atgttcctta aataatttgt   1020

ataatccatc ctcgcactac aatcaatatt aatatttaaa tacaaaacca aaaaaaaaaa   1080

aaaaaaaaaa aaaaaa                                                   1096
```

```
<210> SEQ ID NO 2
<211> LENGTH: 491
<212> TYPE: DNA
<213> ORGANISM: Lygus hesperus

<400> SEQUENCE: 2

caaacaggcc gaaatcgaga ggaagcgcgc tgaagtgcgc aagaggatgg aggaagcctc     60

taaggcgaag aaagccaaga agggtttcat gaccccggaa aggaagaaga aactccgact    120

cctgctgagg aaaaaagccg ctgaggaact gaagaaggag caggaacgca aagcagctga    180

gaggaggcga acgattgagg agcgctgcgg gcaaattgcc gacgtcgaca acgccaatga    240

agcaaccttg aagaaactct gcacagacta ccataagcga attgacgctc tggagaggag    300

taaaattgac atcgaattcg aagtggagag acgtgacctt gagatcgccg acctcaacag    360

ccaggtcaac gacctccgtg gtaaattcgt caaacctacc ttgaaaaagg tttccaagta    420

cgaaaacaaa ttcgccaagc tccagaagaa ggctgccgag ttcaacttca gaaaccaact    480

caaggtcgtc a                                                         491
```

```
<210> SEQ ID NO 3
<211> LENGTH: 431
<212> TYPE: DNA
<213> ORGANISM: Lygus hesperus

<400> SEQUENCE: 3

atgggcatca tgtcgaaagc tgaactcgct tgtgtttact ccgctctcat cctcatcgac     60

gacgatgtcg ccgtgacggg tgagaagatt caaaccatcc tgaaggctgc cagtgtcgac    120

atcgagccgt actggcccgg tctgttcgcc aaggccctcg agggtatcaa ccccaaagac    180

ctcatctcct ccattggaag cggagttggt gctggagcgc cggctgtcgg tggagctgca    240

cctgccgccg ctgctgcccc tgccgctgag gctaagaagg aagagaagaa gaaggtcgaa    300

agcgatccag aatccgatga tgacatgggc ttcggtcttt tcgactaaga gcattccaca    360

gcgggttctc atttgttttt aagattttct tttaaaaaat aaaacttcca aaaaaaaaaa    420

aaaaaaaaaa g                                                         431
```

```
<210> SEQ ID NO 4
<211> LENGTH: 332
<212> TYPE: DNA
<213> ORGANISM: Lygus hesperus

<400> SEQUENCE: 4

gggcatcatg tcgaaagctg aactcgcttg tgtttactcc gctctcatcc tcatcgacga     60
```

```
cgatgtcgcc gtgacgggtg agaagattca aaccatcctg aaggctgcca gtgtcgacat    120

cgagccgtac tggcccggtc tgttcgccaa ggccctcgag ggtatcaacc ccaaagacct    180

catctcctcc attggaagcg gagttggtgc tggagcgccg gctgtcggtg gagctgcacc    240

tgccgccgct gctgcccctg ccgctgaggc taagaaggaa gagaagaaga aggtcgaaag    300

cgatccagaa tccgatgatg acatgggctt cg                                  332


<210> SEQ ID NO 5
<211> LENGTH: 468
<212> TYPE: DNA
<213> ORGANISM: Lygus hesperus

<400> SEQUENCE: 5

atgggggcag gtcttctcca taaccataga ttatcttcgt gtatcgtgtc gggctttcgg     60

ctgaggtcct aattagtaaa taatgattcc gcctacgtcg cggcctcagg tcactgtcta    120

cagtgacaaa aatgaggcca ccgggactct cctcaacctc ccggctgtct tcaacgcccc    180

cattcgcccc gatgttgtga acttcgttca ccaaaatgtc gctaaaaacc acaggcagcc    240

ctactgtgtc tccgctcaag ctggtcatca gacttcagct gagtcctggg gtaccggtcg    300

tgctgtggct cgtatccccc gtgttcgcgg aggtggtact caccgctcag gtcagggtgc    360

ttttggcaac atgtgtcgcg gcggtaggat gttcgctccc actcgcccat ggcgtcgttg    420

gcaccgcaaa atcaacgtta accaaaaaaa aaaaaaaaaa aaaaaaaa                  468


<210> SEQ ID NO 6
<211> LENGTH: 429
<212> TYPE: DNA
<213> ORGANISM: Lygus hesperus

<400> SEQUENCE: 6

gggcaggtct tctccataac catagattat cttcgtgtat cgtgtcgggc tttcggctga     60

ggtcctaatt agtaaataat gattccgcct acgtcgcggc ctcaggtcac tgtctacagt    120

gacaaaaatg aggccaccgg gactctcctc aacctcccgg ctgtcttcaa cgccccccatt    180

cgccccgatg ttgtgaactt cgttcaccaa aatgtcgcta aaaaccacag gcagccctac    240

tgtgtctccg ctcaagctgg tcatcagact tcagctgagt cctggggtac cggtcgtgct    300

gtggctcgta tcccccgtgt tcgcggaggt ggtactcacc gctcaggtca gggtgctttt    360

ggcaacatgt gtcgcggcgg taggatgttc gctcccactc gcccatggcg tcgttggcac    420

cgcaaaatc                                                            429


<210> SEQ ID NO 7
<211> LENGTH: 523
<212> TYPE: DNA
<213> ORGANISM: Lygus hesperus

<400> SEQUENCE: 7

atgggatctc tatgctgaaa aggtcgccac cagaggtttg tgtgctattg cacaagctga     60

atccctccgt tacaaactca ttggcggtct tgctgtccga ggggcttgct atggtgtcct    120

tcgcttcatc atggaaaatg gtgccaaggg ttgcgaagtc gtagtatctg gaaaactgcg    180

tggtcagaga gccaagtcaa tgaagttcgt ggatggtttg atgatccaca gtggggatcc    240

ctgtaacgaa tatgttgata ctgctacccg acatgtgctc cttagacaag gtgtcctggg    300

aataaaggtg aagattatgt tgccgtggga cgttaccggc aaaaatgggc cgaagaaccc    360

tcttcccgac cacgtcagcg ttctcttacc taaggaggag ctaccaaatt tggccgttag    420
```

tgtgcctgga tccgacatca aaccaaagcc tgaagtacca gcacccgctt tgtgaatata 480
aacttctttt ttgtaaaaaa aaaaaaaaaa aaaaaaaaaa aaa 523

<210> SEQ ID NO 8
<211> LENGTH: 431
<212> TYPE: DNA
<213> ORGANISM: Lygus hesperus

<400> SEQUENCE: 8
attgcacaag ctgaatccct ccgttacaaa ctcattggcg gtcttgctgt ccgaggggct 60
tgctatggtg tccttcgctt catcatggaa aatggtgcca agggttgcga agtcgtagta 120
tctggaaaac tgcgtggtca gagagccaag tcaatgaagt tcgtggatgg tttgatgatc 180
cacagtgggg atccctgtaa cgaatatgtt gatactgcta cccgacatgt gctccttaga 240
caaggtgtcc tgggaataaa ggtgaagatt atgttgccgt gggacgttac cggcaaaaat 300
gggccgaaga accctcttcc cgaccacgtc agcgttctct tacctaagga ggagctacca 360
aatttggccg ttagtgtgcc tggatccgac atcaaaccaa agcctgaagt accagcaccc 420
gctttgtgaa t 431

<210> SEQ ID NO 9
<211> LENGTH: 823
<212> TYPE: DNA
<213> ORGANISM: Lygus hesperus

<400> SEQUENCE: 9
catggggaca ctctcttttt cttcatcgcg tggctcgctg ccgtgtggtt agggagtttc 60
ctactttaat tttttagtgt aattcatctt caaaatgacg tcgaaggttt ctcgtgagac 120
cctctacgag tgcatcaatg gagtcatcca gtcctcccag gagaagaaga ggaacttcgt 180
ggagactgtg gagatccaga tcggtctgaa gaactacgat ccccagaagg acaagcgttt 240
ctcgggaact gtcaagctga agcacattcc aaggcctaaa atgcaggttt gcatcctcgg 300
agatcaacag cattgcgacg aggccaaagc caacaacgtg ccctacatgg acgtcgaggc 360
tctgaagaag ctcaacaaaa acaagaagct cgtcaagaaa ttggccaaga aatacgacgc 420
tttcctcgcc tcagaagccc tcatcaagca gatccccagg ctcctcggac ccggtctcaa 480
caaggcgggc aagttccctg gtctcctctc tcaccaggag tccatgatga tgaagatcga 540
cgaagtcaag gccaccatca agttccaaat gaagaaggtg ttgtgcctct cagtggctgt 600
cggtcacgtc ggcatgactg ctgatgagct cgtccagaac gtgcacttgt cggtcaactt 660
cctcgtttcg ctcctcaaga agcactggca gaacgtcagg tctctccacg tcaaatccac 720
gatgggacct ccccagaggc tttactaaac atcttgtttt ttacttttga cgaataaaat 780
tcgttttatt ctcgaaaaaa aaaaaaaaaa aaaaaaaaaa aaa 823

<210> SEQ ID NO 10
<211> LENGTH: 607
<212> TYPE: DNA
<213> ORGANISM: Lygus hesperus

<400> SEQUENCE: 10
ccctctacga gtgcatcaat ggagtcatcc agtcctccca ggagaagaag aggaacttcg 60
tggagactgt ggagatccag atcggtctga agaactacga tccccagaag gacaagcgtt 120
tctcgggaac tgtcaagctg aagcacattc caaggcctaa aatgcaggtt tgcatcctcg 180

```
gagatcaaca gcattgcgac gaggccaaag ccaacaacgt gccctacatg gacgtcgagg    240

ctctgaagaa gctcaacaaa aacaagaagc tcgtcaagaa attggccaag aaatacgacg    300

ctttcctcgc ctcagaagcc ctcatcaagc agatccccag gctcctcgga cccggtctca    360

acaaggcggg caagttccct ggtctcctct ctcaccagga gtccatgatg atgaagatcg    420

acgaagtcaa ggccaccatc aagttccaaa tgaagaaggt gttgtgcctc tcagtggctg    480

tcggtcacgt cggcatgact gctgatgagc tcgtccagaa cgtgcacttg tcggtcaact    540

tcctcgtttc gctcctcaag aagcactggc agaacgtcag gtctctccac gtcaaatcca    600

cgatggg                                                              607


<210> SEQ ID NO 11
<211> LENGTH: 435
<212> TYPE: DNA
<213> ORGANISM: Lygus hesperus

<400> SEQUENCE: 11

atgggaccaa taaagatcaa ctttcccaga gaaagacttg ctatgcccag cataatcagg     60

tccgagaaat ccgcaaaaag atggttaaaa acatcagtga cagcatttcc agctgtgatt    120

tgaggagtgt tgtgaacaag ctgatcccag actccatcgc taaagatata gaaaagaatt    180

gccaaggaat ctacccactc cacgatgtgt acattcggaa ggtgaaggtg ttgaagaagc    240

cgaggttcga gctcagcaag ctccttgagc ttcacgtcga tggcaaaggg atcgacgaac    300

ccggcgcgaa agtgacgagg actgacgctt acgagcctcc agttcaagag tctgtctaag    360

taaacatttt atataaagtt aacaaaaaat aaaggtgtct cgcctgacta aaaaaaaaaa    420

aaaaaaaaaa aaaaa                                                     435


<210> SEQ ID NO 12
<211> LENGTH: 353
<212> TYPE: DNA
<213> ORGANISM: Lygus hesperus

<400> SEQUENCE: 12

ccaataaaga tcaactttcc cagagaaaga cttgctatgc ccagcataat caggtccgag     60

aaatccgcaa aaagatggtt aaaaacatca gtgacagcat ttccagctgt gatttgagga    120

gtgttgtgaa caagctgatc ccagactcca tcgctaaaga tatagaaaag aattgccaag    180

gaatctaccc actccacgat gtgtacattc ggaaggtgaa ggtgttgaag aagccgaggt    240

tcgagctcag caagctcctt gagcttcacg tcgatggcaa agggatcgac gaacccggcg    300

cgaaagtgac gaggactgac gcttacgagc ctccagttca agagtctgtc taa           353


<210> SEQ ID NO 13
<211> LENGTH: 474
<212> TYPE: DNA
<213> ORGANISM: Lygus hesperus

<400> SEQUENCE: 13

catgggtacg aatatcgacg gtaaaagaaa ggtgatgttc gccatgaccg ccatcaaagg     60

tgtcggcaga cggtacgcca acattgtcct caagaaggcc gatgtcaact tggacaagag    120

ggccggcgaa tgctccgaag aagaagttga aaagatcgtt accatcatgc aaaaccctag    180

gcaatacaaa attcccaact ggttcctcaa cagacaaaaa gacaccgtcg agggcaaata    240

ctctcagttg acttcctccc tgctggattc caagctccgt gacgaccttg agcgactcaa    300

gaagatcagg gcccacagag gcatgaggca ctactggggt ttgagggtgc gtggtcaaca    360
```

```
cacgaagacc accggaagga gaggacgaac tgttggtgtg tccaagaaga agtaatttta    420

atttcctaat aaattggttt tttcaaaaaa aaaaaaaaaa aaaaaaaaaa aaaa          474


<210> SEQ ID NO 14
<211> LENGTH: 332
<212> TYPE: DNA
<213> ORGANISM: Lygus hesperus

<400> SEQUENCE: 14

gaaaggtgat gttcgccatg accgccatca aaggtgtcgg cagacggtac gccaacattg     60

tcctcaagaa ggccgatgtc aacttggaca agagggccgg cgaatgctcc gaagaagaag    120

ttgaaaagat cgttaccatc atgcaaaacc ctaggcaata caaaattccc aactggttcc    180

tcaacagaca aaaagacacc gtcgagggca aatactctca gttgacttcc tccctgctgg    240

attccaagct ccgtgacgac cttgagcgac tcaagaagat cagggcccac agaggcatga    300

ggcactactg gggtttgagg gtgcgtggtc aa                                  332


<210> SEQ ID NO 15
<211> LENGTH: 440
<212> TYPE: DNA
<213> ORGANISM: Lygus hesperus

<400> SEQUENCE: 15

gtgagttctt ctgttgatta gtttttcctt ccctgaaatt atttcgttga agttaatttg     60

gattaccctg aaagaatccg ctgctttttc tctcgctaaa aatcttttac acccgtcacc    120

acggccccct gtgggcaggc acaagctgaa gcacctgccc gtgcacccta actcgcactt    180

catggacgtc aactgccctg ggtgttataa aatcccaacg gtgttctccc ccgcccagaa    240

cgacttcggc tgctggacct gttccaccat cctctgcctg cccacagggg gccgtgccga    300

cctcaccaaa agatgctcgt ttaggagaaa tcaacattat tattcttggt gggaacactt    360

atttttttttg taattaaatt tcaaactaca aaataacttt tccgaaaaac actacaaaaa    420

aaattaaaaa caaaaaaaaa                                                440


<210> SEQ ID NO 16
<211> LENGTH: 324
<212> TYPE: DNA
<213> ORGANISM: Lygus hesperus

<400> SEQUENCE: 16

cttccctgaa attatttcgt tgaagttaat ttggattacc ctgaaagaat ccgctgcttt     60

ttctctcgct aaaaatcttt tacacccgtc accacggccc cctgtgggca ggcacaagct    120

gaagcacctg cccgtgcacc ctaactcgca cttcatggac gtcaactgcc ctgggtgtta    180

taaaatccca acggtgttct cccccgccca gaacgacttc ggctgctgga cctgttccac    240

catcctctgc ctgcccacag ggggccgtgc cgacctcacc aaaagatgct cgtttaggag    300

aaatcaacat tattattctt ggtg                                           324


<210> SEQ ID NO 17
<211> LENGTH: 357
<212> TYPE: DNA
<213> ORGANISM: Lygus hesperus

<400> SEQUENCE: 17

atgggttcaa gagagttaaa gccaagaggg ccaagaagga cgacggtgag atatttgccg     60
```

```
ctaaaaagga agtctacaag ccctctgagc agaggaaagc agaccagaaa aacattgaca    120

aacagaccct gaaagccatc aagcgactca agggagacgc ttgcctcatg aggaaatacc    180

tttgcaccat gttcggattc aggagcagtc aatatcccca ccgtatgaag ttttaatatg    240

ttttcagcca ataaataagt gaaagtttct ctttttttatt actacagact caaattttta    300

ttttctgaaa attattaaaa attcttaatg gcaaaaaaaa aaaaaaaaaa aaaaaaa      357


<210> SEQ ID NO 18
<211> LENGTH: 223
<212> TYPE: DNA
<213> ORGANISM: Lygus hesperus

<400> SEQUENCE: 18

gttcaagaga gttaaagcca agagggccaa gaaggacgac ggtgagatat ttgccgctaa     60

aaaggaagtc tacaagccct ctgagcagag gaaagcagac cagaaaaaca ttgacaaaca    120

gaccctgaaa gccatcaagc gactcaaggg agacgcttgc ctcatgagga aatacctttg    180

caccatgttc ggattcagga gcagtcaata tccccaccgt atg                       223


<210> SEQ ID NO 19
<211> LENGTH: 632
<212> TYPE: DNA
<213> ORGANISM: Lygus hesperus

<400> SEQUENCE: 19

atgggacctt ttttccgtgt gtctggctta ggcctcgcgt gttcttgtat ttttacggga     60

aatttagtga aaaagtgtaa atttaacgcg taaaaatggg tcgtatgcac gcacctggta    120

agggtatttc ccagtcagct ctcccctatc gtcgtagcgt cccaacatgg ctgaagctca    180

ctcctgacga cgtcaaggat cagattttca aactcaccaa gaaaggactg actccatctc    240

agatcggtgt catcctcagg gattctcacg gtgtggctca agtcagattc gtcaccgggt    300

cgaagatcct caggatcatg aaagccatcg gcctcgctcc tgacctccca gaggacctct    360

acttcctcat caaaaaagcc gttgctatca ggaaacatct tgaaagaaat aggaaagaca    420

aagactctaa attcggactt atccccgtcg agtccaggat ccacaggttg gcaagatact    480

acaaaaccaa gggcaccctt ccacccacct ggaaatacga gtccagcacc gcctctgctc    540

tggtggcttg aatattcaac tttttatttg tctactgttt aattaatata atgtgattta    600

gcaaaaaaaa aaaaaaaaaa aaaaaaaaaa aa                                   632


<210> SEQ ID NO 20
<211> LENGTH: 457
<212> TYPE: DNA
<213> ORGANISM: Lygus hesperus

<400> SEQUENCE: 20

gggtcgtatg cacgcacctg gtaagggtat ttcccagtca gctctcccct atcgtcgtag     60

cgtcccaaca tggctgaagc tcactcctga cgacgtcaag gatcagattt tcaaactcac    120

caagaaagga ctgactccat ctcagatcgg tgtcatcctc agggattctc acggtgtggc    180

tcaagtcaga ttcgtcaccg ggtcgaagat cctcaggatc atgaaagcca tcggcctcgc    240

tcctgacctc ccagaggacc tctacttcct catcaaaaaa gccgttgcta tcaggaaaca    300

tcttgaaaga aataggaaag acaaagactc taaattcgga cttatccccg tcgagtccag    360

gatccacagg ttggcaagat actacaaaac caagggcacc cttccaccca cctggaaata    420

cgagtccagc accgcctctg ctctggtggc ttgaata                              457
```

<210> SEQ ID NO 21
<211> LENGTH: 407
<212> TYPE: DNA
<213> ORGANISM: Lygus hesperus

<400> SEQUENCE: 21

```
atgggaccgt ttgcctcaca atccagaaca gacaggctgc catatccgtc gtcccctctg     60

cagcctccct cgtaatcaag gccctcaaag agcccccgag ggacaggaag aagaacaaga    120

acatcaaaca cgacggtaac ctgagtatgg atgacattct cggaattgcc aaaaccatga    180

ggccgaggtc gatgtccagg aaactggaag gaaccgtcaa ggaaatcctt gggacagctc    240

agtctgtcgg atgcacgatc gaaggccgag ctccccacga cgtcatcgac tccatcaaca    300

acggcgaaat ggaaatccct gacgaataaa ctgttcatga gtttatggat tttatataaa    360

aaataaaaag ttgaaaaatc caaaaaaaaa aaaaaaaaag aaaaaaa                  407
```

<210> SEQ ID NO 22
<211> LENGTH: 302
<212> TYPE: DNA
<213> ORGANISM: Lygus hesperus

<400> SEQUENCE: 22

```
accgtttgcc tcacaatcca gaacagacag gctgccatat ccgtcgtccc ctctgcagcc     60

tccctcgtaa tcaaggccct caaagagccc ccgagggaca ggaagaagaa caagaacatc    120

aaacacgacg gtaacctgag tatggatgac attctcggaa ttgccaaaac catgaggccg    180

aggtcgatgt ccaggaaact ggaaggaacc gtcaaggaaa tccttgggac agctcagtct    240

gtcggatgca cgatcgaagg ccgagctccc cacgacgtca tcgactccat caacaacggc    300

ga                                                                   302
```

<210> SEQ ID NO 23
<211> LENGTH: 794
<212> TYPE: DNA
<213> ORGANISM: Lygus hesperus

<400> SEQUENCE: 23

```
catggggagt caatttggat ctatcgccag atgaagatgt ctcctgccgt gttcgctgtt     60

ctgctggtac tttcagcttc ccaggtcttg ggagatgatg catccaagtt ccaacacgag    120

gaaatcatgg aagtcctcag ctcggtcaac aaaaccgtca acaaattgta cgacttgatg    180

tccacgcaga aggaaagaga tattgacttt atcgagaaga aaatggatga gacgtaccag    240

caactcagga acaagaggga ggcgccggct gagaaccctg aagccattga caagatccaa    300

aacgcgttca aaagctttca agacggcgtc aaggacttcg tcaagtccgc ttcttcctcg    360

gacctctaca agaaggttca ggaaatcggc gaggacctgt agaacaaagg caaagagctc    420

ggagagaagc tgcaagaaac catcaataac gccagaacga aaaactcaga cgagaagaag    480

gactaaactg aggattttga ctctgcacaa acgcccgttg gtgtttaaac gtatttctta    540

cgtttattat catcggggtt catgaaatca aaaatacacc atcgcatacc acctcgaaaa    600

gaacataata tatgtgaaaa gacaagaaaa ggtgttcaat tgtgtcttta actggtggtt    660

atcacgattc acatgaaata ctactaagaa aacccaaaaa ccgtcatgaa acccgaagta    720

tgcttctgta ttacctaatt gtgctgataa ttcttaataa aatattatac tgagaaaaaa    780

aaaaaaaaaa aaaa                                                      794
```

<210> SEQ ID NO 24
<211> LENGTH: 278
<212> TYPE: DNA
<213> ORGANISM: Lygus hesperus

<400> SEQUENCE: 24
ttctgctggt actttcagct tcccaggtct tgggagatga tgcatccaag ttccaacacg 60
aggaaatcat ggaagtcctc agctcggtca acaaaaccgt caacaaattg tacgacttga 120
tgtccacgca gaaggaaaga gatattgact ttatcgagaa gaaaatggat gagacgtacc 180
agcaactcag gaacaagagg gaggcgccgg ctgagaaccc tgaagccatt gacaagatcc 240
aaaacgcgtt caaaagcttt caagacggcg tcaaggac 278

<210> SEQ ID NO 25
<211> LENGTH: 437
<212> TYPE: DNA
<213> ORGANISM: Lygus hesperus

<400> SEQUENCE: 25
atgggatcca ataataacca ttaaggcaat tggacatcaa tgatactgaa catatgaata 60
ttcagatatc aaaaatatcg aaatagaatc atatataaaa ccaactaacg cattagaaaa 120
taacgaattc cgattacttg aagtagacaa tcgaatcgta ttacctataa aatcaactat 180
ccgaattcta gttacatcat ctgatgtaat tcattcatga accatcccaa gtttgggaat 240
caaaattgat ggcacaccag gacgattaaa tcaagggaga ataaacataa accgaccagg 300
actaatatat gggcaatgtt ctgaaatttg tggagcaaac cacagattta taccaatcgt 360
aattgaaaga gtttcaatta atcaatttat aaactgatta aattcaaaat aaaaaaaaaa 420
aaaaaaaaaa aaaaaaa 437

<210> SEQ ID NO 26
<211> LENGTH: 327
<212> TYPE: DNA
<213> ORGANISM: Lygus hesperus

<400> SEQUENCE: 26
aacgcagagt acatgggatc caataataac cattaaggca attggacatc aatgatactg 60
aacatatgaa tattcagata tcaaaaatat cgaaatagaa tcatatataa aaccaactaa 120
cgcattagaa aataacgaat tccgattact tgaagtagac aatcgaatcg tattacctat 180
aaaatcaact atccgaattc tagttacatc atctgatgta attcattcat gaaccatccc 240
aagtttggga atcaaaattg atggcacacc aggacgatta aatcaaggga gaataaacat 300
aaaccgacca ggactaatat atgggca 327

<210> SEQ ID NO 27
<211> LENGTH: 42
<212> TYPE: DNA
<213> ORGANISM: Artificial
<220> FEATURE:
<223> OTHER INFORMATION: Primer

<400> SEQUENCE: 27
gcgtaatacg actcactata ggcaaacagg ccgaaatcga ga 42

<210> SEQ ID NO 28
<211> LENGTH: 23
<212> TYPE: DNA
<213> ORGANISM: Artificial

<220> FEATURE:
<223> OTHER INFORMATION: Primer

<400> SEQUENCE: 28
tgacgacctt gagttggttt ctg 23

<210> SEQ ID NO 29
<211> LENGTH: 20
<212> TYPE: DNA
<213> ORGANISM: Artificial
<220> FEATURE:
<223> OTHER INFORMATION: Primer

<400> SEQUENCE: 29
caaacaggcc gaaatcgaga 20

<210> SEQ ID NO 30
<211> LENGTH: 45
<212> TYPE: DNA
<213> ORGANISM: Artificial
<220> FEATURE:
<223> OTHER INFORMATION: Primer

<400> SEQUENCE: 30
gcgtaatacg actcactata ggtgacgacc ttgagttggt ttctg 45

<210> SEQ ID NO 31
<211> LENGTH: 42
<212> TYPE: DNA
<213> ORGANISM: Artificial
<220> FEATURE:
<223> OTHER INFORMATION: Primer

<400> SEQUENCE: 31
gcgtaatacg actcactata gggggcatca tgtcgaaagc tg 42

<210> SEQ ID NO 32
<211> LENGTH: 20
<212> TYPE: DNA
<213> ORGANISM: Artificial
<220> FEATURE:
<223> OTHER INFORMATION: Primer

<400> SEQUENCE: 32
cgaagcccat gtcatcatcg 20

<210> SEQ ID NO 33
<211> LENGTH: 20
<212> TYPE: DNA
<213> ORGANISM: Artificial
<220> FEATURE:
<223> OTHER INFORMATION: Primer

<400> SEQUENCE: 33
gggcatcatg tcgaaagctg 20

<210> SEQ ID NO 34
<211> LENGTH: 42
<212> TYPE: DNA
<213> ORGANISM: Artificial
<220> FEATURE:
<223> OTHER INFORMATION: Primer

<400> SEQUENCE: 34
gcgtaatacg actcactata ggcgaagccc atgtcatcat cg 42

<210> SEQ ID NO 35
<211> LENGTH: 44
<212> TYPE: DNA
<213> ORGANISM: Artificial
<220> FEATURE:
<223> OTHER INFORMATION: Primer

<400> SEQUENCE: 35
gcgtaatacg actcactata gggggcaggt cttctccata acca 44

<210> SEQ ID NO 36
<211> LENGTH: 20
<212> TYPE: DNA
<213> ORGANISM: Artificial
<220> FEATURE:
<223> OTHER INFORMATION: Primer

<400> SEQUENCE: 36
gattttgcgg tgccaacgac 20

<210> SEQ ID NO 37
<211> LENGTH: 22
<212> TYPE: DNA
<213> ORGANISM: Artificial
<220> FEATURE:
<223> OTHER INFORMATION: Primer

<400> SEQUENCE: 37
gggcaggtct tctccataac ca 22

<210> SEQ ID NO 38
<211> LENGTH: 42
<212> TYPE: DNA
<213> ORGANISM: Artificial
<220> FEATURE:
<223> OTHER INFORMATION: Primer

<400> SEQUENCE: 38
gcgtaatacg actcactata gggattttgc ggtgccaacg ac 42

<210> SEQ ID NO 39
<211> LENGTH: 44
<212> TYPE: DNA
<213> ORGANISM: Artificial
<220> FEATURE:
<223> OTHER INFORMATION: Primer

<400> SEQUENCE: 39
gcgtaatacg actcactata ggattgcaca agctgaatcc ctcc 44

<210> SEQ ID NO 40
<211> LENGTH: 20
<212> TYPE: DNA
<213> ORGANISM: Artificial
<220> FEATURE:
<223> OTHER INFORMATION: Primer

<400> SEQUENCE: 40
attcacaaag cgggtgctgg 20

<210> SEQ ID NO 41
<211> LENGTH: 22
<212> TYPE: DNA
<213> ORGANISM: Artificial
<220> FEATURE:
<223> OTHER INFORMATION: Primer

<400> SEQUENCE: 41
attgcacaag ctgaatccct cc 22

<210> SEQ ID NO 42
<211> LENGTH: 42
<212> TYPE: DNA
<213> ORGANISM: Artificial
<220> FEATURE:
<223> OTHER INFORMATION: Primer

<400> SEQUENCE: 42
gcgtaatacg actcactata ggattcacaa agcgggtgct gg 42

<210> SEQ ID NO 43
<211> LENGTH: 44
<212> TYPE: DNA
<213> ORGANISM: Artificial
<220> FEATURE:
<223> OTHER INFORMATION: Primer

<400> SEQUENCE: 43
gcgtaatacg actcactata ggccctctac gagtgcatca atgg 44

<210> SEQ ID NO 44
<211> LENGTH: 20
<212> TYPE: DNA
<213> ORGANISM: Artificial
<220> FEATURE:
<223> OTHER INFORMATION: Primer

<400> SEQUENCE: 44
cccatcgtgg atttgacgtg 20

<210> SEQ ID NO 45
<211> LENGTH: 22
<212> TYPE: DNA
<213> ORGANISM: Artificial
<220> FEATURE:
<223> OTHER INFORMATION: Primer

<400> SEQUENCE: 45
ccctctacga gtgcatcaat gg 22

<210> SEQ ID NO 46
<211> LENGTH: 42
<212> TYPE: DNA
<213> ORGANISM: Artificial
<220> FEATURE:
<223> OTHER INFORMATION: Primer

<400> SEQUENCE: 46
gcgtaatacg actcactata ggcccatcgt ggatttgacg tg 42

<210> SEQ ID NO 47
<211> LENGTH: 47
<212> TYPE: DNA
<213> ORGANISM: Artificial
<220> FEATURE:
<223> OTHER INFORMATION: Primer

<400> SEQUENCE: 47
gcgtaatacg actcactata ggccaataaa gatcaacttt cccagag 47

<210> SEQ ID NO 48

<211> LENGTH: 25
<212> TYPE: DNA
<213> ORGANISM: Artificial
<220> FEATURE:
<223> OTHER INFORMATION: Primer

<400> SEQUENCE: 48
ttagacagac tcttgaactg gaggc 25

<210> SEQ ID NO 49
<211> LENGTH: 25
<212> TYPE: DNA
<213> ORGANISM: Artificial
<220> FEATURE:
<223> OTHER INFORMATION: Primer

<400> SEQUENCE: 49
ccaataaaga tcaactttcc cagag 25

<210> SEQ ID NO 50
<211> LENGTH: 47
<212> TYPE: DNA
<213> ORGANISM: Artificial
<220> FEATURE:
<223> OTHER INFORMATION: Primer

<400> SEQUENCE: 50
gcgtaatacg actcactata ggttagacag actcttgaac tggaggc 47

<210> SEQ ID NO 51
<211> LENGTH: 44
<212> TYPE: DNA
<213> ORGANISM: Artificial
<220> FEATURE:
<223> OTHER INFORMATION: Primer

<400> SEQUENCE: 51
gcgtaatacg actcactata gggaaaggtg atgttcgcca tgac 44

<210> SEQ ID NO 52
<211> LENGTH: 20
<212> TYPE: DNA
<213> ORGANISM: Artificial
<220> FEATURE:
<223> OTHER INFORMATION: Primer

<400> SEQUENCE: 52
ttgaccacgc accctcaaac 20

<210> SEQ ID NO 53
<211> LENGTH: 22
<212> TYPE: DNA
<213> ORGANISM: Artificial
<220> FEATURE:
<223> OTHER INFORMATION: Primer

<400> SEQUENCE: 53
gaaaggtgat gttcgccatg ac 22

<210> SEQ ID NO 54
<211> LENGTH: 42
<212> TYPE: DNA
<213> ORGANISM: Artificial
<220> FEATURE:
<223> OTHER INFORMATION: Primer

<400> SEQUENCE: 54
gcgtaatacg actcactata ggttgaccac gcaccctcaa ac 42

<210> SEQ ID NO 55
<211> LENGTH: 47
<212> TYPE: DNA
<213> ORGANISM: Artificial
<220> FEATURE:
<223> OTHER INFORMATION: Primer

<400> SEQUENCE: 55
gcgtaatacg actcactata ggcttccctg aaattatttc gttgaag 47

<210> SEQ ID NO 56
<211> LENGTH: 28
<212> TYPE: DNA
<213> ORGANISM: Artificial
<220> FEATURE:
<223> OTHER INFORMATION: Primer

<400> SEQUENCE: 56
caccaagaat aataatgttg atttctcc 28

<210> SEQ ID NO 57
<211> LENGTH: 25
<212> TYPE: DNA
<213> ORGANISM: Artificial
<220> FEATURE:
<223> OTHER INFORMATION: Primer

<400> SEQUENCE: 57
cttccctgaa attatttcgt tgaag 25

<210> SEQ ID NO 58
<211> LENGTH: 50
<212> TYPE: DNA
<213> ORGANISM: Artificial
<220> FEATURE:
<223> OTHER INFORMATION: Primer

<400> SEQUENCE: 58
gcgtaatacg actcactata ggcaccaaga ataataatgt tgatttctcc 50

<210> SEQ ID NO 59
<211> LENGTH: 47
<212> TYPE: DNA
<213> ORGANISM: Artificial
<220> FEATURE:
<223> OTHER INFORMATION: Primer

<400> SEQUENCE: 59
gcgtaatacg actcactata gggttcaaga gagttaaagc caagagg 47

<210> SEQ ID NO 60
<211> LENGTH: 22
<212> TYPE: DNA
<213> ORGANISM: Artificial
<220> FEATURE:
<223> OTHER INFORMATION: Primer

<400> SEQUENCE: 60
catacggtgg ggatattgac tg 22

<210> SEQ ID NO 61
<211> LENGTH: 25
<212> TYPE: DNA

<213> ORGANISM: Artificial
<220> FEATURE:
<223> OTHER INFORMATION: Primer

<400> SEQUENCE: 61
gttcaagaga gttaaagcca agagg 25

<210> SEQ ID NO 62
<211> LENGTH: 44
<212> TYPE: DNA
<213> ORGANISM: Artificial
<220> FEATURE:
<223> OTHER INFORMATION: Primer

<400> SEQUENCE: 62
gcgtaatacg actcactata ggcatacggt ggggatattg actg 44

<210> SEQ ID NO 63
<211> LENGTH: 42
<212> TYPE: DNA
<213> ORGANISM: Artificial
<220> FEATURE:
<223> OTHER INFORMATION: Primer

<400> SEQUENCE: 63
gcgtaatacg actcactata gggggtcgta tgcacgcacc tg 42

<210> SEQ ID NO 64
<211> LENGTH: 23
<212> TYPE: DNA
<213> ORGANISM: Artificial
<220> FEATURE:
<223> OTHER INFORMATION: Primer

<400> SEQUENCE: 64
tattcaagcc accagagcag agg 23

<210> SEQ ID NO 65
<211> LENGTH: 20
<212> TYPE: DNA
<213> ORGANISM: Artificial
<220> FEATURE:
<223> OTHER INFORMATION: Primer

<400> SEQUENCE: 65
gggtcgtatg cacgcacctg 20

<210> SEQ ID NO 66
<211> LENGTH: 45
<212> TYPE: DNA
<213> ORGANISM: Artificial
<220> FEATURE:
<223> OTHER INFORMATION: Primer

<400> SEQUENCE: 66
gcgtaatacg actcactata ggtattcaag ccaccagagc agagg 45

<210> SEQ ID NO 67
<211> LENGTH: 42
<212> TYPE: DNA
<213> ORGANISM: Artificial
<220> FEATURE:
<223> OTHER INFORMATION: Primer

<400> SEQUENCE: 67
gcgtaatacg actcactata ggaccgtttg cctcacaatc ca 42

<210> SEQ ID NO 68
<211> LENGTH: 20
<212> TYPE: DNA
<213> ORGANISM: Artificial
<220> FEATURE:
<223> OTHER INFORMATION: Primer

<400> SEQUENCE: 68
tcgccgttgt tgatggagtc 20

<210> SEQ ID NO 69
<211> LENGTH: 20
<212> TYPE: DNA
<213> ORGANISM: Artificial
<220> FEATURE:
<223> OTHER INFORMATION: Primer

<400> SEQUENCE: 69
accgtttgcc tcacaatcca 20

<210> SEQ ID NO 70
<211> LENGTH: 42
<212> TYPE: DNA
<213> ORGANISM: Artificial
<220> FEATURE:
<223> OTHER INFORMATION: Primer

<400> SEQUENCE: 70
gcgtaatacg actcactata ggtcgccgtt gttgatggag tc 42

<210> SEQ ID NO 71
<211> LENGTH: 45
<212> TYPE: DNA
<213> ORGANISM: Artificial
<220> FEATURE:
<223> OTHER INFORMATION: Primer

<400> SEQUENCE: 71
gcgtaatacg actcactata ggggtatcaa cgcagagtac atggg 45

<210> SEQ ID NO 72
<211> LENGTH: 20
<212> TYPE: DNA
<213> ORGANISM: Artificial
<220> FEATURE:
<223> OTHER INFORMATION: Primer

<400> SEQUENCE: 72
gtccttgacg ccgtcttgaa 20

<210> SEQ ID NO 73
<211> LENGTH: 23
<212> TYPE: DNA
<213> ORGANISM: Artificial
<220> FEATURE:
<223> OTHER INFORMATION: Primer

<400> SEQUENCE: 73
ggtatcaacg cagagtacat ggg 23

<210> SEQ ID NO 74
<211> LENGTH: 42
<212> TYPE: DNA
<213> ORGANISM: Artificial
<220> FEATURE:

```
<223> OTHER INFORMATION: Primer

<400> SEQUENCE: 74

gcgtaatacg actcactata gggtccttga cgccgtcttg aa                        42


<210> SEQ ID NO 75
<211> LENGTH: 44
<212> TYPE: DNA
<213> ORGANISM: Artificial
<220> FEATURE:
<223> OTHER INFORMATION: Primer

<400> SEQUENCE: 75

gcgtaatacg actcactata ggtgcccata tattagtcct ggtc                      44


<210> SEQ ID NO 76
<211> LENGTH: 20
<212> TYPE: DNA
<213> ORGANISM: Artificial
<220> FEATURE:
<223> OTHER INFORMATION: Primer

<400> SEQUENCE: 76

aacgcagagt acatgggatc                                                 20


<210> SEQ ID NO 77
<211> LENGTH: 22
<212> TYPE: DNA
<213> ORGANISM: Artificial
<220> FEATURE:
<223> OTHER INFORMATION: Primer

<400> SEQUENCE: 77

tgcccatata ttagtcctgg tc                                              22


<210> SEQ ID NO 78
<211> LENGTH: 42
<212> TYPE: DNA
<213> ORGANISM: Artificial
<220> FEATURE:
<223> OTHER INFORMATION: Primer

<400> SEQUENCE: 78

gcgtaatacg actcactata ggaacgcaga gtacatggga tc                        42


<210> SEQ ID NO 79
<211> LENGTH: 197
<212> TYPE: PRT
<213> ORGANISM: Lygus hesperus

<400> SEQUENCE: 79

Met Ala Asp Asp Glu Ala Lys Lys Ala Lys Gln Ala Glu Ile Glu Arg
1               5                   10                  15

Lys Arg Ala Glu Val Arg Lys Arg Met Glu Glu Ala Ser Lys Ala Lys
            20                  25                  30

Lys Ala Lys Lys Gly Phe Met Thr Pro Glu Arg Lys Lys Lys Leu Arg
        35                  40                  45

Leu Leu Leu Arg Lys Lys Ala Ala Glu Glu Leu Lys Lys Glu Gln Glu
    50                  55                  60

Arg Lys Ala Ala Glu Arg Arg Arg Thr Ile Glu Glu Arg Cys Gly Gln
65                  70                  75                  80

Ile Ala Asp Val Asp Asn Ala Asn Glu Ala Thr Leu Lys Lys Leu Cys
                85                  90                  95
```

```
Thr Asp Tyr His Lys Arg Ile Asp Ala Leu Glu Arg Ser Lys Ile Asp
            100                 105                 110

Ile Glu Phe Glu Val Glu Arg Arg Asp Leu Glu Ile Ala Asp Leu Asn
        115                 120                 125

Ser Gln Val Asn Asp Leu Arg Gly Lys Phe Val Lys Pro Thr Leu Lys
    130                 135                 140

Lys Val Ser Lys Tyr Glu Asn Lys Phe Ala Lys Leu Gln Lys Lys Ala
145                 150                 155                 160

Ala Glu Phe Asn Phe Arg Asn Gln Leu Lys Val Val Lys Lys Lys Glu
                165                 170                 175

Phe Thr Leu Glu Glu Glu Asp Lys Glu Pro Lys Lys Ser Glu Lys Ala
            180                 185                 190

Glu Trp Gln Lys Lys
        195


<210> SEQ ID NO 80
<211> LENGTH: 115
<212> TYPE: PRT
<213> ORGANISM: Lygus hesperus

<400> SEQUENCE: 80

Met Gly Ile Met Ser Lys Ala Glu Leu Ala Cys Val Tyr Ser Ala Leu
1               5                   10                  15

Ile Leu Ile Asp Asp Asp Val Ala Val Thr Gly Glu Lys Ile Gln Thr
            20                  25                  30

Ile Leu Lys Ala Ala Ser Val Asp Ile Glu Pro Tyr Trp Pro Gly Leu
        35                  40                  45

Phe Ala Lys Ala Leu Glu Gly Ile Asn Pro Lys Asp Leu Ile Ser Ser
    50                  55                  60

Ile Gly Ser Gly Val Gly Ala Gly Ala Pro Ala Val Gly Gly Ala Ala
65                  70                  75                  80

Pro Ala Ala Ala Ala Ala Pro Ala Ala Glu Ala Lys Lys Glu Glu Lys
                85                  90                  95

Lys Lys Val Glu Ser Asp Pro Glu Ser Asp Asp Asp Met Gly Phe Gly
            100                 105                 110

Leu Phe Asp
        115


<210> SEQ ID NO 81
<211> LENGTH: 121
<212> TYPE: PRT
<213> ORGANISM: Lygus hesperus

<400> SEQUENCE: 81

Met Ile Pro Pro Thr Ser Arg Pro Gln Val Thr Val Tyr Ser Asp Lys
1               5                   10                  15

Asn Glu Ala Thr Gly Thr Leu Leu Asn Leu Pro Ala Val Phe Asn Ala
            20                  25                  30

Pro Ile Arg Pro Asp Val Val Asn Phe Val His Gln Asn Val Ala Lys
        35                  40                  45

Asn His Arg Gln Pro Tyr Cys Val Ser Ala Gln Ala Gly His Gln Thr
    50                  55                  60

Ser Ala Glu Ser Trp Gly Thr Gly Arg Ala Val Ala Arg Ile Pro Arg
65                  70                  75                  80

Val Arg Gly Gly Gly Thr His Arg Ser Gly Gln Gly Ala Phe Gly Asn
                85                  90                  95
```

```
Met Cys Arg Gly Gly Arg Met Phe Ala Pro Thr Arg Pro Trp Arg Arg
            100                 105                 110

Trp His Arg Lys Ile Asn Val Asn Gln
        115                 120


<210> SEQ ID NO 82
<211> LENGTH: 133
<212> TYPE: PRT
<213> ORGANISM: Lygus hesperus

<400> SEQUENCE: 82

Trp Asp Leu Tyr Ala Glu Lys Val Ala Thr Arg Gly Leu Cys Ala Ile
1               5                   10                  15

Ala Gln Ala Glu Ser Leu Arg Tyr Lys Leu Ile Gly Gly Leu Ala Val
            20                  25                  30

Arg Gly Ala Cys Tyr Gly Val Leu Arg Phe Ile Met Glu Asn Gly Ala
        35                  40                  45

Lys Gly Cys Glu Val Val Val Ser Gly Lys Leu Arg Gly Gln Arg Ala
    50                  55                  60

Lys Ser Met Lys Phe Val Asp Gly Leu Met Ile His Ser Gly Asp Pro
65                  70                  75                  80

Cys Asn Glu Tyr Val Asp Thr Ala Thr Arg His Val Leu Leu Arg Gln
                85                  90                  95

Gly Val Leu Gly Ile Lys Val Lys Ile Met Leu Pro Trp Asp Val Thr
            100                 105                 110

Gly Lys Asn Gly Pro Lys Asn Pro Leu Pro Asp His Val Ser Val Leu
        115                 120                 125

Leu Pro Lys Glu Glu
    130


<210> SEQ ID NO 83
<211> LENGTH: 217
<212> TYPE: PRT
<213> ORGANISM: Lygus hesperus

<400> SEQUENCE: 83

Met Thr Ser Lys Val Ser Arg Glu Thr Leu Tyr Glu Cys Ile Asn Gly
1               5                   10                  15

Val Ile Gln Ser Ser Gln Glu Lys Lys Arg Asn Phe Val Glu Thr Val
            20                  25                  30

Glu Ile Gln Ile Gly Leu Lys Asn Tyr Asp Pro Gln Lys Asp Lys Arg
        35                  40                  45

Phe Ser Gly Thr Val Lys Leu Lys His Ile Pro Arg Pro Lys Met Gln
    50                  55                  60

Val Cys Ile Leu Gly Asp Gln Gln His Cys Asp Glu Ala Lys Ala Asn
65                  70                  75                  80

Asn Val Pro Tyr Met Asp Val Glu Ala Leu Lys Lys Leu Asn Lys Asn
                85                  90                  95

Lys Lys Leu Val Lys Lys Leu Ala Lys Lys Tyr Asp Ala Phe Leu Ala
            100                 105                 110

Ser Glu Ala Leu Ile Lys Gln Ile Pro Arg Leu Leu Gly Pro Gly Leu
        115                 120                 125

Asn Lys Ala Gly Lys Phe Pro Gly Leu Leu Ser His Gln Glu Ser Met
    130                 135                 140

Met Met Lys Ile Asp Glu Val Lys Ala Thr Ile Lys Phe Gln Met Lys
145                 150                 155                 160
```

```
Lys Val Leu Cys Leu Ser Val Ala Val Gly His Val Gly Met Thr Ala
                165                 170                 175

Asp Glu Leu Val Gln Asn Val His Leu Ser Val Asn Phe Leu Val Ser
            180                 185                 190

Leu Leu Lys Lys His Trp Gln Asn Val Arg Ser Leu His Val Lys Ser
        195                 200                 205

Thr Met Gly Pro Pro Gln Arg Leu Tyr
    210                 215


<210> SEQ ID NO 84
<211> LENGTH: 118
<212> TYPE: PRT
<213> ORGANISM: Lygus hesperus

<400> SEQUENCE: 84

Gly Thr Asn Lys Asp Gln Leu Ser Gln Arg Lys Thr Cys Tyr Ala Gln
1               5                   10                  15

His Asn Gln Val Arg Glu Ile Arg Lys Lys Met Val Lys Asn Ile Ser
            20                  25                  30

Asp Ser Ile Ser Ser Cys Asp Leu Arg Ser Val Val Asn Lys Leu Ile
        35                  40                  45

Pro Asp Ser Ile Ala Lys Asp Ile Glu Lys Asn Cys Gln Gly Ile Tyr
    50                  55                  60

Pro Leu His Asp Val Tyr Ile Arg Lys Val Lys Val Leu Lys Lys Pro
65                  70                  75                  80

Arg Phe Glu Leu Ser Lys Leu Leu Glu Leu His Val Asp Gly Lys Gly
                85                  90                  95

Ile Asp Glu Pro Gly Ala Lys Val Thr Arg Thr Asp Ala Tyr Glu Pro
            100                 105                 110

Pro Val Gln Glu Ser Val
        115


<210> SEQ ID NO 85
<211> LENGTH: 128
<212> TYPE: PRT
<213> ORGANISM: Lygus hesperus

<400> SEQUENCE: 85

Lys Val Met Phe Ala Met Thr Ala Ile Lys Gly Val Gly Arg Arg Tyr
1               5                   10                  15

Ala Asn Ile Val Leu Lys Lys Ala Asp Val Asn Leu Asp Lys Arg Ala
            20                  25                  30

Gly Glu Cys Ser Glu Glu Glu Val Glu Lys Ile Val Thr Ile Met Gln
        35                  40                  45

Asn Pro Arg Gln Tyr Lys Ile Pro Asn Trp Phe Leu Asn Arg Gln Lys
    50                  55                  60

Asp Thr Val Glu Gly Lys Tyr Ser Gln Leu Thr Ser Ser Leu Leu Asp
65                  70                  75                  80

Ser Lys Leu Arg Asp Asp Leu Glu Arg Leu Lys Lys Ile Arg Ala His
                85                  90                  95

Arg Gly Met Arg His Tyr Trp Gly Leu Arg Val Arg Gly Gln His Thr
            100                 105                 110

Lys Thr Thr Gly Arg Arg Gly Arg Thr Val Gly Val Ser Lys Lys Lys
        115                 120                 125


<210> SEQ ID NO 86
```

```
<211> LENGTH: 122
<212> TYPE: PRT
<213> ORGANISM: Lygus hesperus

<400> SEQUENCE: 86

Val Leu Leu Leu Ile Ser Phe Ser Phe Pro Glu Ile Ile Ser Leu Lys
1               5                   10                  15

Leu Ile Trp Ile Thr Leu Lys Glu Ser Ala Ala Phe Ser Leu Ala Lys
            20                  25                  30

Asn Leu Leu His Pro Ser Pro Arg Pro Pro Val Gly Arg His Lys Leu
        35                  40                  45

Lys His Leu Pro Val His Pro Asn Ser His Phe Met Asp Val Asn Cys
    50                  55                  60

Pro Gly Cys Tyr Lys Ile Pro Thr Val Phe Ser Pro Ala Gln Asn Asp
65                  70                  75                  80

Phe Gly Cys Trp Thr Cys Ser Thr Ile Leu Cys Leu Pro Thr Gly Gly
                85                  90                  95

Arg Ala Asp Leu Thr Lys Arg Cys Ser Phe Arg Arg Asn Gln His Tyr
            100                 105                 110

Tyr Ser Trp Trp Glu His Leu Phe Phe Leu
        115                 120


<210> SEQ ID NO 87
<211> LENGTH: 77
<212> TYPE: PRT
<213> ORGANISM: Lygus hesperus

<400> SEQUENCE: 87

Gly Phe Lys Arg Val Lys Ala Lys Arg Ala Lys Lys Asp Asp Gly Glu
1               5                   10                  15

Ile Phe Ala Ala Lys Lys Glu Val Tyr Lys Pro Ser Glu Gln Arg Lys
            20                  25                  30

Ala Asp Gln Lys Asn Ile Asp Lys Gln Thr Leu Lys Ala Ile Lys Arg
        35                  40                  45

Leu Lys Gly Asp Ala Cys Leu Met Arg Lys Tyr Leu Cys Thr Met Phe
    50                  55                  60

Gly Phe Arg Ser Ser Gln Tyr Pro His Arg Met Lys Phe
65                  70                  75


<210> SEQ ID NO 88
<211> LENGTH: 151
<212> TYPE: PRT
<213> ORGANISM: Lygus hesperus

<400> SEQUENCE: 88

Met Gly Arg Met His Ala Pro Gly Lys Gly Ile Ser Gln Ser Ala Leu
1               5                   10                  15

Pro Tyr Arg Arg Ser Val Pro Thr Trp Leu Lys Leu Thr Pro Asp Asp
            20                  25                  30

Val Lys Asp Gln Ile Phe Lys Leu Thr Lys Lys Gly Leu Thr Pro Ser
        35                  40                  45

Gln Ile Gly Val Ile Leu Arg Asp Ser His Gly Val Ala Gln Val Arg
    50                  55                  60

Phe Val Thr Gly Ser Lys Ile Leu Arg Ile Met Lys Ala Ile Gly Leu
65                  70                  75                  80

Ala Pro Asp Leu Pro Glu Asp Leu Tyr Phe Leu Ile Lys Lys Ala Val
                85                  90                  95
```

```
Ala Ile Arg Lys His Leu Glu Arg Asn Arg Lys Asp Lys Asp Ser Lys
            100                 105                 110

Phe Gly Leu Ile Pro Val Glu Ser Arg Ile His Arg Leu Ala Arg Tyr
        115                 120                 125

Tyr Lys Thr Lys Gly Thr Leu Pro Pro Thr Trp Lys Tyr Glu Ser Ser
    130                 135                 140

Thr Ala Ser Ala Leu Val Ala
145                 150


<210> SEQ ID NO 89
<211> LENGTH: 108
<212> TYPE: PRT
<213> ORGANISM: Lygus hesperus

<400> SEQUENCE: 89

Gly Thr Val Cys Leu Thr Ile Gln Asn Arg Gln Ala Ala Ile Ser Val
1               5                   10                  15

Val Pro Ser Ala Ala Ser Leu Val Ile Lys Ala Leu Lys Glu Pro Pro
            20                  25                  30

Arg Asp Arg Lys Lys Asn Lys Asn Ile Lys His Asp Gly Asn Leu Ser
        35                  40                  45

Met Asp Asp Ile Leu Gly Ile Ala Lys Thr Met Arg Pro Arg Ser Met
    50                  55                  60

Ser Arg Lys Leu Glu Gly Thr Val Lys Glu Ile Leu Gly Thr Ala Gln
65                  70                  75                  80

Ser Val Gly Cys Thr Ile Glu Gly Arg Ala Pro His Asp Val Ile Asp
                85                  90                  95

Ser Ile Asn Asn Gly Glu Met Glu Ile Pro Asp Glu
            100                 105


<210> SEQ ID NO 90
<211> LENGTH: 133
<212> TYPE: PRT
<213> ORGANISM: Lygus hesperus

<400> SEQUENCE: 90

His Gly Glu Ser Ile Trp Ile Tyr Arg Gln Met Lys Met Ser Pro Ala
1               5                   10                  15

Val Phe Ala Val Leu Leu Val Leu Ser Ala Ser Gln Val Leu Gly Asp
            20                  25                  30

Asp Ala Ser Lys Phe Gln His Glu Glu Ile Met Glu Val Leu Ser Ser
        35                  40                  45

Val Asn Lys Thr Val Asn Lys Leu Tyr Asp Leu Met Ser Thr Gln Lys
    50                  55                  60

Glu Arg Asp Ile Asp Phe Ile Glu Lys Lys Met Asp Glu Thr Tyr Gln
65                  70                  75                  80

Gln Leu Arg Asn Lys Arg Glu Ala Pro Ala Glu Asn Pro Glu Ala Ile
                85                  90                  95

Asp Lys Ile Gln Asn Ala Phe Lys Ser Phe Gln Asp Gly Val Lys Asp
            100                 105                 110

Phe Val Lys Ser Ala Ser Ser Ser Asp Leu Tyr Lys Lys Val Gln Glu
        115                 120                 125

Ile Gly Glu Asp Leu
    130


<210> SEQ ID NO 91
<211> LENGTH: 118
```

```
<212> TYPE: PRT
<213> ORGANISM: Lygus hesperus

<400> SEQUENCE: 91

Thr Tyr Glu Tyr Ser Asp Ile Lys Asn Ile Glu Ile Glu Ser Tyr Ile
1               5                   10                  15

Lys Pro Thr Asn Ala Leu Glu Asn Asn Glu Phe Arg Leu Leu Glu Val
            20                  25                  30

Asp Asn Arg Ile Val Leu Pro Ile Lys Ser Thr Ile Arg Ile Leu Val
        35                  40                  45

Thr Ser Ser Asp Val Ile His Ser Thr Ile Pro Ser Leu Gly Ile Lys
    50                  55                  60

Ile Asp Gly Thr Pro Gly Arg Leu Asn Gln Gly Arg Ile Asn Ile Asn
65                  70                  75                  80

Arg Pro Gly Leu Ile Tyr Gly Gln Cys Ser Glu Ile Cys Gly Ala Asn
                85                  90                  95

His Arg Phe Ile Pro Ile Val Ile Glu Arg Val Ser Ile Asn Gln Phe
            100                 105                 110

Ile Asn Leu Asn Ser Lys
        115


<210> SEQ ID NO 92
<211> LENGTH: 20
<212> TYPE: DNA
<213> ORGANISM: Artificial
<220> FEATURE:
<223> OTHER INFORMATION: Adaptor

<400> SEQUENCE: 92

aagcagtggt atcaacgcag                                                  20


<210> SEQ ID NO 93
<211> LENGTH: 20
<212> TYPE: DNA
<213> ORGANISM: Artificial
<220> FEATURE:
<223> OTHER INFORMATION: Primer

<400> SEQUENCE: 93

aagcagtggt atcaacgcag                                                  20


<210> SEQ ID NO 94
<211> LENGTH: 42
<212> TYPE: DNA
<213> ORGANISM: Artificial
<220> FEATURE:
<223> OTHER INFORMATION: Primer

<400> SEQUENCE: 94

gcgtaatacg actcactata ggaagcagtg gtatcaacgc ag                         42


<210> SEQ ID NO 95
<211> LENGTH: 717
<212> TYPE: DNA
<213> ORGANISM: Lygus hesperus

<400> SEQUENCE: 95

aaagtgtggt tctcttcgtc cgaccatgag ttcgctcaaa ctgcagaaga ggctcgccgc      60

ctcggtgatg agatgcggca agaagaaagt gtggttggac cctaatgaaa tcaacgaaat     120

cgccaacacc aactctaggc aaaacatccg taagctgatc aaggatggtt tgatcatcaa     180
```

```
aaagcctgtg gctgtccact ccagagcccg cgtccgtaaa aacacagaag ccagacggaa    240

gggtcgtcat tgtggcttcg gtaagaggaa gggtaccgcc aacgccagaa tgcctgtgaa    300

ggtcctgtgg gtcaacagaa tgagagtcct gcgacggctc cttaaaaaat acagagaagc    360

caagaagatc gataggcaaa tgtaccacga cctttacatg aaagccaaag gtaacgtctt    420

caaaaacaag agggtactga tggacttcat tcacaagaag aaggctgaaa aggcgagatc    480

aaagatgttg aaggaccagg cagaggcgag acgtttcaag gtcaaggagg cgaagaagag    540

gcgcgaggag aggatcgcca ccaagaagca agagatcatg caggcgtacg cccgagaaga    600

cgaggctgcc gtcaaaaagt gatctcgccc cctccgtttt taaattttaa acaaaaaacg    660

tattttgtac aaaaatttac aaaaaaaaaa aaaaaaaaaa aaaaaaaaaa aaaaaaa       717
```

<210> SEQ ID NO 96
<211> LENGTH: 2304
<212> TYPE: DNA
<213> ORGANISM: Lygus hesperus

<400> SEQUENCE: 96

```
atgacgacct acgaggagtt cattcaacag agcgaggagc gcgacggtat caggttcact     60

tggaacgtct ggccatcaag tcgcatcgaa gccaccaggt tggtcgtacc cgtaggatgt    120

ctctatcaac cactaaaaga acgcacggat cttccagcta ttcaatacga tcccgttcta    180

tgcactagga atacctgtag agccatactc aacccgatgt gccaagtaaa ctatagggca    240

aagttgtggg tgtgtaactt ctgtttccag aggaatccgt tcccaccaca atacgccgca    300

atttccgagc agcatcagcc tgctgagttg attccatcat tctcaactat agagtatact    360

atatctagag ctcaattttt gcctcctata ttcctattgg tggtggatac gtgtttggat    420

gatgacgagc taggagctct gaaagattcg ttacaaacgt ctctatcttt gctaccaacc    480

aactccctag ttggtctgat cacgtttggt aaaatggtcc aagttcacga acttgggtgt    540

gaaggttgtt cccggagcta cgtgttcaga ggcaccaagg atttgacgtc caagcaagta    600

caggacatgc ttgggatcgg aaaggtttcc gcttctcctc agcaacagca gcaaagggca    660

atgggcggtc agcagccatt ccccaccaat cggttcattc agccgattca aagttgtgac    720

atgagcctca ccgacttgtt gggcgaaatg cagcgtgatc catggccagt gggtcagggt    780

aagcgacctc ttagatcaac gggtgctgct ctagctattg ccattgggtt gttggagtgc    840

tcctacccca acacgggagc aaaagtcatg ttgttccttg gtggcccttg ttcccaaggg    900

cctggtcaag ttgtcaatga tgacctgagg gaacctatcc gctctcatca tgacatccag    960

aaagataatg cccgctacat gaaaaaagcc attaaacatt acgattcttt ggcattgaga   1020

gcagccacta atgggcattc agtagacatt tattcctgtg ctttagatca gacaggtttg   1080

gcggaaatga agcaatgttg caattctact gggggtcata tggtgatggg tgacaccttc   1140

aactccactt tgttcaaaca gacgttccag agggtgctct cccgtgatca aaaaggcgaa   1200

ttcaaaatgg ctttcaatgg cgtagttgaa gtcaaaacct cccgagagct aaaagttatg   1260

ggagccattg ggccttgcgt ttcattgaat acgaaaggtc cgtgtgttag tgaaactgac   1320

atagggcttg gaggaacttg ccagtggaag ttctgcacat ttaaccaaaa taccactgct   1380

gccatgttct ttgaggtagt aaaccaacac gctgctccta tccctcaagg tggaagagga   1440

tgtatacagt tcataactca ataccagcat gcgtcgggcc aaaggcgcat ccgagtaacc   1500

actgtagcca ggaattgggc tgatgcgact accaacatgc accatgttag tgcaggattt   1560

gatcaggaag ctggagcggt actcatggcc aggatggtcg ttcacagagc tgaaactgat   1620
```

```
gatggacctg atgtcatgag atgggctgat cgcatgttga ttcgtctttg ccagaaattc   1680

ggcgagtaca acaaggatga tccaaatagt ttccgcctcc cagaaaactt ctcgctttac   1740

ccacagttca tgtatcactt gagaaggtcc caattcttgc aggtattcaa caacagccca   1800

gacgaaacgt cgtactatcg tcacatcttg atgcgggaag atttgtcgca gagcttgatc   1860

atgattcagc cgatcctgta cagttacagt ttcaacggtc cagaaccagt ccttttggac   1920

acttccagca ttcaacctga tcggatcctg ctgatggaca ccttcttcca aatcctcatc   1980

ttccacggcg agaccatcgc ccagtggcgt gcccaaaggt accaggacct acctgaatat   2040

gagaacttca agcagctcct acaggctcct gtagacgatg ctaaggaaat cctgcacact   2100

cggttcccca tgccgaggta cattgacacc gaacagggcg gatcacaagc tagattcctt   2160

ctctccaaag tcaacccatc ccaaactcac aacaacatgt acggctatgg aggggaattt   2220

ggagcccctg tgctcactga tgatgtttcc ctccaagtct tcatggaaca ccttaaaaag   2280

ctagccgttt catttactgc ctag                                          2304
```

<210> SEQ ID NO 97
<211> LENGTH: 311
<212> TYPE: DNA
<213> ORGANISM: Artificial
<220> FEATURE:
<223> OTHER INFORMATION: GUS

<400> SEQUENCE: 97

```
ccagcgtatc gtgctgcgtt tcgatgcggt cactcattac ggcaaagtgt gatggagcat     60

cagggcggct atacgccatt tgaagccgat gtcacgccgt atgttattgc cgggaaaagt    120

gtacgtatct gaaatcaaaa aactcgacgg cctgtgggca ttcagtctgg atcgcgaaaa    180

ctgtggaatt gatccagcgc cgtcgtcggt gaacaggtat ggaatttcgc cgattttgcg    240

acctcgcaag gcatattcgg gtgaaggtta tctctatgaa ctgtgcgtca cagccaaaag    300

ccagacagag t                                                         311
```

<210> SEQ ID NO 98
<211> LENGTH: 170
<212> TYPE: DNA
<213> ORGANISM: Artificial
<220> FEATURE:
<223> OTHER INFORMATION: Intron

<400> SEQUENCE: 98

```
ctcgagcctg agagaaaagc atgaagtata cccataacta acccattagt tatgcattta     60

tgttatatct attcatgctt ctactttaga taatcaatca ccaaacaatg agaatctcaa    120

cggtcgcaat aatgttcatg aaaatgtagt gtgtacactt accttctaga               170
```

<210> SEQ ID NO 99
<211> LENGTH: 198
<212> TYPE: PRT
<213> ORGANISM: Lygus hesperus

<400> SEQUENCE: 99

```
Met Ser Ser Leu Lys Leu Gln Lys Arg Leu Ala Ala Ser Val Met Arg
1               5                   10                  15

Cys Gly Lys Lys Lys Val Trp Leu Asp Pro Asn Glu Ile Asn Glu Ile
            20                  25                  30

Ala Asn Thr Asn Ser Arg Gln Asn Ile Arg Lys Leu Ile Lys Asp Gly
        35                  40                  45
```

```
Leu Ile Ile Lys Lys Pro Val Ala Val His Ser Arg Ala Arg Val Arg
    50                  55                  60

Lys Asn Thr Glu Ala Arg Arg Lys Gly Arg His Cys Gly Phe Gly Lys
65                  70                  75                  80

Arg Lys Gly Thr Ala Asn Ala Arg Met Pro Val Lys Val Leu Trp Val
                85                  90                  95

Asn Arg Met Arg Val Leu Arg Arg Leu Leu Lys Lys Tyr Arg Glu Ala
            100                 105                 110

Lys Lys Ile Asp Arg Gln Met Tyr His Asp Leu Tyr Met Lys Ala Lys
        115                 120                 125

Gly Asn Val Phe Lys Asn Lys Arg Val Leu Met Asp Phe Ile His Lys
    130                 135                 140

Lys Lys Ala Glu Lys Ala Arg Ser Lys Met Leu Lys Asp Gln Ala Glu
145                 150                 155                 160

Ala Arg Arg Phe Lys Val Lys Glu Ala Lys Lys Arg Arg Glu Glu Arg
                165                 170                 175

Ile Ala Thr Lys Lys Gln Glu Ile Met Gln Ala Tyr Ala Arg Glu Asp
            180                 185                 190

Glu Ala Ala Val Lys Lys
        195
```

<210> SEQ ID NO 100
<211> LENGTH: 767
<212> TYPE: PRT
<213> ORGANISM: Lygus hesperus

<400> SEQUENCE: 100

```
Met Thr Thr Tyr Glu Glu Phe Ile Gln Gln Ser Glu Glu Arg Asp Gly
1               5                   10                  15

Ile Arg Phe Thr Trp Asn Val Trp Pro Ser Ser Arg Ile Glu Ala Thr
            20                  25                  30

Arg Leu Val Val Pro Val Gly Cys Leu Tyr Gln Pro Leu Lys Glu Arg
        35                  40                  45

Thr Asp Leu Pro Ala Ile Gln Tyr Asp Pro Val Leu Cys Thr Arg Asn
    50                  55                  60

Thr Cys Arg Ala Ile Leu Asn Pro Met Cys Gln Val Asn Tyr Arg Ala
65                  70                  75                  80

Lys Leu Trp Val Cys Asn Phe Cys Phe Gln Arg Asn Pro Phe Pro Pro
                85                  90                  95

Gln Tyr Ala Ala Ile Ser Glu Gln His Gln Pro Ala Glu Leu Ile Pro
            100                 105                 110

Ser Phe Ser Thr Ile Glu Tyr Thr Ile Ser Arg Ala Gln Phe Leu Pro
        115                 120                 125

Pro Ile Phe Leu Leu Val Val Asp Thr Cys Leu Asp Asp Asp Glu Leu
    130                 135                 140

Gly Ala Leu Lys Asp Ser Leu Gln Thr Ser Leu Ser Leu Leu Pro Thr
145                 150                 155                 160

Asn Ser Leu Val Gly Leu Ile Thr Phe Gly Lys Met Val Gln Val His
                165                 170                 175

Glu Leu Gly Cys Glu Gly Cys Ser Arg Ser Tyr Val Phe Arg Gly Thr
            180                 185                 190

Lys Asp Leu Thr Ser Lys Gln Val Gln Asp Met Leu Gly Ile Gly Lys
        195                 200                 205

Val Ser Ala Ser Pro Gln Gln Gln Gln Gln Arg Ala Met Gly Gly Gln
```

```
    210                 215                 220

Gln Pro Phe Pro Thr Asn Arg Phe Ile Gln Pro Ile Gln Ser Cys Asp
225                 230                 235                 240

Met Ser Leu Thr Asp Leu Leu Gly Glu Met Gln Arg Asp Pro Trp Pro
                245                 250                 255

Val Gly Gln Gly Lys Arg Pro Leu Arg Ser Thr Gly Ala Ala Leu Ala
            260                 265                 270

Ile Ala Ile Gly Leu Leu Glu Cys Ser Tyr Pro Asn Thr Gly Ala Lys
        275                 280                 285

Val Met Leu Phe Leu Gly Gly Pro Cys Ser Gln Gly Pro Gly Gln Val
    290                 295                 300

Val Asn Asp Asp Leu Arg Glu Pro Ile Arg Ser His His Asp Ile Gln
305                 310                 315                 320

Lys Asp Asn Ala Arg Tyr Met Lys Lys Ala Ile Lys His Tyr Asp Ser
                325                 330                 335

Leu Ala Leu Arg Ala Ala Thr Asn Gly His Ser Val Asp Ile Tyr Ser
            340                 345                 350

Cys Ala Leu Asp Gln Thr Gly Leu Ala Glu Met Lys Gln Cys Cys Asn
        355                 360                 365

Ser Thr Gly Gly His Met Val Met Gly Asp Thr Phe Asn Ser Thr Leu
    370                 375                 380

Phe Lys Gln Thr Phe Gln Arg Val Leu Ser Arg Asp Gln Lys Gly Glu
385                 390                 395                 400

Phe Lys Met Ala Phe Asn Gly Val Val Glu Val Lys Thr Ser Arg Glu
                405                 410                 415

Leu Lys Val Met Gly Ala Ile Gly Pro Cys Val Ser Leu Asn Thr Lys
            420                 425                 430

Gly Pro Cys Val Ser Glu Thr Asp Ile Gly Leu Gly Gly Thr Cys Gln
        435                 440                 445

Trp Lys Phe Cys Thr Phe Asn Gln Asn Thr Thr Ala Ala Met Phe Phe
    450                 455                 460

Glu Val Val Asn Gln His Ala Ala Pro Ile Pro Gln Gly Gly Arg Gly
465                 470                 475                 480

Cys Ile Gln Phe Ile Thr Gln Tyr Gln His Ala Ser Gly Gln Arg Arg
                485                 490                 495

Ile Arg Val Thr Thr Val Ala Arg Asn Trp Ala Asp Ala Thr Thr Asn
            500                 505                 510

Met His His Val Ser Ala Gly Phe Asp Gln Glu Ala Gly Ala Val Leu
        515                 520                 525

Met Ala Arg Met Val Val His Arg Ala Glu Thr Asp Asp Gly Pro Asp
    530                 535                 540

Val Met Arg Trp Ala Asp Arg Met Leu Ile Arg Leu Cys Gln Lys Phe
545                 550                 555                 560

Gly Glu Tyr Asn Lys Asp Asp Pro Asn Ser Phe Arg Leu Pro Glu Asn
                565                 570                 575

Phe Ser Leu Tyr Pro Gln Phe Met Tyr His Leu Arg Arg Ser Gln Phe
            580                 585                 590

Leu Gln Val Phe Asn Asn Ser Pro Asp Glu Thr Ser Tyr Tyr Arg His
        595                 600                 605

Ile Leu Met Arg Glu Asp Leu Ser Gln Ser Leu Ile Met Ile Gln Pro
    610                 615                 620

Ile Leu Tyr Ser Tyr Ser Phe Asn Gly Pro Glu Pro Val Leu Leu Asp
625                 630                 635                 640
```

```
Thr Ser Ser Ile Gln Pro Asp Arg Ile Leu Leu Met Asp Thr Phe Phe
                645                 650                 655

Gln Ile Leu Ile Phe His Gly Glu Thr Ile Ala Gln Trp Arg Ala Gln
            660                 665                 670

Arg Tyr Gln Asp Leu Pro Glu Tyr Glu Asn Phe Lys Gln Leu Leu Gln
        675                 680                 685

Ala Pro Val Asp Asp Ala Lys Glu Ile Leu His Thr Arg Phe Pro Met
    690                 695                 700

Pro Arg Tyr Ile Asp Thr Glu Gln Gly Gly Ser Gln Ala Arg Phe Leu
705                 710                 715                 720

Leu Ser Lys Val Asn Pro Ser Gln Thr His Asn Asn Met Tyr Gly Tyr
                725                 730                 735

Gly Gly Glu Phe Gly Ala Pro Val Leu Thr Asp Asp Val Ser Leu Gln
            740                 745                 750

Val Phe Met Glu His Leu Lys Lys Leu Ala Val Ser Phe Thr Ala
        755                 760                 765


<210> SEQ ID NO 101
<211> LENGTH: 511
<212> TYPE: DNA
<213> ORGANISM: Lygus hesperus

<400> SEQUENCE: 101

ggtgatgaga tgcggcaaga agaaagtgtg gttggaccct aatgaaatca acgaaatcgc      60

caacaccaac tctaggcaaa acatccgtaa gctgatcaag gatggtttga tcatcaaaaa     120

gcctgtggct gtccactcca gagcccgcgt ccgtaaaaac acagaagcca gacggaaggg     180

tcgtcactgt ggcttcggta agaggaaggg taccgccaac gccagaatgc ctgtgaaggt     240

cctgtgggtc aacagaatga gagtcctgcg acggctcctt aaaaaataca gagaagccaa     300

gaagatcgat aggcaaatgt accacgacct ttacatgaaa gccaaaggta acgtcttcaa     360

aaacaagagg gtactgatgg acttcattca caagaagaag gctgaaaagg cgagatcaaa     420

gatgttgaag gaccaggcag aggcgagacg tctcaaggtc aaggaggcga agaagaggcg     480

cgaggagagg atcgccacca agaagcaaga g                                    511


<210> SEQ ID NO 102
<211> LENGTH: 1145
<212> TYPE: DNA
<213> ORGANISM: Lygus hesperus

<400> SEQUENCE: 102

tgggttgttg gagtgctcct accccaacac gggagcaaaa gtcatgttgt tccttggtgg      60

cccttgttcc caagggcctg gtcaagttgt caatgatgac ctgagggaac ctatccgctc     120

tcatcatgac atccagaaag ataatgcccg ctacatgaaa aaagccatta aacattacga     180

ttctttggca ttgagagcag ccactaatgg gcattcagta gacatttatt cctgtgcttt     240

agatcagaca ggtttggcgg aaatgaagca atgttgcaat tctactgggg gtcatatggt     300

gatgggtgac accttcaact ccactttgtt caaacagacg ttccagaggg tgctctcccg     360

tgatcaaaaa ggcgaattca aaatggcttt caatggcgta gttgaagtca aaacctcccg     420

agagctaaaa gttatgggag ccattgggcc ttgcgtttca ttgaatacga aaggtccgtg     480

tgttagtgaa actgacatag ggcttggagg aacttgccag tggaagttct gcacatttaa     540

ccaaaatacc actgctgcca tgttctttga ggtagtaaac caacacgctg ctcctatccc     600
```

```
tcaaggtgga agaggatgta tacagttcat aactcaatac cagcatgcgt cgggccaaag    660

gcgcatccga gtaaccactg tagccaggaa ttgggctgat gcgactacca acatgcacca    720

tgttagtgca ggatttgatc aggaagctgg agcggtactc atggccagga tggtcgttca    780

cagagctgaa actgatgatg gacctgatgt catgagatgg gctgatcgca tgttgattcg    840

tctttgccag aaattcggcg agtacaacaa ggatgatcca aatagtttcc gcctcccaga    900

aaacttctcg ctttacccac agttcatgta tcacttgaga aggtcccaat tcttgcaggt    960

attcaacaac agcccagacg aaacgtcgta ctatcgtcac atcttgatgc gggaagattt   1020

gtcgcagagc ttgatcatga ttcagccgat cctgtacagt tacagtttca acggtccaga   1080

accagtcctt ttggacactt ccagcattca acctgatcgg atcctgctga tggacacctt   1140

cttcc                                                               1145
```

<210> SEQ ID NO 103
<211> LENGTH: 258
<212> TYPE: DNA
<213> ORGANISM: Artificial
<220> FEATURE:
<223> OTHER INFORMATION: GFP

<400> SEQUENCE: 103

```
agatacccag atcatatgaa acggcatgac tttttcaaga gtgccatgcc cgaaggttat     60

gtacaggaaa gaactatatt tttcaaagat gacgggaact acaagacacg taagtttaaa    120

cagttcggta ctaactaacc atacatattt aaattttcag gtgctgaagt caagtttgaa    180

ggtgataccc ttgttaatag aatcgagtta aaaggtattg attttaaaga agatggaaac    240

attcttggac acaaattg                                                  258
```

<210> SEQ ID NO 104
<211> LENGTH: 745
<212> TYPE: DNA
<213> ORGANISM: Artificial
<220> FEATURE:
<223> OTHER INFORMATION: Pt coral fluorescent protein

<400> SEQUENCE: 104

```
agtgtaataa cttactttga gtctaccgtc atgagtgcaa ttaaaccagt catgaagatt     60

gaattggtca tggaaggaga ggtgaacggg cacaagttca cgatcacggg agagggacaa    120

ggcaagcctt acgagggaac acagactcta aaccttacag tcactaaagg cgtgcccctt    180

cctttcgctt tcgatatctt gtcaacagca ttccagtatg gcaacagggt atttaccaaa    240

tacccagatg atataccgga ctatttcaag cagacctttc cggaaggata ttcgtgggaa    300

agaactttca aatatgaaga gggcgtttgc accacaaaga gtgacataag cctcaagaaa    360

ggccaaccag actgctttca atataaaatt aactttaaag gggagaagct tgaccccaac    420

ggcccaatta tgcagaagaa gaccctgaaa tgggagccat ccactgagag gatgtacatg    480

gacgtggata aagacggtgc aaaggtgctg aagggcgatg ttaatgcggc cctgttgctt    540

gaaggaggtg gccattatcg ttgtgacttt aacagtactt acaaggcgaa gaaaactgtg    600

tccttcccag catatcactt tgtggaccac cgcattgaga ttttgagcca caatacggat    660

tacagcaagg ttacactgta tgaagttgcc gtggctcgca attctcctct tcagattatg    720

gcgccccagt aaaggcttaa cgaaa                                          745
```

<210> SEQ ID NO 105
<211> LENGTH: 42

<212> TYPE: DNA
<213> ORGANISM: Artificial
<220> FEATURE:
<223> OTHER INFORMATION: Primer

<400> SEQUENCE: 105
gcgtaatacg actcactata ggtgatgaga tgcggcaaga ag 42

<210> SEQ ID NO 106
<211> LENGTH: 22
<212> TYPE: DNA
<213> ORGANISM: Artificial
<220> FEATURE:
<223> OTHER INFORMATION: Primer

<400> SEQUENCE: 106
ctcttgcttc ttggtggcga tc 22

<210> SEQ ID NO 107
<211> LENGTH: 22
<212> TYPE: DNA
<213> ORGANISM: Artificial
<220> FEATURE:
<223> OTHER INFORMATION: Primer

<400> SEQUENCE: 107
ggtgatgaga tgcggcaaga ag 22

<210> SEQ ID NO 108
<211> LENGTH: 44
<212> TYPE: DNA
<213> ORGANISM: Artificial
<220> FEATURE:
<223> OTHER INFORMATION: Primer

<400> SEQUENCE: 108
gcgtaatacg actcactata ggctcttgct tcttggtggc gatc 44

<210> SEQ ID NO 109
<211> LENGTH: 44
<212> TYPE: DNA
<213> ORGANISM: Artificial
<220> FEATURE:
<223> OTHER INFORMATION: Primer

<400> SEQUENCE: 109
gcgtaatacg actcactata ggtgggttgt tggagtgctc ctac 44

<210> SEQ ID NO 110
<211> LENGTH: 22
<212> TYPE: DNA
<213> ORGANISM: Artificial
<220> FEATURE:
<223> OTHER INFORMATION: Primer

<400> SEQUENCE: 110
ggaagaaggt gtccatcagc ag 22

<210> SEQ ID NO 111
<211> LENGTH: 22
<212> TYPE: DNA
<213> ORGANISM: Artificial
<220> FEATURE:
<223> OTHER INFORMATION: Primer

<400> SEQUENCE: 111
tgggttgttg gagtgctcct ac 22

<210> SEQ ID NO 112
<211> LENGTH: 44
<212> TYPE: DNA
<213> ORGANISM: Artificial
<220> FEATURE:
<223> OTHER INFORMATION: Primer

<400> SEQUENCE: 112
gcgtaatacg actcactata ggggaagaag gtgtccatca gcag 44

<210> SEQ ID NO 113
<211> LENGTH: 46
<212> TYPE: DNA
<213> ORGANISM: Artificial
<220> FEATURE:
<223> OTHER INFORMATION: Primer

<400> SEQUENCE: 113
gcgtaatacg actcactata ggagataccc agatcatatg aaacgg 46

<210> SEQ ID NO 114
<211> LENGTH: 24
<212> TYPE: DNA
<213> ORGANISM: Artificial
<220> FEATURE:
<223> OTHER INFORMATION: Primer

<400> SEQUENCE: 114
caatttgtgt ccaagaatgt ttcc 24

<210> SEQ ID NO 115
<211> LENGTH: 24
<212> TYPE: DNA
<213> ORGANISM: Artificial
<220> FEATURE:
<223> OTHER INFORMATION: Primer

<400> SEQUENCE: 115
agatacccag atcatatgaa acgg 24

<210> SEQ ID NO 116
<211> LENGTH: 46
<212> TYPE: DNA
<213> ORGANISM: Artificial
<220> FEATURE:
<223> OTHER INFORMATION: Primer

<400> SEQUENCE: 116
gcgtaatacg actcactata ggcaatttgt gtccaagaat gtttcc 46

<210> SEQ ID NO 117
<211> LENGTH: 43
<212> TYPE: DNA
<213> ORGANISM: Artificial
<220> FEATURE:
<223> OTHER INFORMATION: Primer

<400> SEQUENCE: 117
gcgtaatacg actcactata ggagtgtaat aacttacttt gag 43

<210> SEQ ID NO 118
<211> LENGTH: 20
<212> TYPE: DNA
<213> ORGANISM: Artificial

<220> FEATURE:
<223> OTHER INFORMATION: Primer

<400> SEQUENCE: 118
tttcgttaag cctttactgg 20

<210> SEQ ID NO 119
<211> LENGTH: 21
<212> TYPE: DNA
<213> ORGANISM: Artificial
<220> FEATURE:
<223> OTHER INFORMATION: Primer

<400> SEQUENCE: 119
agtgtaataa cttactttga g 21

<210> SEQ ID NO 120
<211> LENGTH: 42
<212> TYPE: DNA
<213> ORGANISM: Artificial
<220> FEATURE:
<223> OTHER INFORMATION: Primer

<400> SEQUENCE: 120
gcgtaatacg actcactata ggtttcgtta agcctttact gg 42

<210> SEQ ID NO 121
<211> LENGTH: 473
<212> TYPE: DNA
<213> ORGANISM: Lygus hesperus

<400> SEQUENCE: 121
tgccgggccg ctcgccgaac catctgggaa gcttggaatg ggctcgactg ccgaactgat 60
caactttttc ggtccacacc ttttctatca actccttata ccgctccagg atgccgcctt 120
caaacagttt tttcttgtcg tcataagatc tggtgtcaac tcttcgttca tatttggagg 180
cgacttggat tttgggtggg tacttgccgg tgagggcctc agggtccaag ccttttttca 240
aggctttgtg ccgaagttgt tgcttctgtc tttccttcag ttctttaaga tcgtagtctt 300
gcctcttttg cctttcctca agatcgtatt tctcggtctc aagtttgaca atggcttccc 360
agagttcctg agctttgatg cgtagcctgt ctatgctcat attttctatc gccaggggct 420
tgagcctaat gctgagggag atacgtttct cttcctccag ctgctccttg gtc 473

<210> SEQ ID NO 122
<211> LENGTH: 773
<212> TYPE: DNA
<213> ORGANISM: Lygus hesperus

<400> SEQUENCE: 122
gctgctcgcc gtccagttcg ttttcgagtt ccctgacacg ttgttccagc ttggcgatgg 60
ccttcttgcc tcccttgagg gcgttgtttt cggcttcgtc caacctgact tggagttcct 120
tgatttgcgt ttccagagcc ttgcggagct tctcctgggt ctgagcgtgg tcctgttctg 180
ccctgagttc atcagctaac ctagcggcat caaccattgc cttcttggcc ttctcttcgg 240
agttcttggc ttcgttgaga agttcgtcga ggtcagcatg aagtgtctgc aactctccct 300
caagcttgcg tttggcggct gaggcgctgg tagcttgggc agccaactcg ttgatctgtt 360
cgtgggcatc tccaagttct tgttcggctt ggcgcctgcc cctgtcggcc tgttcgagga 420
gagtgcgcga ctcctcgagc tcgtttccga gagcgttggc cctcctttcg gcgattccga 480

```
gttgttcacg agcatcgtcg cgtgcccttt gttcttcctc aagagcggtc tgtacgtcct    540

tgagttgttg ttggtatttc ttgatggtct tctgggcttc ggcgttagcc ttgttggcgt    600

ggtcgagagc gatttcgagt tcgttgatgt cggcttcaag cttcttcttc atgcgaagag    660

cctcagcctt acccttggct tcagcctcca agctggcttg catggagtcg agtgcccgtt    720

ggtggttctt cctggtgttc tcgaactcct cctcctttc ctggatccgc cgg           773


<210> SEQ ID NO 123
<211> LENGTH: 771
<212> TYPE: DNA
<213> ORGANISM: Lygus hesperus

<400> SEQUENCE: 123

tggacgccat caagaagaaa atgcaggcga tgaagatgga gaaggacacg gccatggaca     60

aggccgacac ctgcgagggg caggccaagg acgctaacac ccgcgccgac aaaatccttg    120

aagatgtgag ggacctccaa aagaaactca accaggtaga aagtgatctc gaaaggacca    180

agagggaact cgagacgaaa accaccgaac tcgaagagaa ggagaaggcc aacaccaacg    240

ctgagagcga ggtcgcctcc ctcaacagga aagtccagat ggttgaagag gacttggaaa    300

gatctgaaga aaggtccggc accgcacaac aaaaactgtc cgaagcctcc cacgccgctg    360

atgaagcctc tcgtatgtgc aaagtattgg agaacaggtc acaacaggat gaggagagga    420

tggaccagct caccaaccag ctgaaagaag cccgactcct cgctgaagac gccgacggca    480

aatcggatga ggtatcaagg aagctggcct tcgttgaaga cgaactggaa gtagctgaag    540

atcgtgtcaa atctggagac tcgaagatca tggagcttga ggaggagttg aaagttgtcg    600

gtaacagctt gaaatctctc gaagtttcag aggagaaggc caaccagcga gtcgaagagt    660

acaaacgtca aatcaagcaa ctgactgtca agttgaagga ggctgaagct cgcgctgagt    720

tcgccgaaaa gacagtcaag aagttgcaga aagaggtgga ccggctggag g             771


<210> SEQ ID NO 124
<211> LENGTH: 257
<212> TYPE: DNA
<213> ORGANISM: Lygus hesperus

<400> SEQUENCE: 124

tgcgggccct ggggcagaat cccacagaat ctgacgtgaa gaagttcacc caccagcaca     60

aaccagatga aagaatcagc ttcgaggtgt ttctcccgat ataccaagcc atatcgaagg    120

gtaggacgtc agacacagct gaagacttca tcgagggtct cagacacttt gacaaagatg    180

gaaatggctt catttcaaca gctgagcttc gccacttgct cacaactttg ggcgaaaaac    240

tgaccgacga cgaggtg                                                   257


<210> SEQ ID NO 125
<211> LENGTH: 410
<212> TYPE: DNA
<213> ORGANISM: Lygus hesperus

<400> SEQUENCE: 125

gccacctcca acgtgtttgc catgttcgat caggctcaga ttcaagaatt caaggaggca     60

ttcaacatga tcgaccagaa cagggacggc ttcgtggata aggaagacct ccatgacatg    120

ctcgcttccc taggtaagaa cccctcagac gagtatctcg aggggatgat gaacgaggcg    180

cctggtccca tcaacttcac aatgttcctc accctcttcg gtgagcggct tcagggaact    240

gatccggagg aggttatcaa gaacgcattt gggtgttttg acgaagacaa caacggattc    300
```

```
atcaacgagg aaagactgcg cgagctgctc acctccatgg gggacaggtt cactgatgaa    360

gacgtggacg aaatgtaccg agaggccccc atcaagaacg gcatgttcga               410


<210> SEQ ID NO 126
<211> LENGTH: 1021
<212> TYPE: DNA
<213> ORGANISM: Lygus hesperus

<400> SEQUENCE: 126

tgttcatcct ggagcaggag gagtatcaga gagaaggtat tgaatggaag ttcatcgact     60

tcggacttga tcttcagccg accattgatc tcattgataa gccaatggga gtcatggctc    120

tcctggatga agaatgttgg ttccccaaag ccactgacaa gaccttcgtt gagaagctgg    180

tcggtgctca cagcgttcac cccaaattca tcaaaactga tttccgtgga gtcgccgact    240

ttgctgtcgt ccattatgcc ggaaaagtcg attattcggc ggcgcagtgg ctgatgaaga    300

acatggaccc tctgaacgaa aacgtcgtgc agctcctcca gaactcgcaa gatccgttcg    360

tcatccacat ctggaaggac gcagagatcg tcggcatggc tcaccaagct ctcagcgaca    420

ctcagtttgg agctcgtacc aggaagggta tgttccgaac cgtgtctcaa ctctacaaag    480

accagctgtc caaactcatg atcacacttc gcaacacgaa ccccaacttc gtccgttgca    540

tcctccccaa ccacgagaag agagctggca agatcgatgc tcctttggtg ctggatcagc    600

tcagatgcaa cggtgtgttg gaaggcatca gaatttgcag acaaggtttc ccgaatagaa    660

tcccattcca ggaattccgg caaagatacg agctcttaac tcccaatgtc atccccaaag    720

ggttcatgga cggtaaaaag gcttgcgaga agatgatcaa cgctctcgaa ctggacccta    780

atctctacag agttggtcag tccaagatat tcttcagagc tggagtctta gctcatctag    840

aagaagagcg cgactataag attactgatc tgatagccaa tttccgggct ttctgtaggg    900

gatatcttgc ccgaaggaac taccaaaagc gtcttcagca gctcaacgcc attcgtatta    960

tccagcgaaa ttgctcagct tacttgaagt tgaggaactg gcaatggtgg cggctgtaca   1020

c                                                                   1021


<210> SEQ ID NO 127
<211> LENGTH: 325
<212> TYPE: DNA
<213> ORGANISM: Lygus hesperus

<400> SEQUENCE: 127

cggtcatcat ctccatgaac tcgtcgaagt caacagttcc ggaaccgtca gaatcaattt     60

cagcaatcat catgtcaagt tcttgggagg tgattttgtc gtcgagttcc ttcaggattt    120

ccctcaagac gtcagtggta atgtaaccgt tcccttcctt gtcgtagagc ctgaaggcct    180

ccctcagttc ttgctgcatg gcctcagcat cttgtgtctc atcttctgtc aggaaaccgg    240

cagccaaggc tacgaactcc tcaaattcaa gttgtccaga gccatcagcg tcgacctccg    300

caatgatctc ctccaggatc ttctt                                          325


<210> SEQ ID NO 128
<211> LENGTH: 463
<212> TYPE: DNA
<213> ORGANISM: Lygus hesperus

<400> SEQUENCE: 128

cggtcatcat ctccatgaac tcgtcgaagt cgacagttcc ggatccgtca gagtcgatct     60
```

```
cctcgatgat catgtccagc tcctcgttgg tcagctgctc gtccaattca tgaaggattt    120

ctttgaggca ggaggtcggg atgtagccat taccttcttt gtcgtagaga cggaaggctt    180

ctcgcagctc tttctgcatg gcttcatcgt cttcctcaac aatgaacttg gctgccaacg    240

tgatgaactc ttcaaactcc agccttcccg atttgtcagc gtcaacttct tcgatgagtt    300

catcgagaat cttcttgttg aagggttgac ccatgagtct gaggatgtcg gccaccatgt    360

ccgtcgggat ggaacccgag tgatcccggt cgaaagcgtt caacgcgatg gtcatgatgg    420

ggataattcg gttaattctg ttagaccagt ccgattagtg acg                      463
```

<210> SEQ ID NO 129
<211> LENGTH: 413
<212> TYPE: DNA
<213> ORGANISM: Lygus hesperus

<400> SEQUENCE: 129

```
atgggtgaag gagggtgcct gctcagagca gtcctccagg atgacggcta tggacaacgc     60

ctcgaagaac gccgctgaga tgatcgacaa gctgaccttg acgttcaaca ggactcggca    120

agccgtcatc accagggagc tcatcgaaat catctccggt gcctctgctt tggagtaacg    180

tctcagctca cccagccacc tcccgtagat ccactagtgc tgcgagagac cgagtacctc    240

gttctattca ccctgtacat ttcttaatca atattattgg aattcgattc gatagtcgta    300

tgctgggaaa tatcttgttc atattcatga tacttgttca acattgttct ggtaaataat    360

ttatgtaata caggttgagt taccaaaaaa aaaaaaaaaa aaaaaaaaaa aaa           413
```

<210> SEQ ID NO 130
<211> LENGTH: 449
<212> TYPE: DNA
<213> ORGANISM: Lygus hesperus

<400> SEQUENCE: 130

```
gcagctggag gaagagaaac gtatctccct cagcattagg ctcaagcccc tggcgataga     60

aaatatgagc atagacaggc tacgcatcaa agctcaggaa ctctgggaag ccattgtcaa    120

acttgagacc gagaaatacg atcttgagga aaggcaaaag aggcaagact acgatcttaa    180

agaactgaag gaaagacaga agcaacaact tcggcacaaa gccttgaaaa aaggcttgga    240

ccctgaggcc ctcaccggca agtacccacc caaaatccaa gtcgcctcca aatatgaacg    300

aagagttgac accagatctt atgacgacaa gaaaaaactg tttgaaggcg gcatcctgga    360

gcggtataag gagttgatag aaaaggtgtg gaccgaaaaa gttgatcagt tcggcagtcg    420

agcccattcc aagcttccca gatggttcg                                      449
```

<210> SEQ ID NO 131
<211> LENGTH: 719
<212> TYPE: DNA
<213> ORGANISM: Lygus hesperus

<400> SEQUENCE: 131

```
aggagttcga gaacaccagg aagaaccacc aacgggcact cgactccatg caagccagct     60

tggaggctga agccaagggt aaggctgagg ctcttcgcat gaagaagaag cttgaagccg    120

acatcaacga actcgaaatc gctctcgacc acgccaacaa ggctaacgcc gaagcccaga    180

agaccatcaa gaaataccaa caacaactca aggacgtaca gaccgctctt gaggaagaac    240

aaagggcacg cgacgatgct cgtgaacaac tcggaatcgc cgaaaggagg gccaacgctc    300

tcggaaacga gctcgaggag tcgcgcactc tcctcgaaca ggccgacagg ggcaggcgcc    360
```

```
aagccgaaca agaacttgga gatgcccacg aacagatcaa cgagttggct gcccaagcta    420

ccagcgcctc agccgccaaa cgcaagcttg agggagagtt gcagacactt catgctgacc    480

tcgacgaact tctcaacgaa gccaagaact ccgaagagaa ggccaagaag gcaatggttg    540

atgccgctag gttagctgat gaactcaggg cagaacagga ccacgctcag acccaggaga    600

agctccgcaa ggctctggaa acgcaaatca aggaactcca agtcaggttg gacgaagccg    660

aaaacaacgc cctcaaggga ggcaagaagg ccatcgccaa gctggaacaa cgtgtcagg     719
```

<210> SEQ ID NO 132
<211> LENGTH: 737
<212> TYPE: DNA
<213> ORGANISM: Lygus hesperus

<400> SEQUENCE: 132

```
gcaggcgatg aagatggaga aggacacggc catggacaag gccgacacct gcgaggggca     60

ggccaaggac gctaacaccc gcgccgacaa aatccttgaa gatgtgaggg acctccaaaa    120

gaaactcaac caggtagaaa gtgatctcga aaggaccaag agggaactcg agacgaaaac    180

caccgaactc gaagagaagg agaaggccaa caccaacgct gagagcgagg tcgcctccct    240

caacaggaaa gtccagatgg ttgaagagga cttggaaaga tctgaagaaa ggtccggcac    300

cgcacaacaa aaactgtccg aagcctccca cgccgctgat gaagcctctc gtatgtgcaa    360

agtattggag aacaggtcac aacaggatga ggagaggatg gaccagctca ccaaccagct    420

gaaagaagcc cgactcctcg ctgaagacgc cgacggcaaa tcggatgagg tatcaaggaa    480

gctggccttc gttgaagacg aactggaagt agctgaagat cgtgtcaaat ctggagactc    540

gaagatcatg gagcttgagg aggagttgaa agttgtcggt aacagcttga aatctctcga    600

agtttcagag gagaaggcca accagcgagt cgaagagtac aaacgtcaaa tcaagcaact    660

gactgtcaag ttgaaggagg ctgaagctcg cgctgagttc gccgaaaaga cagtcaagaa    720

gttgcagaaa gaggtgg                                                   737
```

<210> SEQ ID NO 133
<211> LENGTH: 205
<212> TYPE: DNA
<213> ORGANISM: Lygus hesperus

<400> SEQUENCE: 133

```
cagaatccca cagaatctga cgtgaagaag ttcacccacc agcacaaacc agatgaaaga     60

atcagcttcg aggtgtttct cccgatatac caagccatat cgaagggtag gacgtcagac    120

acagctgaag acttcatcga gggtctcaga cactttgaca aagatggaaa tggcttcatt    180

tcaacagctg agcttcgcca cttgc                                          205
```

<210> SEQ ID NO 134
<211> LENGTH: 326
<212> TYPE: DNA
<213> ORGANISM: Lygus hesperus

<400> SEQUENCE: 134

```
ggaggcattc aacatgatcg accagaacag ggacggcttc gtggataagg aagacctcca     60

tgacatgctc gcttccctag gtaagaaccc ctcagacgag tatctcgagg ggatgatgaa    120

cgaggcgcct ggtcccatca acttcacaat gttcctcacc ctcttcggtg agcggcttca    180

gggaactgat ccggaggagg ttatcaagaa cgcatttggg tgttttgacg aagacaacaa    240
```

```
cggattcatc aacgaggaaa gactgcgcga gctgctcacc tccatggggg acaggttcac    300

tgatgaagac gtggacgaaa tgtacc                                        326


<210> SEQ ID NO 135
<211> LENGTH: 944
<212> TYPE: DNA
<213> ORGANISM: Lygus hesperus

<400> SEQUENCE: 135

gacttgatct tcagccgacc attgatctca ttgataagcc aatgggagtc atggctctcc     60

tggatgaaga atgttggttc cccaaagcca ctgacaagac cttcgttgag aagctggtcg    120

gtgctcacag cgttcacccc aaattcatca aaactgattt ccgtggagtc gccgactttg    180

ctgtcgtcca ttatgccgga aaagtcgatt attcggcggc gcagtggctg atgaagaaca    240

tggaccctct gaacgaaaac gtcgtgcagc tcctccagaa ctcgcaagat ccgttcgtca    300

tccacatctg gaaggacgca gagatcgtcg gcatggctca ccaagctctc agcgacactc    360

agtttggagc tcgtaccagg aagggtatgt tccgaaccgt gtctcaactc tacaaagacc    420

agctgtccaa actcatgatc acacttcgca acacgaaccc caacttcgtc cgttgcatcc    480

tccccaacca cgagaagaga gctggcaaga tcgatgctcc tttggtgctg gatcagctca    540

gatgcaacgg tgtgttggaa ggcatcagaa tttgcagaca aggtttcccg aatagaatcc    600

cattccagga attccggcaa agatacgagc tcttaactcc caatgtcatc cccaaagggt    660

tcatggacgg taaaaaggct tgcgagaaga tgatcaacgc tctcgaactg gaccctaatc    720

tctacagagt tggtcagtcc aagatattct tcagagctgg agtcttagct catctagaag    780

aagagcgcga ctataagatt actgatctga tagccaattt ccgggctttc tgtaggggat    840

atcttgcccg aaggaactac caaaagcgtc ttcagcagct caacgccatt cgtattatcc    900

agcgaaattg ctcagcttac ttgaagttga ggaactggca atgg                     944


<210> SEQ ID NO 136
<211> LENGTH: 318
<212> TYPE: DNA
<213> ORGANISM: Lygus hesperus

<400> SEQUENCE: 136

atcctggagg agatcattgc ggaggtcgac gctgatggct ctggacaact tgaatttgag     60

gagttcgtag ccttggctgc cggtttcctg acagaagatg agacacaaga tgctgaggcc    120

atgcagcaag aactgaggga ggccttcagg ctctacgaca aggaagggaa cggttacatt    180

accactgacg tcttgaggga aatcctgaag gaactcgacg acaaaatcac ctcccaagaa    240

cttgacatga tgattgctga aattgattct gacggttccg gaactgttga cttcgacgag    300

ttcatggaga tgatgacc                                                  318


<210> SEQ ID NO 137
<211> LENGTH: 423
<212> TYPE: DNA
<213> ORGANISM: Lygus hesperus

<400> SEQUENCE: 137

atccccatca tgaccatcgc gttgaacgct ttcgaccggg atcactcggg ttccatcccg     60

acggacatgg tggccgacat cctcagactc atgggtcaac ccttcaacaa gaagattctc    120

gatgaactca tcgaagaagt tgacgctgac aaatcgggaa ggctggagtt tgaagagttc    180

atcacgttgg cagccaagtt cattgttgag gaagacgatg aagccatgca gaaagagctg    240
```

```
cgagaagcct tccgtctcta cgacaaagaa ggtaatggct acatcccgac ctcctgcctc    300

aaagaaatcc ttcatgaatt ggacgagcag ctgaccaacg aggagctgga catgatcatc    360

gaggagatcg actctgacgg atccggaact gtcgacttcg acgagttcat ggagatgatg    420

acc                                                                  423
```

<210> SEQ ID NO 138
<211> LENGTH: 252
<212> TYPE: DNA
<213> ORGANISM: Lygus hesperus

<400> SEQUENCE: 138

```
ggtgaaggag ggtgcctgct cagagcagtc ctccaggatg acggctatgg acaacgcctc     60

gaagaacgcc gctgagatga tcgacaagct gaccttgacg ttcaacagga ctcggcaagc    120

cgtcatcacc agggagctca tcgaaatcat ctccggtgcc tctgctttgg agtaacgtct    180

cagctcaccc agccacctcc cgtagatcca ctagtgctgc gagagaccga gtacctcgtt    240

ctattcaccc tg                                                        252
```

<210> SEQ ID NO 139
<211> LENGTH: 1110
<212> TYPE: DNA
<213> ORGANISM: Lygus hesperus

<400> SEQUENCE: 139

```
gtctccgctc aagctggtca tcagacttca gctgagtcct ggggtaccgg tcgtgctgtg     60

gctcgtatcc cccgtgttcg cggaggtggt actcaccgct caggtcaggg tgcttttggc    120

aacatgtgtc gcggcggtag gatgttcgct cccactcgcc catggcgtcg ttggcaccgc    180

aagatcaacg ttaaccaaaa acgttatgcc gtcgtgtccg ccatcgctgc atccggcgtc    240

ccagccctcg tcatgtccaa aggacacatg gtgcaaagcg tccctgaatt ccccccttgtt    300

gtgtctgaca aagttcagga atacactaaa accaaacagg ctgtcatctt ccttcaccgc    360

atcaaagcct ggcaagacat ccagaaagtg tacaagtcga agaggttccg tgctggtaag    420

ggtaaaatga ggaaccgcag gaggatccag aggcgtggac ccctcatcat ctacgaccag    480

gatcagggtc tgaacagggc tttccgtaac attcccggcg tcgatttgat cgaagtgagc    540

cgcctcaact tgctgaagct cgctccagga ggtcacatcg gccggttcgt catctggact    600

cagtcggcct tcgagaagtt ggacgccctc tacggcacct ggaagaagaa gtccaccctc    660

aaggctggat acaatctccc catgcccaag atggccaaca ccgacctttc ccgcctcttc    720

aaggccccgg agatcaaggc tgtcctcagg aatcccaaga agaccatcgt acgacgagtg    780

cgcaaactga accctctccg caacaccagg gctatgctgc gtctcaaccc atacgctgct    840

gtcctcaaga ggaaggccat ccttgatcaa aggaagttga aactccagaa gctcgtagaa    900

gctgccaaga agggagatac caagctgtcg ccccgcgtcg agcgtcacct gaagatgatc    960

gagagaagga aagccctgat caagaaagcc aaggctgcca agcccaagaa gcccaaaacg   1020

gccaagaaac ccaagaccgc cgagaaggca ccagcacccg ccaagaaggc ggcagcgccc   1080

aaaaaggcca ccacccctgc caagaaatga                                    1110
```

<210> SEQ ID NO 140
<211> LENGTH: 729
<212> TYPE: DNA
<213> ORGANISM: Lygus hesperus

<400> SEQUENCE: 140

```
atggccaatg ctaagcctat ttctaagaag aagaagtttg tgtctgacgg tgtcttcaaa     60

gccgaattga acgaatttct taccagagaa ctcgctgaag aggggtactc aggtgttgag    120

gtccgagtga cccccaacaa gacagaaatt atcatcatgg cgacaaggac acaaagcgtt    180

cttggtgata agggccgccg aatcagggag ctcacgtctg tagttcagaa aagattcaat    240

ttcaagcctc agactttgga tctctatgct gaaaaggtcg ccaccagagg tttgtgtgct    300

attgcacaag ctgaatccct ccgttacaaa ctcattggcg gtcttgctgt ccgagggget    360

tgctatggtg tccttcgctt catcatggaa aatggtgcca agggttgcga agtcgtagta    420

tctggaaaac tgcgtggtca gagagccaag tcaatgaagt tcgtggatgg tttgatgatc    480

cacagtgggg atccctgtaa cgaatatgtt gatactgcta cccgacatgt gctccttaga    540

caaggtgtcc tgggaataaa ggtgaagatt atgttgccgt gggacgttac cggcaaaaat    600

gggccgaaga accctcttcc cgaccacgtc agcgttctct tacctaagga ggagctacca    660

aatttggccg ttagtgtgcc tggatccgac atcaaaccaa agcctgaagt accagcaccc    720

gctttgtga                                                            729
```

<210> SEQ ID NO 141
<211> LENGTH: 789
<212> TYPE: DNA
<213> ORGANISM: Lygus hesperus

<400> SEQUENCE: 141

```
atggctgttg gtaaaaataa gggtctatcg aaaggaggaa agaagggagt taaaaaaaag     60

gtagtggacc ctttcaccag gaaggattgg tacgatgtta aggctccttc catgttcaaa    120

aagcgtcaag ttggcaaaac tttggtcaac cgaactcagg gaaccaagat tgcttctgaa    180

gggttgaaag gacgagtttt cgaagtttcg ctcgctgata tccaggagga cactgatgcc    240

gagcgctcct tcaggaaatt caggctcatc gctgaagatg tccaagccag aaacgtcctt    300

accaatttcc acggtatgga tttgaccact gacaaactcc ggagcatggt caagaagtgg    360

cagactctca tcgaagccaa cgttgacgtc aagaccaccg acggctacct cctgcgcgtc    420

ttctgcatag gattcaccaa taaagatcaa ctttcccaga gaaagacttg ctatgcccag    480

cataatcagg tccgagaaat ccgcaaaaag atggttaaaa acatcagtga cagcatttcc    540

agctgtgatt tgaggagtgt tgtgaacaag ctgatcccag actccatcgc taaagatata    600

gaaaagaatt gccaaggaat ctacccactc cacgatgtgt acattcggaa ggtgaaggtg    660

ttgaagaagc cgaggttcga gctcagcaag ctccttgagc ttcacgtcga tggcaaaggg    720

atcgacgaac ccggcgcgaa agtgacgagg actgacgctt acgagcctcc agttcaagag    780

tctgtctaa                                                            789
```

<210> SEQ ID NO 142
<211> LENGTH: 473
<212> TYPE: DNA
<213> ORGANISM: Lygus hesperus

<400> SEQUENCE: 142

```
gaccaaggag cagctggagg aagagaaacg tatctccctc agcattaggc tcaagcccct     60

ggcgatagaa aatatgagca tagacaggct acgcatcaaa gctcaggaac tctgggaagc    120

cattgtcaaa cttgagaccg agaaatacga tcttgaggaa aggcaaaaga ggcaagacta    180

cgatcttaaa gaactgaagg aaagacagaa gcaacaactt cggcacaaag ccttgaaaaa    240
```

```
aggcttggac cctgaggccc tcaccggcaa gtacccaccc aaaatccaag tcgcctccaa    300

atatgaacga agagttgaca ccagatctta tgacgacaag aaaaaactgt ttgaaggcgg    360

catcctggag cggtataagg agttgataga aaaggtgtgg accgaaaaag ttgatcagtt    420

cggcagtcga gcccattcca agcttcccag atggttcggc gagcggcccg gca           473
```

<210> SEQ ID NO 143
<211> LENGTH: 1463
<212> TYPE: DNA
<213> ORGANISM: Lygus hesperus

<400> SEQUENCE: 143

```
gggtctcagc tgaggcacat tccatctcgt cgcaaatctt tcctgcatct ctcctgggtg     60

acctttaggt gaccaatcac atccatcatg tcggacgagg agtattcgga gtcggaggaa    120

gagacccagc cggaaccaca gaaaaaacca gaggctgaag gaggcggcga cccagaattc    180

gtcaagcgta aggaagccca gacctcagcc ttagacgagc agcttaaaga ctatatcgca    240

gaatggagga aacaaagagc tcgcgaagaa gaagacctca agaagctgaa ggagaagcaa    300

gccaagcgca aggtcgctcg ggcagaagaa gaaaagagat tggcggaaaa gaagaagcag    360

gaagaagaac gacgtgtgag ggaagcagaa gagaagaaac agagggaaat cgaagagaag    420

aggcgaaggc ttgaagaggc cgagaagaag agacaagcca tgatggctgc tctcaaggac    480

cagagcaaaa cgaagggacc caattttgtc gttaataaga aagccgaaac ccttggcatg    540

tcctccgctc aaattgagcg caacaagact aaggaacagc ttgaggaaga aaaacgtatc    600

tccctcagca ttaggctcaa gcccctggcg atagaaaata tgagcataga caggctacgc    660

ataaaagctc aggaactctg ggaagccatt gtcaaacttg agaccgagaa atacgatctt    720

gaggaaaggc aaaagaggca agactacgat cttaaagaac tgaaggaaag acagaagcaa    780

caacttcggc acaaagcctt gaaaaaaggc ttggaccctg aggccctcac cggcaagtac    840

ccacccaaaa tccaagtcgc ctccaaatat gaacgaagag ttgacaccag atcttatgac    900

gacaagaaaa aactgtttga aggcggcatc ctggagcggt ataaggagtt gatagaaaag    960

gtgtggaccg aaaaagttga tcagttcggc agtcgagccc attccaagct tcccagatgg   1020

ttcggcgagc ggcccggcaa gaagaaggat gcccctgaaa gcccggaaga agaggaagtg   1080

aaggtagaag atgaacctga agctgaacca agcttcatgc tcgacgaaga agaagaagaa   1140

gcggaagaag aggaggcgga agaggaagag gaagccgagg aagaggagga agaagaagag   1200

gaagaggaag aggaggagga ggaagaagaa taggtctttt tcaacatttc actgcaccca   1260

cagttccacg gtctttccgc ccacaaactc aatctgtgct cacgagatct tagcaggaaa   1320

agtattgcga cccgataaga acaaattaaa ttatttttgg aatatctcgt tcagttattt   1380

cgtgagaaac aattttattc atgtaaacga ttaaaagatc ccatacattt ccaaaaaaaa   1440

aaaaaaaaaa aaaaaaaaaa aaa                                           1463
```

<210> SEQ ID NO 144
<211> LENGTH: 773
<212> TYPE: DNA
<213> ORGANISM: Lygus hesperus

<400> SEQUENCE: 144

```
ccggcggatc caggaaaagg aggaggagtt cgagaacacc aggaagaacc accaacgggc     60

actcgactcc atgcaagcca gcttggaggc tgaagccaag ggtaaggctg aggctcttcg    120
```

```
catgaagaag aagcttgaag ccgacatcaa cgaactcgaa atcgctctcg accacgccaa    180

caaggctaac gccgaagccc agaagaccat caagaaatac caacaacaac tcaaggacgt    240

acagaccgct cttgaggaag aacaaagggc acgcgacgat gctcgtgaac aactcggaat    300

cgccgaaagg agggccaacg ctctcggaaa cgagctcgag gagtcgcgca ctctcctcga    360

acaggccgac aggggcaggc gccaagccga acaagaactt ggagatgccc acgaacagat    420

caacgagttg gctgcccaag ctaccagcgc ctcagccgcc aaacgcaagc ttgagggaga    480

gttgcagaca cttcatgctg acctcgacga acttctcaac gaagccaaga actccgaaga    540

gaaggccaag aaggcaatgg ttgatgccgc taggttagct gatgaactca gggcagaaca    600

ggaccacgct cagacccagg agaagctccg caaggctctg gaaacgcaaa tcaaggaact    660

ccaagtcagg ttggacgaag ccgaaaacaa cgccctcaag ggaggcaaga aggccatcgc    720

caagctggaa caacgtgtca gggaactcga aaacgaactg gacggcgagc agc          773
```

<210> SEQ ID NO 145
<211> LENGTH: 5446
<212> TYPE: DNA
<213> ORGANISM: Lygus hesperus

<400> SEQUENCE: 145

```
tcaggaaaac tggctggtgc tgatattgag acctatctgc tggagaaggc tcgtgtcatc     60

tcccaacaaa cactcgagag atcctaccac attttctacc agatgatgtc tggagctgtc    120

aagggcgtca aggaaatgtg cttgctggtc gacgatatct atacgtacaa cttcatatcc    180

cagggtaaag tcagcattgc aggcgttgat gacggagagg aaatggttct gaccgatcaa    240

gccttcgaca tcttgggttt caccaagcaa gagaaggaag acatctacaa gatcaccgcc    300

gctgtcattc acatgggtac catgaagttc aagcaaaggg gtcgtgaaga gcaggctgaa    360

gccgatggaa ctgaggaagg cggtaaggtc ggtgtgctcc tcggtatcga cggtgacgac    420

ttgtacaaga atatgtgcaa gcccagaatc aaggtcggaa ctgagttcgt gacccaggga    480

aagaacgtca accaggtctc atactctctc ggtgccatgt ccaagggtat gttcgatcgt    540

ctcttcaaat tcttggtcaa gaaatgtaac gaaactctgg acaccaaaca gaagagacag    600

cacttcattg gtgtactgga tattgccggg ttcgaaattt tcgacttcaa cggttttgag    660

caactgtgta tcaacttcac caacgagaaa ttgcaacaat tcttcaacca ccacatgttc    720

gtactcgagc aagaagagta caagagggaa ggcattaact gggctttcat tgatttcgga    780

atggacttgc tcgcttgtat tgaactgatt gagaagccca tgggtatctt gtccatcctt    840

gaagaagagt ctatgttccc caaggctact gacaagacct ttgaggacaa actcatcacc    900

aaccacttgg gcaaatctcc caacttcagg aagcccgccg ttccaaagcc tggccaacaa    960

gctggtcact tcgccatcgc tcactacgct ggttgcgtgt catacaacat caccggctgg   1020

cttgagaaga acaaggatcc gttgaacgac actgttgtcg atcagtacaa gaagggaacc   1080

aacaaactgt tgtgcgagat cttcgctgat catcctggcc aatctggtgc ccctggtggt   1140

gatgctggtg gcaagggtgg tcgtggcaag aaaggtggtg gcttcgccac tgtgtcatct   1200

tcctacaagg aacaattgaa caacttgatg accactttga agagcacaca gcctcacttc   1260

gtccgttgta tcatccccaa cgaattgaaa cagcccggtg ttattgattc tcacttggtc   1320

atgcaccagc tgacttgtaa cggtgtactt gaaggcatcc gtatttgccg taaaggcttc   1380

cccaacagga tgaactaccc tgacttcaag ctccgataca agatccttaa ccccgctgcc   1440

gtggacagag agagtgatat cctcaaggct gctggtctcg tccttgagtc aactgggctc   1500
```

```
gaccctgata tgtaccgtct cggccacacc aaggtgttct tcagggccgg agttttgggt   1560
caacttgaag aattgcgtga cgacaggctt agcaagatca tcggatggat gcaggccttc   1620
atgcgcggtt acctcgtcag gaaggagtac aagaagctcc aggaacagag gttagccctc   1680
caagttgtcc agcgcaactt gagaaggtac ctccaactga ggacctggcc ctggtggaag   1740
atgtggtcca gggtcaagcc cctcctcaac gtcgccaacg tcgaagagga gatgcggaaa   1800
ctcgaagagt tggtcgccga gacccaggcc gctttggaga aggaggagaa gctgaggaag   1860
gaggccgaag cccttaacgc caagcttctc caagagaaga ccgaccttct caggaacttg   1920
gaaggagaga agggatccat cagcggtatc caggaacgat gtgccaagct gcaagcccaa   1980
aaggccgatc ttgagtctca actcatggac acccaagaaa ggctgcagaa cgaagaagat   2040
gccaggaacc agctcttcca acagaagaag aaattggaac aagaagccgc tgccctcaag   2100
aaggacatcg aagatctcga actctccaac caaaagaccg accaagataa ggccagcaag   2160
gaacaccaaa tcagaaacct caatgacgag atcgctcacc aagatgactt gatcaacaag   2220
ctcaacaagg agaagaaaat ccagagcgaa ctcaaccaaa agactgctga agaacttcag   2280
gccgctgaag acaaaatcaa ccacctcacc aaggttaagg tcaagcttga acagaccttg   2340
gatgaactcg aagacaccct cgaacgtgaa aagaaactcc gaggagatgt cgaaaaggcc   2400
aagaggaaga ctgaaggcga cctcaagctc actcaggaag ccgttgccga tcttgaaagg   2460
aacaagaaag aactcgaaca gaccatccag aggaaagaca aggaaattgc ttccctcacc   2520
gccaagctcg aagacgaaca atccatcgtc aacaagactg gcaaacagat caaggaactc   2580
cagagccgca ttgaagagct cgaggaggaa gtcgaggctg agaggcaagc ccgcggaaag   2640
gctgagaagc aacgtgctga cctcgcccgc gaacttgagg aactcggcga gaggttagag   2700
gaagctggtg gtgccacctc tgcccagatc gagctcaaca agaagcgtga agctgagatg   2760
agcaaactca ggagggacct ggaagaagcc aacatccagc acgaaggcac gctcgccaac   2820
ctccgcaaga agcacaacga tgctgtcagt gagatgggag accaaatcga ccagctcaac   2880
aaacttaaga ccaaggttga aaaggagaag tctcaatacc tcggtgaact caacgacgtc   2940
cgcgcctcca ttgaccactt gaccaacgag aaggctgcca ctgaaaaggt tgccaagcaa   3000
ctgcaacacc aaatcaatga agttcaaggc aaacttgatg aagctaacag gacgctcaac   3060
gacttcgatg ctgccaagaa gaagttgtct attgagaact ctgacctcct cagacagttg   3120
gaggaagctg agagccaagt ttctcaactt agcaagatca agatctccct caccactcaa   3180
ctcgaggaca ctaagcgtct cgccgatgag gaagctaggg aacgcgcaac ccttcttggc   3240
aagttccgca acttggaaca cgaccttgac aacctgaggg aacaggtgga ggaagaagcc   3300
gaagctaagg ctgatatcca acgtcaactc agcaaggcca acgctgaagc tcagttgtgg   3360
cgcagcaagt acgaaagcga gggtgttgcc cgcgctgagg agcttgagga ggccaagagg   3420
aaactccagg cccgtttggc tgaggctgag gagaccattg agtccctcaa ccagaaggtt   3480
atcgcccttg agaagacgaa gcagcgcctt gccactgaag tcgaggatct gcagctcgag   3540
gtcgaccgtg ccaacgccat tgccaatgcc gctgaaaaga aggctaaggc tattgacaag   3600
atcattggtg aatggaaact caaggttgat gaccttgctg ctgagcttga tgctagtcaa   3660
aaggaatgca gaaactactc cactgagctc ttcaggctca agggagctta tgaagaagga   3720
caggaacaac ttgaagctgt ccgcagggag aacaagaacc ttgctgatga agtcaaggac   3780
ttgctcgacc agatcggtga gggtggccgc aacatccacg aaattgagaa gcagcgcaag   3840
```

```
aggctcgaag ttgagaagga cgaacttcag gccgctcttg aggaggctga agccgctctt   3900
gaacaggagg agaacaaagt actcagggct caacttgagc tcagccaggt gcgtcaagaa   3960
attgaccgcc gcatccagga gaaggaagag gagttcgaga acaccaggaa gaaccaccaa   4020
cgggcactcg actccatgca agccagcttg gaggctgaag ccaagggtaa ggctgaggct   4080
cttcgcatga agaagaagct tgaagccgac atcaacgaac tcgaaatcgc tctcgaccac   4140
gccaacaagg ctaacgccga agcccagaag accatcaaga aataccaaca acaactcaag   4200
gacgtacaga ccgctcttga ggaagaacaa agggcacgcg acgatgctcg tgaacaactc   4260
ggaatcgccg aaaggagggc caacgctctc ggaaacgagc tcgaggagtc gcgcactctc   4320
ctcgaacagg ccgacagggg caggcgccaa gccgaacaag aacttggaga tgcccacgaa   4380
cagatcaacg agttggctgc ccaagctacc agcgcctcag ccgccaaacg caagcttgag   4440
ggagagttgc agacacttca tgctgacctc gacgaacttc tcaacgaagc caagaactcc   4500
gaagagaagg ccaagaaggc aatggttgat gccgctaggt tagctgatga actcagggca   4560
gaacaggacc acgctcagac ccaggagaag ctccgcaagg ctctggaaac gcaaatcaag   4620
gaactccaag tcaggttgga cgaagccgaa aacaacgccc tcaagggagg caagaaggcc   4680
atcgccaagc tggaacaacg tgtcagggaa ctcgaaaacg aactggacgg cgagcagagg   4740
agacacgccg acgcacaaaa gaacctccgt aaatccgagc gtagaattaa ggagctcagt   4800
ttccagtccg acgaggaccg taagaaccac gaacgcatgc aagacctcgt agacaaactg   4860
caacagaaga tcaagactta caagaggcag attgaagaag ccgaagaaat cgcggccctt   4920
aacctcgcca aattccgcaa agcacaacaa gaactcgaag aagctgaaga acgcgctgat   4980
ctcgctgaac aggctgtttc caaattcaga acaaagggtg gacgcgcagg atctgctgcc   5040
agagcgatga gccctgtcgg ccagaagtga aggaacgaat aagcggacgt ataagctatc   5100
aatacctcgc acacaaacct gccaggcctc aatttgacgg caatgccttc ccaccacgat   5160
tcgatctaca tcccgacgac ttttaagatc tttgatagca acgcaaaaca tcaaatgaaa   5220
atcttttaaa ttttatgtat ttattttgac ctattttatt aagttattgt taatacaaac   5280
ataattccat gagctagata tctagccaac gaaccatcac aatcacgatt attcgaactg   5340
tacgatagaa gcattatttg tacagctgga ccatttacaa aatatttttg cttcgaataa   5400
taaagagttt atatcgcgaa aaaaaaaaaa aaaaaaaaaa aaaaaa                  5446
```

<210> SEQ ID NO 146
<211> LENGTH: 964
<212> TYPE: DNA
<213> ORGANISM: Lygus hesperus

<400> SEQUENCE: 146

```
tcctcctctg gtgcccgact cttcaaatac ccaaatccag tcatgtcttc ccgtaaaacc     60
gctggccgca gggcgaccac caagaagcgc gctcagcgtg cgacgtcaaa cgtattcgcc    120
atgttcgatc aggctcagat tcaagaattc aaggaggcat tcaacatgat cgaccagaac    180
agggacggct tcgtggataa ggaagacctc catgacatgc tcgcttccct aggtaagaac    240
ccctcagacg agtatctcga ggggatgatg aacgaggcgc ctggtcccat caacttcaca    300
atgttcctca ccctcttcgg tgagcggctt cagggaactg atccggagga ggttatcaag    360
aacgcatttg ggtgttttga cgaagacaac aacggattca tcaacgagga aagactgcgc    420
gagctgctca cctccatggg ggacaggttc actgatgaag acgtggacga aatgtaccga    480
gaggccccca tcaagaacgg catgttcgac tacatcgaat tcactcggat cctcaagcac    540
```

```
ggagccaaag acaaagacga gcagtgacct atcaaatcct cgtcaacctc ccttcagtaa    600

tttgaaacca atccatcaaa ttttgtttaa aactcttact taaaatccga tcatctacgt    660

cactttgcca ccaatcggta ttattttttg agccgttcct acataaatcg aattaatttt    720

atacctacga atcatattgt tggaaatttc tctcttgtac ttatactttc tgttatttcc    780

taatttttct aactaaccaa gttagtcgtt agtttttatt cattccttta taaattatta    840

gttatccatt tttaatcatc ttgaagttat ttgtttttcg agtggtagaa tatttataca    900

ttttccaata tataatggtt tattcattct taaaaaacga aaaaaaagaa aaaaaaaaaa    960

aaaa                                                                 964
```

<210> SEQ ID NO 147
<211> LENGTH: 5872
<212> TYPE: DNA
<213> ORGANISM: Lygus hesperus

<400> SEQUENCE: 147

```
gatcttacct gcctgaacga ggcgtccgtt cttcacaaca tcaaggacag atattactcc     60

ggattgattt atacgtattc gggactcttc tgcgtggtgg tcaaccctta caagaaactg    120

ccaatctaca cagagagaat catggagaaa tacaaaggcg tcaaaagaca cgacctccct    180

ccacacgtat tcgccatcac agacacagct taccgttcta tgctgcaaga tagggaagat    240

caatcgatac tctgcaccgg cgaatcgggt gcggggaaaa ccgaaaacac gaaaaaagta    300

atccagtact tggcctacgt tgcagcctcg aaacccaaat cttccgcatc cccacatacg    360

gcccagagtc aagctctgat cattggagaa ctcgaacaac agctgcttca agctaaccca    420

attttggaag cattcggaaa cgccaagact gttaaaaacg ataattcttc tcgattcggt    480

aaattcattc gtatcaattt cgacgcatca ggctacatcg caggagccaa catagaaacg    540

tatcttctag agaaatctag ggccatcaga caagcgaaag atgagcgaac gttccacatc    600

ttttaccaac ttctggccgg agcatctgca gaacaaagaa aggagttcat cctcgaagat    660

ccgaaaaact accctttcct cagcagcggg atggtgtctg tgcctggagt tgacgatggt    720

gttgatttcc aagcaactat cgcctccatg tccatcatgg gcatgaccaa cgacgatctt    780

tccgctctct tccgcatcgt cagtgccgtc atgctgttcg gcagcatgca gttcaagcag    840

gagcgaaaca gcgaccaggc gacgctccca gacaacactg tagcgcaaaa aatcgcccac    900

ctccttggtc tctcaatcac agagatgacc aaagcgttcc tcaggcctag aatcaaagta    960

ggacgggatt tcgtcaccaa ggctcaaact aaggaacaag ttgagttcgc agtggaagcc   1020

atttcgaaag cctgctacga acgtatgttc cgatggctcg tcaacagaat caaccgctcc   1080

ctggatcgta ccaaaaggca gggagcatct ttcattggta ttcttgatat ggctggtttc   1140

gaaatctttg agatcaactc cttcgagcag ctttgtatca attacaccaa tgagaaactt   1200

caacaactct tcaaccacac catgttcatt ttggagcaag aggagtacca gagagaaggt   1260

attgaatgga agttcatcga cttcggactt gatcttcagc cgaccattga tctcattgat   1320

aagccaatgg gagtcatggc tctcctggat gaagaatgtt ggttccccaa agccactgac   1380

aagaccttcg ttgagaagct ggtcggtgct cacagcgttc accccaaatt catcaaaact   1440

gatttccgtg gagtcgccga ctttgctgtc gtccattatg ccggaaaagt cgattattcg   1500

gcggcgcagt ggctgatgaa gaacatggac cctctgaacg aaaacgtcgt gcagctcctc   1560

cagaactcgc aagatccgtt cgtcatccac atctggaagg acgcagagat cgtcggcatg   1620
```

```
gctcaccaag ctctcagcga cactcagttt ggagctcgta ccaggaaggg tatgttccga   1680
accgtgtctc aactctacaa agaccagctg tccaaactca tgatcacact tcgcaacacg   1740
aaccccaact tcgtccgttg catcctcccc aaccacgaga agagagctgg caagatcgat   1800
gctcctttgg tgctggatca gctcagatgc aacggtgtgt tggaaggcat cagaatttgc   1860
agacaaggtt tcccgaatag aatcccattc caggaattcc ggcaaagata cgagctctta   1920
actcccaatg tcatccccaa agggttcatg gacggtaaaa aggcttgcga gaagatgatc   1980
aacgctctcg aactggaccc taatctctac agagttggtc agtccaagat attcttcaga   2040
gctggagtct tagctcatct agaagaagag cgcgactata agattactga tctgatagcc   2100
aatttccggg ctttctgtag gggatatctt gcccgaagga actaccaaaa gcgtcttcag   2160
cagctcaacg ccattcgtat tatccagcga aattgctcag cttacttgaa gttgaggaac   2220
tggcaatggt ggcggctgta caccaaggtc aaacctctgc ttgaagtgac gaaacaagaa   2280
gagaagctga cgcaaaagga agacgaactg aagcaggtcc gcgagaaact ggacaaccag   2340
gtgaggtcca aggaagagta tgaaaagagg cttcaggacg ctttggagga gaaagctgct   2400
ctggcagagc aacttcaggc agaagtagag ctgtgtgcgg aagccgaaga aatgagagcc   2460
aggctcgctg tgaggaagca agaactagag gaaattctcc acgatctaga agccagaata   2520
gaggaagaag agcaacgaaa cacggtcctc atcaacgaaa agaagaagtt gaccctcaac   2580
atcgccgacc tcgaagaaca actggaagag gaagaaggag ctcgacagaa actccaactc   2640
gaaaaagtcc agatcgaagc tcggctgaag aaaatggaag aggacctcgc tctggccgaa   2700
gacaccaaca ccaaagtcgt aaaggagaag aaagtgttgg aagagagggc tagtgacttg   2760
gcccagaccc tcgctgagga agaagaaaaa gctaaacacc tcgcgaagct caagaccaag   2820
cacgagacga cgatagcgga attggaagag aggttgctca aagacaatca gcagaggcag   2880
gaaatggata ggaacaagag gaagatcgaa tcagaggtga atgatttgaa agaacaaatt   2940
aacgagaaga aggtccaagt agaggagctt cagttgcaac tcgggaagag ggaagaggaa   3000
atcgctcaag ctctgatgag aattgacgag gaaggagcag gcaaagctca gactcaaaag   3060
gctctcaggg aattggagtc tcagctggct gagctacaag aggatctaga ggctgaaaag   3120
gccgctcgcg ccaaggccga aaagcagaag cgcgacctca acgaagaact cgagtccctc   3180
aagaatgaac ttcttgactc actggacacg acagcagctc aacaggaatt gaggaccaag   3240
agagaacacg aactggcaac gctcaagaaa acattagaag aggaaacgca cattcacgaa   3300
gtatctctca ccgaaatgag gcacaaacac actcaagaag tcgctgcact caacgaacag   3360
ttggagcaac tcaaaaaggc caaatctgca ctcgaaaaat cgaaagcaca acttgaaggg   3420
gaagctgctg agctcgccaa cgaactggaa acagcaggaa cgagcaaggg cgagagtgaa   3480
aggaaacgga agcaggccga atcgtctctg caggagctct cgtcgcgact cttggaaatg   3540
gagagaacca aagccgagct ccaagagagg gtccagaaac tgtctgcaga agccgactct   3600
gtcaatcagc agttggaagc agcggaactg aaagcatcag cagccctcaa ggcatctggt   3660
accttggaga ctcagctcca ggaggcgcaa gtgctcctgg aagaggaaac tcggcagaag   3720
ctgtcgttga ccaccaaact gaaaggcctc gaaagcgaaa gagatgctct caaagagcaa   3780
ctctacgaag aggacgaggg taggaagaac ctagaaaaac agatggcgat actcaatcaa   3840
caagtagctg aaagcaagaa gaagtctgaa gaagaaacgg aaaaaataac tgaactcgaa   3900
gaaagtcgca aaaaattgct caaagacata gaaattcttc aaaggcaagt cgaagaactt   3960
caagttacca acgacaaatt agagaaaggc aagaagaagc tgcagtcaga actggaagac   4020
```

```
ctcaccatcg acctggagtc tcagagaaca aaggtggtcg agctcgagaa gaaacaaaga   4080

aatttcgaca aagttttggc cgaagaaaaa gcgttgtcgc aacaaatcac gcacgagagg   4140

gatgcggctg aaagagaagc ccgtgaaaag gaaactagag tactgtcgct gacgcgagaa   4200

ctcgatgaat tcatggagaa aatcgaggaa ctggagagaa gcaaacggca actccaggct   4260

gaactagacg agctggtcaa caaccaaggc accaccgaca aaagcgtgca cgaattggaa   4320

agggcgaaac gagttctgga gtcacaactt gcagagcaga aagcacaaaa tgaagagctt   4380

gaagatgaac tccaaatgac ggaagacgcc aaattgaggc tcgaagtcaa catgcaagct   4440

ctgagagctc aattcgaaag agatctacag ggcaaagaag agtcgggaga agaaaagagg   4500

agaggattgc tgaaacagct gagggacatt gaggctgaac ttgaagacga gagaaaacaa   4560

aggaccgctg ctgttgcctc tagaaagaag attgaagcgg atttcaaaga tgtagaacag   4620

caactggaaa tgcacactaa ggtaaaggaa gatcttcaga agcaactgaa gaaatgccag   4680

gtccaactga aggacgcaat cagagacgcg gaagaggctc ggctcggtcg ggaagagctg   4740

caggctgccg ctaaagaggc cgaaaggaag tggaagggtt tggaaacgga gctcattcaa   4800

gtgcaagagg atttgatggc gagcgaaagg cagcggcggg cagcggaagc cgaaagggat   4860

gaagtcgttg aagaagccaa caagaatgtc aagagcttat cgaatcttct cgacgaaaag   4920

aagaggctcg aagcccaatg ctcaggcctg gaagaggaac tcgaagaaga acttagcaac   4980

aatgaggccc tccaagacaa agcgagaaaa gcacaactca gcgttgagca acttaatgca   5040

gaacttgctg ccgaacggag taatgtgcag aaacttgagg gaacgagatt gtcgatggaa   5100

aggcaaaaca aggaactgaa ggccaaactg aacgaactgg aaacgttaca acgcaacaag   5160

ttcaaggcca atgcgtctct ggaggctaag attaccaatc ttgaagagca actggaaaat   5220

gaagccaagg aaaagctact tctccagaaa ggcaacagga agctcgacaa gaaaatcaaa   5280

gacctcctcg ttcaattgga ggatgaaagg aggcatgccg accagtataa agaacaagtc   5340

gagaagatca acgtcagggt gaagacgcta aagcgaactt tggacgacgc cgaagaagaa   5400

atgagtaggg agaagaccca gaagaggaaa gcacttcgcg aattggaaga cctcagggag   5460

aactacgatt ccctactccg agagaacgat aacctcaaaa acaaactcag gcggggcggc   5520

ggtatttccg ggatctcgag caggctcgga ggctccaagc gaggttccat ccccggagag   5580

gattcccagg gtctcaacaa caccacagac gaatcagtcg atggtgacga tatctcgaat   5640

ccttaaacgc tacttggatt taccagccag catccaactt tccactgaag acgtctccca   5700

taaacgttga aagagacccg tcgaggaaga aaaaaaggct ctttaagaaa aactattctg   5760

ccttttttcaa aactttgtac ttaaaagtac tttcgcttaa caatgaaaga agaataaaaa   5820

tgtaaagttt tcatttatac aaaaaaaaaa aaaaaaaaaa aaaaaaaaaa aa           5872
```

<210> SEQ ID NO 148
<211> LENGTH: 325
<212> TYPE: DNA
<213> ORGANISM: Lygus hesperus

<400> SEQUENCE: 148

```
aagaagatcc tggaggagat cattgcggag gtcgacgctg atggctctgg acaacttgaa     60

tttgaggagt tcgtagcctt ggctgccggt ttcctgacag aagatgagac acaagatgct    120

gaggccatgc agcaagaact gagggaggcc ttcaggctct acgacaagga agggaacggt    180

tacattacca ctgacgtctt gagggaaatc ctgaaggaac tcgacgacaa aatcacctcc    240
```

caagaacttg acatgatgat tgctgaaatt gattctgacg gttccggaac tgttgacttc 300
gacgagttca tggagatgat gaccg 325

<210> SEQ ID NO 149
<211> LENGTH: 428
<212> TYPE: DNA
<213> ORGANISM: Lygus hesperus

<400> SEQUENCE: 149
aattatcccc atcatgacca tcgcgttgaa cgctttcgac cgggatcact cgggttccat 60
cccgacggac atggtggccg acatcctcag actcatgggt caacccttca acaagaagat 120
tctcgatgaa ctcatcgaag aagttgacgc tgacaaatcg ggaaggctgg agtttgaaga 180
gttcatcacg ttggcagcca agttcattgt tgaggaagac gatgaagcca tgcagaaaga 240
gctgcgagaa gccttccgtc tctacgacaa agaaggtaat ggctacatcc cgacctcctg 300
cctcaaagaa atccttcatg aattggacga gcagctgacc aacgaggagc tggacatgat 360
catcgaggag atcgactctg acggatccgg aactgtcgac ttcgacgagt tcatggagat 420
gatgaccg 428

<210> SEQ ID NO 150
<211> LENGTH: 538
<212> TYPE: DNA
<213> ORGANISM: Lygus hesperus

<400> SEQUENCE: 150
gcttctttta caaatcgcac cacgccgact taattcattc ccggagggtt taaattttat 60
cgaagcagca tggtgcggat gaatgtgctg agcgatgctc tgaaaagcat caacaatgct 120
gagaagaggg gcaaaaggca ggtgctcctg aggccttgtt ccaaagtcat cattaaattc 180
cttacagtga tgatgaagaa aggttatatc ggcgaattcg aaatagtaga tgatcacaga 240
tctggtaaaa tcgtcgtcaa cctcaacggc agattgaaca aatgtggagt tatatcgccc 300
agattcgacg tacccatcac acaaatcgaa aaatggacga acaacctcct gccttcccga 360
cagttcggtt atgtcgtact caccactagt ggagggatca tggatcacga agaagccagg 420
cgaaaacatc ttgggggtaa aatattaggg tttttctttt aataaaaaaa gacgagatgt 480
aaattaataa aactctttta cgtttcgcta aaaaaaaaaa aaaaaaaaaa aaaaaaaa 538

<210> SEQ ID NO 151
<211> LENGTH: 405
<212> TYPE: DNA
<213> ORGANISM: Lygus hesperus

<400> SEQUENCE: 151
ccacgccgac ttaattcatt cccggagggt ttaaatttta tcgaagcagc atggtgcgga 60
tgaatgtgct gagcgatgct ctgaaaagca tcaacaatgc tgagaagagg ggcaaaaggc 120
aggtgctcct gaggccttgt tccaaagtca tcattaaatt ccttacagtg atgatgaaga 180
aaggttatat cggcgaattc gaaatagtag atgatcacag atctggtaaa atcgtcgtca 240
acctcaacgg cagattgaac aaatgtggag ttatatcgcc cagattcgac gtacccatca 300
cacaaatcga aaaatggacg aacaacctcc tgccttcccg acagttcggt tatgtcgtac 360
tcaccactag tggagggatc atggatcacg aagaagccag gcgaa 405

<210> SEQ ID NO 152
<211> LENGTH: 470

```
<212> TYPE: DNA
<213> ORGANISM: Lygus hesperus

<400> SEQUENCE: 152

tgtcgatggc ggtcttaaca tcccccattc caccaagagg ttccctgggt acgacagtga    60

gtctaaggaa ttcaacgctg aggtccacag gaagcacatt ttcggcattc acgtcgctga   120

ctacatgcgt cagctggctg aagaggatga cgatgcttac aagaagcagt tctcgcagta   180

tgtcaagaac ggagtcactg ctgacagcat tgaaagtatc tacaagaagg ctcacgaagc   240

aatccgagct gatccaactc gcaaaccact tgagaagaag gaagtcaaga agaagaggtg   300

gaaccgcgcc aagctttcct tgtctgaaag gaagaacacc atcaaccaaa agaaggcaac   360

ttatctcaag aaagtggaag ctggagaaat cgaataagtt tttatattcc tgacattacc   420

cattaaaggt ttcgttttaa cctaaaaaaa aaaaaaaaaa aaaaaaaaaa              470


<210> SEQ ID NO 153
<211> LENGTH: 387
<212> TYPE: DNA
<213> ORGANISM: Lygus hesperus

<400> SEQUENCE: 153

tgtcgatggc ggtcttaaca tcccccattc caccaagagg ttccctgggt acgacagtga    60

gtctaaggaa ttcaacgctg aggtccacag gaagcacatt ttcggcattc acgtcgctga   120

ctacatgcgt cagctggctg aagaggatga cgatgcttac aagaagcagt tctcgcagta   180

tgtcaagaac ggagtcactg ctgacagcat tgaaagtatc tacaagaagg ctcacgaagc   240

aatccgagct gatccaactc gcaaaccact tgagaagaag gaagtcaaga agaagaggtg   300

gaaccgcgcc aagctttcct tgtctgaaag gaagaacacc atcaaccaaa agaaggcaac   360

ttatctcaag aaagtggaag ctggaga                                       387


<210> SEQ ID NO 154
<211> LENGTH: 745
<212> TYPE: DNA
<213> ORGANISM: Lygus hesperus

<400> SEQUENCE: 154

gtcctacgtg tttccggaaa aacgtgcatt tcgcgtaccc ctcgtggtga tccgttttca    60

tagaaataat ccaaaatggc tcccaagggg aataatatga ttcccaatgg ccatttccac   120

aaggattggc agaggttcat caaaacctgg ttcaaccagc ctgcccgcaa gttgaggagg   180

agaaacaaga ggttggagaa ggcccaacgg ctcgcgcccc gccccgcggg acctcttcgc   240

cccgctgtca gatgtcccac cgtcaggtac cacaccaagc tacgacctgg acgtggcttc   300

accttggaag aaatcaagag agccggtctg tgcaaaggat tcgcgatgtc catcggaatc   360

gctgtcgacc ccagaagaag gaataaatcc atcgagtccc tccaactcaa tgtacagaga   420

ctcaaggagt acagggctaa gcttatcctc ttcccacaca agaatgccaa gaaactgaag   480

aagggagaag ctactgagga agagaggaag gtggccaccc aacagcccct gccagttatg   540

cccatcaagc aaccagtcat caaattcaag gctcgcgtca ttacagacga tgagaagaaa   600

tactctgcct tcaccgccct ccgcaaggga cgagcagacc aaaggttggt cggtatccgt   660

gctaagcgcg caaaggaagc cgcagaaaac gccgaagacc cctctaaagc tcctaaaaaa   720

aaaaaaaaaa aaaaaaaaaa aaaaa                                         745


<210> SEQ ID NO 155
```

<211> LENGTH: 527
<212> TYPE: DNA
<213> ORGANISM: Lygus hesperus

<400> SEQUENCE: 155

```
aacgtgcatt tcgcgtaccc ctcgtggtga tccgttttca tagaaataat ccaaaatggc     60

tcccaagggg aataatatga ttcccaatgg ccatttccac aaggattggc agaggttcat    120

caaaacctgg ttcaaccagc ctgcccgcaa gttgaggagg agaaacaaga ggttggagaa    180

ggcccaacgg ctcgcgcccc gccccgcggg acctcttcgc cccgctgtca gatgtcccac    240

cgtcaggtac cacaccaagc tacgacctgg acgtggcttc accttggaag aaatcaagag    300

agccggtctg tgcaaaggat tcgcgatgtc catcggaatc gctgtcgacc ccagaagaag    360

gaataaatcc atcgagtccc tccaactcaa tgtacagaga ctcaaggagt acagggctaa    420

gcttatcctc ttcccacaca agaatgccaa gaaactgaag aagggagaag ctactgagga    480

agagaggaag gtggccaccc aacagcccct gccagttatg cccatca                  527
```

<210> SEQ ID NO 156
<211> LENGTH: 576
<212> TYPE: DNA
<213> ORGANISM: Lygus hesperus

<400> SEQUENCE: 156

```
gccttattga acgtggtcga cagaaaactc ggtttctgag ctcatctcaa catggatatc     60

gaagaaccgg ccgcggcccc tacggagccc tcggacgtca acaccgccct tcaagaggtc    120

ctcaaggccg cccttcaaca cggagtcgtc gtccacggta tccacgagtc cgccaaggcc    180

ctcgacaaga ggcaagcttt gttgtgcgtc ctcgctgaga actgcgacga gccgatgtac    240

aagaagctgg tacaagccct ctgctcagag caccacatcc ccctcgtcaa agtagattcc    300

aataagaaac tcggcgaatg gacgggcctt tgcaagatcg acaagaccgg caaatctagg    360

aaaatcgtcg gctgctcttg tgtcgtcatc aaggactggg gtgaggacac gccccacttg    420

gacctcctca aggactacat cagggacgtc ttctaagaag tttctcctca atttcctttt    480

tataatgatt taacaactga gaattaataa taaaaatgtt aaattaaaca aaaaaatctc    540

aaaactgtaa aaaaaaagaa gaaaaaaaaa aaaaaa                              576
```

<210> SEQ ID NO 157
<211> LENGTH: 442
<212> TYPE: DNA
<213> ORGANISM: Lygus hesperus

<400> SEQUENCE: 157

```
ccttattgaa cgtggtcgac agaaaactcg gtttctgagc tcatctcaac atggatatcg     60

aagaaccggc cgcggcccct acggagccct cggacgtcaa caccgccctt caagaggtcc    120

tcaaggccgc ccttcaacac ggagtcgtcg tccacggtat ccacgagtcc gccaaggccc    180

tcgacaagag gcaagctttg ttgtgcgtcc tcgctgagaa ctgcgacgag ccgatgtaca    240

agaagctggt acaagccctc tgctcagagc accacatccc cctcgtcaaa gtagattcca    300

ataagaaact cggcgaatgg acgggccttt gcaagatcga caagaccggc aaatctagga    360

aaatcgtcgg ctgctcttgt gtcgtcatca aggactgggg tgaggacacg ccccacttgg    420

acctcctcaa ggactacatc ag                                             442
```

<210> SEQ ID NO 158
<211> LENGTH: 601

<212> TYPE: DNA
<213> ORGANISM: Lygus hesperus

<400> SEQUENCE: 158

```
ctttcatttg tatagtacgg acgggtagtt tagttgtgtc ggttcatcgt aattcatcgg     60

ctgaatcatg aagatgaata aattggtcac ttcctcgagg aggaagaaca ggaagaggca    120

cttcaccgcc ccatcccaca tccgtagaaa gttgatgtcg gcaccactgt ccaaagaact    180

taggcagaag tacaacgtcc gaactatgcc tgtgaggaag gacgatgaag tccaggttgt    240

acgaggacac tacaaaggcc aacaggttgg caaagtcctc caggtgtaca ggaagaagtt    300

cattatttac attgagcgga tccaaagaga aaaagccaat ggtgccagcg tttacgttgg    360

cattcacccc tcaaagtgtg tgatcgtcaa attgaaggtc gacaaggata ggaaagaaat    420

ccttgacaga agatccaaag gacgtgactt ggcacttggc aaggacaagg gcaaatacac    480

cgaagacagt acgactgcta tggacacgtc ttaaattaat ttggtttatt tggttcctta    540

actccgttct tctttaataa tgactttttt aaagcaaaaa aaaaaaaaaa aaaaaaaaaa    600

a                                                                    601
```

<210> SEQ ID NO 159
<211> LENGTH: 448
<212> TYPE: DNA
<213> ORGANISM: Lygus hesperus

<400> SEQUENCE: 159

```
gtacggacgg gtagtttagt tgtgtcggtt catcgtaatt catcggctga atcatgaaga     60

tgaataaatt ggtcacttcc tcgaggagga agaacaggaa gaggcacttc accgccccat    120

cccacatccg tagaaagttg atgtcggcac cactgtccaa agaacttagg cagaagtaca    180

acgtccgaac tatgcctgtg aggaaggacg atgaagtcca ggttgtacga ggacactaca    240

aaggccaaca ggttggcaaa gtcctccagg tgtacaggaa gaagttcatt atttacattg    300

agcggatcca aagagaaaaa gccaatggtg ccagcgttta cgttggcatt cacccctcaa    360

agtgtgtgat cgtcaaattg aaggtcgaca aggataggaa agaaatcctt gacagaagat    420

ccaaaggacg tgacttggca cttggcaa                                       448
```

<210> SEQ ID NO 160
<211> LENGTH: 456
<212> TYPE: DNA
<213> ORGANISM: Lygus hesperus

<400> SEQUENCE: 160

```
ggctgttgtc ggctggtcat atcccgtttt ccacgtggtg tgtcgagtta tttttcttgt     60

aaattcgcat ttaaaatcgg atttataacc gaaattcatt atggaaaagc cagtagtttt    120

ggcccgtgtc atcaaaatcc tcggacgtac cggctcacag ggccaatgta cgcaagtgaa    180

ggtggagttc attggtgagc agaaccgaca gatcatcagg aacgtgaaag gaccagttag    240

agaaggcgac atcctcacac tcctagagtc tgaaagagaa gcgagaagac tgaggtagtg    300

ggaggtggcg atgcgttacg ttattttact tcattcaaca tttgaaaaaa accatcttcg    360

tgacaaaaaa catcttcacg caactatttg tattacctat gtttcgtaaa taaagtaacc    420

tcgttactta aaaaaaaaaa aaaaaaaaaa aaaaaa                              456
```

<210> SEQ ID NO 161
<211> LENGTH: 321
<212> TYPE: DNA

<213> ORGANISM: Lygus hesperus

<400> SEQUENCE: 161

```
ctgttgtcgg ctggtcatat cccgttttcc acgtggtgtg tcgagttatt tttcttgtaa     60

attcgcattt aaaatcggat ttataaccga aattcattat ggaaaagcca gtagttttgg    120

cccgtgtcat caaaatcctc ggacgtaccg gctcacaggg ccaatgtacg caagtgaagg    180

tggagttcat tggtgagcag aaccgacaga tcatcaggaa cgtgaaagga ccagttagag    240

aaggcgacat cctcacactc ctagagtctg aaagagaagc gagaagactg aggtagtggg    300

aggtggcgat gcgttacgtt a                                              321
```

<210> SEQ ID NO 162
<211> LENGTH: 865
<212> TYPE: DNA
<213> ORGANISM: Lygus hesperus

<400> SEQUENCE: 162

```
aatcccggat tcatcgtttt attgaattgt ttttcgaagt ttctggtatt atcgttaaat     60

tagtctgtta agccctcatc cgtgatttgg caagttgttg attgttctat tttccttttt    120

ccagaaaatg gggagacgtc cagcgaggtg ttatcggtac tgtaaaaaca agccataccc    180

ccaaatcccg gttctgtcgt ggtgtccccg accccaagat caggatcttc gatctgggaa    240

agaagaaggc ccgcgtggaa gacttccccc tctgcgttca cctcgtctcc gatgagtacg    300

agcagctgtc ctccgaagcc ctcgaggcag gacgtatctg ctgcaacaag tacctcgtca    360

agaactgcgg caaggaccag ttccacatca ggatgaggct ccaccccttc cacgtcatta    420

ggatcaacaa aatgttatcg tgcgctggag ctgataggct ccagacaggg atgagaggag    480

cgttcggaaa gccgcaagga accgtcgctc gcgtccgcat cggtcagccc atcatgagcg    540

tccgctcgtc cgacaggtac aaggccgccg tcatcaaggc tctgaggaga gccaaattca    600

agttccctgg tcgccagaag atctacgttt ccaagaaatg ggcttcacc aagttcgacc     660

gcgaagagta cgagggcctt aggaacgaca acaaactagc gaatgacggc tgcaacgtca    720

aattgaggcc ggatcacgga cctttgcagg cgtggaggaa ggctcagctt gacatcgctg    780

ctggcctcta aattactttc caatggtttt ataaatcaac aaataaaact cgttttatgt    840

aaaaaaaaaa aaaaaaaaaa aaaaa                                          865
```

<210> SEQ ID NO 163
<211> LENGTH: 792
<212> TYPE: DNA
<213> ORGANISM: Lygus hesperus

<400> SEQUENCE: 163

```
ggttcctttc tcagattttg actttgccgt gttgtctctc ccaattttcc aaaatgggga     60

gacgtccagc gaggtgttat cggtactgta aaaacaagcc ataccccaaa tcccggttct    120

gtcgtggtgt ccccgacccc aagatcagga tcttcgatct gggaaagaag aaggcccgcg    180

tggaagactt cccccctctgc gttcacctcg tctccgatga gtacgagcag ctgtcctccg    240

aagccctcga ggcaggacgt atctgctgca acaagtacct cgtcaagaac tgcggcaagg    300

accagttcca catcaggatg aggctccacc ccttccacgt cattaggatc aacaaaatgt    360

tatcgtgcgc tggagctgat aggctccaga cagggatgag aggagcattc ggaaagccgc    420

aaggaaccgt cgctcgcgtc cgcatcggtc agcccatcat gagcgtccgc tcgtccgaca    480

ggtacaaggc cgccgtcatc gaggctctga ggagagccaa attcaagttc cctggtcgcc    540
```

agaagatcta cgtttccaag aaatggggct tcaccaagtt cgaccgcgaa gagtacgagg 600
gccttaggaa cgacaacaaa ctagcgaatg gcggctgcaa cgtcaaattg aggccggatc 660
acggaccttt gcaggcgtgg aggaaggctc agcttgacat cgctgctggc ctctaaatta 720
ctttccaatg gttttataaa tcaacaaata aaactcgttt tatctaaaaa aaaaaaaaaa 780
aaaaaaaaaa aa 792

<210> SEQ ID NO 164
<211> LENGTH: 645
<212> TYPE: DNA
<213> ORGANISM: Lygus hesperus

<400> SEQUENCE: 164
agccctcatc cgtgatttgg caagttgttg attgttctat tttccttttt ccagaaaatg 60
gggagacgtc cagcgaggtg ttatcggtac tgtaaaaaca agccataccc ccaaatcccg 120
gttctgtcgt ggtgtccccg accccaagat caggatcttc gatctgggaa agaagaaggc 180
ccgcgtggaa gacttccccc tctgcgttca cctcgtctcc gatgagtacg agcagctgtc 240
ctccgaagcc ctcgaggcag gacgtatctg ctgcaacaag tacctcgtca agaactgcgg 300
caaggaccag ttccacatca ggatgaggct ccaccccttc cacgtcatta ggatcaacaa 360
aatgttatcg tgcgctggag ctgataggct ccagacaggg atgagaggag cgttcggaaa 420
gccgcaagga accgtcgctc gcgtccgcat cggtcagccc atcatgagcg tccgctcgtc 480
cgacaggtac aaggccgccg tcatcaaggc tctgaggaga gccaaattca agttccctgg 540
tcgccagaag atctacgttt ccaagaaatg ggcttcacc aagttcgacc gcgaagagta 600
cgagggcctt aggaacgaca acaaactagc gaatgacggc tgcaa 645

<210> SEQ ID NO 165
<211> LENGTH: 619
<212> TYPE: DNA
<213> ORGANISM: Lygus hesperus

<400> SEQUENCE: 165
gctttaccga ttccgttctt gtttagtcca cgtttctctg ctcattcgtg cagattttaa 60
aacatgacca actccaaagg ttatcgtcgc ggaacgaggg atctcttctc gaggcccttc 120
cgtcaccatg gtgtcatccc actctcaacg tacatgaaag tataccgagt aggagacatc 180
gtatctatca aaggtaatgg agcagtgcaa aaaggtatgc cccacaaagt ttaccacggc 240
aagaccggac gagtctacaa tgttacacct cgcgcccttg gtgttattgt caacaagagg 300
gttcgtggaa aaatccttcc caagaggatc aacatcagga ttgaacacgt caaccacagt 360
aaatgcagag aagatttctt gaagcgagtg cgagaaaatg aaaggctccg caaattcgcc 420
aaagaaactg gcaccagggt tgaactcaaa agacagcctg ctcagccacg ccctgcacac 480
tttgtacaag ctaaagaagt cccagagctg ctggccccca taccttacga gttcatcgct 540
taaaaaattt tcaattccat cttaacttta tatatttgaa taaaattgtg ttctcaaaaa 600
aaaaaaaaaa aaaaaaaaa 619

<210> SEQ ID NO 166
<211> LENGTH: 461
<212> TYPE: DNA
<213> ORGANISM: Lygus hesperus

<400> SEQUENCE: 166

```
acgtttctct gctcattcgt gcagatttta aaacatgacc aactccaaag gttatcgtcg      60

cggaacgagg gatctcttct cgaggccctt ccgtcaccat ggtgtcatcc cactctcaac     120

gtacatgaaa gtataccgag taggagacat cgtatctatc aaaggtaatg gagcagtgca     180

aaaaggtatg ccccacaaag tttaccacgg caagaccgga cgagtctaca atgttacacc     240

tcgcgccctt ggtgttattg tcaacaagag ggttcgtgga aaaatccttc ccaagaggat     300

caacatcagg attgaacacg tcaaccacag taaatgcaga gaagatttct tgaagcgagt     360

gcgagaaaat gaaaggctcc gcaaattcgc caaagaaact ggcaccaggg ttgaactcaa     420

aagacagcct gctcagccac gccctgcaca ctttgtacaa g                         461
```

```
<210> SEQ ID NO 167
<211> LENGTH: 481
<212> TYPE: DNA
<213> ORGANISM: Lygus hesperus

<400> SEQUENCE: 167

caacgtacat gaaagtatac cgagtaggag acatcgtatc tatcaaaggt aatggagcag      60

tgcaaaaagg tatgccccac aaagtttacc acggcaagac cggacgagtc tataatgtta     120

cacctcgcgc ccttggtgtt attgtcaaca agagggttcg tggaaaaatc cttcccaaga     180

ggatcaacat caggattgaa cacgtcaacc acagtaaatg cagagaagat ttcttgaagc     240

gagtgcgaga aaatgagagg ctccgcaaat tcgccaaaga aactggcacc agggttgaac     300

tcaaaagaca gcctgctcag ccacgccctg cacactttgt acaagctaaa gaagtcccag     360

agctgctggc cccatacct tacgagttca tcgcttaaac aattttcaat tccatcttaa      420

ctttatatat ttgaataaaa ttgtgttccc taaaaaaaaa aaaaaaaaaa aaaaaaaaaa     480

a                                                                     481
```

```
<210> SEQ ID NO 168
<211> LENGTH: 747
<212> TYPE: DNA
<213> ORGANISM: Lygus hesperus

<400> SEQUENCE: 168

gcataaatat atagggcgat tgatttagcg gccgcgaatt cgcccttaag cagtggtatc      60

aacgcagagg gggggtcttc tctcccggtt ttcttcttgc ccgaatcgtc catcctgatg     120

ttggggtcac tgtcaccacg accatacccc aatttggggt atggcttggt tgtcccctac     180

ccataaatcc tgattggaca tctccccatt atgaaagact gcgagaaaca cccctgcccc     240

cggctttaaa ccccacggcta agggggggatt cgcgggcggc aaatttcatt cggcccatag   300

tgagtcgtat tacaattcac tggcgtcct ttttacacct tcggaccggg aaaaacctgg      360

cggttaccca aaatccgtta tttgccacat ccccctttac tccactgggt tatataacaa     420

agaggcccct tccaatgtcc tttcccaaaa gtgcgcagcc ctatactaat ggcctttaaa     480

ggaaccccta ttaaaaaaaa aaccccttaac cacaggttgg tgatgtaacc aaggaaaata    540

atgaacacac cgggccaaag aaggtgatac ccctggtctt ggcgaccgcc tgtcaaatct     600

tcctcccgga acgaaacccg tagtggcatc gaggaataac cttgcgcatc atagactcca     660

aatggccact gtggccgctc tcgattcatg gaagaaatga gatgacccct accccgcgca     720

aaaggattca gaaccaatac cagaatc                                         747
```

```
<210> SEQ ID NO 169
<211> LENGTH: 1052
```

<212> TYPE: DNA
<213> ORGANISM: Lygus hesperus
<220> FEATURE:
<221> NAME/KEY: misc_feature
<222> LOCATION: (662)..(665)
<223> OTHER INFORMATION: n is a, c, g, or t

<400> SEQUENCE: 169

```
ggttttcttc ttgcccgaat cgtccatcct gatgttgggg tcactgtcac cacgaccata     60
ccccaatttg ggtatggct tggttgtccc ctacccataa atcctgattg gacatctccc    120
cattatgaaa gactgcgaga aacacccctg cccccggctt taaacccacg gctaaggggg    180
gattcgcggg cggcaaattt cattcggccc atagtgagtc gtattacaat tcactgggcg    240
tcctttttac accttcggac cgggaaaaac ctggcggtta cccaaaatcc gttatttgcc    300
acatccccct ttactccact gggttatata acaaagaggc cccttccaat gtcctttccc    360
aaaagtgcgc agccctatac taatggcctt taaaggaacc cctattaaaa aaaaaaccct    420
taaccacagg ttggtgatgt aaccaaggaa aataatgaac acaccgggcc aaagaaggtg    480
ataccccctgg tcttggcgac cgcctgtcaa atcttcctcc cggaacgaaa cccgtagtgg    540
catcgaggaa taaccttgcg catcatagac tccaaatggc cactgtggcc gctctcgatt    600
catggaagaa atgagatgac ccctaccccg cgcaaaagga ttcagaacca ataccagaat    660
cnnnntagca aaacggctat ttcccggttc tttgtcggat tcttttgcca gggccatgcc    720
ttttcccgga atggaaggcg ggctgtttga gaaacgcatt aaatgggatt agtccattca    780
taggccaccc aaggaaacca ctttaatttc gggttggtag gttgagagaa atggtgaggg    840
gtaacaattt tacaccggga accgtttatg cccagaatta ccccagcttc gaattaaccc    900
cccctaaagg ggatagttcc gccgggttaa aagaaattcg ccttaaacca gtgttttaaa    960
gcaggagaca gaagtgtttc tcgcaagctt tcaaaatggg gagatgtcca atcaggattt   1020
atgggtaggg tacaaccaag ccgaacccca aa                                1052
```

<210> SEQ ID NO 170
<211> LENGTH: 555
<212> TYPE: DNA
<213> ORGANISM: Lygus hesperus

<400> SEQUENCE: 170

```
tagcaaaacg gctatttccc ggttctttgt cggattcttt tgccagggcc atgccttttc     60
ccggaatgga aggcgggctg tttgagaaac gcattaaatg ggattagtcc attcataggc    120
cacccaagga aaccacttta atttcgggtt ggtaggttga gagaaatggt gaggggtaac    180
aattttacac cgggaaccgt ttatgcccag aattacccca gcttcgaatt aacccccccct    240
aaaggggata gttccgccgg gttaaaagaa attcgcctta aaccagtgtt ttaaagcagg    300
agacagaagt gtttctcgca agctttcaaa atggggagat gtccaatcag gatttatggg    360
tagggtacaa ccaagccgaa ccccaaatcc ctgttctgtc gtggtgacag tgaccccaag    420
atctggatgt tcgttttggg aaagaagaaa accgggaggg accacttcct cctctgcgtt    480
gataccactg cttaagggcg aattcgttta aacctgcagg actagtccct tagtgagggt    540
aatctagcag cccac                                                   555
```

<210> SEQ ID NO 171
<211> LENGTH: 1052
<212> TYPE: DNA
<213> ORGANISM: Lygus hesperus
<220> FEATURE:

<221> NAME/KEY: misc_feature
<222> LOCATION: (662)..(665)
<223> OTHER INFORMATION: n is a, c, g, or t

<400> SEQUENCE: 171
ggttttcttc ttgcccgaat cgtccatcct gatgttgggg tcactgtcac cacgaccata 60
ccccaatttg ggtatggct tggttgtccc ctacccataa atcctgattg gacatctccc 120
cattatgaaa gactgcgaga aacaccccctg cccccggctt taaacccacg gctaaggggg 180
gattcgcggg cggcaaattt cattcggccc atagtgagtc gtattacaat tcactgggcg 240
tcctttttac accttcggac cgggaaaaac ctggcggtta cccaaaatcc gttatttgcc 300
acatccccct ttactccact gggttatata acaaagaggc cccttccaat gtcctttccc 360
aaaagtgcgc agccctatac taatggcctt taaaggaacc cctattaaaa aaaaaaccct 420
taaccacagg ttggtgatgt aaccaaggaa aataatgaac acaccgggcc aaagaaggtg 480 ataccccctgg tcttggcgac cgcctgtcaa atcttcctcc cggaacgaaa cccgtagtgg 540
catcgaggaa taaccttgcg catcatagac tccaaatggc cactgtggcc gctctcgatt 600
catggaagaa atgagatgac ccctaccccg cgcaaaagga ttcagaacca ataccagaat 660
cnnnntagca aaacggctat ttcccggttc tttgtcggat tcttttgcca gggccatgcc 720
ttttcccgga atggaaggcg ggctgtttga gaaacgcatt aaatgggatt agtccattca 780
taggccaccc aaggaaacca ctttaatttc gggttggtag gttgagagaa atggtgaggg 840
gtaacaattt tacaccggga accgtttatg cccagaatta ccccagcttc gaattaaccc 900
cccctaaagg ggatagttcc gccgggttaa aagaaattcg ccttaaacca gtgttttaaa 960
gcaggagaca gaagtgtttc tcgcaagctt tcaaaatggg gagatgtcca atcaggattt 1020
atgggtaggg tacaaccaag ccgaacccca aa 1052

<210> SEQ ID NO 172
<211> LENGTH: 1175
<212> TYPE: DNA
<213> ORGANISM: Lygus hesperus

<400> SEQUENCE: 172
ctcagcgaga tccctaagac aacgcctgcc acgtgggaga atatcggaca cgcctcccca 60
gagtgcggaa aggggaacgg cgttccgtat cggtcaaggt gcaagcttcg gaaccggagg 120
acgaccgttg caaggtgcaa ggggcaggta tcttgtattt tcattgtgcg tgtcgacatc 180
taccaaactg agacttggag ttcgatattt tgacgatggg gccgggggcc ggaggcaaaa 240
cgacaaacac aggcaccgtg accgtgttcc ggtccctggc ctgcgttgcc ttacgttcac 300
atcttgttct tgcgctttct ctggttttac gataacccta ctacgagttt agtagagccg 360
atcccgtagc cgaagccaaa gcccaagcgc tccgtatccg agaacgcgga agagcacgaa 420
ctccccaaac ccctccgccc ctccccccgcg cgtatccgaa acacaaatgc agcgggcagt 480
acaggttttg gaaggggacg cgggcagtga gcgcaatgca agtaaatgtg attagctcat 540
ggctacgcag ccctgctttt tcagtttcgg ttcggatcgt tagggggtgt gggattggga 600
gcggattcaa tctggacagg aaacagctat gaccaaggtc acgccaagct ctgaattaac 660
cctcaggaaa gggactagtc cggcaggttg aaacgaactc gcccctaagc agtggtatca 720
gagcacagtg gtttttttt tttgtttttt ttcgtagaaa aaaatatgta ttaagtcaat 780
taattaaatc attggttttc tggcttcaca acaggtggca cgtgctgtgc tcggagaaat 840
ttatgaacta tgttctgttc ttcaatgagg aaagatgaga tgatccattc tcagacacat 900

```
tcagacagag gacaccaccg taagccctat ccacagtctg tccacgtaag gggatcgtgt    960

ccccttccat gggcagagca gggagagggc cgtaagcttg ttcttgcgtc atcaacatgt   1020

gggggtaatg ttggtcatag cgatgttcgg tacacaagag aaccacctgg tgtaatcatt   1080

acagcacagc aatactctgt gttttgtaag ataacaaaaa aggtacttaa gacgctgaac   1140

cattttctac gatcggaaaa caaaaaaaaa gaaaa                              1175
```

<210> SEQ ID NO 173
<211> LENGTH: 1023
<212> TYPE: DNA
<213> ORGANISM: Lygus hesperus

<400> SEQUENCE: 173

```
tcagcgagat ccctaagaca acgcctgcca cgtgggagaa tatcggacac gcctccccag     60

agtgcggaaa ggggaacggc gttccgtatc ggtcaaggtg caagcttcgg aaccggagga    120

cgaccgttgc aaggtgcaag gggcaggtat cttgtatttt cattgtgcgt gtcgacatct    180

accaaactga gacttggagt tcgatatttt gacgatgggg ccgggggccg gaggcaaaac    240

gacaaacaca ggcaccgtga ccgtgttccg gtccctggcc tgcgttgcct tacgttcaca    300

tcttgttctt gcgctttctc tggttttacg ataaccctac tacgagttta gtagagccga    360

tcccgtagcc gaagccaaag cccaagcgct ccgtatccga gaacgcggaa gagcacgaac    420

tccccaaacc cctccgcccc tcccccgcgc gtatccgaaa cacaaatgca gcgggcagta    480

caggttttgg aaggggacgc gggcagtgag cgcaatgcaa gtaaatgtga ttagctcatg    540

gctacgcagc cctgcttttt cagtttcggt tcggatcgtt agggggtgtg ggattgggag    600

cggattcaat ctggacagga aacagctatg accaaggtca cgccaagctc tgaattaacc    660

ctcaggaaag ggactagtcc ggcaggttga aacgaactcg cccctaagca gtggtatcag    720

agcacagtgg tttttttttt ttgttttttt tcgtagaaaa aaatatgtat taagtcaatt    780

aattaaatca ttggttttct ggcttcacaa caggtggcac gtgctgtgct cggagaaatt    840

tatgaactat gttctgttct tcaatgagga aagatgagat gatccattct cagacacatt    900

cagacagagg acaccaccgt aagccctatc cacagtctgt ccacgtaagg ggatcgtgtc    960

cccttccatg ggcagagcag ggagagggcc gtaagcttgt tcttgcgtca tcaacatgtg   1020

ggg                                                                 1023
```

<210> SEQ ID NO 174
<211> LENGTH: 454
<212> TYPE: DNA
<213> ORGANISM: leptinotarsa decemlineata

<400> SEQUENCE: 174

```
ccaagaaggc caagaagggg tttatgaccc ctgagaggaa gaagaaactt aggttattgc     60

tgagaaagaa agcagcagaa gaactgaaaa aagaacaaga acgcaaagct gccgaaagga    120

gacgtattat tgaagagaga tgcggaaaac caaaactcat tgatgaggca aatgaagagc    180

aggtgaggaa ctattgcaag ttatatcacg gtagaatagc taaactggag gaccagaaat    240

ttgatttgga ataccttgtc aaaaagaaag acatggagat cgccgaattg aacagtcaag    300

tcaacgacct caggggtaaa ttcgtcaaac ccactctcaa gaaagtatcc aaatacgaga    360

acaaatttgc taaactccaa aagaaagcag cagaattcaa tttccgtaat caactgaaag    420

ttgtaaagaa gaaggagttc accctggagg agga                               454
```

<210> SEQ ID NO 175
<211> LENGTH: 431
<212> TYPE: DNA
<213> ORGANISM: leptinotarsa decemlineata

<400> SEQUENCE: 175

```
ggtttatgac ccctgagagg aagaagaaac ttaggttatt gctgagaaag aaagcagcag     60

aagaactgaa aaaagaacaa gaacgcaaag ctgccgaaag gagacgtatt attgaagaga    120

gatgcggaaa accaaaactc attgatgagg caaatgaaga gcaggtgagg aactattgca    180

agttatatca cggtagaata gctaaactgg aggaccagaa atttgatttg gaataccttg    240

tcaaaaagaa agacatggag atcgccgaat tgaacagtca agtcaacgac ctcaggggta    300

aattcgtcaa acccactctc aagaaagtat ccaaatacga gaacaaattt gctaaactcc    360

aaaagaaagc agcagaattc aatttccgta atcaactgaa agttgtaaag aagaaggagt    420

tcaccctgga g                                                          431
```

<210> SEQ ID NO 176
<211> LENGTH: 888
<212> TYPE: DNA
<213> ORGANISM: leptinotarsa decemlineata

<400> SEQUENCE: 176

```
agcagtggta tcaacgcaga gtacgcgggg acatcgagga gaagaggcaa cgcctcgaag     60

aggctgaaaa gaaacgccag gccatgatgc aggccctcaa ggaccagaac aagaacaagg    120

ggcccaactt caccatcacc aagagggatg cttcatctaa cctttctgcc gctcagttgg    180

aacgcaacaa gaccaaggag caactcgagg aagagaagaa aatttccctt tccatccgca    240

tcaagccctt ggtcgttgat ggtctgggcg tagataaact ccgtctgaaa gcacaagaac    300

tttgggaatg catcgtcaag ttggagactg aaaagtacga cttggaagag aggcagaaac    360

gtcaagacta cgatctcaaa gagctgaaag aaagacagaa acaacagctg agacacaaag    420

ccttgaagaa gggtctagac ccagaagccc taaccggcaa atacccgcct aaaatccaag    480

tagcctccaa atatgaacgt cgtgttgaca cgaggtcgta tggagacaaa aagaagctat    540

tcgaaggggg attagaagaa atcattaaag agaccaatga aaagagctgg aaagagaaat    600

ttggacagtt cgattccaga caaaaggcaa gacttcccaa gtggttcggt gaacgtcctg    660

gcaaaaaacc tggagatccc gaaactccag aaggcgagga ggagggcaaa caagtcattg    720

atgaggatga cgacctcaag gagcctgtaa tcgaagctga aattgaagaa gaggaggaag    780

aagaggaagt cgaggtcgat gaagaagaag aggatgacga agaagaagaa gaagaagagt    840

gaatgccaaa ggcagaagat aatcatgaaa tcaacattag ataacgtc                  888
```

<210> SEQ ID NO 177
<211> LENGTH: 404
<212> TYPE: DNA
<213> ORGANISM: leptinotarsa decemlineata

<400> SEQUENCE: 177

```
caaggaccag aacaagaaca aggggcccaa cttcaccatc accaagaggg atgcttcatc     60

taacctttct gccgctcagt tggaacgcaa caagaccaag gagcaactcg aggaagagaa    120

gaaaatttcc ctttccatcc gcatcaagcc cttggtcgtt gatggtctgg gcgtagataa    180

actccgtctg aaagcacaag aactttggga atgcatcgtc aagttggaga ctgaaaagta    240

cgacttggaa gagaggcaga aacgtcaaga ctacgatctc aaagagctga aagaaagaca    300
```

```
gaaacaacag ctgagacaca aagccttgaa gaagggtcta gacccagaag ccctaaccgg    360

caaatacccg cctaaaatcc aagtagcctc caaatatgaa cgtc                     404
```

<210> SEQ ID NO 178
<211> LENGTH: 1155
<212> TYPE: DNA
<213> ORGANISM: leptinotarsa decemlineata

<400> SEQUENCE: 178

```
gctcttcaga atgaacttga agaatctcgt acactgttgg aacaagctga ccgtgcccgt     60

cgccaagcag aacaagaatt gggagatgct cacgaacaat tgaatgatct tggtgcacag    120

aatggttctc tgtctgccgc caagaggaaa ctggaaactg aactccaaac tctccattcc    180

gatcttgatg aacttctcaa tgaagccaag aactctgagg agaaggctaa gaaagccatg    240

gtcgatgcag ctcgtcttgc agatgaactg agagcagaac aagatcatgc acaaactcag    300

gagaaacttc gtaaagcctt agaatcacaa atcaaggacc ttcaagttcg tctcgacgag    360

gctgaagcta acgccctcaa aggaggtaag aaagcaatcg ctaaacttga acaacgcgtc    420

agggaattgg agaatgagtt agatggtgaa caaagacgac acgccgatgc tcaaaagaat    480

ttgagaaagt ccgaacgtcg catcaaggag ctcagcctcc aagctgaaga agaccgtaag    540

aaccacgaaa aaatgcaaga cttagtcgac aaacttcaac agaaaatcaa gacccacaag    600

aggcaaatag aagaagctga agaaatagcg gctctcaatt tggccaaatt ccgtaaagca    660

caacaggaat tggaagaagc agaagagcgt gcagaccttg ctgaacaagc aattgtcaaa    720

ttccgtacca agggacgttc tggatcagca gctaggggag ccagccctgc gcctcagcga    780

cagcgtccca cattcggaat gggagattca cttggaggtg ccttccctcc aaggttcgat    840

cttgcacccg actttgaatg aatctgacat tgtgttataa gtgtaaggtg aacattctat    900

cgcagtgtaa atatcatccc aatgcgaatc aattctacat tcagtttaag tcattctatc    960

tctcaaaata ataatagtgt catccattct cactatcaaa tcaagacaag agatgatgat   1020

cagagaacac gtatcacatc tacagcaaac cctcagtcct cggcatctct gataatattt   1080

tcaattatcg agattgatga tatcgggtgt tgaatgctga tgaatagaag gcgccctatg   1140

gaaataagag agaag                                                    1155
```

<210> SEQ ID NO 179
<211> LENGTH: 523
<212> TYPE: DNA
<213> ORGANISM: leptinotarsa decemlineata

<400> SEQUENCE: 179

```
gaatctcgta cactgttgga acaagctgac cgtgcccgtc gccaagcaga acaagaattg     60

ggagatgctc acgaacaatt gaatgatctt ggtgcacaga atggttctct gtctgccgcc    120

aagaggaaac tggaaactga actccaaact ctccattccg atcttgatga acttctcaat    180

gaagccaaga actctgagga gaaggctaag aaagccatgg tcgatgcagc tcgtcttgca    240

gatgaactga gagcagaaca agatcatgca caaactcagg agaaacttcg taaagcctta    300

gaatcacaaa tcaaggacct tcaagttcgt ctcgacgagg ctgaagctaa cgccctcaaa    360

ggaggtaaga aagcaatcgc taaacttgaa caacgcgtca gggaattgga gaatgagtta    420

gatggtgaac aaagacgaca cgccgatgct caaaagaatt tgagaaagtc cgaacgtcgc    480

atcaaggagc tcagcctcca agctgaagaa gaccgtaaga acc                      523
```

<210> SEQ ID NO 180
<211> LENGTH: 865
<212> TYPE: DNA
<213> ORGANISM: nilaparvata lugens

<400> SEQUENCE: 180

```
ctaggagtat ctcctacgta attcggtgct tgagccaact gcagctactc actttttttcc     60

aggttcagtg gtagggacgc aaacacagct aaaatggcgg acgatgaggc aaagaaggca    120

aagcaggcgg aaatcgaccg caagagagcc gaggtccgca agcggatgga ggaagcctcc    180

aaggccaaga aggccaagaa aggtttcatg acgcctgaca gaaagaagaa gctcaggttg    240

ttgctgagga aaaaggctgc tgaggaattg aagaaggaac aggagaggaa agccgcggaa    300

aggagaagga tcatcgagga gaggtgtggc aaggctgttg atctcgatga cggaagtgaa    360

gagaaagtca aggcaacttt aaaaacctat cacgacagaa ttggaaaatt ggaggatgaa    420

aaatttgacc tggaatatat tgtaaaaaag aaagacttcg agatcgctga cctcaacagc    480

caggtgaatg acctccgtgg taaatttgtc aagccaacct tgaaaaaagt ctccaaatat    540

gagaacaaat tcgccaagct ccagaagaaa gcagctgaat tcaatttcag aaatcagctc    600

aaagttgtca agaagaagga attcaccttg gaagaagaag acaaggagcc gaagaaatcg    660

gagaaagccg aatggcagaa gaaatgaact cacatcacct cttcataata ttgtcccaca    720

cttctacaac cttcatcaaa taacttttat tcgagtaaac ttactgttac taacaaaatt    780

acaaaaccaa actcttatca tcaacgtagg caatgtgctc aacttatttc ttaaacatat    840

tgtccagcta tttattgaaa ttaaa                                          865
```

<210> SEQ ID NO 181
<211> LENGTH: 269
<212> TYPE: DNA
<213> ORGANISM: nilaparvata lugens

<400> SEQUENCE: 181

```
aagaagaagc tcaggttgtt gctgaggaaa aaggctgctg aggaattgaa gaaggaacag     60

gagaggaaag ccgcggaaag gagaaggatc atcgaggaga ggtgtggcaa ggctgttgat    120

ctcgatgacg gaagtgaaga gaaagtcaag gcaactttaa aaacctatca cgacagaatt    180

ggaaaattgg aggatgaaaa atttgacctg gaatatattg taaaaaagaa agacttcgag    240

atcgctgacc tcaacagcca ggtgaatga                                      269
```

<210> SEQ ID NO 182
<211> LENGTH: 553
<212> TYPE: DNA
<213> ORGANISM: nilaparvata lugens

<400> SEQUENCE: 182

```
aatgatggcg gctctcaagg accagagcaa atcgaaagga cccaacttca ccgtaaacaa     60

gaaaacagac ttgaacatga cgtcagctca aatggaaagg aacaagacta aggagcagct    120

ggaggaggag aagaagatct ctctgtcgtt ccgcatcaag ccgttggcca tcgagaacat    180

gagcatcaac gcactgcgcg ccaaggccca ggaactgtgg gactgcatcg tcaagctcga    240

aactgagaag tacgatctgg aggaacgcca gaagaggcag gactacgatc tcaaagaatt    300

gaaagaaaga caaaagcaac agctgaggca taaagccctc aaaaaaggtc tagaccctga    360

ggctctcaca ggaaagtacc caccaaaaat ccaagttgcc tccaaatatg aaagacgtgt    420

agatacaagg tcatacgacg acaagaagaa gctcttcgaa ggtggctggg acacattaac    480
```

```
atcagaaacc aatgagaaaa tatggaagag cagaaacgat cagttttcaa atcgtagcaa    540

ggctaaactg cca                                                       553


<210> SEQ ID NO 183
<211> LENGTH: 470
<212> TYPE: DNA
<213> ORGANISM: nilaparvata lugens

<400> SEQUENCE: 183

atgatggcgg ctctcaagga ccagagcaaa tcgaaaggac ccaacttcac cgtaaacaag     60

aaaacagact tgaacatgac gtcagctcaa atggaaagga acaagactaa ggagcagctg    120

gaggaggaga agaagatctc tctgtcgttc cgcatcaagc cgttggccat cgagaacatg    180

agcatcaacg cactgcgcgc caaggcccag gaactgtggg actgcatcgt caagctcgaa    240

actgagaagt acgatctgga ggaacgccag aagaggcagg actacgatct caaagaattg    300

aaagaaagac aaaagcaaca gctgaggcat aaagccctca aaaaaggtct agaccctgag    360

gctctcacag gaaagtaccc accaaaaatc caagttgcct ccaaatatga aagacgtgta    420

gatacaaggt catacgacga caagaagaag ctcttcgaag gtggctggga               470


<210> SEQ ID NO 184
<211> LENGTH: 367
<212> TYPE: DNA
<213> ORGANISM: nilaparvata lugens

<400> SEQUENCE: 184

tgccttcgac cgtgaaaggt ctggaagtat cccaacagac atggtcgccg acatcctcag     60

gctcatggga cagcctttca acaagaagat cctcgacgaa ctcattgagg aagttgatgc    120

tgacaaatct ggccgtcttg agtttgacga attcgtgact ctggccgcca aattcattgt    180

tgaggaagac gatgaggcaa tgcagaagga attgaaggaa gctttcagat tatacgacaa    240

ggaaggtaac ggctacatcc ccacatcatg tctgaaggaa atcttaaggg aacttgacga    300

tcagctgaca aacgaggaac tcaacatgat gattgatgag atcgactctg acggatcagg    360

aactgtt                                                              367


<210> SEQ ID NO 185
<211> LENGTH: 204
<212> TYPE: DNA
<213> ORGANISM: nilaparvata lugens

<400> SEQUENCE: 185

acatcctcag gctcatggga cagcctttca acaagaagat cctcgacgaa cttattgagg     60

aggttgatgc tgacaagtct ggccgtctag agtttgacga attcgtgact ctggccgcca    120

aattcattgt tgaggaagac gatgaggcaa tgcagaagga attgaaggaa gctttcagat    180

tatacgacaa ggaaggtaac ggct                                           204


<210> SEQ ID NO 186
<211> LENGTH: 221
<212> TYPE: DNA
<213> ORGANISM: nilaparvata lugens

<400> SEQUENCE: 186

cgtaaaaact ctgaccggca agaccatcac cttggaagtg gagccttccg ataccattga     60

aaacgtgaag gccaagatcc aagacaagga gggaattcct cccgaccagc agagacttat    120
```

```
cttcgctgga aagcaactgg aggatggcag aaccctgtcc gactacaaca tccaaaaaga    180

atctacactc cacttggttc tcagacttcg tggtggaact a                        221


<210> SEQ ID NO 187
<211> LENGTH: 221
<212> TYPE: DNA
<213> ORGANISM: nilaparvata lugens

<400> SEQUENCE: 187

cgtaaaaact ctgaccggca agaccatcac cttggaagtg gagccttccg ataccattga     60

aaacgtgaag gccaagatcc aagacaagga gggaattcct cccgaccagc agagacttat    120

cttcgctgga aagcaactgg aggatggcag aaccctgtcc gactacaaca tccaaaaaga    180

atctacactc cacttggttc tcagacttcg tggtggaact a                        221


<210> SEQ ID NO 188
<211> LENGTH: 759
<212> TYPE: DNA
<213> ORGANISM: Acyrthosiphon pisum

<400> SEQUENCE: 188

atggccgacg atgaagctaa gaaagcaaaa caggcggaaa tcgaccgcaa gagggccgaa     60

gtgcgcaagc gtatggaaga ggcgtccaag gccaagaagg ccaagaaggg tttcatgacc    120

ccagacagaa agaagaaact ccgtctgttg ttgaaaaaaa aggcggccga agagttgaag    180

aaagaacaag aacgcaaagc tgccgaacga aggcggatca tcgaagagcg gtgcggacaa    240

ccgaagaaca tcgacgacgc cggcgaagag gagcttgcgg aaatctgcga agaactatgg    300

aaacgggttt acaccgtaga gggcataaaa tttgacttgg aaagggatat caggatgaaa    360

gttttcgaga tcagcgaatt gaacagccaa gtcaatgact tacgaggaaa attcgtcaaa    420

ccaacattga agaaggtttc caaatacgaa aacaaattcg caaaactcca aaagaaagcg    480

gcggagttca acttcagaaa ccaactgaaa gtagtgaaga aaaaggagtt caccttggaa    540

gaagaagaca aagagaaaaa acccgattgg tccaaaaagg gagacgaaaa gaagggcgaa    600

ggagaagacg gcgacggtac cgaagacgaa aagaccgacg acggtttgac caccgaaggc    660

gaatcggtcg cgggcgatct aacggacgcg acggaagacg cgcagagcga caacgagata    720

ctcgaaccag aacccgtggt tgaacccgaa ccagaacca                           759


<210> SEQ ID NO 189
<211> LENGTH: 759
<212> TYPE: DNA
<213> ORGANISM: Acyrthosiphon pisum

<400> SEQUENCE: 189

atggccgacg atgaagctaa gaaagcaaaa caggcggaaa tcgaccgcaa gagggccgaa     60

gtgcgcaagc gtatggaaga ggcgtccaag gccaagaagg ccaagaaggg tttcatgacc    120

ccagacagaa agaagaaact ccgtctgttg ttgaaaaaaa aggcggccga agagttgaag    180

aaagaacaag aacgcaaagc tgccgaacga aggcggatca tcgaagagcg gtgcggacaa    240

ccgaagaaca tcgacgacgc cggcgaagag gagcttgcgg aaatctgcga agaactatgg    300

aaacgggttt acaccgtaga gggcataaaa tttgacttgg aaagggatat caggatgaaa    360

gttttcgaga tcagcgaatt gaacagccaa gtcaatgact tacgaggaaa attcgtcaaa    420

ccaacattga agaaggtttc caaatacgaa aacaaattcg caaaactcca aaagaaagcg    480

gcggagttca acttcagaaa ccaactgaaa gtagtgaaga aaaaggagtt caccttggaa    540
```

gaagaagaca aagagaaaaa acccgattgg tccaaaaagg gagacgaaaa gaagggcgaa 600
ggagaagacg gcgacggtac cgaagacgaa aagaccgacg acggtttgac caccgaaggc 660
gaatcggtcg cgggcgatct aacggacgcg acggaagacg cgcagagcga caacgagata 720
ctcgaaccag aacccgtggt tgaacccgaa ccagaacca 759

<210> SEQ ID NO 190
<211> LENGTH: 759
<212> TYPE: DNA
<213> ORGANISM: Acyrthosiphon pisum

<400> SEQUENCE: 190
atggccgacg atgaagctaa gaaagcaaaa caggcggaaa tcgaccgcaa gagggccgaa 60
gtgcgcaagc gtatggaaga ggcgtccaag gccaagaagg ccaagaaggg tttcatgacc 120
ccagacagaa agaagaaact ccgtctgttg ttgaaaaaaa aggcggccga agagttgaag 180
aaagaacaag aacgcaaagc tgccgaacga aggcggatca tcgaagagcg gtgcggacaa 240
ccgaagaaca tcgacgacgc cggcgaagag gagcttgcgg aaatctgcga agaactatgg 300
aaacgggttt acaccgtaga gggcataaaa tttgacttgg aaagggatat caggatgaaa 360
gttttcgaga tcagcgaatt gaacagccaa gtcaatgact tacgaggaaa attcgtcaaa 420
ccaacattga agaaggtttc caaatacgaa aacaaattcg caaaactcca aaagaaagcg 480
gcggagttca acttcagaaa ccaactgaaa gtagtgaaga aaaaggagtt caccttggaa 540
gaagaagaca aagagaaaaa acccgattgg tccaaaaagg gagacgaaaa gaagggcgaa 600
ggagaagacg gcgacggtac cgaagacgaa aagaccgacg acggtttgac caccgaaggc 660
gaatcggtcg cgggcgatct aacggacgcg acggaagacg cgcagagcga caacgagata 720
ctcgaaccag aacccgtggt tgaacccgaa ccagaacca 759

<210> SEQ ID NO 191
<211> LENGTH: 759
<212> TYPE: DNA
<213> ORGANISM: Acyrthosiphon pisum

<400> SEQUENCE: 191
atggccgacg atgaagctaa gaaagcaaaa caggcggaaa tcgaccgcaa gagggccgaa 60
gtgcgcaagc gtatggaaga ggcgtccaag gccaagaagg ccaagaaggg tttcatgacc 120
ccagacagaa agaagaaact ccgtctgttg ttgaaaaaaa aggcggccga agagttgaag 180
aaagaacaag aacgcaaagc tgccgaacga aggcggatca tcgaagagcg gtgcggacaa 240
ccgaagaaca tcgacgacgc cggcgaagag gagcttgcgg aaatctgcga agaactatgg 300
aaacgggttt acaccgtaga gggcataaaa tttgacttgg aaagggatat caggatgaaa 360
gttttcgaga tcagcgaatt gaacagccaa gtcaatgact tacgaggaaa attcgtcaaa 420
ccaacattga agaaggtttc caaatacgaa aacaaattcg caaaactcca aaagaaagcg 480
gcggagttca acttcagaaa ccaactgaaa gtagtgaaga aaaaggagtt caccttggaa 540
gaagaagaca aagagaaaaa acccgattgg tccaaaaagg gagacgaaaa gaagggcgaa 600
ggagaagacg gcgacggtac cgaagacgaa aagaccgacg acggtttgac caccgaaggc 660
gaatcggtcg cgggcgatct aacggacgcg acggaagacg cgcagagcga caacgagata 720
ctcgaaccag aacccgtggt tgaacccgaa ccagaacca 759

<210> SEQ ID NO 192

<211> LENGTH: 759
<212> TYPE: DNA
<213> ORGANISM: Acyrthosiphon pisum

<400> SEQUENCE: 192
atggccgacg atgaagctaa gaaagcaaaa caggcggaaa tcgaccgcaa gagggccgaa 60
gtgcgcaagc gtatggaaga ggcgtccaag gccaagaagg ccaagaaggg tttcatgacc 120
ccagacagaa agaagaaact ccgtctgttg ttgaaaaaaa aggcggccga agagttgaag 180
aaagaacaag aacgcaaagc tgccgaacga aggcggatca tcgaagagcg gtgcggacaa 240
ccgaagaaca tcgacgacgc cggcgaagag gagcttgcgg aaatctgcga agaactatgg 300
aaacgggttt acaccgtaga gggcataaaa tttgacttgg aaagggatat caggatgaaa 360
gttttcgaga tcagcgaatt gaacagccaa gtcaatgact tacgaggaaa attcgtcaaa 420
ccaacattga agaaggtttc caaatacgaa aacaaattcg caaaactcca aaagaaagcg 480
gcggagttca acttcagaaa ccaactgaaa gtagtgaaga aaaaggagtt caccttggaa 540
gaagaagaca aagagaaaaa acccgattgg tccaaaaagg gagacgaaaa gaagggcgaa 600
ggagaagacg gcgacggtac cgaagacgaa aagaccgacg acggtttgac caccgaaggc 660
gaatcggtcg cgggcgatct aacggacgcg acggaagacg cgcagagcga caacgagata 720
ctcgaaccag aacccgtggt tgaacccgaa ccagaacca 759

<210> SEQ ID NO 193
<211> LENGTH: 759
<212> TYPE: DNA
<213> ORGANISM: Acyrthosiphon pisum

<400> SEQUENCE: 193
atggccgacg atgaagctaa gaaagcaaaa caggcggaaa tcgaccgcaa gagggccgaa 60
gtgcgcaagc gtatggaaga ggcgtccaag gccaagaagg ccaagaaggg tttcatgacc 120
ccagacagaa agaagaaact ccgtctgttg ttgaaaaaaa aggcggccga agagttgaag 180
aaagaacaag aacgcaaagc tgccgaacga aggcggatca tcgaagagcg gtgcggacaa 240
ccgaagaaca tcgacgacgc cggcgaagag gagcttgcgg aaatctgcga agaactatgg 300
aaacgggttt acaccgtaga gggcataaaa tttgacttgg aaagggatat caggatgaaa 360
gttttcgaga tcagcgaatt gaacagccaa gtcaatgact tacgaggaaa attcgtcaaa 420
ccaacattga agaaggtttc caaatacgaa aacaaattcg caaaactcca aaagaaagcg 480
gcggagttca acttcagaaa ccaactgaaa gtagtgaaga aaaaggagtt caccttggaa 540
gaagaagaca aagagaaaaa acccgattgg tccaaaaagg gagacgaaaa gaagggcgaa 600
ggagaagacg gcgacggtac cgaagacgaa aagaccgacg acggtttgac caccgaaggc 660
gaatcggtcg cgggcgatct aacggacgcg acggaagacg cgcagagcga caacgagata 720
ctcgaaccag aacccgtggt tgaacccgaa ccagaacca 759

<210> SEQ ID NO 194
<211> LENGTH: 759
<212> TYPE: DNA
<213> ORGANISM: Acyrthosiphon pisum

<400> SEQUENCE: 194
atggccgacg atgaagctaa gaaagcaaaa caggcggaaa tcgaccgcaa gagggccgaa 60
gtgcgcaagc gtatggaaga ggcgtccaag gccaagaagg ccaagaaggg tttcatgacc 120
ccagacagaa agaagaaact ccgtctgttg ttgaaaaaaa aggcggccga agagttgaag 180

```
aaagaacaag aacgcaaagc tgccgaacga aggcggatca tcgaagagcg gtgcggacaa    240

ccgaagaaca tcgacgacgc cggcgaagag gagcttgcgg aaatctgcga agaactatgg    300

aaacgggttt acaccgtaga gggcataaaa tttgacttgg aaagggatat caggatgaaa    360

gttttcgaga tcagcgaatt gaacagccaa gtcaatgact tacgaggaaa attcgtcaaa    420

ccaacattga agaaggtttc caaatacgaa aacaaattcg caaaactcca aaagaaagcg    480

gcggagttca acttcagaaa ccaactgaaa gtagtgaaga aaaaggagtt caccttggaa    540

gaagaagaca aagagaaaaa acccgattgg tccaaaaagg gagacgaaaa gaagggcgaa    600

ggagaagacg gcgacggtac cgaagacgaa aagaccgacg acggtttgac caccgaaggc    660

gaatcggtcg cgggcgatct aacggacgcg acggaagacg cgcagagcga caacgagata    720

ctcgaaccag aacccgtggt tgaacccgaa ccagaacca                           759
```

```
<210> SEQ ID NO 195
<211> LENGTH: 759
<212> TYPE: DNA
<213> ORGANISM: Acyrthosiphon pisum

<400> SEQUENCE: 195

atggccgacg atgaagctaa gaaagcaaaa caggcggaaa tcgaccgcaa gagggccgaa     60

gtgcgcaagc gtatggaaga ggcgtccaag gccaagaagg ccaagaaggg tttcatgacc    120

ccagacagaa agaagaaact ccgtctgttg ttgaaaaaaa aggcggccga agagttgaag    180

aaagaacaag aacgcaaagc tgccgaacga aggcggatca tcgaagagcg gtgcggacaa    240

ccgaagaaca tcgacgacgc cggcgaagag gagcttgcgg aaatctgcga agaactatgg    300

aaacgggttt acaccgtaga gggcataaaa tttgacttgg aaagggatat caggatgaaa    360

gttttcgaga tcagcgaatt gaacagccaa gtcaatgact tacgaggaaa attcgtcaaa    420

ccaacattga agaaggtttc caaatacgaa aacaaattcg caaaactcca aaagaaagcg    480

gcggagttca acttcagaaa ccaactgaaa gtagtgaaga aaaaggagtt caccttggaa    540

gaagaagaca aagagaaaaa acccgattgg tccaaaaagg gagacgaaaa gaagggcgaa    600

ggagaagacg gcgacggtac cgaagacgaa aagaccgacg acggtttgac caccgaaggc    660

gaatcggtcg cgggcgatct aacggacgcg acggaagacg cgcagagcga caacgagata    720

ctcgaaccag aacccgtggt tgaacccgaa ccagaacca                           759
```

```
<210> SEQ ID NO 196
<211> LENGTH: 759
<212> TYPE: DNA
<213> ORGANISM: Acyrthosiphon pisum

<400> SEQUENCE: 196

atggccgacg atgaagctaa gaaagcaaaa caggcggaaa tcgaccgcaa gagggccgaa     60

gtgcgcaagc gtatggaaga ggcgtccaag gccaagaagg ccaagaaggg tttcatgacc    120

ccagacagaa agaagaaact ccgtctgttg ttgaaaaaaa aggcggccga agagttgaag    180

aaagaacaag aacgcaaagc tgccgaacga aggcggatca tcgaagagcg gtgcggacaa    240

ccgaagaaca tcgacgacgc cggcgaagag gagcttgcgg aaatctgcga agaactatgg    300

aaacgggttt acaccgtaga gggcataaaa tttgacttgg aaagggatat caggatgaaa    360

gttttcgaga tcagcgaatt gaacagccaa gtcaatgact tacgaggaaa attcgtcaaa    420

ccaacattga agaaggtttc caaatacgaa aacaaattcg caaaactcca aaagaaagcg    480
```

```
gcggagttca acttcagaaa ccaactgaaa gtagtgaaga aaaaggagtt caccttggaa    540

gaagaagaca aagagaaaaa acccgattgg tccaaaaagg gagacgaaaa gaagggcgaa    600

ggagaagacg gcgacggtac cgaagacgaa aagaccgacg acggtttgac caccgaaggc    660

gaatcggtcg cgggcgatct aacggacgcg acggaagacg cgcagagcga caacgagata    720

ctcgaaccag aacccgtggt tgaacccgaa ccagaacca                           759
```

<210> SEQ ID NO 197
<211> LENGTH: 759
<212> TYPE: DNA
<213> ORGANISM: Acyrthosiphon pisum

<400> SEQUENCE: 197

```
atggccgacg atgaagctaa gaaagcaaaa caggcggaaa tcgaccgcaa gagggccgaa     60

gtgcgcaagc gtatggaaga ggcgtccaag gccaagaagg ccaagaaggg tttcatgacc    120

ccagacagaa agaagaaact ccgtctgttg ttgaaaaaaa aggcggccga agagttgaag    180

aaagaacaag aacgcaaagc tgccgaacga aggcggatca tcgaagagcg gtgcggacaa    240

ccgaagaaca tcgacgacgc cggcgaagag gagcttgcgg aaatctgcga agaactatgg    300

aaacgggttt acaccgtaga gggcataaaa tttgacttgg aaagggatat caggatgaaa    360

gttttcgaga tcagcgaatt gaacagccaa gtcaatgact tacgaggaaa attcgtcaaa    420

ccaacattga agaaggtttc caaatacgaa aacaaattcg caaaactcca aaagaaagcg    480

gcggagttca acttcagaaa ccaactgaaa gtagtgaaga aaaaggagtt caccttggaa    540

gaagaagaca aagagaaaaa acccgattgg tccaaaaagg gagacgaaaa gaagggcgaa    600

ggagaagacg gcgacggtac cgaagacgaa aagaccgacg acggtttgac caccgaaggc    660

gaatcggtcg cgggcgatct aacggacgcg acggaagacg cgcagagcga caacgagata    720

ctcgaaccag aacccgtggt tgaacccgaa ccagaacca                           759
```

<210> SEQ ID NO 198
<211> LENGTH: 759
<212> TYPE: DNA
<213> ORGANISM: Acyrthosiphon pisum

<400> SEQUENCE: 198

```
atggccgacg atgaagctaa gaaagcaaaa caggcggaaa tcgaccgcaa gagggccgaa     60

gtgcgcaagc gtatggaaga ggcgtccaag gccaagaagg ccaagaaggg tttcatgacc    120

ccagacagaa agaagaaact ccgtctgttg ttgaaaaaaa aggcggccga agagttgaag    180

aaagaacaag aacgcaaagc tgccgaacga aggcggatca tcgaagagcg gtgcggacaa    240

ccgaagaaca tcgacgacgc cggcgaagag gagcttgcgg aaatctgcga agaactatgg    300

aaacgggttt acaccgtaga gggcataaaa tttgacttgg aaagggatat caggatgaaa    360

gttttcgaga tcagcgaatt gaacagccaa gtcaatgact tacgaggaaa attcgtcaaa    420

ccaacattga agaaggtttc caaatacgaa aacaaattcg caaaactcca aaagaaagcg    480

gcggagttca acttcagaaa ccaactgaaa gtagtgaaga aaaaggagtt caccttggaa    540

gaagaagaca aagagaaaaa acccgattgg tccaaaaagg gagacgaaaa gaagggcgaa    600

ggagaagacg gcgacggtac cgaagacgaa aagaccgacg acggtttgac caccgaaggc    660

gaatcggtcg cgggcgatct aacggacgcg acggaagacg cgcagagcga caacgagata    720

ctcgaaccag aacccgtggt tgaacccgaa ccagaacca                           759
```

<210> SEQ ID NO 199
<211> LENGTH: 759
<212> TYPE: DNA
<213> ORGANISM: Acyrthosiphon pisum

<400> SEQUENCE: 199

```
atggccgacg atgaagctaa gaaagcaaaa caggcggaaa tcgaccgcaa gagggccgaa     60

gtgcgcaagc gtatggaaga ggcgtccaag gccaagaagg ccaagaaggg tttcatgacc    120

ccagacagaa agaagaaact ccgtctgttg ttgaaaaaaa aggcggccga agagttgaag    180

aaagaacaag aacgcaaagc tgccgaacga aggcggatca tcgaagagcg gtgcggacaa    240

ccgaagaaca tcgacgacgc cggcgaagag gagcttgcgg aaatctgcga agaactatgg    300

aaacgggttt acaccgtaga gggcataaaa tttgacttgg aaagggatat caggatgaaa    360

gttttcgaga tcagcgaatt gaacagccaa gtcaatgact tacgaggaaa attcgtcaaa    420

ccaacattga agaaggtttc caaatacgaa aacaaattcg caaaactcca aaagaaagcg    480

gcggagttca acttcagaaa ccaactgaaa gtagtgaaga aaaaggagtt caccttggaa    540

gaagaagaca aagagaaaaa acccgattgg tccaaaaagg gagacgaaaa gaagggcgaa    600

ggagaagacg gcgacggtac cgaagacgaa aagaccgacg acggtttgac caccgaaggc    660

gaatcggtcg cgggcgatct aacggacgcg acggaagacg cgcagagcga caacgagata    720

ctcgaaccag aacccgtggt tgaacccgaa ccagaacca                           759
```

<210> SEQ ID NO 200
<211> LENGTH: 541
<212> TYPE: DNA
<213> ORGANISM: Acyrthosiphon pisum

<400> SEQUENCE: 200

```
cggtaatgcg atgcggtaag aagaaggtat ggttggatcc aaacgaaata aatgaaattg     60

ccaacaccaa ttccagacaa aatattcgta agttgatcaa agatggtttg atcattaaaa    120

agccagtagc tgtacactct agggctcgtg cacgtaaaaa tgcagatgcc agaagaaaag    180

gtcgtcattg tggttttggt aaaaggaagg gtactgctaa tgctcgaaca cctcaaaaag    240

acctttgggt gaaaagaatg cgagtattaa ggcggttgct taaaaaatac cgtgaagcaa    300

agaaaattga caaccatctt taccatcagt tatacatgaa ggctaagggt aatgttttca    360

agaacaaacg tgtattgatg gagttcatcc acaaaaagaa ggcagagaag gcccgtgcca    420

agatgttgag tgatcaagct gaagctagac gtcaaaaggt taaggaagct aggaaacgta    480

aagaagcaag atttttacaa aataggaagg aacttttggc tgcatacgcc cgagaagatg    540

a                                                                    541
```

<210> SEQ ID NO 201
<211> LENGTH: 541
<212> TYPE: DNA
<213> ORGANISM: Acyrthosiphon pisum

<400> SEQUENCE: 201

```
cggtaatgcg atgcggtaag aagaaggtat ggttggatcc aaacgaaata aatgaaattg     60

ccaacaccaa ttccagacaa aatattcgta agttgatcaa agatggtttg atcattaaaa    120

agccagtagc tgtacactct agggctcgtg cacgtaaaaa tgcagatgcc agaagaaaag    180

gtcgtcattg tggttttggt aaaaggaagg gtactgctaa tgctcgaaca cctcaaaaag    240

acctttgggt gaaaagaatg cgagtattaa ggcggttgct taaaaaatac cgtgaagcaa    300
```

```
agaaaattga caaccatctt taccatcagt tatacatgaa ggctaagggt aatgttttca    360

agaacaaacg tgtattgatg gagttcatcc acaaaaagaa ggcagagaag gcccgtgcca    420

agatgttgag tgatcaagct gaagctagac gtcaaaaggt taaggaagct aggaaacgta    480

aagaagcaag atttttacaa aataggaagg aacttttggc tgcatacgcc cgagaagatg    540

a                                                                    541
```

<210> SEQ ID NO 202
<211> LENGTH: 823
<212> TYPE: DNA
<213> ORGANISM: Acyrthosiphon pisum

<400> SEQUENCE: 202

```
gttgtagtcg gaaagggtac gtccgtcttc aagttgtttt ccggcaaaga tcaaacgttg     60

ttggtctggt gggatacctt ctttgtcttg gatcttggct tttacatttt caatggaatc    120

agatgattcc acctccaatg taatggtctt tccagtgagg gtctttacaa agatttgcat    180

accaccacgg agacgcaaca ctaagtgaag ggtagattct ttctggatgt tgtagtcaga    240

aagtgtgcgt ccgtcttcaa gttgctttcc ggcaaagatc aaacgttgtt ggtcaggtgg    300

aataccttct ttgtcttgga tcttagcttt tacattttca atggaatctg atgactcaac    360

ttccaatgta atggtctttc cagtgagggt ctttacaaag atttgcatac caccacggag    420

acgcaacact aagtgaaggg tagattcttt ctggatgttg tagtcggaaa gggtacgtcc    480

gtcttcaagt tgctttccgg caaagatcaa acgttgttgg tctggtggga taccttcttt    540

gtcttggatc ttggctttta cattttcaat ggaatcagat gattccacct ccaatgtaat    600

ggtctttcca gtgagggtct ttacaaagat ttgcatacca ccacggagac gcaacactaa    660

gtgaagggta gattctttct ggatgttgta gtcggaaagg gtacgtccgt cttcaagttg    720

ctttccagca aagatcaaac gttgctggtc tggtgggata ccttccttgt cttggatctt    780

ggccttaaca ttttcaatgg aatctgatga ctcaacttcc aaa                      823
```

<210> SEQ ID NO 203
<211> LENGTH: 823
<212> TYPE: DNA
<213> ORGANISM: Acyrthosiphon pisum

<400> SEQUENCE: 203

```
gttgtagtcg gaaagggtac gtccgtcttc aagttgtttt ccggcaaaga tcaaacgttg     60

ttggtctggt gggatacctt ctttgtcttg gatcttggct tttacatttt caatggaatc    120

agatgattcc acctccaatg taatggtctt tccagtgagg gtctttacaa agatttgcat    180

accaccacgg agacgcaaca ctaagtgaag ggtagattct ttctggatgt tgtagtcaga    240

aagtgtgcgt ccgtcttcaa gttgctttcc ggcaaagatc aaacgttgtt ggtcaggtgg    300

aataccttct ttgtcttgga tcttagcttt tacattttca atggaatctg atgactcaac    360

ttccaatgta atggtctttc cagtgagggt ctttacaaag atttgcatac caccacggag    420

acgcaacact aagtgaaggg tagattcttt ctggatgttg tagtcggaaa gggtacgtcc    480

gtcttcaagt tgctttccgg caaagatcaa acgttgttgg tctggtggga taccttcttt    540

gtcttggatc ttggctttta cattttcaat ggaatcagat gattccacct ccaatgtaat    600

ggtctttcca gtgagggtct ttacaaagat ttgcatacca ccacggagac gcaacactaa    660

gtgaagggta gattctttct ggatgttgta gtcggaaagg gtacgtccgt cttcaagttg    720

ctttccagca aagatcaaac gttgctggtc tggtgggata ccttccttgt cttggatctt    780
```

ggccttaaca ttttcaatgg aatctgatga ctcaacttcc aaa 823

<210> SEQ ID NO 204
<211> LENGTH: 172
<212> TYPE: DNA
<213> ORGANISM: Acyrthosiphon pisum

<400> SEQUENCE: 204
aagacttgct tcatcctact gcaattgaag aacgcaggaa acacaaatta aagcgccttg 60
ttcaacaccc aaactctttt ttcatggatg tcaaatgccc tggatgttat aaaattacaa 120
ctgtattcag tcacgctcag agtgtagtta tatgtaccgg atgttccaca at 172

<210> SEQ ID NO 205
<211> LENGTH: 172
<212> TYPE: DNA
<213> ORGANISM: Acyrthosiphon pisum

<400> SEQUENCE: 205
aagacttgct tcatcctact gcaattgaag aacgcaggaa acacaaatta aagcgccttg 60
ttcaacaccc aaactctttt ttcatggatg tcaaatgccc tggatgttat aaaattacaa 120
ctgtattcag tcacgctcag agtgtagtta tatgtaccgg atgttccaca at 172

<210> SEQ ID NO 206
<211> LENGTH: 25
<212> TYPE: DNA
<213> ORGANISM: Artificial
<220> FEATURE:
<223> OTHER INFORMATION: Primer

<400> SEQUENCE: 206
cgaaccatct gggaagcttg gaatg 25

<210> SEQ ID NO 207
<211> LENGTH: 25
<212> TYPE: DNA
<213> ORGANISM: Artificial
<220> FEATURE:
<223> OTHER INFORMATION: Primer

<400> SEQUENCE: 207
gcagctggag gaagagaaac gtatc 25

<210> SEQ ID NO 208
<211> LENGTH: 47
<212> TYPE: DNA
<213> ORGANISM: Artificial
<220> FEATURE:
<223> OTHER INFORMATION: Primer

<400> SEQUENCE: 208
gcgtaatacg actcactata ggcgaaccat ctgggaagct tggaatg 47

<210> SEQ ID NO 209
<211> LENGTH: 46
<212> TYPE: DNA
<213> ORGANISM: Artificial
<220> FEATURE:
<223> OTHER INFORMATION: Primer

<400> SEQUENCE: 209
gcgtaatacg actcactata ggcagctgga ggaagagaaa cgtatc 46

<210> SEQ ID NO 210
<211> LENGTH: 20
<212> TYPE: DNA
<213> ORGANISM: Artificial
<220> FEATURE:
<223> OTHER INFORMATION: Primer

<400> SEQUENCE: 210
agttcgagaa caccaggaag 20

<210> SEQ ID NO 211
<211> LENGTH: 22
<212> TYPE: DNA
<213> ORGANISM: Artificial
<220> FEATURE:
<223> OTHER INFORMATION: Primer

<400> SEQUENCE: 211
cctgacacgt tgttccagct tg 22

<210> SEQ ID NO 212
<211> LENGTH: 45
<212> TYPE: DNA
<213> ORGANISM: Artificial
<220> FEATURE:
<223> OTHER INFORMATION: Primer

<400> SEQUENCE: 212
gcgtaatacg actcactata ggaggagttc gagaacacca ggaag 45

<210> SEQ ID NO 213
<211> LENGTH: 44
<212> TYPE: DNA
<213> ORGANISM: Artificial
<220> FEATURE:
<223> OTHER INFORMATION: Primer

<400> SEQUENCE: 213
gcgtaatacg actcactata ggcctgacac gttgttccag cttg 44

<210> SEQ ID NO 214
<211> LENGTH: 20
<212> TYPE: DNA
<213> ORGANISM: Artificial
<220> FEATURE:
<223> OTHER INFORMATION: Primer

<400> SEQUENCE: 214
gcaggcgatg aagatggaga 20

<210> SEQ ID NO 215
<211> LENGTH: 24
<212> TYPE: DNA
<213> ORGANISM: Artificial
<220> FEATURE:
<223> OTHER INFORMATION: Primer

<400> SEQUENCE: 215
ccacctcttt ctgcaacttc ttga 24

<210> SEQ ID NO 216
<211> LENGTH: 42
<212> TYPE: DNA
<213> ORGANISM: Artificial
<220> FEATURE:
<223> OTHER INFORMATION: Primer

<400> SEQUENCE: 216
gcgtaatacg actcactata gggcaggcga tgaagatgga ga 42

<210> SEQ ID NO 217
<211> LENGTH: 46
<212> TYPE: DNA
<213> ORGANISM: Artificial
<220> FEATURE:
<223> OTHER INFORMATION: Primer

<400> SEQUENCE: 217
gcgtaatacg actcactata ggccacctct ttctgcaact tcttga 46

<210> SEQ ID NO 218
<211> LENGTH: 25
<212> TYPE: DNA
<213> ORGANISM: Artificial
<220> FEATURE:
<223> OTHER INFORMATION: Primer

<400> SEQUENCE: 218
cagaatccca cagaatctga cgtga 25

<210> SEQ ID NO 219
<211> LENGTH: 20
<212> TYPE: DNA
<213> ORGANISM: Artificial
<220> FEATURE:
<223> OTHER INFORMATION: Primer

<400> SEQUENCE: 219
gcaagtggcg aagctcagct 20

<210> SEQ ID NO 220
<211> LENGTH: 47
<212> TYPE: DNA
<213> ORGANISM: Artificial
<220> FEATURE:
<223> OTHER INFORMATION: Primer

<400> SEQUENCE: 220
gcgtaatacg actcactata ggcagaatcc cacagaatct gacgtga 47

<210> SEQ ID NO 221
<211> LENGTH: 41
<212> TYPE: DNA
<213> ORGANISM: Artificial
<220> FEATURE:
<223> OTHER INFORMATION: Primer

<400> SEQUENCE: 221
gcgtaatacg actcactata ggcaagtggc gaagctcagc t 41

<210> SEQ ID NO 222
<211> LENGTH: 21
<212> TYPE: DNA
<213> ORGANISM: Artificial
<220> FEATURE:
<223> OTHER INFORMATION: Primer

<400> SEQUENCE: 222
cgtgtttgcc atgttcgatc a 21

<210> SEQ ID NO 223

<211> LENGTH: 23
<212> TYPE: DNA
<213> ORGANISM: Artificial
<220> FEATURE:
<223> OTHER INFORMATION: Primer

<400> SEQUENCE: 223
ggtacatttc gtccacgtct tca 23

<210> SEQ ID NO 224
<211> LENGTH: 43
<212> TYPE: DNA
<213> ORGANISM: Artificial
<220> FEATURE:
<223> OTHER INFORMATION: Primer

<400> SEQUENCE: 224
gcgtaatacg actcactata ggcgtgtttg ccatgttcga tca 43

<210> SEQ ID NO 225
<211> LENGTH: 43
<212> TYPE: DNA
<213> ORGANISM: Artificial
<220> FEATURE:
<223> OTHER INFORMATION: Primer

<400> SEQUENCE: 225
gcgtaatacg actcactata ggtacatttc gtccacgtct tca 43

<210> SEQ ID NO 226
<211> LENGTH: 23
<212> TYPE: DNA
<213> ORGANISM: Artificial
<220> FEATURE:
<223> OTHER INFORMATION: Primer

<400> SEQUENCE: 226
gacttgatct tcagccgacc att 23

<210> SEQ ID NO 227
<211> LENGTH: 23
<212> TYPE: DNA
<213> ORGANISM: Artificial
<220> FEATURE:
<223> OTHER INFORMATION: Primer

<400> SEQUENCE: 227
ccattgccag ttcctcaact tca 23

<210> SEQ ID NO 228
<211> LENGTH: 44
<212> TYPE: DNA
<213> ORGANISM: Artificial
<220> FEATURE:
<223> OTHER INFORMATION: Primer

<400> SEQUENCE: 228
gcgtaatacg actcactata ggacttgatc ttcagccgac catt 44

<210> SEQ ID NO 229
<211> LENGTH: 45
<212> TYPE: DNA
<213> ORGANISM: Artificial
<220> FEATURE:
<223> OTHER INFORMATION: Primer

<400> SEQUENCE: 229
gcgtaatacg actcactata ggccattgcc agttcctcaa cttca 45

<210> SEQ ID NO 230
<211> LENGTH: 21
<212> TYPE: DNA
<213> ORGANISM: Artificial
<220> FEATURE:
<223> OTHER INFORMATION: Primer

<400> SEQUENCE: 230
cgcaatgatc tcctccagga t 21

<210> SEQ ID NO 231
<211> LENGTH: 24
<212> TYPE: DNA
<213> ORGANISM: Artificial
<220> FEATURE:
<223> OTHER INFORMATION: Primer

<400> SEQUENCE: 231
ggtcatcatc tccatgaact cgtc 24

<210> SEQ ID NO 232
<211> LENGTH: 43
<212> TYPE: DNA
<213> ORGANISM: Artificial
<220> FEATURE:
<223> OTHER INFORMATION: Primer

<400> SEQUENCE: 232
gcgtaatacg actcactata ggcgcaatga tctcctccag gat 43

<210> SEQ ID NO 233
<211> LENGTH: 45
<212> TYPE: DNA
<213> ORGANISM: Artificial
<220> FEATURE:
<223> OTHER INFORMATION: Primer

<400> SEQUENCE: 233
gcgtaatacg actcactata gggtcatcat ctccatgaac tcgtc 45

<210> SEQ ID NO 234
<211> LENGTH: 26
<212> TYPE: DNA
<213> ORGANISM: Artificial
<220> FEATURE:
<223> OTHER INFORMATION: Primer

<400> SEQUENCE: 234
cgtcactaat cggactggtc taacag 26

<210> SEQ ID NO 235
<211> LENGTH: 24
<212> TYPE: DNA
<213> ORGANISM: Artificial
<220> FEATURE:
<223> OTHER INFORMATION: Primer

<400> SEQUENCE: 235
ggtcatcatc tccatgaact cgtc 24

<210> SEQ ID NO 236
<211> LENGTH: 48
<212> TYPE: DNA

<213> ORGANISM: Artificial
<220> FEATURE:
<223> OTHER INFORMATION: Primer

<400> SEQUENCE: 236
gcgtaatacg actcactata ggcgtcacta atcggactgg tctaacag 48

<210> SEQ ID NO 237
<211> LENGTH: 45
<212> TYPE: DNA
<213> ORGANISM: Artificial
<220> FEATURE:
<223> OTHER INFORMATION: Primer

<400> SEQUENCE: 237
gcgtaatacg actcactata gggtcatcat ctccatgaac tcgtc 45

<210> SEQ ID NO 238
<211> LENGTH: 23
<212> TYPE: DNA
<213> ORGANISM: Artificial
<220> FEATURE:
<223> OTHER INFORMATION: Primer

<400> SEQUENCE: 238
ggtgaaggag ggtgcctgct cag 23

<210> SEQ ID NO 239
<211> LENGTH: 25
<212> TYPE: DNA
<213> ORGANISM: Artificial
<220> FEATURE:
<223> OTHER INFORMATION: Primer

<400> SEQUENCE: 239
cagggtgaat agaacgaggt actcg 25

<210> SEQ ID NO 240
<211> LENGTH: 40
<212> TYPE: DNA
<213> ORGANISM: Artificial
<220> FEATURE:
<223> OTHER INFORMATION: Primer

<400> SEQUENCE: 240
aatacgactc actatagggc gctatgaaat tccaagcaca 40

<210> SEQ ID NO 241
<211> LENGTH: 47
<212> TYPE: DNA
<213> ORGANISM: Artificial
<220> FEATURE:
<223> OTHER INFORMATION: Primer

<400> SEQUENCE: 241
gcgtaatacg actcactata ggcagggtga atagaacgag gtactcg 47

<210> SEQ ID NO 242
<211> LENGTH: 29
<212> TYPE: DNA
<213> ORGANISM: Artificial
<220> FEATURE:
<223> OTHER INFORMATION: Primer

<400> SEQUENCE: 242
ctcaacgaag gtcttgtcag tggctttgg 29

<210> SEQ ID NO 243
<211> LENGTH: 20
<212> TYPE: DNA
<213> ORGANISM: Artificial
<220> FEATURE:
<223> OTHER INFORMATION: Primer

<400> SEQUENCE: 243
ttcgcctggc ttcttcgtga 20

<210> SEQ ID NO 244
<211> LENGTH: 44
<212> TYPE: DNA
<213> ORGANISM: Artificial
<220> FEATURE:
<223> OTHER INFORMATION: Primer

<400> SEQUENCE: 244
gcgtaatacg actcactata ggccacgccg acttaattca ttcc 44

<210> SEQ ID NO 245
<211> LENGTH: 42
<212> TYPE: DNA
<213> ORGANISM: Artificial
<220> FEATURE:
<223> OTHER INFORMATION: Primer

<400> SEQUENCE: 245
gcgtaatacg actcactata ggttcgcctg gcttcttcgt ga 42

<210> SEQ ID NO 246
<211> LENGTH: 22
<212> TYPE: DNA
<213> ORGANISM: Artificial
<220> FEATURE:
<223> OTHER INFORMATION: Primer

<400> SEQUENCE: 246
tgtcgatggc ggtcttaaca tc 22

<210> SEQ ID NO 247
<211> LENGTH: 24
<212> TYPE: DNA
<213> ORGANISM: Artificial
<220> FEATURE:
<223> OTHER INFORMATION: Primer

<400> SEQUENCE: 247
tctccagctt ccactttctt gaga 24

<210> SEQ ID NO 248
<211> LENGTH: 44
<212> TYPE: DNA
<213> ORGANISM: Artificial
<220> FEATURE:
<223> OTHER INFORMATION: Primer

<400> SEQUENCE: 248
gcgtaatacg actcactata ggtgtcgatg gcggtcttaa catc 44

<210> SEQ ID NO 249
<211> LENGTH: 46
<212> TYPE: DNA
<213> ORGANISM: Artificial
<220> FEATURE:

<223> OTHER INFORMATION: Primer

<400> SEQUENCE: 249
gcgtaatacg actcactata ggtctccagc ttccactttc ttgaga 46

<210> SEQ ID NO 250
<211> LENGTH: 20
<212> TYPE: DNA
<213> ORGANISM: Artificial
<220> FEATURE:
<223> OTHER INFORMATION: Primer

<400> SEQUENCE: 250
aacgtgcatt tcgcgtaccc 20

<210> SEQ ID NO 251
<211> LENGTH: 20
<212> TYPE: DNA
<213> ORGANISM: Artificial
<220> FEATURE:
<223> OTHER INFORMATION: Primer

<400> SEQUENCE: 251
tgatgggcat aactggcagg 20

<210> SEQ ID NO 252
<211> LENGTH: 42
<212> TYPE: DNA
<213> ORGANISM: Artificial
<220> FEATURE:
<223> OTHER INFORMATION: Primer

<400> SEQUENCE: 252
gcgtaatacg actcactata ggaacgtgca tttcgcgtac cc 42

<210> SEQ ID NO 253
<211> LENGTH: 42
<212> TYPE: DNA
<213> ORGANISM: Artificial
<220> FEATURE:
<223> OTHER INFORMATION: Primer

<400> SEQUENCE: 253
gcgtaatacg actcactata ggtgatgggc ataactggca gg 42

<210> SEQ ID NO 254
<211> LENGTH: 22
<212> TYPE: DNA
<213> ORGANISM: Artificial
<220> FEATURE:
<223> OTHER INFORMATION: Primer

<400> SEQUENCE: 254
ccttattgaa cgtggtcgac ag 22

<210> SEQ ID NO 255
<211> LENGTH: 20
<212> TYPE: DNA
<213> ORGANISM: Artificial
<220> FEATURE:
<223> OTHER INFORMATION: Primer

<400> SEQUENCE: 255
ctgatgtagt ccttgaggag 20

<210> SEQ ID NO 256
<211> LENGTH: 44
<212> TYPE: DNA
<213> ORGANISM: Artificial
<220> FEATURE:
<223> OTHER INFORMATION: Primer

<400> SEQUENCE: 256
gcgtaatacg actcactata ggccttattg aacgtggtcg acag 44

<210> SEQ ID NO 257
<211> LENGTH: 42
<212> TYPE: DNA
<213> ORGANISM: Artificial
<220> FEATURE:
<223> OTHER INFORMATION: Primer

<400> SEQUENCE: 257
gcgtaatacg actcactata ggctgatgta gtccttgagg ag 42

<210> SEQ ID NO 258
<211> LENGTH: 26
<212> TYPE: DNA
<213> ORGANISM: Artificial
<220> FEATURE:
<223> OTHER INFORMATION: Primer

<400> SEQUENCE: 258
gtacggacgg gtagtttagt tgtgtc 26

<210> SEQ ID NO 259
<211> LENGTH: 20
<212> TYPE: DNA
<213> ORGANISM: Artificial
<220> FEATURE:
<223> OTHER INFORMATION: Primer

<400> SEQUENCE: 259
ttgccaagtg ccaagtcacg 20

<210> SEQ ID NO 260
<211> LENGTH: 48
<212> TYPE: DNA
<213> ORGANISM: Artificial
<220> FEATURE:
<223> OTHER INFORMATION: Primer

<400> SEQUENCE: 260
gcgtaatacg actcactata gggtacggac gggtagttta gttgtgtc 48

<210> SEQ ID NO 261
<211> LENGTH: 42
<212> TYPE: DNA
<213> ORGANISM: Artificial
<220> FEATURE:
<223> OTHER INFORMATION: Primer

<400> SEQUENCE: 261
gcgtaatacg actcactata ggttgccaag tgccaagtca cg 42

<210> SEQ ID NO 262
<211> LENGTH: 22
<212> TYPE: DNA
<213> ORGANISM: Artificial
<220> FEATURE:
<223> OTHER INFORMATION: Primer

<400> SEQUENCE: 262
ctgttgtcgg ctggtcatat cc 22

<210> SEQ ID NO 263
<211> LENGTH: 20
<212> TYPE: DNA
<213> ORGANISM: Artificial
<220> FEATURE:
<223> OTHER INFORMATION: Primer

<400> SEQUENCE: 263
taacgtaacg catcgccacc 20

<210> SEQ ID NO 264
<211> LENGTH: 44
<212> TYPE: DNA
<213> ORGANISM: Artificial
<220> FEATURE:
<223> OTHER INFORMATION: Primer

<400> SEQUENCE: 264
gcgtaatacg actcactata ggctgttgtc ggctggtcat atcc 44

<210> SEQ ID NO 265
<211> LENGTH: 42
<212> TYPE: DNA
<213> ORGANISM: Artificial
<220> FEATURE:
<223> OTHER INFORMATION: Primer

<400> SEQUENCE: 265
gcgtaatacg actcactata ggtaacgtaa cgcatcgcca cc 42

<210> SEQ ID NO 266
<211> LENGTH: 20
<212> TYPE: DNA
<213> ORGANISM: Artificial
<220> FEATURE:
<223> OTHER INFORMATION: Primer

<400> SEQUENCE: 266
agccctcatc cgtgatttgg 20

<210> SEQ ID NO 267
<211> LENGTH: 20
<212> TYPE: DNA
<213> ORGANISM: Artificial
<220> FEATURE:
<223> OTHER INFORMATION: Primer

<400> SEQUENCE: 267
gatccggcct caatttgacg 20

<210> SEQ ID NO 268
<211> LENGTH: 42
<212> TYPE: DNA
<213> ORGANISM: Artificial
<220> FEATURE:
<223> OTHER INFORMATION: Primer

<400> SEQUENCE: 268
gcgtaatacg actcactata ggagccctca tccgtgattt gg 42

<210> SEQ ID NO 269
<211> LENGTH: 42

<212> TYPE: DNA
<213> ORGANISM: Artificial
<220> FEATURE:
<223> OTHER INFORMATION: Primer

<400> SEQUENCE: 269
gcgtaatacg actcactata gggatccggc ctcaatttga cg 42

<210> SEQ ID NO 270
<211> LENGTH: 22
<212> TYPE: DNA
<213> ORGANISM: Artificial
<220> FEATURE:
<223> OTHER INFORMATION: Primer

<400> SEQUENCE: 270
acgtttctct gctcattcgt gc 22

<210> SEQ ID NO 271
<211> LENGTH: 20
<212> TYPE: DNA
<213> ORGANISM: Artificial
<220> FEATURE:
<223> OTHER INFORMATION: Primer

<400> SEQUENCE: 271
cttgtacaaa gtgtgcaggg 20

<210> SEQ ID NO 272
<211> LENGTH: 44
<212> TYPE: DNA
<213> ORGANISM: Artificial
<220> FEATURE:
<223> OTHER INFORMATION: Primer

<400> SEQUENCE: 272
gcgtaatacg actcactata ggacgtttct ctgctcattc gtgc 44

<210> SEQ ID NO 273
<211> LENGTH: 42
<212> TYPE: DNA
<213> ORGANISM: Artificial
<220> FEATURE:
<223> OTHER INFORMATION: Primer

<400> SEQUENCE: 273
gcgtaatacg actcactata ggcttgtaca aagtgtgcag gg 42

<210> SEQ ID NO 274
<211> LENGTH: 22
<212> TYPE: DNA
<213> ORGANISM: Artificial
<220> FEATURE:
<223> OTHER INFORMATION: Primer

<400> SEQUENCE: 274
ggttttcttc ttgcccgaat cg 22

<210> SEQ ID NO 275
<211> LENGTH: 20
<212> TYPE: DNA
<213> ORGANISM: Artificial
<220> FEATURE:
<223> OTHER INFORMATION: Primer

<400> SEQUENCE: 275
tttggggttc ggcttggttg 20

<210> SEQ ID NO 276
<211> LENGTH: 44
<212> TYPE: DNA
<213> ORGANISM: Artificial
<220> FEATURE:
<223> OTHER INFORMATION: Primer

<400> SEQUENCE: 276
gcgtaatacg actcactata ggggttttct tcttgcccga atcg 44

<210> SEQ ID NO 277
<211> LENGTH: 42
<212> TYPE: DNA
<213> ORGANISM: Artificial
<220> FEATURE:
<223> OTHER INFORMATION: Primer

<400> SEQUENCE: 277
gcgtaatacg actcactata ggtttggggt tcggcttggt tg 42

<210> SEQ ID NO 278
<211> LENGTH: 23
<212> TYPE: DNA
<213> ORGANISM: Artificial
<220> FEATURE:
<223> OTHER INFORMATION: Primer

<400> SEQUENCE: 278
tcagcgagat ccctaagaca acg 23

<210> SEQ ID NO 279
<211> LENGTH: 20
<212> TYPE: DNA
<213> ORGANISM: Artificial
<220> FEATURE:
<223> OTHER INFORMATION: Primer

<400> SEQUENCE: 279
ccccacatgt tgatgacgca 20

<210> SEQ ID NO 280
<211> LENGTH: 45
<212> TYPE: DNA
<213> ORGANISM: Artificial
<220> FEATURE:
<223> OTHER INFORMATION: Primer

<400> SEQUENCE: 280
gcgtaatacg actcactata ggtcagcgag atccctaaga caacg 45

<210> SEQ ID NO 281
<211> LENGTH: 42
<212> TYPE: DNA
<213> ORGANISM: Artificial
<220> FEATURE:
<223> OTHER INFORMATION: Primer

<400> SEQUENCE: 281
gcgtaatacg actcactata ggccccacat gttgatgacg ca 42

<210> SEQ ID NO 282
<211> LENGTH: 23
<212> TYPE: DNA
<213> ORGANISM: Artificial

<220> FEATURE:
<223> OTHER INFORMATION: Primer

<400> SEQUENCE: 282
ggtttatgac ccctgagagg aag 23

<210> SEQ ID NO 283
<211> LENGTH: 22
<212> TYPE: DNA
<213> ORGANISM: Artificial
<220> FEATURE:
<223> OTHER INFORMATION: Primer

<400> SEQUENCE: 283
ctccagggtg aactccttct tc 22

<210> SEQ ID NO 284
<211> LENGTH: 43
<212> TYPE: DNA
<213> ORGANISM: Artificial
<220> FEATURE:
<223> OTHER INFORMATION: Primer

<400> SEQUENCE: 284
gcgtaatacg actcactata ggtttatgac ccctgagagg aag 43

<210> SEQ ID NO 285
<211> LENGTH: 44
<212> TYPE: DNA
<213> ORGANISM: Artificial
<220> FEATURE:
<223> OTHER INFORMATION: Primer

<400> SEQUENCE: 285
gcgtaatacg actcactata ggctccaggg tgaactcctt cttc 44

<210> SEQ ID NO 286
<211> LENGTH: 24
<212> TYPE: DNA
<213> ORGANISM: Artificial
<220> FEATURE:
<223> OTHER INFORMATION: Primer

<400> SEQUENCE: 286
caaggaccag aacaagaaca aggg 24

<210> SEQ ID NO 287
<211> LENGTH: 26
<212> TYPE: DNA
<213> ORGANISM: Artificial
<220> FEATURE:
<223> OTHER INFORMATION: Primer

<400> SEQUENCE: 287
gacgttcata tttggaggct acttgg 26

<210> SEQ ID NO 288
<211> LENGTH: 46
<212> TYPE: DNA
<213> ORGANISM: Artificial
<220> FEATURE:
<223> OTHER INFORMATION: Primer

<400> SEQUENCE: 288
gcgtaatacg actcactata ggcaaggacc agaacaagaa caaggg 46

<210> SEQ ID NO 289
<211> LENGTH: 47
<212> TYPE: DNA
<213> ORGANISM: Artificial
<220> FEATURE:
<223> OTHER INFORMATION: Primer

<400> SEQUENCE: 289
gcgtaatacg actcactata ggacgttcat atttggaggc tacttgg 47

<210> SEQ ID NO 290
<211> LENGTH: 25
<212> TYPE: DNA
<213> ORGANISM: Artificial
<220> FEATURE:
<223> OTHER INFORMATION: Primer

<400> SEQUENCE: 290
aatctcgtac actgttggaa caagc 25

<210> SEQ ID NO 291
<211> LENGTH: 25
<212> TYPE: DNA
<213> ORGANISM: Artificial
<220> FEATURE:
<223> OTHER INFORMATION: Primer

<400> SEQUENCE: 291
ggttcttacg gtcttcttca gcttg 25

<210> SEQ ID NO 292
<211> LENGTH: 47
<212> TYPE: DNA
<213> ORGANISM: Artificial
<220> FEATURE:
<223> OTHER INFORMATION: Primer

<400> SEQUENCE: 292
gcgtaatacg actcactata ggaatctcgt acactgttgg aacaagc 47

<210> SEQ ID NO 293
<211> LENGTH: 45
<212> TYPE: DNA
<213> ORGANISM: Artificial
<220> FEATURE:
<223> OTHER INFORMATION: Primer

<400> SEQUENCE: 293
gcgtaatacg actcactata ggttcttacg gtcttcttca gcttg 45

<210> SEQ ID NO 294
<211> LENGTH: 22
<212> TYPE: DNA
<213> ORGANISM: Artificial
<220> FEATURE:
<223> OTHER INFORMATION: Primer

<400> SEQUENCE: 294
aagaagaagc tcaggttgtt gc 22

<210> SEQ ID NO 295
<211> LENGTH: 20
<212> TYPE: DNA
<213> ORGANISM: Artificial
<220> FEATURE:
<223> OTHER INFORMATION: Primer

<400> SEQUENCE: 295
tcattcacct ggctgttgag 20

<210> SEQ ID NO 296
<211> LENGTH: 44
<212> TYPE: DNA
<213> ORGANISM: Artificial
<220> FEATURE:
<223> OTHER INFORMATION: Primer

<400> SEQUENCE: 296
gcgtaatacg actcactata ggaagaagaa gctcaggttg ttgc 44

<210> SEQ ID NO 297
<211> LENGTH: 42
<212> TYPE: DNA
<213> ORGANISM: Artificial
<220> FEATURE:
<223> OTHER INFORMATION: Primer

<400> SEQUENCE: 297
gcgtaatacg actcactata ggtcattcac ctggctgttg ag 42

<210> SEQ ID NO 298
<211> LENGTH: 20
<212> TYPE: DNA
<213> ORGANISM: Artificial
<220> FEATURE:
<223> OTHER INFORMATION: Primer

<400> SEQUENCE: 298
acatcctcag gctcatggga 20

<210> SEQ ID NO 299
<211> LENGTH: 20
<212> TYPE: DNA
<213> ORGANISM: Artificial
<220> FEATURE:
<223> OTHER INFORMATION: Primer

<400> SEQUENCE: 299
agccgttacc ttccttgtcg 20

<210> SEQ ID NO 300
<211> LENGTH: 42
<212> TYPE: DNA
<213> ORGANISM: Artificial
<220> FEATURE:
<223> OTHER INFORMATION: Primer

<400> SEQUENCE: 300
gcgtaatacg actcactata ggacatcctc aggctcatgg ga 42

<210> SEQ ID NO 301
<211> LENGTH: 42
<212> TYPE: DNA
<213> ORGANISM: Artificial
<220> FEATURE:
<223> OTHER INFORMATION: Primer

<400> SEQUENCE: 301
gcgtaatacg actcactata ggagccgtta ccttccttgt cg 42

<210> SEQ ID NO 302

<211> LENGTH: 20
<212> TYPE: DNA
<213> ORGANISM: Artificial
<220> FEATURE:
<223> OTHER INFORMATION: Primer

<400> SEQUENCE: 302
acatcctcag gctcatggga 20

<210> SEQ ID NO 303
<211> LENGTH: 20
<212> TYPE: DNA
<213> ORGANISM: Artificial
<220> FEATURE:
<223> OTHER INFORMATION: Primer

<400> SEQUENCE: 303
agccgttacc ttccttgtcg 20

<210> SEQ ID NO 304
<211> LENGTH: 42
<212> TYPE: DNA
<213> ORGANISM: Artificial
<220> FEATURE:
<223> OTHER INFORMATION: Primer

<400> SEQUENCE: 304
gcgtaatacg actcactata ggacatcctc aggctcatgg ga 42

<210> SEQ ID NO 305
<211> LENGTH: 42
<212> TYPE: DNA
<213> ORGANISM: Artificial
<220> FEATURE:
<223> OTHER INFORMATION: Primer

<400> SEQUENCE: 305
gcgtaatacg actcactata ggagccgtta ccttccttgt cg 42

<210> SEQ ID NO 306
<211> LENGTH: 24
<212> TYPE: DNA
<213> ORGANISM: Artificial
<220> FEATURE:
<223> OTHER INFORMATION: Primer

<400> SEQUENCE: 306
cgtaaaaact ctgaccggca agac 24

<210> SEQ ID NO 307
<211> LENGTH: 26
<212> TYPE: DNA
<213> ORGANISM: Artificial
<220> FEATURE:
<223> OTHER INFORMATION: Primer

<400> SEQUENCE: 307
tagttccacc acgaagtctg agaacc 26

<210> SEQ ID NO 308
<211> LENGTH: 46
<212> TYPE: DNA
<213> ORGANISM: Artificial
<220> FEATURE:
<223> OTHER INFORMATION: Primer

<400> SEQUENCE: 308
gcgtaatacg actcactata ggcgtaaaaa ctctgaccgg caagac 46

<210> SEQ ID NO 309
<211> LENGTH: 48
<212> TYPE: DNA
<213> ORGANISM: Artificial
<220> FEATURE:
<223> OTHER INFORMATION: Primer

<400> SEQUENCE: 309
gcgtaatacg actcactata ggtagttcca ccacgaagtc tgagaacc 48

<210> SEQ ID NO 310
<211> LENGTH: 21
<212> TYPE: DNA
<213> ORGANISM: Artificial
<220> FEATURE:
<223> OTHER INFORMATION: Primer

<400> SEQUENCE: 310
atggccgacg atgaagctaa g 21

<210> SEQ ID NO 311
<211> LENGTH: 20
<212> TYPE: DNA
<213> ORGANISM: Artificial
<220> FEATURE:
<223> OTHER INFORMATION: Primer

<400> SEQUENCE: 311
tggttgtggt tctggttcgg 20

<210> SEQ ID NO 312
<211> LENGTH: 43
<212> TYPE: DNA
<213> ORGANISM: Artificial
<220> FEATURE:
<223> OTHER INFORMATION: Primer

<400> SEQUENCE: 312
gcgtaatacg actcactata ggatggccga cgatgaagct aag 43

<210> SEQ ID NO 313
<211> LENGTH: 42
<212> TYPE: DNA
<213> ORGANISM: Artificial
<220> FEATURE:
<223> OTHER INFORMATION: Primer

<400> SEQUENCE: 313
gcgtaatacg actcactata ggtggttctg gttcgggttc aa 42

<210> SEQ ID NO 314
<211> LENGTH: 20
<212> TYPE: DNA
<213> ORGANISM: Artificial
<220> FEATURE:
<223> OTHER INFORMATION: Primer

<400> SEQUENCE: 314
cggtaatgcg atgcggtaag 20

<210> SEQ ID NO 315
<211> LENGTH: 20
<212> TYPE: DNA

<213> ORGANISM: Artificial
<220> FEATURE:
<223> OTHER INFORMATION: Primer

<400> SEQUENCE: 315
tcatcttctc gggcgtatgc 20

<210> SEQ ID NO 316
<211> LENGTH: 42
<212> TYPE: DNA
<213> ORGANISM: Artificial
<220> FEATURE:
<223> OTHER INFORMATION: Primer

<400> SEQUENCE: 316
gcgtaatacg actcactata ggcggtaatg cgatgcggta ag 42

<210> SEQ ID NO 317
<211> LENGTH: 42
<212> TYPE: DNA
<213> ORGANISM: Artificial
<220> FEATURE:
<223> OTHER INFORMATION: Primer

<400> SEQUENCE: 317
gcgtaatacg actcactata ggtcatcttc tcgggcgtat gc 42

<210> SEQ ID NO 318
<211> LENGTH: 25
<212> TYPE: DNA
<213> ORGANISM: Artificial
<220> FEATURE:
<223> OTHER INFORMATION: Primer

<400> SEQUENCE: 318
tttggaagtt gagtcatcag attcc 25

<210> SEQ ID NO 319
<211> LENGTH: 24
<212> TYPE: DNA
<213> ORGANISM: Artificial
<220> FEATURE:
<223> OTHER INFORMATION: Primer

<400> SEQUENCE: 319
gttgtagtcg gaaagggtac gtcc 24

<210> SEQ ID NO 320
<211> LENGTH: 47
<212> TYPE: DNA
<213> ORGANISM: Artificial
<220> FEATURE:
<223> OTHER INFORMATION: Primer

<400> SEQUENCE: 320
gcgtaatacg actcactata ggtttggaag ttgagtcatc agattcc 47

<210> SEQ ID NO 321
<211> LENGTH: 46
<212> TYPE: DNA
<213> ORGANISM: Artificial
<220> FEATURE:
<223> OTHER INFORMATION: Primer

<400> SEQUENCE: 321
gcgtaatacg actcactata gggttgtagt cggaaagggt acgtcc 46

<210> SEQ ID NO 322
<211> LENGTH: 23
<212> TYPE: DNA
<213> ORGANISM: Artificial
<220> FEATURE:
<223> OTHER INFORMATION: Primer

<400> SEQUENCE: 322
aagacttgct tcatcctact gca 23

<210> SEQ ID NO 323
<211> LENGTH: 20
<212> TYPE: DNA
<213> ORGANISM: Artificial
<220> FEATURE:
<223> OTHER INFORMATION: Primer

<400> SEQUENCE: 323
attgtggaac atccggtaca 20

<210> SEQ ID NO 324
<211> LENGTH: 45
<212> TYPE: DNA
<213> ORGANISM: Artificial
<220> FEATURE:
<223> OTHER INFORMATION: Primer

<400> SEQUENCE: 324
gcgtaatacg actcactata ggaagacttg cttcatccta ctgca 45

<210> SEQ ID NO 325
<211> LENGTH: 42
<212> TYPE: DNA
<213> ORGANISM: Artificial
<220> FEATURE:
<223> OTHER INFORMATION: Primer

<400> SEQUENCE: 325
gcgtaatacg actcactata ggattgtgga acatccggta ca 42

<210> SEQ ID NO 326
<211> LENGTH: 424
<212> TYPE: PRT
<213> ORGANISM: Lygus hesperus

<400> SEQUENCE: 326

```
Met Ile Pro Pro Thr Ser Arg Pro Gln Val Thr Val Tyr Ser Asp Lys
1               5                   10                  15

Asn Glu Ala Thr Gly Thr Leu Leu Asn Leu Pro Ala Val Phe Asn Ala
            20                  25                  30

Pro Ile Arg Pro Asp Val Val Asn Phe Val His Gln Asn Val Ala Lys
        35                  40                  45

Asn His Arg Gln Pro Tyr Cys Val Ser Ala Gln Ala Gly His Gln Thr
    50                  55                  60

Ser Ala Glu Ser Trp Gly Thr Gly Arg Ala Val Ala Arg Ile Pro Arg
65                  70                  75                  80

Val Arg Gly Gly Gly Thr His Arg Ser Gly Gln Gly Ala Phe Gly Asn
                85                  90                  95

Met Cys Arg Gly Gly Arg Met Phe Ala Pro Thr Arg Pro Trp Arg Arg
            100                 105                 110

Trp His Arg Lys Ile Asn Val Asn Gln Lys Arg Tyr Ala Val Val Ser
```

```
        115                 120                 125

Ala Ile Ala Ala Ser Gly Val Pro Ala Leu Val Met Ser Lys Gly His
    130                 135                 140

Met Val Gln Ser Val Pro Glu Phe Pro Leu Val Val Ser Asp Lys Val
145                 150                 155                 160

Gln Glu Tyr Thr Lys Thr Lys Gln Ala Val Ile Phe Leu His Arg Ile
                165                 170                 175

Lys Ala Trp Gln Asp Ile Gln Lys Val Tyr Lys Ser Lys Arg Phe Arg
            180                 185                 190

Ala Gly Lys Gly Lys Met Arg Asn Arg Arg Arg Ile Gln Arg Arg Gly
        195                 200                 205

Pro Leu Ile Ile Tyr Asp Gln Asp Gln Gly Leu Asn Arg Ala Phe Arg
    210                 215                 220

Asn Ile Pro Gly Val Asp Leu Ile Glu Val Ser Arg Leu Asn Leu Leu
225                 230                 235                 240

Lys Leu Ala Pro Gly Gly His Ile Gly Arg Phe Val Ile Trp Thr Gln
                245                 250                 255

Ser Ala Phe Glu Lys Leu Asp Ala Leu Tyr Gly Thr Trp Lys Lys Lys
            260                 265                 270

Ser Thr Leu Lys Ala Gly Tyr Asn Leu Pro Met Pro Lys Met Ala Asn
        275                 280                 285

Thr Asp Leu Ser Arg Leu Phe Lys Ala Pro Glu Ile Lys Ala Val Leu
    290                 295                 300

Arg Asn Pro Lys Lys Thr Ile Val Arg Arg Val Arg Lys Leu Asn Pro
305                 310                 315                 320

Leu Arg Asn Thr Arg Ala Met Leu Arg Leu Asn Pro Tyr Ala Ala Val
                325                 330                 335

Leu Lys Arg Lys Ala Ile Leu Asp Gln Arg Lys Leu Lys Leu Gln Lys
            340                 345                 350

Leu Val Glu Ala Ala Lys Lys Gly Asp Thr Lys Leu Ser Pro Arg Val
        355                 360                 365

Glu Arg His Leu Lys Met Ile Glu Arg Arg Lys Ala Leu Ile Lys Lys
    370                 375                 380

Ala Lys Ala Ala Lys Pro Lys Lys Pro Lys Thr Ala Lys Lys Pro Lys
385                 390                 395                 400

Thr Ala Glu Lys Ala Pro Ala Pro Ala Lys Lys Ala Ala Ala Pro Lys
                405                 410                 415

Lys Ala Thr Thr Pro Ala Lys Lys
            420


<210> SEQ ID NO 327
<211> LENGTH: 242
<212> TYPE: PRT
<213> ORGANISM: Lygus hesperus

<400> SEQUENCE: 327

Met Ala Asn Ala Lys Pro Ile Ser Lys Lys Lys Lys Phe Val Ser Asp
1               5                   10                  15

Gly Val Phe Lys Ala Glu Leu Asn Glu Phe Leu Thr Arg Glu Leu Ala
            20                  25                  30

Glu Glu Gly Tyr Ser Gly Val Glu Val Arg Val Thr Pro Asn Lys Thr
        35                  40                  45

Glu Ile Ile Ile Met Ala Thr Arg Thr Gln Ser Val Leu Gly Asp Lys
    50                  55                  60
```

```
Gly Arg Arg Ile Arg Glu Leu Thr Ser Val Val Gln Lys Arg Phe Asn
65                  70                  75                  80

Phe Lys Pro Gln Thr Leu Asp Leu Tyr Ala Glu Lys Val Ala Thr Arg
                85                  90                  95

Gly Leu Cys Ala Ile Ala Gln Ala Glu Ser Leu Arg Tyr Lys Leu Ile
            100                 105                 110

Gly Gly Leu Ala Val Arg Gly Ala Cys Tyr Gly Val Leu Arg Phe Ile
        115                 120                 125

Met Glu Asn Gly Ala Lys Gly Cys Glu Val Val Val Ser Gly Lys Leu
    130                 135                 140

Arg Gly Gln Arg Ala Lys Ser Met Lys Phe Val Asp Gly Leu Met Ile
145                 150                 155                 160

His Ser Gly Asp Pro Cys Asn Glu Tyr Val Asp Thr Ala Thr Arg His
                165                 170                 175

Val Leu Leu Arg Gln Gly Val Leu Gly Ile Lys Val Lys Ile Met Leu
            180                 185                 190

Pro Trp Asp Val Thr Gly Lys Asn Gly Pro Lys Asn Pro Leu Pro Asp
        195                 200                 205

His Val Ser Val Leu Leu Pro Lys Glu Glu Leu Pro Asn Leu Ala Val
    210                 215                 220

Ser Val Pro Gly Ser Asp Ile Lys Pro Lys Pro Glu Val Pro Ala Pro
225                 230                 235                 240

Ala Leu
```

<210> SEQ ID NO 328
<211> LENGTH: 262
<212> TYPE: PRT
<213> ORGANISM: Lygus hesperus

<400> SEQUENCE: 328

```
Met Ala Val Gly Lys Asn Lys Gly Leu Ser Lys Gly Gly Lys Lys Gly
1               5                   10                  15

Val Lys Lys Lys Val Val Asp Pro Phe Thr Arg Lys Asp Trp Tyr Asp
            20                  25                  30

Val Lys Ala Pro Ser Met Phe Lys Lys Arg Gln Val Gly Lys Thr Leu
        35                  40                  45

Val Asn Arg Thr Gln Gly Thr Lys Ile Ala Ser Glu Gly Leu Lys Gly
    50                  55                  60

Arg Val Phe Glu Val Ser Leu Ala Asp Ile Gln Glu Asp Thr Asp Ala
65                  70                  75                  80

Glu Arg Ser Phe Arg Lys Phe Arg Leu Ile Ala Glu Asp Val Gln Ala
                85                  90                  95

Arg Asn Val Leu Thr Asn Phe His Gly Met Asp Leu Thr Thr Asp Lys
            100                 105                 110

Leu Arg Ser Met Val Lys Lys Trp Gln Thr Leu Ile Glu Ala Asn Val
        115                 120                 125

Asp Val Lys Thr Thr Asp Gly Tyr Leu Leu Arg Val Phe Cys Ile Gly
    130                 135                 140

Phe Thr Asn Lys Asp Gln Leu Ser Gln Arg Lys Thr Cys Tyr Ala Gln
145                 150                 155                 160

His Asn Gln Val Arg Glu Ile Arg Lys Lys Met Val Lys Asn Ile Ser
                165                 170                 175

Asp Ser Ile Ser Ser Cys Asp Leu Arg Ser Val Val Asn Lys Leu Ile
            180                 185                 190
```

```
Pro Asp Ser Ile Ala Lys Asp Ile Glu Lys Asn Cys Gln Gly Ile Tyr
        195                 200                 205

Pro Leu His Asp Val Tyr Ile Arg Lys Val Lys Val Leu Lys Lys Pro
    210                 215                 220

Arg Phe Glu Leu Ser Lys Leu Leu Glu Leu His Val Asp Gly Lys Gly
225                 230                 235                 240

Ile Asp Glu Pro Gly Ala Lys Val Thr Arg Thr Asp Ala Tyr Glu Pro
                245                 250                 255

Pro Val Gln Glu Ser Val
            260


<210> SEQ ID NO 329
<211> LENGTH: 152
<212> TYPE: PRT
<213> ORGANISM: Lygus hesperus

<400> SEQUENCE: 329

Met Ser Leu Met Leu Pro Glu Lys Phe Gln His Ile Leu Arg Ile Met
1               5                   10                  15

Gly Thr Asn Ile Asp Gly Lys Arg Lys Val Met Phe Ala Met Thr Ala
            20                  25                  30

Ile Lys Gly Val Gly Arg Arg Tyr Ala Asn Ile Val Leu Lys Lys Ala
        35                  40                  45

Asp Val Asn Leu Asp Lys Arg Ala Gly Glu Cys Ser Glu Glu Glu Val
    50                  55                  60

Glu Lys Ile Val Thr Ile Met Gln Asn Pro Arg Gln Tyr Lys Ile Pro
65                  70                  75                  80

Asn Trp Phe Leu Asn Arg Gln Lys Asp Thr Val Glu Gly Lys Tyr Ser
                85                  90                  95

Gln Leu Thr Ser Ser Leu Leu Asp Ser Lys Leu Arg Asp Asp Leu Glu
            100                 105                 110

Arg Leu Lys Lys Ile Arg Ala His Arg Gly Met Arg His Tyr Trp Gly
        115                 120                 125

Leu Arg Val Arg Gly Gln His Thr Lys Thr Thr Gly Arg Arg Gly Arg
    130                 135                 140

Thr Val Gly Val Ser Lys Lys Lys
145                 150


<210> SEQ ID NO 330
<211> LENGTH: 381
<212> TYPE: PRT
<213> ORGANISM: Lygus hesperus

<400> SEQUENCE: 330

Met Ser Asp Glu Glu Tyr Ser Glu Ser Glu Glu Glu Thr Gln Pro Glu
1               5                   10                  15

Pro Gln Lys Lys Pro Glu Ala Glu Gly Gly Gly Asp Pro Glu Phe Val
            20                  25                  30

Lys Arg Lys Glu Ala Gln Thr Ser Ala Leu Asp Glu Gln Leu Lys Asp
        35                  40                  45

Tyr Ile Ala Glu Trp Arg Lys Gln Arg Ala Arg Glu Glu Glu Asp Leu
    50                  55                  60

Lys Lys Leu Lys Glu Lys Gln Ala Lys Arg Lys Val Ala Arg Ala Glu
65                  70                  75                  80

Glu Glu Lys Arg Leu Ala Glu Lys Lys Lys Gln Glu Glu Glu Arg Arg
                85                  90                  95
```

```
Val Arg Glu Ala Glu Glu Lys Lys Gln Arg Glu Ile Glu Glu Lys Arg
            100                 105                 110

Arg Arg Leu Glu Glu Ala Glu Lys Lys Arg Gln Ala Met Met Ala Ala
        115                 120                 125

Leu Lys Asp Gln Ser Lys Thr Lys Gly Pro Asn Phe Val Val Asn Lys
    130                 135                 140

Lys Ala Glu Thr Leu Gly Met Ser Ser Ala Gln Ile Glu Arg Asn Lys
145                 150                 155                 160

Thr Lys Glu Gln Leu Glu Glu Glu Lys Arg Ile Ser Leu Ser Ile Arg
                165                 170                 175

Leu Lys Pro Leu Ala Ile Glu Asn Met Ser Ile Asp Arg Leu Arg Ile
            180                 185                 190

Lys Ala Gln Glu Leu Trp Glu Ala Ile Val Lys Leu Glu Thr Glu Lys
        195                 200                 205

Tyr Asp Leu Glu Glu Arg Gln Lys Arg Gln Asp Tyr Asp Leu Lys Glu
    210                 215                 220

Leu Lys Glu Arg Gln Lys Gln Gln Leu Arg His Lys Ala Leu Lys Lys
225                 230                 235                 240

Gly Leu Asp Pro Glu Ala Leu Thr Gly Lys Tyr Pro Pro Lys Ile Gln
                245                 250                 255

Val Ala Ser Lys Tyr Glu Arg Arg Val Asp Thr Arg Ser Tyr Asp Asp
            260                 265                 270

Lys Lys Lys Leu Phe Glu Gly Gly Ile Leu Glu Arg Tyr Lys Glu Leu
        275                 280                 285

Ile Glu Lys Val Trp Thr Glu Lys Val Asp Gln Phe Gly Ser Arg Ala
    290                 295                 300

His Ser Lys Leu Pro Arg Trp Phe Gly Glu Arg Pro Gly Lys Lys Lys
305                 310                 315                 320

Asp Ala Pro Glu Ser Pro Glu Glu Glu Glu Val Lys Val Glu Asp Glu
                325                 330                 335

Pro Glu Ala Glu Pro Ser Phe Met Leu Asp Glu Glu Glu Glu Glu Ala
            340                 345                 350

Glu Glu Glu Glu Ala Glu Glu Glu Glu Glu Ala Glu Glu Glu Glu Glu
        355                 360                 365

Glu Glu Glu Glu Glu Glu Glu Glu Glu Glu Glu Glu Glu
    370                 375                 380


<210> SEQ ID NO 331
<211> LENGTH: 1689
<212> TYPE: PRT
<213> ORGANISM: Lygus hesperus

<400> SEQUENCE: 331

Ser Gly Lys Leu Ala Gly Ala Asp Ile Glu Thr Tyr Leu Leu Glu Lys
1               5                   10                  15

Ala Arg Val Ile Ser Gln Gln Thr Leu Glu Arg Ser Tyr His Ile Phe
            20                  25                  30

Tyr Gln Met Met Ser Gly Ala Val Lys Gly Val Lys Glu Met Cys Leu
        35                  40                  45

Leu Val Asp Asp Ile Tyr Thr Tyr Asn Phe Ile Ser Gln Gly Lys Val
    50                  55                  60

Ser Ile Ala Gly Val Asp Asp Gly Glu Glu Met Val Leu Thr Asp Gln
65                  70                  75                  80

Ala Phe Asp Ile Leu Gly Phe Thr Lys Gln Glu Lys Glu Asp Ile Tyr
                85                  90                  95
```

```
Lys Ile Thr Ala Ala Val Ile His Met Gly Thr Met Lys Phe Lys Gln
            100                 105                 110

Arg Gly Arg Glu Glu Gln Ala Glu Ala Asp Gly Thr Glu Glu Gly Gly
        115                 120                 125

Lys Val Gly Val Leu Leu Gly Ile Asp Gly Asp Asp Leu Tyr Lys Asn
    130                 135                 140

Met Cys Lys Pro Arg Ile Lys Val Gly Thr Glu Phe Val Thr Gln Gly
145                 150                 155                 160

Lys Asn Val Asn Gln Val Ser Tyr Ser Leu Gly Ala Met Ser Lys Gly
                165                 170                 175

Met Phe Asp Arg Leu Phe Lys Phe Leu Val Lys Lys Cys Asn Glu Thr
            180                 185                 190

Leu Asp Thr Lys Gln Lys Arg Gln His Phe Ile Gly Val Leu Asp Ile
        195                 200                 205

Ala Gly Phe Glu Ile Phe Asp Phe Asn Gly Phe Glu Gln Leu Cys Ile
    210                 215                 220

Asn Phe Thr Asn Glu Lys Leu Gln Gln Phe Phe Asn His His Met Phe
225                 230                 235                 240

Val Leu Glu Gln Glu Glu Tyr Lys Arg Glu Gly Ile Asn Trp Ala Phe
                245                 250                 255

Ile Asp Phe Gly Met Asp Leu Leu Ala Cys Ile Glu Leu Ile Glu Lys
            260                 265                 270

Pro Met Gly Ile Leu Ser Ile Leu Glu Glu Glu Ser Met Phe Pro Lys
        275                 280                 285

Ala Thr Asp Lys Thr Phe Glu Asp Lys Leu Ile Thr Asn His Leu Gly
    290                 295                 300

Lys Ser Pro Asn Phe Arg Lys Pro Ala Val Pro Lys Pro Gly Gln Gln
305                 310                 315                 320

Ala Gly His Phe Ala Ile Ala His Tyr Ala Gly Cys Val Ser Tyr Asn
                325                 330                 335

Ile Thr Gly Trp Leu Glu Lys Asn Lys Asp Pro Leu Asn Asp Thr Val
            340                 345                 350

Val Asp Gln Tyr Lys Lys Gly Thr Asn Lys Leu Leu Cys Glu Ile Phe
        355                 360                 365

Ala Asp His Pro Gly Gln Ser Gly Ala Pro Gly Gly Asp Ala Gly Gly
    370                 375                 380

Lys Gly Gly Arg Gly Lys Lys Gly Gly Gly Phe Ala Thr Val Ser Ser
385                 390                 395                 400

Ser Tyr Lys Glu Gln Leu Asn Asn Leu Met Thr Thr Leu Lys Ser Thr
                405                 410                 415

Gln Pro His Phe Val Arg Cys Ile Ile Pro Asn Glu Leu Lys Gln Pro
            420                 425                 430

Gly Val Ile Asp Ser His Leu Val Met His Gln Leu Thr Cys Asn Gly
        435                 440                 445

Val Leu Glu Gly Ile Arg Ile Cys Arg Lys Gly Phe Pro Asn Arg Met
    450                 455                 460

Asn Tyr Pro Asp Phe Lys Leu Arg Tyr Lys Ile Leu Asn Pro Ala Ala
465                 470                 475                 480

Val Asp Arg Glu Ser Asp Ile Leu Lys Ala Ala Gly Leu Val Leu Glu
                485                 490                 495

Ser Thr Gly Leu Asp Pro Asp Met Tyr Arg Leu Gly His Thr Lys Val
            500                 505                 510
```

```
Phe Phe Arg Ala Gly Val Leu Gly Gln Leu Glu Glu Leu Arg Asp Asp
        515                 520                 525

Arg Leu Ser Lys Ile Ile Gly Trp Met Gln Ala Phe Met Arg Gly Tyr
    530                 535                 540

Leu Val Arg Lys Glu Tyr Lys Lys Leu Gln Glu Gln Arg Leu Ala Leu
545                 550                 555                 560

Gln Val Val Gln Arg Asn Leu Arg Arg Tyr Leu Gln Leu Arg Thr Trp
                565                 570                 575

Pro Trp Trp Lys Met Trp Ser Arg Val Lys Pro Leu Leu Asn Val Ala
            580                 585                 590

Asn Val Glu Glu Glu Met Arg Lys Leu Glu Glu Leu Val Ala Glu Thr
        595                 600                 605

Gln Ala Ala Leu Glu Lys Glu Glu Lys Leu Arg Lys Glu Ala Glu Ala
    610                 615                 620

Leu Asn Ala Lys Leu Leu Gln Glu Lys Thr Asp Leu Leu Arg Asn Leu
625                 630                 635                 640

Glu Gly Glu Lys Gly Ser Ile Ser Gly Ile Gln Glu Arg Cys Ala Lys
                645                 650                 655

Leu Gln Ala Gln Lys Ala Asp Leu Glu Ser Gln Leu Met Asp Thr Gln
            660                 665                 670

Glu Arg Leu Gln Asn Glu Glu Asp Ala Arg Asn Gln Leu Phe Gln Gln
        675                 680                 685

Lys Lys Lys Leu Glu Gln Glu Ala Ala Ala Leu Lys Lys Asp Ile Glu
    690                 695                 700

Asp Leu Glu Leu Ser Asn Gln Lys Thr Asp Gln Asp Lys Ala Ser Lys
705                 710                 715                 720

Glu His Gln Ile Arg Asn Leu Asn Asp Glu Ile Ala His Gln Asp Asp
                725                 730                 735

Leu Ile Asn Lys Leu Asn Lys Glu Lys Lys Ile Gln Ser Glu Leu Asn
            740                 745                 750

Gln Lys Thr Ala Glu Glu Leu Gln Ala Ala Glu Asp Lys Ile Asn His
        755                 760                 765

Leu Thr Lys Val Lys Val Lys Leu Glu Gln Thr Leu Asp Glu Leu Glu
    770                 775                 780

Asp Thr Leu Glu Arg Glu Lys Lys Leu Arg Gly Asp Val Glu Lys Ala
785                 790                 795                 800

Lys Arg Lys Thr Glu Gly Asp Leu Lys Leu Thr Gln Glu Ala Val Ala
                805                 810                 815

Asp Leu Glu Arg Asn Lys Lys Glu Leu Glu Gln Thr Ile Gln Arg Lys
            820                 825                 830

Asp Lys Glu Ile Ala Ser Leu Thr Ala Lys Leu Glu Asp Glu Gln Ser
        835                 840                 845

Ile Val Asn Lys Thr Gly Lys Gln Ile Lys Glu Leu Gln Ser Arg Ile
    850                 855                 860

Glu Glu Leu Glu Glu Glu Val Glu Ala Glu Arg Gln Ala Arg Gly Lys
865                 870                 875                 880

Ala Glu Lys Gln Arg Ala Asp Leu Ala Arg Glu Leu Glu Glu Leu Gly
                885                 890                 895

Glu Arg Leu Glu Glu Ala Gly Gly Ala Thr Ser Ala Gln Ile Glu Leu
            900                 905                 910

Asn Lys Lys Arg Glu Ala Glu Met Ser Lys Leu Arg Arg Asp Leu Glu
        915                 920                 925

Glu Ala Asn Ile Gln His Glu Gly Thr Leu Ala Asn Leu Arg Lys Lys
```

```
    930                 935                 940

His Asn Asp Ala Val Ser Glu Met Gly Asp Gln Ile Asp Gln Leu Asn
945                 950                 955                 960

Lys Leu Lys Thr Lys Val Glu Lys Glu Lys Ser Gln Tyr Leu Gly Glu
                965                 970                 975

Leu Asn Asp Val Arg Ala Ser Ile Asp His Leu Thr Asn Glu Lys Ala
            980                 985                 990

Ala Thr Glu Lys Val Ala Lys Gln  Leu Gln His Gln Ile  Asn Glu Val
        995                 1000                 1005

Gln Gly  Lys Leu Asp Glu Ala  Asn Arg Thr Leu Asn  Asp Phe Asp
    1010                 1015                 1020

Ala Ala  Lys Lys Lys Leu Ser  Ile Glu Asn Ser Asp  Leu Leu Arg
    1025                 1030                 1035

Gln Leu  Glu Glu Ala Glu Ser  Gln Val Ser Gln Leu  Ser Lys Ile
    1040                 1045                 1050

Lys Ile  Ser Leu Thr Thr Gln  Leu Glu Asp Thr Lys  Arg Leu Ala
    1055                 1060                 1065

Asp Glu  Glu Ala Arg Glu Arg  Ala Thr Leu Leu Gly  Lys Phe Arg
    1070                 1075                 1080

Asn Leu  Glu His Asp Leu Asp  Asn Leu Arg Glu Gln  Val Glu Glu
    1085                 1090                 1095

Glu Ala  Glu Ala Lys Ala Asp  Ile Gln Arg Gln Leu  Ser Lys Ala
    1100                 1105                 1110

Asn Ala  Glu Ala Gln Leu Trp  Arg Ser Lys Tyr Glu  Ser Glu Gly
    1115                 1120                 1125

Val Ala  Arg Ala Glu Glu Leu  Glu Glu Ala Lys Arg  Lys Leu Gln
    1130                 1135                 1140

Ala Arg  Leu Ala Glu Ala Glu  Glu Thr Ile Glu Ser  Leu Asn Gln
    1145                 1150                 1155

Lys Val  Ile Ala Leu Glu Lys  Thr Lys Gln Arg Leu  Ala Thr Glu
    1160                 1165                 1170

Val Glu  Asp Leu Gln Leu Glu  Val Asp Arg Ala Asn  Ala Ile Ala
    1175                 1180                 1185

Asn Ala  Ala Glu Lys Lys Ala  Lys Ala Ile Asp Lys  Ile Ile Gly
    1190                 1195                 1200

Glu Trp  Lys Leu Lys Val Asp  Asp Leu Ala Ala Glu  Leu Asp Ala
    1205                 1210                 1215

Ser Gln  Lys Glu Cys Arg Asn  Tyr Ser Thr Glu Leu  Phe Arg Leu
    1220                 1225                 1230

Lys Gly  Ala Tyr Glu Glu Gly  Gln Glu Gln Leu Glu  Ala Val Arg
    1235                 1240                 1245

Arg Glu  Asn Lys Asn Leu Ala  Asp Glu Val Lys Asp  Leu Leu Asp
    1250                 1255                 1260

Gln Ile  Gly Glu Gly Gly Arg  Asn Ile His Glu Ile  Glu Lys Gln
    1265                 1270                 1275

Arg Lys  Arg Leu Glu Val Glu  Lys Asp Glu Leu Gln  Ala Ala Leu
    1280                 1285                 1290

Glu Glu  Ala Glu Ala Ala Leu  Glu Gln Glu Glu Asn  Lys Val Leu
    1295                 1300                 1305

Arg Ala  Gln Leu Glu Leu Ser  Gln Val Arg Gln Glu  Ile Asp Arg
    1310                 1315                 1320

Arg Ile  Gln Glu Lys Glu Glu  Glu Phe Glu Asn Thr  Arg Lys Asn
    1325                 1330                 1335
```

```
His Gln  Arg Ala Leu Asp Ser  Met Gln Ala Ser Leu  Glu Ala Glu
    1340                 1345                 1350

Ala Lys  Gly Lys Ala Glu Ala  Leu Arg Met Lys Lys  Lys Leu Glu
    1355                 1360                 1365

Ala Asp  Ile Asn Glu Leu Glu  Ile Ala Leu Asp His  Ala Asn Lys
    1370                 1375                 1380

Ala Asn  Ala Glu Ala Gln Lys  Thr Ile Lys Lys Tyr  Gln Gln Gln
    1385                 1390                 1395

Leu Lys  Asp Val Gln Thr Ala  Leu Glu Glu Glu Gln  Arg Ala Arg
    1400                 1405                 1410

Asp Asp  Ala Arg Glu Gln Leu  Gly Ile Ala Glu Arg  Arg Ala Asn
    1415                 1420                 1425

Ala Leu  Gly Asn Glu Leu Glu  Glu Ser Arg Thr Leu  Leu Glu Gln
    1430                 1435                 1440

Ala Asp  Arg Gly Arg Arg Gln  Ala Glu Gln Glu Leu  Gly Asp Ala
    1445                 1450                 1455

His Glu  Gln Ile Asn Glu Leu  Ala Ala Gln Ala Thr  Ser Ala Ser
    1460                 1465                 1470

Ala Ala  Lys Arg Lys Leu Glu  Gly Glu Leu Gln Thr  Leu His Ala
    1475                 1480                 1485

Asp Leu  Asp Glu Leu Leu Asn  Glu Ala Lys Asn Ser  Glu Glu Lys
    1490                 1495                 1500

Ala Lys  Lys Ala Met Val Asp  Ala Ala Arg Leu Ala  Asp Glu Leu
    1505                 1510                 1515

Arg Ala  Glu Gln Asp His Ala  Gln Thr Gln Glu Lys  Leu Arg Lys
    1520                 1525                 1530

Ala Leu  Glu Thr Gln Ile Lys  Glu Leu Gln Val Arg  Leu Asp Glu
    1535                 1540                 1545

Ala Glu  Asn Asn Ala Leu Lys  Gly Gly Lys Lys Ala  Ile Ala Lys
    1550                 1555                 1560

Leu Glu  Gln Arg Val Arg Glu  Leu Glu Asn Glu Leu  Asp Gly Glu
    1565                 1570                 1575

Gln Arg  Arg His Ala Asp Ala  Gln Lys Asn Leu Arg  Lys Ser Glu
    1580                 1585                 1590

Arg Arg  Ile Lys Glu Leu Ser  Phe Gln Ser Asp Glu  Asp Arg Lys
    1595                 1600                 1605

Asn His  Glu Arg Met Gln Asp  Leu Val Asp Lys Leu  Gln Gln Lys
    1610                 1615                 1620

Ile Lys  Thr Tyr Lys Arg Gln  Ile Glu Glu Ala Glu  Glu Ile Ala
    1625                 1630                 1635

Ala Leu  Asn Leu Ala Lys Phe  Arg Lys Ala Gln Gln  Glu Leu Glu
    1640                 1645                 1650

Glu Ala  Glu Glu Arg Ala Asp  Leu Ala Glu Gln Ala  Val Ser Lys
    1655                 1660                 1665

Phe Arg  Thr Lys Gly Gly Arg  Ala Gly Ser Ala Ala  Arg Ala Met
    1670                 1675                 1680

Ser Pro  Val Gly Gln Lys
    1685
```

<210> SEQ ID NO 332
<211> LENGTH: 256
<212> TYPE: PRT
<213> ORGANISM: Lygus hesperus

<400> SEQUENCE: 332

```
Asp Ala Ile Lys Lys Lys Met Gln Ala Met Lys Met Glu Lys Asp Thr
1               5                   10                  15

Ala Met Asp Lys Ala Asp Thr Cys Glu Gly Gln Ala Lys Asp Ala Asn
            20                  25                  30

Thr Arg Ala Asp Lys Ile Leu Glu Asp Val Arg Asp Leu Gln Lys Lys
        35                  40                  45

Leu Asn Gln Val Glu Ser Asp Leu Glu Arg Thr Lys Arg Glu Leu Glu
    50                  55                  60

Thr Lys Thr Thr Glu Leu Glu Glu Lys Glu Lys Ala Asn Thr Asn Ala
65                  70                  75                  80

Glu Ser Glu Val Ala Ser Leu Asn Arg Lys Val Gln Met Val Glu Glu
                85                  90                  95

Asp Leu Glu Arg Ser Glu Glu Arg Ser Gly Thr Ala Gln Gln Lys Leu
            100                 105                 110

Ser Glu Ala Ser His Ala Ala Asp Glu Ala Ser Arg Met Cys Lys Val
        115                 120                 125

Leu Glu Asn Arg Ser Gln Gln Asp Glu Glu Arg Met Asp Gln Leu Thr
    130                 135                 140

Asn Gln Leu Lys Glu Ala Arg Leu Leu Ala Glu Asp Ala Asp Gly Lys
145                 150                 155                 160

Ser Asp Glu Val Ser Arg Lys Leu Ala Phe Val Glu Asp Glu Leu Glu
                165                 170                 175

Val Ala Glu Asp Arg Val Lys Ser Gly Asp Ser Lys Ile Met Glu Leu
            180                 185                 190

Glu Glu Glu Leu Lys Val Val Gly Asn Ser Leu Lys Ser Leu Glu Val
        195                 200                 205

Ser Glu Glu Lys Ala Asn Gln Arg Val Glu Glu Tyr Lys Arg Gln Ile
    210                 215                 220

Lys Gln Leu Thr Val Lys Leu Lys Glu Ala Glu Ala Arg Ala Glu Phe
225                 230                 235                 240

Ala Glu Lys Thr Val Lys Lys Leu Gln Lys Glu Val Asp Arg Leu Glu
                245                 250                 255
```

<210> SEQ ID NO 333
<211> LENGTH: 85
<212> TYPE: PRT
<213> ORGANISM: Lygus hesperus

<400> SEQUENCE: 333

```
Arg Ala Leu Gly Gln Asn Pro Thr Glu Ser Asp Val Lys Lys Phe Thr
1               5                   10                  15

His Gln His Lys Pro Asp Glu Arg Ile Ser Phe Glu Val Phe Leu Pro
            20                  25                  30

Ile Tyr Gln Ala Ile Ser Lys Gly Arg Thr Ser Asp Thr Ala Glu Asp
        35                  40                  45

Phe Ile Glu Gly Leu Arg His Phe Asp Lys Asp Gly Asn Gly Phe Ile
    50                  55                  60

Ser Thr Ala Glu Leu Arg His Leu Leu Thr Thr Leu Gly Glu Lys Leu
65                  70                  75                  80

Thr Asp Asp Glu Val
                85
```

<210> SEQ ID NO 334
<211> LENGTH: 174

<212> TYPE: PRT
<213> ORGANISM: Lygus hesperus

<400> SEQUENCE: 334

```
Met Ser Ser Arg Lys Thr Ala Gly Arg Arg Ala Thr Thr Lys Lys Arg
1               5                   10                  15

Ala Gln Arg Ala Thr Ser Asn Val Phe Ala Met Phe Asp Gln Ala Gln
            20                  25                  30

Ile Gln Glu Phe Lys Glu Ala Phe Asn Met Ile Asp Gln Asn Arg Asp
        35                  40                  45

Gly Phe Val Asp Lys Glu Asp Leu His Asp Met Leu Ala Ser Leu Gly
    50                  55                  60

Lys Asn Pro Ser Asp Glu Tyr Leu Glu Gly Met Met Asn Glu Ala Pro
65                  70                  75                  80

Gly Pro Ile Asn Phe Thr Met Phe Leu Thr Leu Phe Gly Glu Arg Leu
                85                  90                  95

Gln Gly Thr Asp Pro Glu Glu Val Ile Lys Asn Ala Phe Gly Cys Phe
            100                 105                 110

Asp Glu Asp Asn Asn Gly Phe Ile Asn Glu Glu Arg Leu Arg Glu Leu
        115                 120                 125

Leu Thr Ser Met Gly Asp Arg Phe Thr Asp Glu Asp Val Asp Glu Met
    130                 135                 140

Tyr Arg Glu Ala Pro Ile Lys Asn Gly Met Phe Asp Tyr Ile Glu Phe
145                 150                 155                 160

Thr Arg Ile Leu Lys His Gly Ala Lys Asp Lys Asp Glu Gln
                165                 170
```

<210> SEQ ID NO 335
<211> LENGTH: 1881
<212> TYPE: PRT
<213> ORGANISM: Lygus hesperus

<400> SEQUENCE: 335

```
Asp Leu Thr Cys Leu Asn Glu Ala Ser Val Leu His Asn Ile Lys Asp
1               5                   10                  15

Arg Tyr Tyr Ser Gly Leu Ile Tyr Thr Tyr Ser Gly Leu Phe Cys Val
            20                  25                  30

Val Val Asn Pro Tyr Lys Lys Leu Pro Ile Tyr Thr Glu Arg Ile Met
        35                  40                  45

Glu Lys Tyr Lys Gly Val Lys Arg His Asp Leu Pro Pro His Val Phe
    50                  55                  60

Ala Ile Thr Asp Thr Ala Tyr Arg Ser Met Leu Gln Asp Arg Glu Asp
65                  70                  75                  80

Gln Ser Ile Leu Cys Thr Gly Glu Ser Gly Ala Gly Lys Thr Glu Asn
                85                  90                  95

Thr Lys Lys Val Ile Gln Tyr Leu Ala Tyr Val Ala Ala Ser Lys Pro
            100                 105                 110

Lys Ser Ser Ala Ser Pro His Thr Ala Gln Ser Gln Ala Leu Ile Ile
        115                 120                 125

Gly Glu Leu Glu Gln Gln Leu Leu Gln Ala Asn Pro Ile Leu Glu Ala
    130                 135                 140

Phe Gly Asn Ala Lys Thr Val Lys Asn Asp Asn Ser Ser Arg Phe Gly
145                 150                 155                 160

Lys Phe Ile Arg Ile Asn Phe Asp Ala Ser Gly Tyr Ile Ala Gly Ala
                165                 170                 175
```

```
Asn Ile Glu Thr Tyr Leu Leu Glu Lys Ser Arg Ala Ile Arg Gln Ala
            180                 185                 190

Lys Asp Glu Arg Thr Phe His Ile Phe Tyr Gln Leu Leu Ala Gly Ala
        195                 200                 205

Ser Ala Glu Gln Arg Lys Glu Phe Ile Leu Glu Asp Pro Lys Asn Tyr
    210                 215                 220

Pro Phe Leu Ser Ser Gly Met Val Ser Val Pro Gly Val Asp Asp Gly
225                 230                 235                 240

Val Asp Phe Gln Ala Thr Ile Ala Ser Met Ser Ile Met Gly Met Thr
                245                 250                 255

Asn Asp Asp Leu Ser Ala Leu Phe Arg Ile Val Ser Ala Val Met Leu
            260                 265                 270

Phe Gly Ser Met Gln Phe Lys Gln Glu Arg Asn Ser Asp Gln Ala Thr
        275                 280                 285

Leu Pro Asp Asn Thr Val Ala Gln Lys Ile Ala His Leu Leu Gly Leu
    290                 295                 300

Ser Ile Thr Glu Met Thr Lys Ala Phe Leu Arg Pro Arg Ile Lys Val
305                 310                 315                 320

Gly Arg Asp Phe Val Thr Lys Ala Gln Thr Lys Glu Gln Val Glu Phe
                325                 330                 335

Ala Val Glu Ala Ile Ser Lys Ala Cys Tyr Glu Arg Met Phe Arg Trp
            340                 345                 350

Leu Val Asn Arg Ile Asn Arg Ser Leu Asp Arg Thr Lys Arg Gln Gly
        355                 360                 365

Ala Ser Phe Ile Gly Ile Leu Asp Met Ala Gly Phe Glu Ile Phe Glu
    370                 375                 380

Ile Asn Ser Phe Glu Gln Leu Cys Ile Asn Tyr Thr Asn Glu Lys Leu
385                 390                 395                 400

Gln Gln Leu Phe Asn His Thr Met Phe Ile Leu Glu Gln Glu Glu Tyr
                405                 410                 415

Gln Arg Glu Gly Ile Glu Trp Lys Phe Ile Asp Phe Gly Leu Asp Leu
            420                 425                 430

Gln Pro Thr Ile Asp Leu Ile Asp Lys Pro Met Gly Val Met Ala Leu
        435                 440                 445

Leu Asp Glu Glu Cys Trp Phe Pro Lys Ala Thr Asp Lys Thr Phe Val
    450                 455                 460

Glu Lys Leu Val Gly Ala His Ser Val His Pro Lys Phe Ile Lys Thr
465                 470                 475                 480

Asp Phe Arg Gly Val Ala Asp Phe Ala Val Val His Tyr Ala Gly Lys
                485                 490                 495

Val Asp Tyr Ser Ala Ala Gln Trp Leu Met Lys Asn Met Asp Pro Leu
            500                 505                 510

Asn Glu Asn Val Val Gln Leu Leu Gln Asn Ser Gln Asp Pro Phe Val
        515                 520                 525

Ile His Ile Trp Lys Asp Ala Glu Ile Val Gly Met Ala His Gln Ala
    530                 535                 540

Leu Ser Asp Thr Gln Phe Gly Ala Arg Thr Arg Lys Gly Met Phe Arg
545                 550                 555                 560

Thr Val Ser Gln Leu Tyr Lys Asp Gln Leu Ser Lys Leu Met Ile Thr
                565                 570                 575

Leu Arg Asn Thr Asn Pro Asn Phe Val Arg Cys Ile Leu Pro Asn His
            580                 585                 590

Glu Lys Arg Ala Gly Lys Ile Asp Ala Pro Leu Val Leu Asp Gln Leu
```

```
        595                 600                 605

Arg Cys Asn Gly Val Leu Glu Gly Ile Arg Ile Cys Arg Gln Gly Phe
    610                 615                 620

Pro Asn Arg Ile Pro Phe Gln Glu Phe Arg Gln Arg Tyr Glu Leu Leu
625                 630                 635                 640

Thr Pro Asn Val Ile Pro Lys Gly Phe Met Asp Gly Lys Lys Ala Cys
                645                 650                 655

Glu Lys Met Ile Asn Ala Leu Glu Leu Asp Pro Asn Leu Tyr Arg Val
            660                 665                 670

Gly Gln Ser Lys Ile Phe Phe Arg Ala Gly Val Leu Ala His Leu Glu
        675                 680                 685

Glu Glu Arg Asp Tyr Lys Ile Thr Asp Leu Ile Ala Asn Phe Arg Ala
    690                 695                 700

Phe Cys Arg Gly Tyr Leu Ala Arg Arg Asn Tyr Gln Lys Arg Leu Gln
705                 710                 715                 720

Gln Leu Asn Ala Ile Arg Ile Ile Gln Arg Asn Cys Ser Ala Tyr Leu
                725                 730                 735

Lys Leu Arg Asn Trp Gln Trp Trp Arg Leu Tyr Thr Lys Val Lys Pro
            740                 745                 750

Leu Leu Glu Val Thr Lys Gln Glu Glu Lys Leu Thr Gln Lys Glu Asp
        755                 760                 765

Glu Leu Lys Gln Val Arg Glu Lys Leu Asp Asn Gln Val Arg Ser Lys
    770                 775                 780

Glu Glu Tyr Glu Lys Arg Leu Gln Asp Ala Leu Glu Glu Lys Ala Ala
785                 790                 795                 800

Leu Ala Glu Gln Leu Gln Ala Glu Val Glu Leu Cys Ala Glu Ala Glu
                805                 810                 815

Glu Met Arg Ala Arg Leu Ala Val Arg Lys Gln Glu Leu Glu Glu Ile
            820                 825                 830

Leu His Asp Leu Glu Ala Arg Ile Glu Glu Glu Glu Gln Arg Asn Thr
        835                 840                 845

Val Leu Ile Asn Glu Lys Lys Lys Leu Thr Leu Asn Ile Ala Asp Leu
    850                 855                 860

Glu Glu Gln Leu Glu Glu Glu Glu Gly Ala Arg Gln Lys Leu Gln Leu
865                 870                 875                 880

Glu Lys Val Gln Ile Glu Ala Arg Leu Lys Lys Met Glu Glu Asp Leu
                885                 890                 895

Ala Leu Ala Glu Asp Thr Asn Thr Lys Val Val Lys Glu Lys Lys Val
            900                 905                 910

Leu Glu Glu Arg Ala Ser Asp Leu Ala Gln Thr Leu Ala Glu Glu Glu
        915                 920                 925

Glu Lys Ala Lys His Leu Ala Lys Leu Lys Thr Lys His Glu Thr Thr
    930                 935                 940

Ile Ala Glu Leu Glu Glu Arg Leu Leu Lys Asp Asn Gln Gln Arg Gln
945                 950                 955                 960

Glu Met Asp Arg Asn Lys Arg Lys Ile Glu Ser Glu Val Asn Asp Leu
                965                 970                 975

Lys Glu Gln Ile Asn Glu Lys Lys Val Gln Val Glu Glu Leu Gln Leu
            980                 985                 990

Gln Leu Gly Lys Arg Glu Glu Glu  Ile Ala Gln Ala Leu  Met Arg Ile
        995                 1000                 1005

Asp Glu  Glu Gly Ala Gly Lys  Ala Gln Thr Gln Lys  Ala Leu Arg
    1010                 1015                 1020
```

```
Glu Leu  Glu Ser Gln Leu Ala  Glu Leu Gln Glu Asp  Leu Glu Ala
    1025                 1030                 1035

Glu Lys  Ala Ala Arg Ala Lys  Ala Glu Lys Gln Lys  Arg Asp Leu
    1040                 1045                 1050

Asn Glu  Glu Leu Glu Ser Leu  Lys Asn Glu Leu Leu  Asp Ser Leu
    1055                 1060                 1065

Asp Thr  Thr Ala Ala Gln Gln  Glu Leu Arg Thr Lys  Arg Glu His
    1070                 1075                 1080

Glu Leu  Ala Thr Leu Lys Lys  Thr Leu Glu Glu Glu  Thr His Ile
    1085                 1090                 1095

His Glu  Val Ser Leu Thr Glu  Met Arg His Lys His  Thr Gln Glu
    1100                 1105                 1110

Val Ala  Ala Leu Asn Glu Gln  Leu Glu Gln Leu Lys  Lys Ala Lys
    1115                 1120                 1125

Ser Ala  Leu Glu Lys Ser Lys  Ala Gln Leu Glu Gly  Glu Ala Ala
    1130                 1135                 1140

Glu Leu  Ala Asn Glu Leu Glu  Thr Ala Gly Thr Ser  Lys Gly Glu
    1145                 1150                 1155

Ser Glu  Arg Lys Arg Lys Gln  Ala Glu Ser Ser Leu  Gln Glu Leu
    1160                 1165                 1170

Ser Ser  Arg Leu Leu Glu Met  Glu Arg Thr Lys Ala  Glu Leu Gln
    1175                 1180                 1185

Glu Arg  Val Gln Lys Leu Ser  Ala Glu Ala Asp Ser  Val Asn Gln
    1190                 1195                 1200

Gln Leu  Glu Ala Ala Glu Leu  Lys Ala Ser Ala Ala  Leu Lys Ala
    1205                 1210                 1215

Ser Gly  Thr Leu Glu Thr Gln  Leu Gln Glu Ala Gln  Val Leu Leu
    1220                 1225                 1230

Glu Glu  Glu Thr Arg Gln Lys  Leu Ser Leu Thr Thr  Lys Leu Lys
    1235                 1240                 1245

Gly Leu  Glu Ser Glu Arg Asp  Ala Leu Lys Glu Gln  Leu Tyr Glu
    1250                 1255                 1260

Glu Asp  Glu Gly Arg Lys Asn  Leu Glu Lys Gln Met  Ala Ile Leu
    1265                 1270                 1275

Asn Gln  Gln Val Ala Glu Ser  Lys Lys Lys Ser Glu  Glu Glu Thr
    1280                 1285                 1290

Glu Lys  Ile Thr Glu Leu Glu  Glu Ser Arg Lys Lys  Leu Leu Lys
    1295                 1300                 1305

Asp Ile  Glu Ile Leu Gln Arg  Gln Val Glu Glu Leu  Gln Val Thr
    1310                 1315                 1320

Asn Asp  Lys Leu Glu Lys Gly  Lys Lys Lys Leu Gln  Ser Glu Leu
    1325                 1330                 1335

Glu Asp  Leu Thr Ile Asp Leu  Glu Ser Gln Arg Thr  Lys Val Val
    1340                 1345                 1350

Glu Leu  Glu Lys Lys Gln Arg  Asn Phe Asp Lys Val  Leu Ala Glu
    1355                 1360                 1365

Glu Lys  Ala Leu Ser Gln Gln  Ile Thr His Glu Arg  Asp Ala Ala
    1370                 1375                 1380

Glu Arg  Glu Ala Arg Glu Lys  Glu Thr Arg Val Leu  Ser Leu Thr
    1385                 1390                 1395

Arg Glu  Leu Asp Glu Phe Met  Glu Lys Ile Glu Glu  Leu Glu Arg
    1400                 1405                 1410
```

```
Ser Lys  Arg Gln Leu Gln Ala  Glu Leu Asp Glu Leu  Val Asn Asn
    1415                 1420                 1425

Gln Gly  Thr Thr Asp Lys Ser  Val His Glu Leu Glu  Arg Ala Lys
    1430                 1435                 1440

Arg Val  Leu Glu Ser Gln Leu  Ala Glu Gln Lys Ala  Gln Asn Glu
    1445                 1450                 1455

Glu Leu  Glu Asp Glu Leu Gln  Met Thr Glu Asp Ala  Lys Leu Arg
    1460                 1465                 1470

Leu Glu  Val Asn Met Gln Ala  Leu Arg Ala Gln Phe  Glu Arg Asp
    1475                 1480                 1485

Leu Gln  Gly Lys Glu Glu Ser  Gly Glu Glu Lys Arg  Arg Gly Leu
    1490                 1495                 1500

Leu Lys  Gln Leu Arg Asp Ile  Glu Ala Glu Leu Glu  Asp Glu Arg
    1505                 1510                 1515

Lys Gln  Arg Thr Ala Ala Val  Ala Ser Arg Lys Lys  Ile Glu Ala
    1520                 1525                 1530

Asp Phe  Lys Asp Val Glu Gln  Gln Leu Glu Met His  Thr Lys Val
    1535                 1540                 1545

Lys Glu  Asp Leu Gln Lys Gln  Leu Lys Lys Cys Gln  Val Gln Leu
    1550                 1555                 1560

Lys Asp  Ala Ile Arg Asp Ala  Glu Glu Ala Arg Leu  Gly Arg Glu
    1565                 1570                 1575

Glu Leu  Gln Ala Ala Ala Lys  Glu Ala Glu Arg Lys  Trp Lys Gly
    1580                 1585                 1590

Leu Glu  Thr Glu Leu Ile Gln  Val Gln Glu Asp Leu  Met Ala Ser
    1595                 1600                 1605

Glu Arg  Gln Arg Arg Ala Ala  Glu Ala Glu Arg Asp  Glu Val Val
    1610                 1615                 1620

Glu Glu  Ala Asn Lys Asn Val  Lys Ser Leu Ser Asn  Leu Leu Asp
    1625                 1630                 1635

Glu Lys  Lys Arg Leu Glu Ala  Gln Cys Ser Gly Leu  Glu Glu Glu
    1640                 1645                 1650

Leu Glu  Glu Glu Leu Ser Asn  Asn Glu Ala Leu Gln  Asp Lys Ala
    1655                 1660                 1665

Arg Lys  Ala Gln Leu Ser Val  Glu Gln Leu Asn Ala  Glu Leu Ala
    1670                 1675                 1680

Ala Glu  Arg Ser Asn Val Gln  Lys Leu Glu Gly Thr  Arg Leu Ser
    1685                 1690                 1695

Met Glu  Arg Gln Asn Lys Glu  Leu Lys Ala Lys Leu  Asn Glu Leu
    1700                 1705                 1710

Glu Thr  Leu Gln Arg Asn Lys  Phe Lys Ala Asn Ala  Ser Leu Glu
    1715                 1720                 1725

Ala Lys  Ile Thr Asn Leu Glu  Glu Gln Leu Glu Asn  Glu Ala Lys
    1730                 1735                 1740

Glu Lys  Leu Leu Leu Gln Lys  Gly Asn Arg Lys Leu  Asp Lys Lys
    1745                 1750                 1755

Ile Lys  Asp Leu Leu Val Gln  Leu Glu Asp Glu Arg  Arg His Ala
    1760                 1765                 1770

Asp Gln  Tyr Lys Glu Gln Val  Glu Lys Ile Asn Val  Arg Val Lys
    1775                 1780                 1785

Thr Leu  Lys Arg Thr Leu Asp  Asp Ala Glu Glu Glu  Met Ser Arg
    1790                 1795                 1800

Glu Lys  Thr Gln Lys Arg Lys  Ala Leu Arg Glu Leu  Glu Asp Leu
```

```
    1805                1810                1815

Arg Glu  Asn Tyr Asp Ser Leu  Leu Arg Glu Asn Asp  Asn Leu Lys
    1820                1825                1830

Asn Lys  Leu Arg Arg Gly Gly  Gly Ile Ser Gly Ile  Ser Ser Arg
    1835                1840                1845

Leu Gly  Gly Ser Lys Arg Gly  Ser Ile Pro Gly Glu  Asp Ser Gln
    1850                1855                1860

Gly Leu  Asn Asn Thr Thr Asp  Glu Ser Val Asp Gly  Asp Asp Ile
    1865                1870                1875

Ser Asn  Pro
    1880
```

<210> SEQ ID NO 336
<211> LENGTH: 108
<212> TYPE: PRT
<213> ORGANISM: Lygus hesperus

<400> SEQUENCE: 336

```
Lys Lys Ile Leu Glu Glu Ile Ile Ala Glu Val Asp Ala Asp Gly Ser
1               5                   10                  15

Gly Gln Leu Glu Phe Glu Glu Phe Val Ala Leu Ala Ala Gly Phe Leu
            20                  25                  30

Thr Glu Asp Glu Thr Gln Asp Ala Glu Ala Met Gln Gln Glu Leu Arg
        35                  40                  45

Glu Ala Phe Arg Leu Tyr Asp Lys Glu Gly Asn Gly Tyr Ile Thr Thr
    50                  55                  60

Asp Val Leu Arg Glu Ile Leu Lys Glu Leu Asp Asp Lys Ile Thr Ser
65                  70                  75                  80

Gln Glu Leu Asp Met Met Ile Ala Glu Ile Asp Ser Asp Gly Ser Gly
                85                  90                  95

Thr Val Asp Phe Asp Glu Phe Met Glu Met Met Thr
            100                 105
```

<210> SEQ ID NO 337
<211> LENGTH: 141
<212> TYPE: PRT
<213> ORGANISM: Lygus hesperus

<400> SEQUENCE: 337

```
Ile Pro Ile Met Thr Ile Ala Leu Asn Ala Phe Asp Arg Asp His Ser
1               5                   10                  15

Gly Ser Ile Pro Thr Asp Met Val Ala Asp Ile Leu Arg Leu Met Gly
            20                  25                  30

Gln Pro Phe Asn Lys Lys Ile Leu Asp Glu Leu Ile Glu Glu Val Asp
        35                  40                  45

Ala Asp Lys Ser Gly Arg Leu Glu Phe Glu Glu Phe Ile Thr Leu Ala
    50                  55                  60

Ala Lys Phe Ile Val Glu Glu Asp Asp Glu Ala Met Gln Lys Glu Leu
65                  70                  75                  80

Arg Glu Ala Phe Arg Leu Tyr Asp Lys Glu Gly Asn Gly Tyr Ile Pro
                85                  90                  95

Thr Ser Cys Leu Lys Glu Ile Leu His Glu Leu Asp Glu Gln Leu Thr
            100                 105                 110

Asn Glu Glu Leu Asp Met Ile Ile Glu Glu Ile Asp Ser Asp Gly Ser
        115                 120                 125

Gly Thr Val Asp Phe Asp Glu Phe Met Glu Met Met Thr
```

```
    130                 135                 140


<210> SEQ ID NO 338
<211> LENGTH: 58
<212> TYPE: PRT
<213> ORGANISM: Lygus hesperus

<400> SEQUENCE: 338

Trp Val Lys Glu Gly Ala Cys Ser Glu Gln Ser Ser Arg Met Thr Ala
1               5                   10                  15

Met Asp Asn Ala Ser Lys Asn Ala Ala Glu Met Ile Asp Lys Leu Thr
            20                  25                  30

Leu Thr Phe Asn Arg Thr Arg Gln Ala Val Ile Thr Arg Glu Leu Ile
        35                  40                  45

Glu Ile Ile Ser Gly Ala Ser Ala Leu Glu
    50                  55


<210> SEQ ID NO 339
<211> LENGTH: 130
<212> TYPE: PRT
<213> ORGANISM: Lygus hesperus

<400> SEQUENCE: 339

Met Val Arg Met Asn Val Leu Ser Asp Ala Leu Lys Ser Ile Asn Asn
1               5                   10                  15

Ala Glu Lys Arg Gly Lys Arg Gln Val Leu Leu Arg Pro Cys Ser Lys
            20                  25                  30

Val Ile Ile Lys Phe Leu Thr Val Met Met Lys Lys Gly Tyr Ile Gly
        35                  40                  45

Glu Phe Glu Ile Val Asp Asp His Arg Ser Gly Lys Ile Val Val Asn
    50                  55                  60

Leu Asn Gly Arg Leu Asn Lys Cys Gly Val Ile Ser Pro Arg Phe Asp
65                  70                  75                  80

Val Pro Ile Thr Gln Ile Glu Lys Trp Thr Asn Asn Leu Leu Pro Ser
                85                  90                  95

Arg Gln Phe Gly Tyr Val Val Leu Thr Thr Ser Gly Gly Ile Met Asp
            100                 105                 110

His Glu Glu Ala Arg Arg Lys His Leu Gly Gly Lys Ile Leu Gly Phe
        115                 120                 125

Phe Phe
    130


<210> SEQ ID NO 340
<211> LENGTH: 131
<212> TYPE: PRT
<213> ORGANISM: Lygus hesperus

<400> SEQUENCE: 340

Val Asp Gly Gly Leu Asn Ile Pro His Ser Thr Lys Arg Phe Pro Gly
1               5                   10                  15

Tyr Asp Ser Glu Ser Lys Glu Phe Asn Ala Glu Val His Arg Lys His
            20                  25                  30

Ile Phe Gly Ile His Val Ala Asp Tyr Met Arg Gln Leu Ala Glu Glu
        35                  40                  45

Asp Asp Asp Ala Tyr Lys Lys Gln Phe Ser Gln Tyr Val Lys Asn Gly
    50                  55                  60

Val Thr Ala Asp Ser Ile Glu Ser Ile Tyr Lys Lys Ala His Glu Ala
65                  70                  75                  80
```

```
Ile Arg Ala Asp Pro Thr Arg Lys Pro Leu Glu Lys Lys Glu Val Lys
                85                  90                  95

Lys Lys Arg Trp Asn Arg Ala Lys Leu Ser Leu Ser Glu Arg Lys Asn
            100                 105                 110

Thr Ile Asn Gln Lys Lys Ala Thr Tyr Leu Lys Lys Val Glu Ala Gly
        115                 120                 125

Glu Ile Glu
    130


<210> SEQ ID NO 341
<211> LENGTH: 214
<212> TYPE: PRT
<213> ORGANISM: Lygus hesperus

<400> SEQUENCE: 341

Met Ala Pro Lys Gly Asn Asn Met Ile Pro Asn Gly His Phe His Lys
1               5                   10                  15

Asp Trp Gln Arg Phe Ile Lys Thr Trp Phe Asn Gln Pro Ala Arg Lys
            20                  25                  30

Leu Arg Arg Arg Asn Lys Arg Leu Glu Lys Ala Gln Arg Leu Ala Pro
        35                  40                  45

Arg Pro Ala Gly Pro Leu Arg Pro Ala Val Arg Cys Pro Thr Val Arg
    50                  55                  60

Tyr His Thr Lys Leu Arg Pro Gly Arg Gly Phe Thr Leu Glu Glu Ile
65                  70                  75                  80

Lys Arg Ala Gly Leu Cys Lys Gly Phe Ala Met Ser Ile Gly Ile Ala
                85                  90                  95

Val Asp Pro Arg Arg Arg Asn Lys Ser Ile Glu Ser Leu Gln Leu Asn
            100                 105                 110

Val Gln Arg Leu Lys Glu Tyr Arg Ala Lys Leu Ile Leu Phe Pro His
        115                 120                 125

Lys Asn Ala Lys Lys Leu Lys Lys Gly Glu Ala Thr Glu Glu Glu Arg
    130                 135                 140

Lys Val Ala Thr Gln Gln Pro Leu Pro Val Met Pro Ile Lys Gln Pro
145                 150                 155                 160

Val Ile Lys Phe Lys Ala Arg Val Ile Thr Asp Asp Glu Lys Lys Tyr
                165                 170                 175

Ser Ala Phe Thr Ala Leu Arg Lys Gly Arg Ala Asp Gln Arg Leu Val
            180                 185                 190

Gly Ile Arg Ala Lys Arg Ala Lys Glu Ala Ala Glu Asn Ala Glu Asp
        195                 200                 205

Pro Ser Lys Ala Pro Lys
    210


<210> SEQ ID NO 342
<211> LENGTH: 134
<212> TYPE: PRT
<213> ORGANISM: Lygus hesperus

<400> SEQUENCE: 342

Met Asp Ile Glu Glu Pro Ala Ala Ala Pro Thr Glu Pro Ser Asp Val
1               5                   10                  15

Asn Thr Ala Leu Gln Glu Val Leu Lys Ala Ala Leu Gln His Gly Val
            20                  25                  30

Val Val His Gly Ile His Glu Ser Ala Lys Ala Leu Asp Lys Arg Gln
        35                  40                  45
```

```
Ala Leu Leu Cys Val Leu Ala Glu Asn Cys Asp Glu Pro Met Tyr Lys
    50                  55                  60

Lys Leu Val Gln Ala Leu Cys Ser Glu His His Ile Pro Leu Val Lys
65                  70                  75                  80

Val Asp Ser Asn Lys Lys Leu Gly Glu Trp Thr Gly Leu Cys Lys Ile
                85                  90                  95

Asp Lys Thr Gly Lys Ser Arg Lys Ile Val Gly Cys Ser Cys Val Val
            100                 105                 110

Ile Lys Asp Trp Gly Glu Asp Thr Pro His Leu Asp Leu Leu Lys Asp
        115                 120                 125

Tyr Ile Arg Asp Val Phe
    130
```

<210> SEQ ID NO 343
<211> LENGTH: 148
<212> TYPE: PRT
<213> ORGANISM: Lygus hesperus

<400> SEQUENCE: 343

```
Met Lys Met Asn Lys Leu Val Thr Ser Ser Arg Arg Lys Asn Arg Lys
1               5                   10                  15

Arg His Phe Thr Ala Pro Ser His Ile Arg Arg Lys Leu Met Ser Ala
            20                  25                  30

Pro Leu Ser Lys Glu Leu Arg Gln Lys Tyr Asn Val Arg Thr Met Pro
        35                  40                  45

Val Arg Lys Asp Asp Glu Val Gln Val Val Arg Gly His Tyr Lys Gly
    50                  55                  60

Gln Gln Val Gly Lys Val Leu Gln Val Tyr Arg Lys Lys Phe Ile Ile
65                  70                  75                  80

Tyr Ile Glu Arg Ile Gln Arg Glu Lys Ala Asn Gly Ala Ser Val Tyr
                85                  90                  95

Val Gly Ile His Pro Ser Lys Cys Val Ile Val Lys Leu Lys Val Asp
            100                 105                 110

Lys Asp Arg Lys Glu Ile Leu Asp Arg Arg Ser Lys Gly Arg Asp Leu
        115                 120                 125

Ala Leu Gly Lys Asp Lys Gly Lys Tyr Thr Glu Asp Ser Thr Thr Ala
    130                 135                 140

Met Asp Thr Ser
145
```

<210> SEQ ID NO 344
<211> LENGTH: 65
<212> TYPE: PRT
<213> ORGANISM: Lygus hesperus

<400> SEQUENCE: 344

```
Met Glu Lys Pro Val Val Leu Ala Arg Val Ile Lys Ile Leu Gly Arg
1               5                   10                  15

Thr Gly Ser Gln Gly Gln Cys Thr Gln Val Lys Val Glu Phe Ile Gly
            20                  25                  30

Glu Gln Asn Arg Gln Ile Ile Arg Asn Val Lys Gly Pro Val Arg Glu
        35                  40                  45

Gly Asp Ile Leu Thr Leu Leu Glu Ser Glu Arg Glu Ala Arg Arg Leu
    50                  55                  60

Arg
65
```

<210> SEQ ID NO 345
<211> LENGTH: 229
<212> TYPE: PRT
<213> ORGANISM: Lygus hesperus

<400> SEQUENCE: 345

```
Leu Phe Tyr Phe Pro Phe Ser Arg Lys Trp Gly Asp Val Gln Arg Gly
1               5                   10                  15

Val Ile Gly Thr Val Lys Thr Ser His Thr Pro Lys Ser Arg Phe Cys
            20                  25                  30

Arg Gly Val Pro Asp Pro Lys Ile Arg Ile Phe Asp Leu Gly Lys Lys
        35                  40                  45

Lys Ala Arg Val Glu Asp Phe Pro Leu Cys Val His Leu Val Ser Asp
    50                  55                  60

Glu Tyr Glu Gln Leu Ser Ser Glu Ala Leu Glu Ala Gly Arg Ile Cys
65                  70                  75                  80

Cys Asn Lys Tyr Leu Val Lys Asn Cys Gly Lys Asp Gln Phe His Ile
                85                  90                  95

Arg Met Arg Leu His Pro Phe His Val Ile Arg Ile Asn Lys Met Leu
            100                 105                 110

Ser Cys Ala Gly Ala Asp Arg Leu Gln Thr Gly Met Arg Gly Ala Phe
        115                 120                 125

Gly Lys Pro Gln Gly Thr Val Ala Arg Val Arg Ile Gly Gln Pro Ile
    130                 135                 140

Met Ser Val Arg Ser Ser Asp Arg Tyr Lys Ala Ala Val Ile Lys Ala
145                 150                 155                 160

Leu Arg Arg Ala Lys Phe Lys Phe Pro Gly Arg Gln Lys Ile Tyr Val
                165                 170                 175

Ser Lys Lys Trp Gly Phe Thr Lys Phe Asp Arg Glu Glu Tyr Glu Gly
            180                 185                 190

Leu Arg Asn Asp Asn Lys Leu Ala Asn Asp Gly Cys Asn Val Lys Leu
        195                 200                 205

Arg Pro Asp His Gly Pro Leu Gln Ala Trp Arg Lys Ala Gln Leu Asp
    210                 215                 220

Ile Ala Ala Gly Leu
225
```

<210> SEQ ID NO 346
<211> LENGTH: 220
<212> TYPE: PRT
<213> ORGANISM: Lygus hesperus

<400> SEQUENCE: 346

```
Met Gly Arg Arg Pro Ala Arg Cys Tyr Arg Tyr Cys Lys Asn Lys Pro
1               5                   10                  15

Tyr Pro Lys Ser Arg Phe Cys Arg Gly Val Pro Asp Pro Lys Ile Arg
            20                  25                  30

Ile Phe Asp Leu Gly Lys Lys Lys Ala Arg Val Glu Asp Phe Pro Leu
        35                  40                  45

Cys Val His Leu Val Ser Asp Glu Tyr Glu Gln Leu Ser Ser Glu Ala
    50                  55                  60

Leu Glu Ala Gly Arg Ile Cys Cys Asn Lys Tyr Leu Val Lys Asn Cys
65                  70                  75                  80

Gly Lys Asp Gln Phe His Ile Arg Met Arg Leu His Pro Phe His Val
                85                  90                  95
```

```
Ile Arg Ile Asn Lys Met Leu Ser Cys Ala Gly Ala Asp Arg Leu Gln
            100                 105                 110

Thr Gly Met Arg Gly Ala Phe Gly Lys Pro Gln Gly Thr Val Ala Arg
        115                 120                 125

Val Arg Ile Gly Gln Pro Ile Met Ser Val Arg Ser Ser Asp Arg Tyr
    130                 135                 140

Lys Ala Ala Val Ile Glu Ala Leu Arg Arg Ala Lys Phe Lys Phe Pro
145                 150                 155                 160

Gly Arg Gln Lys Ile Tyr Val Ser Lys Lys Trp Gly Phe Thr Lys Phe
                165                 170                 175

Asp Arg Glu Glu Tyr Glu Gly Leu Arg Asn Asp Asn Lys Leu Ala Asn
            180                 185                 190

Gly Gly Cys Asn Val Lys Leu Arg Pro Asp His Gly Pro Leu Gln Ala
        195                 200                 205

Trp Arg Lys Ala Gln Leu Asp Ile Ala Ala Gly Leu
    210                 215                 220


<210> SEQ ID NO 347
<211> LENGTH: 159
<212> TYPE: PRT
<213> ORGANISM: Lygus hesperus

<400> SEQUENCE: 347

Met Thr Asn Ser Lys Gly Tyr Arg Arg Gly Thr Arg Asp Leu Phe Ser
1               5                   10                  15

Arg Pro Phe Arg His His Gly Val Ile Pro Leu Ser Thr Tyr Met Lys
            20                  25                  30

Val Tyr Arg Val Gly Asp Ile Val Ser Ile Lys Gly Asn Gly Ala Val
        35                  40                  45

Gln Lys Gly Met Pro His Lys Val Tyr His Gly Lys Thr Gly Arg Val
    50                  55                  60

Tyr Asn Val Thr Pro Arg Ala Leu Gly Val Ile Val Asn Lys Arg Val
65                  70                  75                  80

Arg Gly Lys Ile Leu Pro Lys Arg Ile Asn Ile Arg Ile Glu His Val
                85                  90                  95

Asn His Ser Lys Cys Arg Glu Asp Phe Leu Lys Arg Val Arg Glu Asn
            100                 105                 110

Glu Arg Leu Arg Lys Phe Ala Lys Glu Thr Gly Thr Arg Val Glu Leu
        115                 120                 125

Lys Arg Gln Pro Ala Gln Pro Arg Pro Ala His Phe Val Gln Ala Lys
    130                 135                 140

Glu Val Pro Glu Leu Leu Ala Pro Ile Pro Tyr Glu Phe Ile Ala
145                 150                 155


<210> SEQ ID NO 348
<211> LENGTH: 131
<212> TYPE: PRT
<213> ORGANISM: Lygus hesperus

<400> SEQUENCE: 348

Thr Tyr Met Lys Val Tyr Arg Val Gly Asp Ile Val Ser Ile Lys Gly
1               5                   10                  15

Asn Gly Ala Val Gln Lys Gly Met Pro His Lys Val Tyr His Gly Lys
            20                  25                  30

Thr Gly Arg Val Tyr Asn Val Thr Pro Arg Ala Leu Gly Val Ile Val
        35                  40                  45
```

```
Asn Lys Arg Val Arg Gly Lys Ile Leu Pro Lys Arg Ile Asn Ile Arg
    50                  55                  60

Ile Glu His Val Asn His Ser Lys Cys Arg Glu Asp Phe Leu Lys Arg
65                  70                  75                  80

Val Arg Glu Asn Glu Arg Leu Arg Lys Phe Ala Lys Glu Thr Gly Thr
                85                  90                  95

Arg Val Glu Leu Lys Arg Gln Pro Ala Gln Pro Arg Pro Ala His Phe
            100                 105                 110

Val Gln Ala Lys Glu Val Pro Glu Leu Leu Ala Pro Ile Pro Tyr Glu
        115                 120                 125

Phe Ile Ala
    130


<210> SEQ ID NO 349
<211> LENGTH: 150
<212> TYPE: PRT
<213> ORGANISM: leptinotarsa decemlineata

<400> SEQUENCE: 349

Lys Lys Ala Lys Lys Gly Phe Met Thr Pro Glu Arg Lys Lys Lys Leu
1               5                   10                  15

Arg Leu Leu Leu Arg Lys Lys Ala Ala Glu Glu Leu Lys Lys Glu Gln
            20                  25                  30

Glu Arg Lys Ala Ala Glu Arg Arg Arg Ile Ile Glu Glu Arg Cys Gly
        35                  40                  45

Lys Pro Lys Leu Ile Asp Glu Ala Asn Glu Glu Gln Val Arg Asn Tyr
    50                  55                  60

Cys Lys Leu Tyr His Gly Arg Ile Ala Lys Leu Glu Asp Gln Lys Phe
65                  70                  75                  80

Asp Leu Glu Tyr Leu Val Lys Lys Lys Asp Met Glu Ile Ala Glu Leu
                85                  90                  95

Asn Ser Gln Val Asn Asp Leu Arg Gly Lys Phe Val Lys Pro Thr Leu
            100                 105                 110

Lys Lys Val Ser Lys Tyr Glu Asn Lys Phe Ala Lys Leu Gln Lys Lys
        115                 120                 125

Ala Ala Glu Phe Asn Phe Arg Asn Gln Leu Lys Val Val Lys Lys Lys
    130                 135                 140

Glu Phe Thr Leu Glu Glu
145                 150


<210> SEQ ID NO 350
<211> LENGTH: 279
<212> TYPE: PRT
<213> ORGANISM: leptinotarsa decemlineata

<400> SEQUENCE: 350

Gln Trp Tyr Gln Arg Arg Val Arg Gly Asp Ile Glu Glu Lys Arg Gln
1               5                   10                  15

Arg Leu Glu Glu Ala Glu Lys Lys Arg Gln Ala Met Met Gln Ala Leu
            20                  25                  30

Lys Asp Gln Asn Lys Asn Lys Gly Pro Asn Phe Thr Ile Thr Lys Arg
        35                  40                  45

Asp Ala Ser Ser Asn Leu Ser Ala Ala Gln Leu Glu Arg Asn Lys Thr
    50                  55                  60

Lys Glu Gln Leu Glu Glu Glu Lys Lys Ile Ser Leu Ser Ile Arg Ile
65                  70                  75                  80
```

```
Lys Pro Leu Val Val Asp Gly Leu Gly Val Asp Lys Leu Arg Leu Lys
                85                  90                  95

Ala Gln Glu Leu Trp Glu Cys Ile Val Lys Leu Glu Thr Glu Lys Tyr
            100                 105                 110

Asp Leu Glu Glu Arg Gln Lys Arg Gln Asp Tyr Asp Leu Lys Glu Leu
        115                 120                 125

Lys Glu Arg Gln Lys Gln Gln Leu Arg His Lys Ala Leu Lys Lys Gly
    130                 135                 140

Leu Asp Pro Glu Ala Leu Thr Gly Lys Tyr Pro Pro Lys Ile Gln Val
145                 150                 155                 160

Ala Ser Lys Tyr Glu Arg Arg Val Asp Thr Arg Ser Tyr Gly Asp Lys
                165                 170                 175

Lys Lys Leu Phe Glu Gly Gly Leu Glu Glu Ile Ile Lys Glu Thr Asn
            180                 185                 190

Glu Lys Ser Trp Lys Glu Lys Phe Gly Gln Phe Asp Ser Arg Gln Lys
        195                 200                 205

Ala Arg Leu Pro Lys Trp Phe Gly Glu Arg Pro Gly Lys Lys Pro Gly
    210                 215                 220

Asp Pro Glu Thr Pro Glu Gly Glu Glu Glu Gly Lys Gln Val Ile Asp
225                 230                 235                 240

Glu Asp Asp Asp Leu Lys Glu Pro Val Ile Glu Ala Glu Ile Glu Glu
                245                 250                 255

Glu Glu Glu Glu Glu Glu Val Glu Val Asp Glu Glu Glu Glu Asp Asp
            260                 265                 270

Glu Glu Glu Glu Glu Glu Glu
        275


<210> SEQ ID NO 351
<211> LENGTH: 286
<212> TYPE: PRT
<213> ORGANISM: leptinotarsa decemlineata

<400> SEQUENCE: 351

Ala Leu Gln Asn Glu Leu Glu Glu Ser Arg Thr Leu Leu Glu Gln Ala
1               5                   10                  15

Asp Arg Ala Arg Arg Gln Ala Glu Gln Glu Leu Gly Asp Ala His Glu
            20                  25                  30

Gln Leu Asn Asp Leu Gly Ala Gln Asn Gly Ser Leu Ser Ala Ala Lys
        35                  40                  45

Arg Lys Leu Glu Thr Glu Leu Gln Thr Leu His Ser Asp Leu Asp Glu
    50                  55                  60

Leu Leu Asn Glu Ala Lys Asn Ser Glu Glu Lys Ala Lys Lys Ala Met
65                  70                  75                  80

Val Asp Ala Ala Arg Leu Ala Asp Glu Leu Arg Ala Glu Gln Asp His
                85                  90                  95

Ala Gln Thr Gln Glu Lys Leu Arg Lys Ala Leu Glu Ser Gln Ile Lys
            100                 105                 110

Asp Leu Gln Val Arg Leu Asp Glu Ala Glu Ala Asn Ala Leu Lys Gly
        115                 120                 125

Gly Lys Lys Ala Ile Ala Lys Leu Glu Gln Arg Val Arg Glu Leu Glu
    130                 135                 140

Asn Glu Leu Asp Gly Glu Gln Arg Arg His Ala Asp Ala Gln Lys Asn
145                 150                 155                 160

Leu Arg Lys Ser Glu Arg Arg Ile Lys Glu Leu Ser Leu Gln Ala Glu
```

```
                165                 170                 175

Glu Asp Arg Lys Asn His Glu Lys Met Gln Asp Leu Val Asp Lys Leu
            180                 185                 190

Gln Gln Lys Ile Lys Thr His Lys Arg Gln Ile Glu Glu Ala Glu Glu
        195                 200                 205

Ile Ala Ala Leu Asn Leu Ala Lys Phe Arg Lys Ala Gln Gln Glu Leu
    210                 215                 220

Glu Glu Ala Glu Glu Arg Ala Asp Leu Ala Glu Gln Ala Ile Val Lys
225                 230                 235                 240

Phe Arg Thr Lys Gly Arg Ser Gly Ser Ala Ala Arg Gly Ala Ser Pro
                245                 250                 255

Ala Pro Gln Arg Gln Arg Pro Thr Phe Gly Met Gly Asp Ser Leu Gly
            260                 265                 270

Gly Ala Phe Pro Pro Arg Phe Asp Leu Ala Pro Asp Phe Glu
        275                 280                 285


<210> SEQ ID NO 352
<211> LENGTH: 197
<212> TYPE: PRT
<213> ORGANISM: nilaparvata lugens

<400> SEQUENCE: 352

Met Ala Asp Asp Glu Ala Lys Lys Ala Lys Gln Ala Glu Ile Asp Arg
1               5                   10                  15

Lys Arg Ala Glu Val Arg Lys Arg Met Glu Glu Ala Ser Lys Ala Lys
            20                  25                  30

Lys Ala Lys Lys Gly Phe Met Thr Pro Asp Arg Lys Lys Lys Leu Arg
        35                  40                  45

Leu Leu Leu Arg Lys Lys Ala Ala Glu Glu Leu Lys Lys Glu Gln Glu
    50                  55                  60

Arg Lys Ala Ala Glu Arg Arg Arg Ile Ile Glu Glu Arg Cys Gly Lys
65                  70                  75                  80

Ala Val Asp Leu Asp Asp Gly Ser Glu Glu Lys Val Lys Ala Thr Leu
                85                  90                  95

Lys Thr Tyr His Asp Arg Ile Gly Lys Leu Glu Asp Glu Lys Phe Asp
            100                 105                 110

Leu Glu Tyr Ile Val Lys Lys Lys Asp Phe Glu Ile Ala Asp Leu Asn
        115                 120                 125

Ser Gln Val Asn Asp Leu Arg Gly Lys Phe Val Lys Pro Thr Leu Lys
    130                 135                 140

Lys Val Ser Lys Tyr Glu Asn Lys Phe Ala Lys Leu Gln Lys Lys Ala
145                 150                 155                 160

Ala Glu Phe Asn Phe Arg Asn Gln Leu Lys Val Val Lys Lys Lys Glu
                165                 170                 175

Phe Thr Leu Glu Glu Glu Asp Lys Glu Pro Lys Lys Ser Glu Lys Ala
            180                 185                 190

Glu Trp Gln Lys Lys
        195


<210> SEQ ID NO 353
<211> LENGTH: 184
<212> TYPE: PRT
<213> ORGANISM: nilaparvata lugens

<400> SEQUENCE: 353

Met Met Ala Ala Leu Lys Asp Gln Ser Lys Ser Lys Gly Pro Asn Phe
```

```
1               5                   10                  15

Thr Val Asn Lys Lys Thr Asp Leu Asn Met Thr Ser Ala Gln Met Glu
            20                  25                  30

Arg Asn Lys Thr Lys Glu Gln Leu Glu Glu Glu Lys Lys Ile Ser Leu
        35                  40                  45

Ser Phe Arg Ile Lys Pro Leu Ala Ile Glu Asn Met Ser Ile Asn Ala
    50                  55                  60

Leu Arg Ala Lys Ala Gln Glu Leu Trp Asp Cys Ile Val Lys Leu Glu
65                  70                  75                  80

Thr Glu Lys Tyr Asp Leu Glu Glu Arg Gln Lys Arg Gln Asp Tyr Asp
                85                  90                  95

Leu Lys Glu Leu Lys Glu Arg Gln Lys Gln Gln Leu Arg His Lys Ala
            100                 105                 110

Leu Lys Lys Gly Leu Asp Pro Glu Ala Leu Thr Gly Lys Tyr Pro Pro
        115                 120                 125

Lys Ile Gln Val Ala Ser Lys Tyr Glu Arg Arg Val Asp Thr Arg Ser
    130                 135                 140

Tyr Asp Asp Lys Lys Lys Leu Phe Glu Gly Gly Trp Asp Thr Leu Thr
145                 150                 155                 160

Ser Glu Thr Asn Glu Lys Ile Trp Lys Ser Arg Asn Asp Gln Phe Ser
                165                 170                 175

Asn Arg Ser Lys Ala Lys Leu Pro
            180


<210> SEQ ID NO 354
<211> LENGTH: 122
<212> TYPE: PRT
<213> ORGANISM: nilaparvata lugens

<400> SEQUENCE: 354

Ala Phe Asp Arg Glu Arg Ser Gly Ser Ile Pro Thr Asp Met Val Ala
1               5                   10                  15

Asp Ile Leu Arg Leu Met Gly Gln Pro Phe Asn Lys Lys Ile Leu Asp
            20                  25                  30

Glu Leu Ile Glu Glu Val Asp Ala Asp Lys Ser Gly Arg Leu Glu Phe
        35                  40                  45

Asp Glu Phe Val Thr Leu Ala Ala Lys Phe Ile Val Glu Glu Asp Asp
    50                  55                  60

Glu Ala Met Gln Lys Glu Leu Lys Glu Ala Phe Arg Leu Tyr Asp Lys
65                  70                  75                  80

Glu Gly Asn Gly Tyr Ile Pro Thr Ser Cys Leu Lys Glu Ile Leu Arg
                85                  90                  95

Glu Leu Asp Asp Gln Leu Thr Asn Glu Glu Leu Asn Met Met Ile Asp
            100                 105                 110

Glu Ile Asp Ser Asp Gly Ser Gly Thr Val
        115                 120


<210> SEQ ID NO 355
<211> LENGTH: 73
<212> TYPE: PRT
<213> ORGANISM: nilaparvata lugens

<400> SEQUENCE: 355

Val Lys Thr Leu Thr Gly Lys Thr Ile Thr Leu Glu Val Glu Pro Ser
1               5                   10                  15

Asp Thr Ile Glu Asn Val Lys Ala Lys Ile Gln Asp Lys Glu Gly Ile
```

```
            20                  25                  30

Pro Pro Asp Gln Gln Arg Leu Ile Phe Ala Gly Lys Gln Leu Glu Asp
        35                  40                  45

Gly Arg Thr Leu Ser Asp Tyr Asn Ile Gln Lys Glu Ser Thr Leu His
    50                  55                  60

Leu Val Leu Arg Leu Arg Gly Gly Thr
65                  70


<210> SEQ ID NO 356
<211> LENGTH: 253
<212> TYPE: PRT
<213> ORGANISM: Acyrthosiphon pisum

<400> SEQUENCE: 356

Met Ala Asp Asp Glu Ala Lys Lys Ala Lys Gln Ala Glu Ile Asp Arg
1               5                   10                  15

Lys Arg Ala Glu Val Arg Lys Arg Met Glu Glu Ala Ser Lys Ala Lys
            20                  25                  30

Lys Ala Lys Lys Gly Phe Met Thr Pro Asp Arg Lys Lys Lys Leu Arg
        35                  40                  45

Leu Leu Leu Lys Lys Lys Ala Ala Glu Glu Leu Lys Lys Glu Gln Glu
    50                  55                  60

Arg Lys Ala Ala Glu Arg Arg Arg Ile Ile Glu Glu Arg Cys Gly Gln
65                  70                  75                  80

Pro Lys Asn Ile Asp Asp Ala Gly Glu Glu Glu Leu Ala Glu Ile Cys
                85                  90                  95

Glu Glu Leu Trp Lys Arg Val Tyr Thr Val Glu Gly Ile Lys Phe Asp
            100                 105                 110

Leu Glu Arg Asp Ile Arg Met Lys Val Phe Glu Ile Ser Glu Leu Asn
        115                 120                 125

Ser Gln Val Asn Asp Leu Arg Gly Lys Phe Val Lys Pro Thr Leu Lys
    130                 135                 140

Lys Val Ser Lys Tyr Glu Asn Lys Phe Ala Lys Leu Gln Lys Lys Ala
145                 150                 155                 160

Ala Glu Phe Asn Phe Arg Asn Gln Leu Lys Val Val Lys Lys Lys Glu
                165                 170                 175

Phe Thr Leu Glu Glu Glu Asp Lys Glu Lys Lys Pro Asp Trp Ser Lys
            180                 185                 190

Lys Gly Asp Glu Lys Lys Gly Glu Gly Glu Asp Gly Asp Gly Thr Glu
        195                 200                 205

Asp Glu Lys Thr Asp Asp Gly Leu Thr Thr Glu Gly Glu Ser Val Ala
    210                 215                 220

Gly Asp Leu Thr Asp Ala Thr Glu Asp Ala Gln Ser Asp Asn Glu Ile
225                 230                 235                 240

Leu Glu Pro Glu Pro Val Val Glu Pro Glu Pro Glu Pro
                245                 250


<210> SEQ ID NO 357
<211> LENGTH: 179
<212> TYPE: PRT
<213> ORGANISM: Acyrthosiphon pisum

<400> SEQUENCE: 357

Val Met Arg Cys Gly Lys Lys Lys Val Trp Leu Asp Pro Asn Glu Ile
1               5                   10                  15

Asn Glu Ile Ala Asn Thr Asn Ser Arg Gln Asn Ile Arg Lys Leu Ile
```

```
            20                  25                  30

Lys Asp Gly Leu Ile Ile Lys Lys Pro Val Ala Val His Ser Arg Ala
        35                  40                  45

Arg Ala Arg Lys Asn Ala Asp Ala Arg Arg Lys Gly Arg His Cys Gly
    50                  55                  60

Phe Gly Lys Arg Lys Gly Thr Ala Asn Ala Arg Thr Pro Gln Lys Asp
65                  70                  75                  80

Leu Trp Val Lys Arg Met Arg Val Leu Arg Arg Leu Leu Lys Lys Tyr
                85                  90                  95

Arg Glu Ala Lys Lys Ile Asp Asn His Leu Tyr His Gln Leu Tyr Met
            100                 105                 110

Lys Ala Lys Gly Asn Val Phe Lys Asn Lys Arg Val Leu Met Glu Phe
        115                 120                 125

Ile His Lys Lys Lys Ala Glu Lys Ala Arg Ala Lys Met Leu Ser Asp
    130                 135                 140

Gln Ala Glu Ala Arg Arg Gln Lys Val Lys Glu Ala Arg Lys Arg Lys
145                 150                 155                 160

Glu Ala Arg Phe Leu Gln Asn Arg Lys Glu Leu Leu Ala Ala Tyr Ala
                165                 170                 175

Arg Glu Asp


<210> SEQ ID NO 358
<211> LENGTH: 275
<212> TYPE: PRT
<213> ORGANISM: Acyrthosiphon pisum

<400> SEQUENCE: 358

Gly Leu Glu Val Glu Ser Ser Asp Ser Ile Glu Asn Val Lys Ala Lys
1               5                   10                  15

Ile Gln Asp Lys Glu Gly Ile Pro Pro Asp Gln Gln Arg Leu Ile Phe
            20                  25                  30

Ala Gly Lys Gln Leu Glu Asp Gly Arg Thr Leu Ser Asp Tyr Asn Ile
        35                  40                  45

Gln Lys Glu Ser Thr Leu His Leu Val Leu Arg Leu Arg Gly Gly Met
    50                  55                  60

Gln Ile Phe Val Lys Thr Leu Thr Gly Lys Thr Ile Thr Leu Glu Val
65                  70                  75                  80

Glu Ser Ser Asp Ser Ile Glu Asn Val Lys Ala Lys Ile Gln Asp Lys
                85                  90                  95

Glu Gly Ile Pro Pro Asp Gln Gln Arg Leu Ile Phe Ala Gly Lys Gln
            100                 105                 110

Leu Glu Asp Gly Arg Thr Leu Ser Asp Tyr Asn Ile Gln Lys Glu Ser
        115                 120                 125

Thr Leu His Leu Val Leu Arg Leu Arg Gly Gly Met Gln Ile Phe Val
    130                 135                 140

Lys Thr Leu Thr Gly Lys Thr Ile Thr Leu Glu Val Glu Ser Ser Asp
145                 150                 155                 160

Ser Ile Glu Asn Val Lys Ala Lys Ile Gln Asp Lys Glu Gly Ile Pro
                165                 170                 175

Pro Asp Gln Gln Arg Leu Ile Phe Ala Gly Lys Gln Leu Glu Asp Gly
            180                 185                 190

Arg Thr Leu Ser Asp Tyr Asn Ile Gln Lys Glu Ser Thr Leu His Leu
        195                 200                 205

Val Leu Arg Leu Arg Gly Gly Met Gln Ile Phe Val Lys Thr Leu Thr
```

```
    210                 215                 220

Gly Lys Thr Ile Thr Leu Glu Val Glu Ser Ser Asp Ser Ile Glu Asn
225                 230                 235                 240

Val Lys Ala Lys Ile Gln Asp Lys Glu Gly Ile Pro Pro Asp Gln Gln
                245                 250                 255

Arg Leu Ile Phe Ala Gly Lys Gln Leu Glu Asp Gly Arg Thr Leu Ser
            260                 265                 270

Asp Tyr Asn
        275


<210> SEQ ID NO 359
<211> LENGTH: 56
<212> TYPE: PRT
<213> ORGANISM: Acyrthosiphon pisum

<400> SEQUENCE: 359

Asp Leu Leu His Pro Thr Ala Ile Glu Glu Arg Arg Lys His Lys Leu
1               5                   10                  15

Lys Arg Leu Val Gln His Pro Asn Ser Phe Phe Met Asp Val Lys Cys
            20                  25                  30

Pro Gly Cys Tyr Lys Ile Thr Thr Val Phe Ser His Ala Gln Ser Val
        35                  40                  45

Val Ile Cys Thr Gly Cys Ser Thr
    50                  55


<210> SEQ ID NO 360
<211> LENGTH: 20
<212> TYPE: DNA
<213> ORGANISM: Artificial
<220> FEATURE:
<223> OTHER INFORMATION: Primer

<400> SEQUENCE: 360

atcatgcagg cgtacgcccg                                                   20


<210> SEQ ID NO 361
<211> LENGTH: 19
<212> TYPE: DNA
<213> ORGANISM: Artificial
<220> FEATURE:
<223> OTHER INFORMATION: Primer

<400> SEQUENCE: 361

cggagggggc gagatcact                                                    19


<210> SEQ ID NO 362
<211> LENGTH: 62
<212> TYPE: DNA
<213> ORGANISM: Artificial
<220> FEATURE:
<223> OTHER INFORMATION: Amplicon

<400> SEQUENCE: 362

atcatgcagg cgtacgcccg agaagacgag gctgccgtca aaaagtgatc tcgccccctc      60

cg                                                                      62


<210> SEQ ID NO 363
<211> LENGTH: 22
<212> TYPE: DNA
<213> ORGANISM: Artificial
<220> FEATURE:
<223> OTHER INFORMATION: Primer
```

<400> SEQUENCE: 363
tgtgttggct actggtggct ac 22

<210> SEQ ID NO 364
<211> LENGTH: 25
<212> TYPE: DNA
<213> ORGANISM: Artificial
<220> FEATURE:
<223> OTHER INFORMATION: Primer

<400> SEQUENCE: 364
tcggatggaa ctggacaaat tcaag 25

<210> SEQ ID NO 365
<211> LENGTH: 137
<212> TYPE: DNA
<213> ORGANISM: Artificial
<220> FEATURE:
<223> OTHER INFORMATION: Amplicon

<400> SEQUENCE: 365
tgtgttggct actggtggct acggcagagc ttacttttca tgcacttcag ctcacacttg 60
cacgggagat ggccaagcaa tggtttcacg agctgggctt cccaacgaag atcttgaatt 120
tgtccagttc catccga 137

<210> SEQ ID NO 366
<211> LENGTH: 21
<212> TYPE: DNA
<213> ORGANISM: Artificial
<220> FEATURE:
<223> OTHER INFORMATION: Primer

<400> SEQUENCE: 366
gcaacccgtg ttctccaaag c 21

<210> SEQ ID NO 367
<211> LENGTH: 28
<212> TYPE: DNA
<213> ORGANISM: Artificial
<220> FEATURE:
<223> OTHER INFORMATION: Primer

<400> SEQUENCE: 367
tcaactcgta ttctcgtact ttcaaacc 28

<210> SEQ ID NO 368
<211> LENGTH: 146
<212> TYPE: DNA
<213> ORGANISM: Artificial
<220> FEATURE:
<223> OTHER INFORMATION: Amplicon

<400> SEQUENCE: 368
gcaacccgtg ttctccaaag ccagatacac tgtgcgatcc ttcggtatca ggcgtaacga 60
aaaaatcgcc gttcactgca ctgtcagggg cgccaaagca gaggaaattc tggagcgtgg 120
tttgaaagta cgagaatacg agttga 146

<210> SEQ ID NO 369
<211> LENGTH: 21
<212> TYPE: DNA
<213> ORGANISM: Artificial
<220> FEATURE:

<223> OTHER INFORMATION: Primer

<400> SEQUENCE: 369
atggccgacg atgaagctaa g 21

<210> SEQ ID NO 370
<211> LENGTH: 20
<212> TYPE: DNA
<213> ORGANISM: Artificial
<220> FEATURE:
<223> OTHER INFORMATION: Primer

<400> SEQUENCE: 370
tggttctggt tcgggttcaa 20

<210> SEQ ID NO 371
<211> LENGTH: 20
<212> TYPE: DNA
<213> ORGANISM: Artificial
<220> FEATURE:
<223> OTHER INFORMATION: Primer

<400> SEQUENCE: 371
cggtaatgcg atgcggtaag 20

<210> SEQ ID NO 372
<211> LENGTH: 20
<212> TYPE: DNA
<213> ORGANISM: Artificial
<220> FEATURE:
<223> OTHER INFORMATION: Primer

<400> SEQUENCE: 372
tcatcttctc gggcgtatgc 20

<210> SEQ ID NO 373
<211> LENGTH: 25
<212> TYPE: DNA
<213> ORGANISM: Artificial
<220> FEATURE:
<223> OTHER INFORMATION: Primer

<400> SEQUENCE: 373
tttggaagtt gagtcatcag attcc 25

<210> SEQ ID NO 374
<211> LENGTH: 24
<212> TYPE: DNA
<213> ORGANISM: Artificial
<220> FEATURE:
<223> OTHER INFORMATION: Primer

<400> SEQUENCE: 374
gttgtagtcg gaaagggtac gtcc 24

<210> SEQ ID NO 375
<211> LENGTH: 20
<212> TYPE: DNA
<213> ORGANISM: Artificial
<220> FEATURE:
<223> OTHER INFORMATION: Primer

<400> SEQUENCE: 375
attgtggaac atccggtaca 20

<210> SEQ ID NO 376
<211> LENGTH: 23
<212> TYPE: DNA
<213> ORGANISM: Artificial
<220> FEATURE:
<223> OTHER INFORMATION: Primer

<400> SEQUENCE: 376
aagacttgct tcatcctact gca 23

<210> SEQ ID NO 377
<211> LENGTH: 28
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (20)..(20)
<223> OTHER INFORMATION: n is a, c, g, or t

<400> SEQUENCE: 377
ccaagaaggc caagaagggn ttyatgac 28

<210> SEQ ID NO 378
<211> LENGTH: 29
<212> TYPE: DNA
<213> ORGANISM: Artificial
<220> FEATURE:
<223> OTHER INFORMATION: Primer

<400> SEQUENCE: 378
tcctcctcca gggtgaactc yttyttytt 29

<210> SEQ ID NO 379
<211> LENGTH: 26
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 379
gccaagaagg gcttcatgac nccnga 26

<210> SEQ ID NO 380
<211> LENGTH: 27
<212> TYPE: DNA
<213> ORGANISM: Artificial
<220> FEATURE:
<223> OTHER INFORMATION: Primer

<400> SEQUENCE: 380
gaagttgaac tcggcggcyt tyttytg 27

<210> SEQ ID NO 381
<211> LENGTH: 26
<212> TYPE: DNA
<213> ORGANISM: Artificial
<220> FEATURE:
<223> OTHER INFORMATION: Primer
<220> FEATURE:

<221> NAME/KEY: misc_feature
<222> LOCATION: (24)..(24)
<223> OTHER INFORMATION: n is a, c, g, or t

<400> SEQUENCE: 381
ctggaggagg ccgagaaraa rmgnca 26

<210> SEQ ID NO 382
<211> LENGTH: 22
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (14)..(14)
<223> OTHER INFORMATION: n is a, c, g, or t

<400> SEQUENCE: 382
tgccgggccg ctcnccraac ca 22

<210> SEQ ID NO 383
<211> LENGTH: 28
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 383
agatcgccat cctgaggaan gcnttyra 28

<210> SEQ ID NO 384
<211> LENGTH: 31
<212> TYPE: DNA
<213> ORGANISM: Artificial
<220> FEATURE:
<223> OTHER INFORMATION: Primer

<400> SEQUENCE: 384
cggtcatcat ctccatgaac tcrtcraart c 31

<210> SEQ ID NO 385
<211> LENGTH: 170
<212> TYPE: DNA
<213> ORGANISM: Artificial
<220> FEATURE:
<223> OTHER INFORMATION: Intron

<400> SEQUENCE: 385
tctagaaggt aagtgtacac actacatttt catgaacatt attgcgaccg ttgagattct 60
cattgtttgg tgattgatta tctaaagtag aagcatgaat agatataaca taaactagta 120
actaatgggt tagttatggg tatacttcat gcttttctct caggctcgag 170

<210> SEQ ID NO 386
<211> LENGTH: 521
<212> TYPE: DNA
<213> ORGANISM: leptinotarsa decemlineata

<400> SEQUENCE: 386

```
tcgatttttc atttttcttt tattatttgg agtgggcctg ttgtggtcgt tatcaaaatg     60

ggtaaaataa tgaaatctgg taaagtcgta ttggtccttg gaggccgata cgctggaaga    120

aaggcagtag tcataaaaaa ttacgatgat gggacgtcag ataaacaata tggacatgcc    180

gtggtggctg gaatcgatag gtaccctaga aaaatccaca aacgtatggg caaaggaaaa    240

atgcacaaga ggtccaaaat caagcccttc cttaaggtgc tcaactataa ccatttgatg    300

cctacaagat attcagtgga tttgacttcg gacttgaaag tggcgcccaa agacctcaag    360

gatccagtga agaggaagaa gattaggttc caaaccagag ttaaattcga agagagatac    420

aagcaaggaa aacacaaatg gtttttccag aaattgaggt tctagattct ataaatttaa    480

ccattttgta atccacccac ctttttgttc aaataaattg t                         521
```

<210> SEQ ID NO 387
<211> LENGTH: 475
<212> TYPE: DNA
<213> ORGANISM: leptinotarsa decemlineata

<400> SEQUENCE: 387

```
tatcgcgaaa aatatacaac ttacaaaatg aggaacacgt atgagttgag ccctaaagaa     60

gcagcaaatt tcactcgtcg aaatttagca gatactcttc gaagcaggag tccatatcat    120

gttaatcttc tcttggctgg atatgacaag aaagacgggg ctcagttgta ttacatggat    180

tatctagcgt ctgttgctag tgttgattac gctgcccatg gatacggagg atatttctcc    240

ctttccataa tggatcgcaa ttatttgaaa accctgtcga aagatcaagg atacgaactt    300

ctgaaggaat gtgttaaaga agttcaaaag agacttgcta taaatttacc aaatttcaaa    360

gttcaggtta ttgataaaga tggtattaag gatatgccta atataacttc aaaaggtttg    420

aattgattaa gcaacttcag tttcagattt ttttctaaat aaacatttaa agtgt          475
```

<210> SEQ ID NO 388
<211> LENGTH: 467
<212> TYPE: DNA
<213> ORGANISM: leptinotarsa decemlineata

<400> SEQUENCE: 388

```
gcggggactg gatacatctc taaaacacag aaaaatgaaa ttcttcaagt caggaatata     60

ttctgttgta tttttggcaa ttatattttc tttggtcact gaggaagtgg aaggtcgaag    120

gactatttta agagggcgta aaacactgac gagaacctat tttcgtgaca atgcagtccc    180

agcatacgtc atagtgatac tcgttggaat aggagaaatc attttgggag ctatcctgta    240

tgttataatg aggaaaacga taatagattt tcctttatca gggagttacg cagtggcccc    300

tactcaagaa gcataaatcc cattgaaatt gtgactgttt actttctttg gaaaaatgtg    360

tataataaat acaattcatt tataatattt atatttggaa cttaaaatac ttacaaaatt    420

accatttaca tgatcaaata actaataaag ttctgtctca attataa                  467
```

<210> SEQ ID NO 389
<211> LENGTH: 906
<212> TYPE: DNA
<213> ORGANISM: leptinotarsa decemlineata

<400> SEQUENCE: 389

```
ggattggaag taaaaatata caattcatgc tgtagctgta gtgtaaaaac tgaactgaaa     60

gccataaaat aaagaccttg caagaaacat gtccaagatt aatgaggtgt ctaatttgta    120
```

```
caaacaactg aaatcagaat ggaacacatc caatccaaat ttaagcaaat gtgaaaagct    180

tttgtcagat ttgaagcttg agctaacaca cttaatgttc cttccaactt caaacgccac    240

tgcttcaaaa caagaacttc ttctggcaag agatgttctg gaaattgggg tacaatggag    300

tatagctgca aatgatatac ctgcctttga aagatacatg gcacagttga aatgttatta    360

tttcgattat aagaatcaac ttcccgaatc ttctttcaaa tatcagttac tgggtctgaa    420

tttactattt ttgttatcac aaaatagagt ggcagagttc cacacagaat tagaattgtt    480

gcctgctgac cacattcaga atgatgtata catcaggcac cctccatcta ttgaacagta    540

ccttatggaa ggaagttata ataagatatt tctggcaaag ggaaatgtcc cagcaacaaa    600

ttacaatttt tttatggata tacttctaga tactatcaga ggggagattg cagattgtct    660

agagaaagca tatgaaaaaa tatcaattaa agatgttgct aggatgctat acttgggcag    720

tgaagaatcg gccaaggcct ttgtaacaaa gagtaagaca tggaaattag aaaaggacaa    780

cttctttcac ttcacgcccg aggttaaaaa gacacatgag ccaattctat ccaaagaatt    840

ggcacaacaa gctattgaat atgcaaaaga actggaaatg attgtttaaa gtaataaagt    900

ttttca                                                               906
```

<210> SEQ ID NO 390
<211> LENGTH: 135
<212> TYPE: PRT
<213> ORGANISM: leptinotarsa decemlineata

<400> SEQUENCE: 390

```
Met Gly Lys Ile Met Lys Ser Gly Lys Val Val Leu Val Leu Gly Gly
1               5                   10                  15

Arg Tyr Ala Gly Arg Lys Ala Val Val Ile Lys Asn Tyr Asp Asp Gly
            20                  25                  30

Thr Ser Asp Lys Gln Tyr Gly His Ala Val Val Ala Gly Ile Asp Arg
        35                  40                  45

Tyr Pro Arg Lys Ile His Lys Arg Met Gly Lys Gly Lys Met His Lys
    50                  55                  60

Arg Ser Lys Ile Lys Pro Phe Leu Lys Val Leu Asn Tyr Asn His Leu
65                  70                  75                  80

Met Pro Thr Arg Tyr Ser Val Asp Leu Thr Ser Asp Leu Lys Val Ala
                85                  90                  95

Pro Lys Asp Leu Lys Asp Pro Val Lys Arg Lys Lys Ile Arg Phe Gln
            100                 105                 110

Thr Arg Val Lys Phe Glu Glu Arg Tyr Lys Gln Gly Lys His Lys Trp
        115                 120                 125

Phe Phe Gln Lys Leu Arg Phe
    130                 135
```

<210> SEQ ID NO 391
<211> LENGTH: 141
<212> TYPE: PRT
<213> ORGANISM: leptinotarsa decemlineata

<400> SEQUENCE: 391

```
Tyr Arg Glu Lys Tyr Thr Thr Tyr Lys Met Arg Asn Thr Tyr Glu Leu
1               5                   10                  15

Ser Pro Lys Glu Ala Ala Asn Phe Thr Arg Arg Asn Leu Ala Asp Thr
            20                  25                  30

Leu Arg Ser Arg Ser Pro Tyr His Val Asn Leu Leu Leu Ala Gly Tyr
        35                  40                  45
```

```
Asp Lys Lys Asp Gly Ala Gln Leu Tyr Tyr Met Asp Tyr Leu Ala Ser
    50                  55                  60

Val Ala Ser Val Asp Tyr Ala Ala His Gly Tyr Gly Gly Tyr Phe Ser
65                  70                  75                  80

Leu Ser Ile Met Asp Arg Asn Tyr Leu Lys Thr Leu Ser Lys Asp Gln
                85                  90                  95

Gly Tyr Glu Leu Leu Lys Glu Cys Val Lys Glu Val Gln Lys Arg Leu
            100                 105                 110

Ala Ile Asn Leu Pro Asn Phe Lys Val Gln Val Ile Asp Lys Asp Gly
        115                 120                 125

Ile Lys Asp Met Pro Asn Ile Thr Ser Lys Gly Leu Asn
    130                 135                 140


<210> SEQ ID NO 392
<211> LENGTH: 104
<212> TYPE: PRT
<213> ORGANISM: leptinotarsa decemlineata

<400> SEQUENCE: 392

Arg Gly Leu Asp Thr Ser Leu Lys His Arg Lys Met Lys Phe Phe Lys
1               5                   10                  15

Ser Gly Ile Tyr Ser Val Val Phe Leu Ala Ile Ile Phe Ser Leu Val
            20                  25                  30

Thr Glu Glu Val Glu Gly Arg Arg Thr Ile Leu Arg Gly Arg Lys Thr
        35                  40                  45

Leu Thr Arg Thr Tyr Phe Arg Asp Asn Ala Val Pro Ala Tyr Val Ile
    50                  55                  60

Val Ile Leu Val Gly Ile Gly Glu Ile Ile Leu Gly Ala Ile Leu Tyr
65                  70                  75                  80

Val Ile Met Arg Lys Thr Ile Ile Asp Phe Pro Leu Ser Gly Ser Tyr
                85                  90                  95

Ala Val Ala Pro Thr Gln Glu Ala
            100


<210> SEQ ID NO 393
<211> LENGTH: 266
<212> TYPE: PRT
<213> ORGANISM: leptinotarsa decemlineata

<400> SEQUENCE: 393

Met Ser Lys Ile Asn Glu Val Ser Asn Leu Tyr Lys Gln Leu Lys Ser
1               5                   10                  15

Glu Trp Asn Thr Ser Asn Pro Asn Leu Ser Lys Cys Glu Lys Leu Leu
            20                  25                  30

Ser Asp Leu Lys Leu Glu Leu Thr His Leu Met Phe Leu Pro Thr Ser
        35                  40                  45

Asn Ala Thr Ala Ser Lys Gln Glu Leu Leu Leu Ala Arg Asp Val Leu
    50                  55                  60

Glu Ile Gly Val Gln Trp Ser Ile Ala Ala Asn Asp Ile Pro Ala Phe
65                  70                  75                  80

Glu Arg Tyr Met Ala Gln Leu Lys Cys Tyr Tyr Phe Asp Tyr Lys Asn
                85                  90                  95

Gln Leu Pro Glu Ser Ser Phe Lys Tyr Gln Leu Leu Gly Leu Asn Leu
            100                 105                 110

Leu Phe Leu Leu Ser Gln Asn Arg Val Ala Glu Phe His Thr Glu Leu
        115                 120                 125
```

```
Glu Leu Leu Pro Ala Asp His Ile Gln Asn Asp Val Tyr Ile Arg His
    130                 135                 140

Pro Pro Ser Ile Glu Gln Tyr Leu Met Glu Gly Ser Tyr Asn Lys Ile
145                 150                 155                 160

Phe Leu Ala Lys Gly Asn Val Pro Ala Thr Asn Tyr Asn Phe Phe Met
                165                 170                 175

Asp Ile Leu Leu Asp Thr Ile Arg Gly Glu Ile Ala Asp Cys Leu Glu
            180                 185                 190

Lys Ala Tyr Glu Lys Ile Ser Ile Lys Asp Val Ala Arg Met Leu Tyr
        195                 200                 205

Leu Gly Ser Glu Glu Ser Ala Lys Ala Phe Val Thr Lys Ser Lys Thr
    210                 215                 220

Trp Lys Leu Glu Lys Asp Asn Phe Phe His Phe Thr Pro Glu Val Lys
225                 230                 235                 240

Lys Thr His Glu Pro Ile Leu Ser Lys Glu Leu Ala Gln Gln Ala Ile
                245                 250                 255

Glu Tyr Ala Lys Glu Leu Glu Met Ile Val
            260                 265


<210> SEQ ID NO 394
<211> LENGTH: 750
<212> TYPE: DNA
<213> ORGANISM: Leptinotarsa decemlineata

<400> SEQUENCE: 394

cgcccagcag tggtatcaac gcagagtacg cgggagacat tcaagtcttg tgatagtgca      60

ggcacggcag ttcaaataaa ctggtgcctt caatttattt atatatttat actttttac      120

tagaaaccaa atactaacca atcaacatgt gtgacgaaga ggttgccgca ttagtcgtag     180

acaatggatc tggtatgtgc aaagctggat ttgctgggga tgatgccccc cgtgcagttt     240

tcccatccat tgttggtcgt ccaagacatc aaggagttat ggtaggaatg ggccaaaagg     300

actcgtatgt aggagatgaa gcccaaagca aaagaggtat ccttaccttg aaatacccca     360

ttgaacacgg tattgtcaca aactgggatg atatggagaa aatctggcac catacettct     420

acaatgaact tcgagttgcc cccgaagagc accctgtttt gttgacagag gcaccattga     480

accccaaagc caacagggag aagatgaccc agatcatgtt tgaaaccttc aatacccccg     540

ccatgtacgt cgccatccaa gctgtattgt ctctgtatgc ttctggtcgt acaactggta     600

ttgtgctgga ttctggagat ggtgtttctc acacagtacc aatctatgaa ggttatgccc     660

ttcctcatgc catccttcgt ttggacttgg ctggtagaga cttgactgat taccttatga     720

aaattctgac tgaacgtggt tactctttca                                      750


<210> SEQ ID NO 395
<211> LENGTH: 204
<212> TYPE: PRT
<213> ORGANISM: Leptinotarsa decemlineata

<400> SEQUENCE: 395

Pro Ile Asn Met Cys Asp Glu Glu Val Ala Ala Leu Val Val Asp Asn
1               5                   10                  15

Gly Ser Gly Met Cys Lys Ala Gly Phe Ala Gly Asp Asp Ala Pro Arg
            20                  25                  30

Ala Val Phe Pro Ser Ile Val Gly Arg Pro Arg His Gln Gly Val Met
        35                  40                  45
```

```
Val Gly Met Gly Gln Lys Asp Ser Tyr Val Gly Asp Glu Ala Gln Ser
    50                  55                  60

Lys Arg Gly Ile Leu Thr Leu Lys Tyr Pro Ile Glu His Gly Ile Val
65                  70                  75                  80

Thr Asn Trp Asp Asp Met Glu Lys Ile Trp His His Thr Phe Tyr Asn
                85                  90                  95

Glu Leu Arg Val Ala Pro Glu Glu His Pro Val Leu Leu Thr Glu Ala
            100                 105                 110

Pro Leu Asn Pro Lys Ala Asn Arg Glu Lys Met Thr Gln Ile Met Phe
        115                 120                 125

Glu Thr Phe Asn Thr Pro Ala Met Tyr Val Ala Ile Gln Ala Val Leu
    130                 135                 140

Ser Leu Tyr Ala Ser Gly Arg Thr Thr Gly Ile Val Leu Asp Ser Gly
145                 150                 155                 160

Asp Gly Val Ser His Thr Val Pro Ile Tyr Glu Gly Tyr Ala Leu Pro
                165                 170                 175

His Ala Ile Leu Arg Leu Asp Leu Ala Gly Arg Asp Leu Thr Asp Tyr
            180                 185                 190

Leu Met Lys Ile Leu Thr Glu Arg Gly Tyr Ser Phe
        195                 200
```

<210> SEQ ID NO 396
<211> LENGTH: 44
<212> TYPE: DNA
<213> ORGANISM: Artificial
<220> FEATURE:
<223> OTHER INFORMATION: Primer

<400> SEQUENCE: 396
gcgtaatacg actcactata ggatgtgtga cgaagaggtt gccg 44

<210> SEQ ID NO 397
<211> LENGTH: 24
<212> TYPE: DNA
<213> ORGANISM: Artificial
<220> FEATURE:
<223> OTHER INFORMATION: Primer

<400> SEQUENCE: 397
gtcaacaaaa cagggtgctc ttcg 24

<210> SEQ ID NO 398
<211> LENGTH: 22
<212> TYPE: DNA
<213> ORGANISM: Artificial
<220> FEATURE:
<223> OTHER INFORMATION: Primer

<400> SEQUENCE: 398
atgtgtgacg aagaggttgc cg 22

<210> SEQ ID NO 399
<211> LENGTH: 46
<212> TYPE: DNA
<213> ORGANISM: Artificial
<220> FEATURE:
<223> OTHER INFORMATION: Primer

<400> SEQUENCE: 399
gcgtaatacg actcactata gggtcaacaa aacagggtgc tcttcg 46

<210> SEQ ID NO 400
<211> LENGTH: 320
<212> TYPE: DNA
<213> ORGANISM: Leptinotarsa decemlineata

<400> SEQUENCE: 400

```
atgtgtgacg aagaggttgc cgcattagtc gtagacaatg gatctggtat gtgcaaagct     60

ggatttgctg gggatgatgc cccccgtgca gttttcccat ccattgttgg tcgtccaaga    120

catcaaggag ttatggtagg aatgggccaa aaggactcgt atgtaggaga tgaagcccaa    180

agcaaaagag gtatccttac cttgaaatac cccattgaac acggtattgt cacaaactgg    240

gatgatatgg agaaaatctg gcaccatacc ttctacaatg aacttcgagt tgcccccgaa    300

gagcaccctg ttttgttgac                                                320
```

<210> SEQ ID NO 401
<211> LENGTH: 1152
<212> TYPE: DNA
<213> ORGANISM: Artificial
<220> FEATURE:
<223> OTHER INFORMATION: Hairpin

<400> SEQUENCE: 401

```
tgacgacctt gagttggttt ctgaagttga actcggcagc cttcttctgg agcttggcga     60

atttgttttc gtacttggaa accttttca aggtaggttt gacgaattta ccacggaggt    120

cgttgacctg gctgttgagg tcggcgatct caaggtcacg tctctccact tcgaattcga    180

tgtcaatttt actcctctcc agagcgtcaa ttcgcttatg gtagtctgtg cagagtttct    240

tcaaggttgc ttcattggcg ttgtcgacgt cggcaatttg cccgcagcgc tcctcaatcg    300

ttcgcctcct ctcagctgct ttgcgttcct gctccttctt cagttcctca gcggcttttt    360

tcctcagcag gagtcggagt ttcttcttcc tttccggggt catgaaaccc ttcttggctt    420

tcttcgcctt agaggcttcc tccatcctct tgcgcacttc agcgcgcttc ctctcgattt    480

cggcctgttt gtctagaagg taagtgtaca cactacattt tcatgaacat tattgcgacc    540

gttgagattc tcattgtttg gtgattgatt atctaaagta gaagcatgaa tagatataac    600

ataaactagt aactaatggg ttagttatgg gtatacttca tgcttttctc tcaggctcga    660

gcaaacaggc cgaaatcgag aggaagcgcg ctgaagtgcg caagaggatg gaggaagcct    720

ctaaggcgaa gaaagccaag aagggtttca tgaccccgga aaggaagaag aaactccgac    780

tcctgctgag gaaaaaagcc gctgaggaac tgaagaagga gcaggaacgc aaagcagctg    840

agaggaggcg aacgattgag gagcgctgcg ggcaaattgc cgacgtcgac aacgccaatg    900

aagcaacctt gaagaaactc tgcacagact accataagcg aattgacgct ctggagagga    960

gtaaaattga catcgaattc gaagtggaga gacgtgacct tgagatcgcc gacctcaaca   1020

gccaggtcaa cgacctccgt ggtaaattcg tcaaacctac cttgaaaaag gtttccaagt   1080

acgaaaacaa attcgccaag ctccagaaga aggctgccga gttcaacttc agaaaccaac   1140

tcaaggtcgt ca                                                       1152
```

<210> SEQ ID NO 402
<211> LENGTH: 1192
<212> TYPE: DNA
<213> ORGANISM: Artificial
<220> FEATURE:
<223> OTHER INFORMATION: Hairpin

<400> SEQUENCE: 402

```
ctcttgcttc ttggtggcga tcctctcctc gcgcctcttc ttcgcctcct tgaccttgag     60

acgtctcgcc tctgcctggt ccttcaacat ctttgatctc gccttttcag ccttcttctt    120

gtgaatgaag tccatcagta ccctcttgtt tttgaagacg ttacctttgg ctttcatgta    180

aaggtcgtgg tacatttgcc tatcgatctt cttggcttct ctgtattttt taaggagccg    240

tcgcaggact ctcattctgt tgacccacag gaccttcaca ggcattctgg cgttggcggt    300

acccttcctc ttaccgaagc cacagtgacg acccttccgt ctggcttctg tgtttttacg    360

gacgcgggct ctggagtgga cagccacagg ctttttgatg atcaaaccat ccttgatcag    420

cttacggatg ttttgcctag agttggtgtt ggcgatttcg ttgatttcat tagggtccaa    480

ccacactttc ttcttgccgc atctcatcac ctctagaagg taagtgtaca cactacattt    540

tcatgaacat tattgcgacc gttgagattc tcattgtttg gtgattgatt atctaaagta    600

gaagcatgaa tagatataac ataaactagt aactaatggg ttagttatgg gtatacttca    660

tgcttttctc tcaggctcga gggtgatgag atgcggcaag aagaaagtgt ggttggaccc    720

taatgaaatc aacgaaatcg ccaacaccaa ctctaggcaa aacatccgta agctgatcaa    780

ggatggtttg atcatcaaaa agcctgtggc tgtccactcc agagcccgcg tccgtaaaaa    840

cacagaagcc agacggaagg gtcgtcactg tggcttcggt aagaggaagg gtaccgccaa    900

cgccagaatg cctgtgaagg tcctgtgggt caacagaatg agagtcctgc gacggctcct    960

taaaaaatac agagaagcca agaagatcga taggcaaatg taccacgacc tttacatgaa   1020

agccaaaggt aacgtcttca aaaacaagag ggtactgatg gacttcattc acaagaagaa   1080

ggctgaaaag gcgagatcaa agatgttgaa ggaccaggca gaggcgagac gtctcaaggt   1140

caaggaggcg aagaagaggc gcgaggagag gatcgccacc aagaagcaag ag           1192
```

<210> SEQ ID NO 403
<211> LENGTH: 792
<212> TYPE: DNA
<213> ORGANISM: Artificial
<220> FEATURE:
<223> OTHER INFORMATION: Hairpin

<400> SEQUENCE: 403

```
actctgtctg gcttttggct gtgacgcaca gttcatagag ataaccttca cccgaatatg     60

ccttgcgagg tcgcaaaatc ggcgaaattc catacctgtt caccgacgac ggcgctggat    120

caattccaca gttttcgcga tccagactga atgcccacag gccgtcgagt tttttgattt    180

cagatacgta cacttttccc ggcaataaca tacggcgtga catcggcttc aaatggcgta    240

tagccgccct gatgctccat cacactttgc cgtaatgagt gaccgcatcg aaacgcagca    300

cgatacgctg gtctagaagg taagtgtaca cactacattt tcatgaacat tattgcgacc    360

gttgagattc tcattgtttg gtgattgatt atctaaagta gaagcatgaa tagatataac    420

ataaactagt aactaatggg ttagttatgg gtatacttca tgcttttctc tcaggctcga    480

gccagcgtat cgtgctgcgt ttcgatgcgg tcactcatta cggcaaagtg tgatggagca    540

tcagggcggc tatacgccat ttgaagccga tgtcacgccg tatgttattg ccgggaaaag    600

tgtacgtatc tgaaatcaaa aaactcgacg gcctgtgggc attcagtctg gatcgcgaaa    660

actgtggaat tgatccagcg ccgtcgtcgg tgaacaggta tggaatttcg ccgattttgc    720

gacctcgcaa ggcatattcg ggtgaaggtt atctctatga actgtgcgtc acagccaaaa    780

gccagacaga gt                                                         792
```

<210> SEQ ID NO 404
<211> LENGTH: 839
<212> TYPE: DNA
<213> ORGANISM: leptinotarsa decemlineata

<400> SEQUENCE: 404

```
cagtcagcac cgagtccttg ttgactgctc acattttcca tcgtttctac cagaacaaca     60

gcaacaactt tcatcatggc ggacgacgag gaaaagagga ggaaacaagc ggaaattgaa    120

cgcaagaggg ctgaggtcag ggctcgcatg gaagaggcct ccaaggccaa aaaagccaag    180

aaaggtttca tgaccccctga gaggaagaag aaacttaggt tattgctgag aaagaaagca    240

gcagaagaac tgaaaaaaga acaagaacgc aaagctgccg aaaggcgtat tattgaagag    300

agatgcggaa aaccaaaact cattgatgag gcaaatgaag agcaggtgag gaactattgc    360

aagttatatc acggtagaat agctaaactg gaggaccaga aatttgattt ggaatacctt    420

gtcaaaaaga aagacatgga gatcgccgaa ttgaacagtc aagtcaacga cctcaggggt    480

aaattcgtca aacccactct caagaaagta tccaaatacg agaacaaatt tgctaaactc    540

caaaagaaag cagcagaatt caatttccgt aatcaactga aagttgtaaa gaagaaggag    600

ttcaccctgg aggaggaaga caaagaaaag aagcccgatt ggtcgaagaa gggagacgaa    660

aagaaggtac aagaagtgga agcatgatct gtccctacaa tttaatattt cccttcgtcc    720

gtggaaattt tacaacttaa gatatattta ttttattcgc ttcttatgag actatgaaag    780

tgatgtctgc atgtatatta ttcgttttat gtatgtatta aaaaaagaac ttgattgaa     839
```

<210> SEQ ID NO 405
<211> LENGTH: 203
<212> TYPE: PRT
<213> ORGANISM: leptinotarsa decemlineata

<400> SEQUENCE: 405

```
Met Ala Asp Asp Glu Glu Lys Arg Arg Lys Gln Ala Glu Ile Glu Arg
1               5                   10                  15

Lys Arg Ala Glu Val Arg Ala Arg Met Glu Glu Ala Ser Lys Ala Lys
            20                  25                  30

Lys Ala Lys Lys Gly Phe Met Thr Pro Glu Arg Lys Lys Lys Leu Arg
        35                  40                  45

Leu Leu Leu Arg Lys Lys Ala Ala Glu Glu Leu Lys Lys Glu Gln Glu
    50                  55                  60

Arg Lys Ala Ala Glu Arg Arg Ile Ile Glu Glu Arg Cys Gly Lys Pro
65                  70                  75                  80

Lys Leu Ile Asp Glu Ala Asn Glu Glu Gln Val Arg Asn Tyr Cys Lys
                85                  90                  95

Leu Tyr His Gly Arg Ile Ala Lys Leu Glu Asp Gln Lys Phe Asp Leu
            100                 105                 110

Glu Tyr Leu Val Lys Lys Lys Asp Met Glu Ile Ala Glu Leu Asn Ser
        115                 120                 125

Gln Val Asn Asp Leu Arg Gly Lys Phe Val Lys Pro Thr Leu Lys Lys
    130                 135                 140

Val Ser Lys Tyr Glu Asn Lys Phe Ala Lys Leu Gln Lys Lys Ala Ala
145                 150                 155                 160

Glu Phe Asn Phe Arg Asn Gln Leu Lys Val Val Lys Lys Lys Glu Phe
                165                 170                 175
```

-continued

```
Thr Leu Glu Glu Glu Asp Lys Glu Lys Lys Pro Asp Trp Ser Lys Lys
            180                 185                 190

Gly Asp Glu Lys Lys Val Gln Glu Val Glu Ala
        195                 200
```

DOWN-REGULATING GENE EXPRESSION IN INSECT PESTS

RELATED APPLICATIONS

This application is a continuation-in-part of PCT/EP2012/057332, filed Apr. 20, 2012, which claims the benefit under 35 U.S.C. §119(e) of U.S. provisional application 61/477,371 filed Apr. 20, 2011, and U.S. provisional application 61/508,826 filed Jul. 18, 2011, each of which is incorporated by reference in its entirety herein.

SEQUENCE LISTING

The instant application contains a Sequence Listing which has been submitted in ASCII format via EFS-Web and is hereby incorporated by reference in its entirety.

FIELD OF THE INVENTION

The present invention relates generally to genetic control of infestation by insect pest species, particularly prevention and/or control of pest infestation of plants. More specifically, the invention relates to down-regulation of expression of target genes in insect pest species by interfering ribonucleic acid (RNA) molecules. Compositions and combinations containing the interfering RNA molecules of the invention for use in topical applications, for example in the form of insecticides, are also provided.

BACKGROUND TO THE INVENTION

There exists an abundance of insect pest species that can infect or infest a wide variety of environments and host organisms. Insect pests include a variety of species from the insect Orders Hemiptera (true bugs), Coleoptera (beetles), Siphonaptera (fleas), Dichyoptera (cockroaches and mantids), Lepidoptera (moths and butterflies), Orthoptera (e.g. grasshoppers) and Diptera (true flies). Pest infestation can lead to significant damage. Insect pests that infest plant species are particularly problematic in agriculture as they can cause serious damage to crops and significantly reduce plant yields. A wide variety of different types of plant are susceptible to pest infestation including commercial crops such as rice, cotton, soybean, potato and corn.

Traditionally, infestation with insect pests has been prevented or controlled through the use of chemical pesticides. However, these chemicals are not always suitable for use in the treatment of crops as they can be toxic to other species and can cause significant environmental damage. Over more recent decades, researchers have developed more environmentally-friendly methods of controlling pest infestation. For example, microorganisms such as *Bacillus thuringiensis* bacteria that naturally express proteins toxic to insect pests have been used. Scientists have also isolated the genes encoding these insecticidal proteins and used them to generate transgenic crops resistant to insect pests e.g. corn and cotton plants genetically engineered to produce proteins of the Cry family. Although bacterial toxins have been highly successful in controlling certain types of pest, they are not effective against all pest species. Researchers have therefore looked for other more targeted approaches to pest control and in particular to RNA interference or 'gene silencing' as a means to control pests at the genetic level.

RNA interference or 'RNAi' is a process whereby the expression of genes in the context of a cell or whole organism is down-regulated in a sequence-specific manner. RNAi is now a well-established technique in the art for inhibiting or down-regulating gene expression in a wide variety of organisms including pest organisms such as fungi, nematodes and insects. Furthermore, previous studies have shown that down-regulation of target genes in insect pest species can be used as a means to control pest infestation.

WO2007/074405 describes methods of inhibiting expression of target genes in invertebrate pests including Colorado potato beetle. Furthermore, WO2009/091864 describes compositions and methods for the suppression of target genes from insect pest species including pests from the *Lygus* genus.

Although the use of RNAi for down-regulating gene expression in pest species is known in the art, the success of this technique for use as a pest control measure depends on selection of the most appropriate target genes, namely those wherein loss of function results in significant disruption of an essential biological process and/or death of the organism. The present invention is thus directed towards the down-regulation of particular target genes in insect pests as a means to achieve more effective prevention and/or control of insect pest infestation, particularly of plants.

SUMMARY OF THE INVENTION

The current inventors sought to identify improved means for preventing and/or controlling insect pest infestation using genetic approaches. In particular, they investigated the use of RNAi to down-regulate genes in such a way as to impair the ability of the insect pest to survive, grow, colonize specific environments and/or infest host organisms and thus limit the damage caused by the pest. Therefore, in accordance with one aspect of the invention, there is provided an interfering ribonucleic acid (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or having a nucleotide sequence that, when the two sequences are optimally aligned and compared, is at least 75%, preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (ii) is selected from the group of genes having a nucleotide sequence consisting of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iii) is selected from the group of genes having a nucleotide sequence comprising a fragment of at least 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000 or 3000 contiguous nucleotides of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or having a nucleotide sequence that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iv) is selected from the group of genes having a nucleotide sequence comprising a fragment of at least 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000 or 3000 contiguous nucleotides of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (v) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or (vi) is selected from the group of genes having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389.

In a particular aspect of the invention, interfering RNA molecules of the current invention comprise at least one double-stranded region, typically the silencing element of the interfering RNA, comprising a sense RNA strand annealed by complementary basepairing to an antisense RNA strand wherein the sense strand of the dsRNA molecule comprises a sequence of nucleotides complementary to a sequence of nucleotides located within the RNA transcript of the target gene.

In one embodiment, the present invention relates to an interfering ribonucleic acid (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233 or the complement thereof, or having a nucleotide sequence so that, when the two sequences are optimally aligned and compared, is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233 or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233.

These target genes encode proteins within the troponin/myofilament complex.

In a further embodiment, the present invention relates to an interfering ribonucleic acid (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or having a nucleotide sequence so that, when the two sequences are optimally aligned and compared, is at least 75% preferably at least 80%, 85%, 90%, 95%, 98% or 99% identical to any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (ii) is selected from the group of genes having a nucleotide sequence comprising a fragment of at least 21 contiguous nucleotides of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or having a nucleotide sequence so that, when said gene comprising said fragment is optimally aligned and compared with any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, said nucleotide sequence is at least 75% preferably at least 80%, 85%, 90%, 95%, 98% or 99% identical to any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (iii) is selected from the group of genes having a nucleotide sequence comprising a fragment of at least 21 contiguous nucleotides of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, and wherein when said fragment is optimally aligned and compared with the corresponding fragment in any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, said nucleotide sequence of said fragment is at least 75% preferably at least 80%, 85%, 90%, 95%, 98% or 99% identical to said corresponding fragment of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (iv) is an insect pest orthologue of a gene having a nucleotide sequence comprising any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273.

These target genes encode insect ribosomal proteins.

In certain embodiments, the present invention relates to an interfering RNA molecule which comprises at least one double-stranded region, typically the silencing element of the interfering RNA molecule, comprising a sense RNA strand annealed by complementary basepairing to an antisense RNA strand wherein the sense strand of the dsRNA molecule comprises a sequence of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000 or 3000 contiguous nucleotides, that is at least 75% preferably at least 80%, 85%, 90%, 95%, 98%, 99% or 100% complementary to a sequence of nucleotides located within the RNA transcript of a target gene from the troponin/myofilament complex.

In one embodiment, the target gene encodes an insect wings up A (troponin I) protein (e.g. an insect orthologue of the CG7178 Dm protein), said target gene being represented by SEQ ID NOs 1, 2, 174, 404, 175, 180, 181, 188 and 189. In a preferred embodiment, the insect orthologue has at least 85%, 90%, 92%, 94%, 96%, 98%, 99% or 100% amino acid sequence identity to one or more of SEQ ID NOs. 79, 349, 405, 352 or 356.

In one embodiment, the target gene encodes an upheld protein (e.g. an insect orthologue of the CG7107 Dm protein), said target gene being represented by SEQ ID NOs 121, 130, 142, 143, 176, 177, 182 and 183. In a preferred embodiment, the insect orthologue has at least 85%, 90%, 92%, 94%, 96%, 98%, 99% or 100% amino acid sequence identity to one or more of SEQ ID NOs. 330, 350 or 353.

In one embodiment, the target gene encodes the tropomyosin 1 protein (e.g. an insect orthologue of the CG4898 Dm protein), or the tropomyosin 2 protein (e.g. an insect orthologue of the CG4843 Dm protein), said target gene being represented by SEQ ID NOs 123 and 132. In a preferred embodiment, the insect orthologue has at least 85%, 90%, 92%, 94%, 96%, 98%, 99% or 100% amino acid sequence identity to SEQ ID NO. 332.

In one embodiment, the target gene encodes the myosin heavy chain (e.g. an insect orthologue of the CG17927 Dm protein), said target gene being represented by SEQ ID NOs 122, 131, 144, 145, 178 and 179. In a preferred embodiment, the insect orthologue has at least 85%, 90%, 92%, 94%, 96%, 98%, 99% or 100% amino acid sequence identity to one or more of SEQ ID NOs. 331 or 351.

In one embodiment, the target gene encodes the myosin light chain cytoplasmic protein (e.g. an insect orthologue of the CG3201 Dm protein), said target gene being represented by SEQ ID NOs 124 and 133. In a preferred embodiment, the insect orthologue has at least 85%, 90%, 92%, 94%, 96%, 98%, 99% or 100% amino acid sequence identity to SEQ ID NO. 333.

In one embodiment, the target gene encodes the spaghetti squash protein (e.g. an insect orthologue of the CG3595 Dm protein), said target gene being represented by SEQ ID NOs 125 and 134. In a preferred embodiment, the insect orthologue has at least 85%, 90%, 92%, 94%, 96%, 98%, 99% or 100% identity to SEQ ID NO. 334.

In one embodiment, the target gene encodes the zipper protein (e.g. an insect orthologue of the CG15792 Dm protein), said target gene being represented by SEQ ID NOs 126 and 135. In a preferred embodiment, the insect orthologue has at least 85%, 90%, 92%, 94%, 96%, 98%, 99% or 100% identity to SEQ ID NO. 335.

In one embodiment, the target gene encodes the troponin C (e.g. an insect orthologue of the CG2981, CG7930, CG9073, CG6514, CG12408, CG9073, CG7930, CG2981, CG12408 or CG6514 Dm protein), said target gene being represented by SEQ ID NOs 127 and 136, or 128 and 137, or 184 and 185. In a preferred embodiment, the insect orthologue has at least 85%, 90%, 92%, 94%, 96%, 98%, 99% or 100% amino acid sequence identity to one or more of SEQ ID NOs. 336, 337 and 354.

According to another embodiment the present invention relates to an interfering RNA molecule which comprises at least one double-stranded region, typically the silencing element of the interfering RNA molecule, comprising a sense RNA strand annealed by complementary basepairing to an antisense RNA strand wherein the sense strand of the dsRNA molecule comprises a sequence of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000 or 3000 contiguous nucleotides, that is at least 75% preferably at least 80%, 85%, 90%, 95%, 98%, 99% or 100% complementary to a sequence of nucleotides located within the RNA transcript of a target gene that encodes an insect ribosomal protein.

In one embodiment, the target gene encodes ribosomal protein S3A (e.g. an insect orthologue of the CG2168 Dm protein), said target gene being represented by SEQ ID NOs 11, 12 and 141. In a preferred embodiment, the insect orthologue has at least 85%, 90%, 92%, 94%, 96%, 98%, 99% or 100% amino acid sequence identity to one or both of SEQ ID NO. 84 or 328.

In one embodiment, the target gene encodes the ribosomal protein LP1 (e.g. an insect orthologue of the CG4087 Dm protein), said target gene being represented by SEQ ID NO 3 and 4. In a preferred embodiment, the insect orthologue has at least 85%, 90%, 92%, 94%, 96%, 98%, 99% or 100% amino acid sequence identity to SEQ ID NO. 80.

In one embodiment, the target gene encodes the ribosomal protein S3 (e.g. an insect orthologue of the CG6779 Dm protein), said target gene being represented by SEQ ID NOs 7 and 8. In a preferred embodiment, the insect orthologue has at least 85%, 90%, 92%, 94%, 96%, 98%, 99% or 100% amino acid sequence identity to SEQ ID NO. 82.

In one embodiment, the target gene encodes the ribosomal protein L10Ab (e.g. an insect orthologue of the CG7283 Dm protein) represented by SEQ ID NOs 9 and 10. In a preferred embodiment, the insect orthologue has at least 85%, 90%, 92%, 94%, 96%, 98%, 99% or 100% amino acid sequence identity to SEQ ID NO. 83.

In one embodiment, the target gene encodes the ribosomal protein S18 (e.g. an insect orthologue of the CG8900 Dm protein), said target gene being represented by SEQ ID NO 13 and 14. In a preferred embodiment, the insect orthologue has at least 85%, 90%, 92%, 94%, 96%, 98%, 99% or 100% amino acid sequence identity to SEQ ID NO. 85.

In one embodiment, the target gene encodes the ribosomal protein L4 (e.g. an insect orthologue of the CG5502 Dm protein), said target gene represented by SEQ ID NO 5 and 6. In a preferred embodiment, the insect orthologue has at least 85%, 90%, 92%, 94%, 96%, 98%, 99% or 100% amino acid sequence identity to SEQ ID NO. 81.

In one embodiment, the target gene encodes the ribosomal protein S27 (e.g. an insect orthologue of the CG10423 Dm protein), said target gene being represented by SEQ ID NO 15 and 16, 204 and 205. In a preferred embodiment, the insect orthologue has at least 85%, 90%, 92%, 94%, 96%, 98%, 99% or 100% amino acid sequence identity to one or both of SEQ ID NOs. 86 and 359.

In one embodiment, the target gene encodes the ribosomal protein L6 (e.g. an insect orthologue of the CG11522 Dm protein), said target gene being represented by SEQ ID NO 17 and 18. In a preferred embodiment, the insect orthologue has at least 85%, 90%, 92%, 94%, 96%, 98%, 99% or 100% amino acid sequence identity to SEQ ID NO. 87.

In one embodiment, the target gene encodes the ribosomal protein S13 (e.g. an insect orthologue of the CG13389 Dm protein), said target gene being represented by SEQ ID NO 19 and 20. In a preferred embodiment, the insect orthologue has at least 85%, 90%, 92%, 94%, 96%, 98%, 99% or 100% amino acid sequence identity to SEQ ID NO. 88.

In one embodiment, the target gene encodes the ribosomal protein L12 (e.g. an insect orthologue of the CG3195 Dm protein), said target gene being represented by SEQ ID NOs 21 and 22. In a preferred embodiment, the insect orthologue has at least 85%, 90%, 92%, 94%, 96%, 98%, 99% or 100% amino acid sequence identity to SEQ ID NO. 89.

In one embodiment, the target gene encodes the ribosomal protein L26 (e.g. an insect orthologue of the CG6846 Dm protein), said target gene being represented by SEQ ID NOs 158 and 159. In a preferred embodiment, the insect orthologue has at least 85%, 90%, 92%, 94%, 96%, 98%, 99% or 100% amino acid sequence identity to SEQ ID NO. 343.

In one embodiment, the target gene encodes the ribosomal protein L21 (e.g. an insect orthologue of the CG12775 Dm protein), said target gene being represented by SEQ ID NO 165, 166 and 167. In a preferred embodiment, the insect orthologue has at least 85%, 90%, 92%, 94%, 96%, 98%, 99% or 100% amino acid sequence identity to SEQ ID NOs 347 and 348.

In one embodiment, the target gene encodes the ribosomal protein S12 (e.g. an insect orthologue of the CG11271 Dm protein), said target gene being represented by SEQ ID NOs 156 and 157. In a preferred embodiment, the insect orthologue has at least 85%, 90%, 92%, 94%, 96%, 98%, 99% or 100% amino acid sequence identity to SEQ ID NO. 342.

In one embodiment, the target gene encodes the ribosomal protein S28b (e.g. an insect orthologue of the CG2998 Dm protein), said target gene being represented by SEQ ID NOs 160 and 161. In a preferred embodiment, the insect orthologue has at least 85%, 90%, 92%, 94%, 96%, 98%, 99% or 100% amino acid sequence identity to SEQ ID NO. 344.

In one embodiment, the target gene encodes the ribosomal protein L13 (e.g. an insect orthologue of the CG4651 Dm protein), said target gene being represented by SEQ ID NOs. 154 and 155. In a preferred embodiment, the insect orthologue has at least 85%, 90%, 92%, 94%, 96%, 98%, 99% or 100% amino acid sequence identity to SEQ ID NO. 341.

In one embodiment, the target gene encodes the ribosomal protein L10 (e.g. an insect orthologue of the CG17521 Dm protein), said target gene being represented by SEQ ID NOs. 163 and 164. In a preferred embodiment, the insect orthologue has at least 85%, 90%, 92%, 94%, 96%, 98%, 99% or 100% amino acid sequence identity to SEQ ID NO. 345.

In one embodiment, the target gene encodes the ribosomal protein L5 (e.g. an insect orthologue of the CG17489 Dm protein), said target gene being represented by SEQ ID NOs. 152 and 153. In a preferred embodiment, the insect orthologue has at least 85%, 90%, 92%, 94%, 96%, 98%, 99% or 100% amino acid sequence identity to SEQ ID NO. 340.

In one embodiment, the target gene encodes the ribosomal protein S15Aa (e.g. an insect orthologue of the CG2033 Dm protein), said target gene being represented by SEQ ID NOs. 150 and 151. In a preferred embodiment, the insect orthologue has at least 85%, 90%, 92%, 94%, 96%, 98%, 99% or 100% amino acid sequence identity to SEQ ID NO. 339.

In one embodiment, the target gene encodes the ribosomal protein L19 (e.g. an insect orthologue of the CG2746 Dm protein), said target gene being represented by SEQ ID NOs. 200 and 201. In a preferred embodiment, the insect orthologue has at least 85%, 90%, 92%, 94%, 96%, 98%, 99% or 100% amino acid sequence identity to SEQ ID NO. 357.

In one embodiment, the target gene encodes the ribosomal protein L27 (e.g. an insect orthologue of the CG4759 Dm protein), said target gene being represented by SEQ ID NO. 386. In a preferred embodiment, the insect orthologue has at least 85%, 90%, 92%, 94%, 96%, 98%, 99% or 100% amino acid sequence identity to SEQ ID NO. 390.

In one embodiment, the target gene encodes the mitochondrial cytochrome c oxidase subunit II protein (e.g. an insect orthologue of the CG34069 Dm protein), said target gene being represented by SEQ ID NO 25 and 26. In a preferred embodiment, the insect orthologue has at least 85%, 90%, 92%, 94%, 96%, 98%, 99% or 100% amino acid sequence identity to SEQ ID NO. 91.

In one embodiment, the target gene encodes the ATP synthase-γ chain (e.g. an insect orthologue of the CG7610 Dm protein), said target gene being represented by SEQ ID NOs 129 and 138. In a preferred embodiment, the insect orthologue has at least 85%, 90%, 92%, 94%, 96%, 98%, 99% or 100% amino acid sequence identity to SEQ ID NO. 338.

In one embodiment, the target gene encodes the ubiquitin-5E (e.g. an insect orthologue of the CG32744 Dm protein) said target gene being represented by SEQ ID NOs. 186 and 187, 202 and 203. In a preferred embodiment, the insect orthologue has at least 85%, 90%, 92%, 94%, 96%, 98%, 99% or 100% amino acid sequence identity to one or both of SEQ ID NOs. 355 and 358.

In one embodiment, the target gene encodes the proteasome beta-type subunit (e.g. an insect orthologue of the CG17331 Dm protein) said target gene being represented by SEQ ID NO. 387. In a preferred embodiment, the insect orthologue has at least 85%, 90%, 92%, 94%, 96%, 98%, 99% or 100% amino acid sequence identity to SEQ ID NO. 391.

In one embodiment, the target gene encodes the protein which is an insect orthologue of the CG13704 Dm protein, said target gene being represented by SEQ ID NO. 388. In a preferred embodiment, the insect orthologue has at least 85%, 90%, 92%, 94%, 96%, 98%, 99% or 100% amino acid sequence identity to SEQ ID NO. 392.

In one embodiment, the target gene encodes the Rpn12 protein (e.g. an insect orthologue of the CG4157 Dm protein) said target gene being represented by SEQ ID NO. 389. In a preferred embodiment, the insect orthologue has at least 85%, 90%, 92%, 94%, 96%, 98%, 99% or 100% amino acid sequence identity to SEQ ID NO. 393.

In accordance with a second aspect of the invention, there is provided a composition for preventing and/or controlling insect pest infestation comprising at least one interfering ribonucleic acid (RNA) and at least one suitable carrier, excipient or diluent, wherein the interfering RNA functions upon uptake by the pest to down-regulate the expression of a target gene within said pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or having a nucleotide sequence so that, when the two sequences are optimally aligned and compared, is at least 75% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence of said fragment is at least 75% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, wherein the two orthologous genes are similar in sequence to such a degree that when the two genes are optimally aligned and compared, the orthologue has a sequence that is at least 75% identical to any of the sequences represented by SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or (v) is selected from the group of genes having a nucleotide sequence encoding an amino acid sequence that, when the two amino acid sequences are optimally aligned and compared, is at least 85% identical to the amino acid sequence encoded by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389.

The composition of the invention may be used for the prevention and/or control of pest infestation. In certain embodiments, the composition may be used as a pesticide for a plant or for propagation or reproductive material of a plant. In a further aspect, provided herein is a combination for preventing and/or controlling pest infestation comprising the composition of the invention and at least one other active agent.

In a further aspect, provided herein is a method for down-regulating expression of a target gene in an insect pest species in order to prevent and/or control pest infestation, comprising contacting said pest species with an effective amount of at least one interfering ribonucleic acid (RNA), wherein the interfering RNA functions upon uptake by the pest to down-regulate the expression of a target gene within said pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or having a nucleotide sequence so that, when the two sequences are optimally aligned and compared, is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs. SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389.

In accordance with a further aspect of the invention, there is provided an isolated polynucleotide selected from the group consisting of:

(i) a polynucleotide which comprises at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (ii) a polynucleotide which consists of at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iii) a polynucleotide which comprises at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, that, when the two sequences are optimally aligned and compared, said polynucleotide is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iv) a polynucleotide which comprises a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein said fragment or said complement has a nucleotide sequence that, when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389 or the complement thereof, or (v) a polynucleotide which consists of a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein said fragment or said complement has a nucleotide sequence that, when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389 or the complement thereof, or (vi) a polynucleotide encoding an amino acid sequence that, when the two amino acid sequences are optimally aligned and compared, is at least 70% preferably at least 75%, 80%, 85%, 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, and wherein said polynucleotide is no longer than 10000, 9000, 8000, 7000, 6000, 5000, 4000, 3000, 2000 or 1500 nucleotides.

The amino acid sequences encoded by the target genes of the present invention are represented by SEQ ID NOs 79, 349, 405, 352, 356, 80, 326, 81, 327, 82, 83, 328, 84, 329, 85, 86, 359, 87 to 91, 330, 350, 353, 331, 351, 332 to 336, 337, 354, 338 to 344, 346, 345, 347, 348, 357, 355, 358, 390 to 393, respectively.

In a particular aspect of the invention, the isolated polynucleotide is part of an interfering RNA molecule, typically part of the silencing element, comprising at least one double-stranded region comprising a sense RNA strand annealed by complementary basepairing to an antisense RNA strand wherein the sense strand of the dsRNA molecule comprises a sequence of nucleotides complementary to a sequence of nucleotides located within the RNA transcript of the target gene. More particularly, the isolated polynucleotide is cloned in a DNA construct in a sense and antisense orientation so that the upon transcription of the sense and antisense polynucleotide a dsRNA molecule is formed, which functions upon uptake by a pest to inhibit or down-regulate the expression of a target gene within said pest.

In one embodiment the present invention relates to an isolated polynucleotide that is cloned in a DNA construct in a sense and antisense orientation so that the upon transcription of the sense and antisense polynucleotide a dsRNA molecule is formed, which functions upon uptake by an insect to inhibit or down-regulate the expression of a target gene within the troponin/myofilament complex.

In one embodiment, the target gene encodes an insect wings up A (troponin I) protein (e.g. an insect orthologue of the CG7178 Dm protein), said target gene being represented by SEQ ID NOs 1, 2, 174, 404, 175, 180, 181, 188 and 189. In a preferred embodiment, the insect orthologue has at least 85%, 90%, 92%, 94%, 96%, 98%, 99% or 100% amino acid sequence identity to one or more of SEQ ID NOs. 79, 349, 405, 352 or 356.

In one embodiment, the target gene encodes an upheld protein (e.g. an insect orthologue of the CG7107 Dm protein), said target gene being represented by SEQ ID NOs 121, 130, 142, 143, 176, 177, 182 and 183. In a preferred embodiment, the insect orthologue has at least 85%, 90%, 92%, 94%, 96%, 98%, 99% or 100% amino acid sequence identity to one or more of SEQ ID NOs. 330, 350 or 353.

In one embodiment, the target gene encodes the tropomyosin 1 protein (e.g. an insect orthologue of the CG4898 Dm protein), or the tropomyosin 2 protein (e.g. an insect orthologue of the CG4843 Dm protein), said target gene being represented by SEQ ID NOs 123 and 132. In a preferred embodiment, the insect orthologue has at least 85%, 90%, 92%, 94%, 96%, 98%, 99% or 100% amino acid sequence identity to SEQ ID NO. 332.

In one embodiment, the target gene encodes the myosin heavy chain (e.g. an insect orthologue of the CG17927 Dm protein), said target gene being represented by SEQ ID NOs 122, 131, 144, 145, 178 and 179. In a preferred embodiment, the insect orthologue has at least 85%, 90%, 92%, 94%, 96%, 98%, 99% or 100% amino acid sequence identity to one or more of SEQ ID NOs. 331 or 351.

In one embodiment, the target gene encodes the myosin light chain cytoplasmic protein (e.g. an insect orthologue of the CG3201 Dm protein), said target gene being represented by SEQ ID NOs 124 and 133. In a preferred embodiment, the insect orthologue has at least 85%, 90%, 92%, 94%, 96%, 98%, 99% or 100% amino acid sequence identity to SEQ ID NO. 333.

In one embodiment, the target gene encodes the spaghetti squash protein (e.g. an insect orthologue of the CG3595 Dm protein), said target gene being represented by SEQ ID NOs 125 and 134. In a preferred embodiment, the insect orthologue has at least 85%, 90%, 92%, 94%, 96%, 98%, 99% or 100% identity to SEQ ID NO. 334.

In one embodiment, the target gene encodes the zipper protein (e.g. an insect orthologue of the CG15792 Dm protein), said target gene being represented by SEQ ID NOs 126 and 135. In a preferred embodiment, the insect orthologue has at least 85%, 90%, 92%, 94%, 96%, 98%, 99% or 100% identity to SEQ ID NO. 335.

In one embodiment, the target gene encodes the troponin C (e.g. an insect orthologue of the CG2981, CG7930, CG9073, CG6514, CG12408, CG9073, CG7930, CG2981, CG12408 or CG6514 Dm protein), said target gene being represented by SEQ ID NOs 127 and 136, or 128 and 137, or 184 and 185. In a preferred embodiment, the insect orthologue has at least 85%, 90%, 92%, 94%, 96%, 98%, 99% or 100% amino acid sequence identity to one or more of SEQ ID NOs. 336, 337 and 354.

According to other embodiments, the present invention relates to an isolated polynucleotide that is cloned in a DNA construct in a sense and antisense orientation so that the upon transcription of the sense and antisense polynucleotide a dsRNA molecule is formed, which functions upon uptake by an insect to inhibit or down-regulate the expression of a target gene that encodes an insect ribosomal protein.

In one embodiment, the target gene encodes ribosomal protein S3A (e.g. an insect orthologue of the CG2168 Dm protein), said target gene being represented by SEQ ID NOs 11, 12 and 141. In a preferred embodiment, the insect orthologue has at least 85%, 90%, 92%, 94%, 96%, 98%, 99% or 100% amino acid sequence identity to one or both of SEQ ID NO. 84 or 328.

In one embodiment, the target gene encodes the ribosomal protein LP1 (e.g. an insect orthologue of the CG4087 Dm protein), said target gene being represented by SEQ ID NO 3 and 4. In a preferred embodiment, the insect orthologue has at least 85%, 90%, 92%, 94%, 96%, 98%, 99% or 100% amino acid sequence identity to SEQ ID NO. 80.

In one embodiment, the target gene encodes the ribosomal protein S3 (e.g. an insect orthologue of the CG6779 Dm protein), said target gene being represented by SEQ ID NOs 7 and 8. In a preferred embodiment, the insect orthologue has at least 85%, 90%, 92%, 94%, 96%, 98%, 99% or 100% amino acid sequence identity to SEQ ID NO. 82.

In one embodiment, the target gene encodes the ribosomal protein L10Ab (e.g. an insect orthologue of the CG7283 Dm protein) represented by SEQ ID NOs 9 and 10. In a preferred embodiment, the insect orthologue has at least 85%, 90%, 92%, 94%, 96%, 98%, 99% or 100% amino acid sequence identity to SEQ ID NO. 83.

In one embodiment, the target gene encodes the ribosomal protein S18 (e.g. an insect orthologue of the CG8900 Dm protein), said target gene being represented by SEQ ID NO 13 and 14. In a preferred embodiment, the insect orthologue has at least 85%, 90%, 92%, 94%, 96%, 98%, 99% or 100% amino acid sequence identity to SEQ ID NO. 85.

In one embodiment, the target gene encodes the ribosomal protein L4 (e.g. an insect orthologue of the CG5502 Dm protein), said target gene represented by SEQ ID NO 5 and 6. In a preferred embodiment, the insect orthologue has at least 85%, 90%, 92%, 94%, 96%, 98%, 99% or 100% amino acid sequence identity to SEQ ID NO. 81.

In one embodiment, the target gene encodes the ribosomal protein S27 (e.g. an insect orthologue of the CG10423 Dm protein), said target gene being represented by SEQ ID NO 15 and 16, 204 and 205. In a preferred embodiment, the insect orthologue has at least 85%, 90%, 92%, 94%, 96%, 98%, 99% or 100% amino acid sequence identity to one or both of SEQ ID NOs. 86 and 359.

In one embodiment, the target gene encodes the ribosomal protein L6 (e.g. an insect orthologue of the CG11522 Dm protein), said target gene being represented by SEQ ID NO 17 and 18. In a preferred embodiment, the insect orthologue has at least 85%, 90%, 92%, 94%, 96%, 98%, 99% or 100% amino acid sequence identity to SEQ ID NO. 87.

In one embodiment, the target gene encodes the ribosomal protein S13 (e.g. an insect orthologue of the CG13389 Dm protein), said target gene being represented by SEQ ID NO 19 and 20. In a preferred embodiment, the insect orthologue has at least 85%, 90%, 92%, 94%, 96%, 98%, 99% or 100% amino acid sequence identity to SEQ ID NO. 88.

In one embodiment, the target gene encodes the ribosomal protein L12 (e.g. an insect orthologue of the CG3195 Dm protein), said target gene being represented by SEQ ID NOs 21 and 22. In a preferred embodiment, the insect orthologue has at least 85%, 90%, 92%, 94%, 96%, 98%, 99% or 100% amino acid sequence identity to SEQ ID NO. 89.

In one embodiment, the target gene encodes the ribosomal protein L26 (e.g. an insect orthologue of the CG6846 Dm protein), said target gene being represented by SEQ ID NOs 158 and 159. In a preferred embodiment, the insect orthologue has at least 85%, 90%, 92%, 94%, 96%, 98%, 99% or 100% amino acid sequence identity to SEQ ID NO. 343.

In one embodiment, the target gene encodes the ribosomal protein L21 (e.g. an insect orthologue of the CG12775 Dm protein), said target gene being represented by SEQ ID NO 165, 166 and 167. In a preferred embodiment, the insect orthologue has at least 85%, 90%, 92%, 94%, 96%, 98%, 99% or 100% amino acid sequence identity to SEQ ID NOs 347 and 348.

In one embodiment, the target gene encodes the ribosomal protein S12 (e.g. an insect orthologue of the CG11271 Dm protein), said target gene being represented by SEQ ID NOs 156 and 157. In a preferred embodiment, the insect orthologue has at least 85%, 90%, 92%, 94%, 96%, 98%, 99% or 100% amino acid sequence identity to SEQ ID NO. 342.

In one embodiment, the target gene encodes the ribosomal protein S28b (e.g. an insect orthologue of the CG2998 Dm protein), said target gene being represented by SEQ ID NOs 160 and 161. In a preferred embodiment, the insect orthologue has at least 85%, 90%, 92%, 94%, 96%, 98%, 99% or 100% amino acid sequence identity to SEQ ID NO. 344.

In one embodiment, the target gene encodes the ribosomal protein L13 (e.g. an insect orthologue of the CG4651 Dm protein), said target gene being represented by SEQ ID NOs. 154 and 155. In a preferred embodiment, the insect orthologue has at least 85%, 90%, 92%, 94%, 96%, 98%, 99% or 100% amino acid sequence identity to SEQ ID NO. 341.

In one embodiment, the target gene encodes the ribosomal protein L10 (e.g. an insect orthologue of the CG17521 Dm protein), said target gene being represented by SEQ ID NOs. 163 and 164. In a preferred embodiment, the insect orthologue has at least 85%, 90%, 92%, 94%, 96%, 98%, 99% or 100% amino acid sequence identity to SEQ ID NO. 345.

In one embodiment, the target gene encodes the ribosomal protein L5 (e.g. an insect orthologue of the CG17489 Dm protein), said target gene being represented by SEQ ID NOs. 152 and 153. In a preferred embodiment, the insect orthologue has at least 85%, 90%, 92%, 94%, 96%, 98%, 99% or 100% amino acid sequence identity to SEQ ID NO. 340.

In one embodiment, the target gene encodes the ribosomal protein S15Aa (e.g. an insect orthologue of the CG2033 Dm protein), said target gene being represented by SEQ ID NOs. 150 and 151. In a preferred embodiment, the insect orthologue has at least 85%, 90%, 92%, 94%, 96%, 98%, 99% or 100% amino acid sequence identity to SEQ ID NO. 339.

In one embodiment, the target gene encodes the ribosomal protein L19 (e.g. an insect orthologue of the CG2746 Dm protein), said target gene being represented by SEQ ID NOs. 200 and 201. In a preferred embodiment, the insect orthologue has at least 85%, 90%, 92%, 94%, 96%, 98%, 99% or 100% amino acid sequence identity to SEQ ID NO. 357.

In one embodiment, the target gene encodes the ribosomal protein L27 (e.g. an insect orthologue of the CG4759 Dm protein), said target gene being represented by SEQ ID NO. 386. In a preferred embodiment, the insect orthologue has at least 85%, 90%, 92%, 94%, 96%, 98%, 99% or 100% amino acid sequence identity to SEQ ID NO. 390.

Preferably, the methods of the invention find practical application in the prevention and/or control of insect pest infestation, in particular, control of pest infestation of crop plants such as but not limited to cotton, potato, rice, strawberries, alfalfa, soy, tomato, canola, sunflower, sorghum, pearl millet, corn, eggplant, pepper and tobacco. In addition, the interfering RNA of the invention may be introduced into the plants to be protected by routine genetic engineering techniques.

In all aspects of the invention, in preferred embodiments the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or having a nucleotide sequence so that, when the two sequences are optimally aligned and compared, is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233 or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233 said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233 or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233.

These target genes encode proteins within the troponin/myofilament complex.

In all aspects of the invention, in preferred embodiments, the target gene (i) is selected from the group of genes having a nucleotide sequence comprising any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or having a nucleotide sequence so that, when the two sequences are optimally aligned and compared, is at least 75% preferably at least 80%, 85%, 90%, 95%, 98% or 99% identical to any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (ii) is selected from the group of genes having a nucleotide sequence comprising a fragment of at least 21 contiguous nucleotides of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or having a nucleotide sequence so that, when said gene comprising said fragment is optimally aligned and compared with any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, said nucleotide sequence is at least 75% preferably at least 80%, 85%, 90%, 95%, 98% or 99% identical to any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (iii) is selected from the group of genes having a nucleotide sequence comprising a fragment of at least 21 contiguous nucleotides of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, and wherein when said fragment is optimally aligned and compared with the corresponding fragment in any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, said nucleotide sequence of said fragment is at least 75% preferably at least 80%, 85%, 90%, 95%, 98% or 99% identical to said corresponding fragment of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (iv) is an insect pest orthologue of a gene having a nucleotide sequence comprising any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or (v) is selected from the group of genes having a nucleotide sequence encoding an amino acid sequence that, when the two amino acid sequences are optimally aligned and compared, is at least 85% identical to the amino acid sequence encoded by any of SEQ ID NOs. 3, 4, 31 to 34, 139, 5, 6, to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273.

These target genes encode insect ribosomal proteins.

In all aspects of the invention, in preferred embodiments, the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, or the complement thereof, or having a nucleotide sequence so that, when the two sequences are optimally aligned and compared, is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313. In preferred embodiments, this target gene may encode an insect the troponin I protein (e.g. an insect orthologue of the CG7178 Dm protein). The insect troponin I protein may have an amino acid sequence which is at least 85%, 90%, 92%, 94%, 96%, 98%, 99% identical to the amino acid sequence as presented in any of SEQ ID NOs 79, 349, 405, 352 or 356 (when said encoded proteins are optimally aligned).

BRIEF DESCRIPTION OF THE TABLES AND FIGURES

Table 1 *Lygus hesperus* novel targets identified from first screen.

Table 1B *Lygus hesperus* novel targets in Lh594 pathway.

Table 1C *Lygus hesperus* novel targets identified from second round screen.

Table 2 Polynucleotide sequences of target genes identified in *Lygus hesperus*.

Table 3 Amino acid sequences of target genes identified in *Lygus hesperus*.

Table 4 dsRNAs (sense strand represented by equivalent DNA sequence) corresponding to *Lygus hesperus* target genes and primers for producing the dsRNAs.

Table 5 *Lygus hesperus* targets ranking according to dose response curves (DRCs) and compared to bench mark targets Lh423 & Lh105.

Table 6 *Lygus hesperus* targets from second round screen-ranking according to DRCs and compared to bench mark targets Lh423 & Lh594.

Table 7 Polynucleotide sequences of target genes identified in Colorado potato beetle (CPB).

Table 8 Amino acid sequences of target genes identified in CPB.

Table 9 dsRNAs (sense strand represented by equivalent DNA sequence) corresponding to CPB target genes and primers for producing the dsRNAs.

Table 10 Polynucleotide sequences of target genes identified in brown plant hopper (BPH).

Table 11 Amino acid sequences of target genes identified in BPH.

Table 12 dsRNAs (sense strand represented by equivalent DNA sequence) corresponding to BPH target genes and primers for producing the dsRNAs.

Table 13 Primers used for amplification of aphid cDNAs, based on pea aphid genomic sequence.

Table 14 Polynucleotide sequences of target genes identified in aphids.

Table 15 Amino acid sequences of target genes identified in aphids.

Table 16 dsRNAs (sense strand represented by equivalent DNA sequence) corresponding to aphid target genes and primers for producing the dsRNAs.

Table 17 Degenerate primers used for amplification of CPB Ld594 cDNA

Table 18 Degenerate primers used for amplification of BPH cDNAs

Table 19: *Leptinotarsa decemlineata* novel targets from the screen.

Table 20: *Nilaparvata lugens* novel identified target.

Table 21: *Acyrthosiphon pisum* novel identified targets.

FIG. 1: Plates Lh001_009 second confirmation assay. Dark bars: mortality at day 3 to 6, light bars: mortality at day 6 to 8. Candidate clones are named using the "Lygxxx" screening codes and the "Lhxxx" target nomenclature codes.

Figure 2:
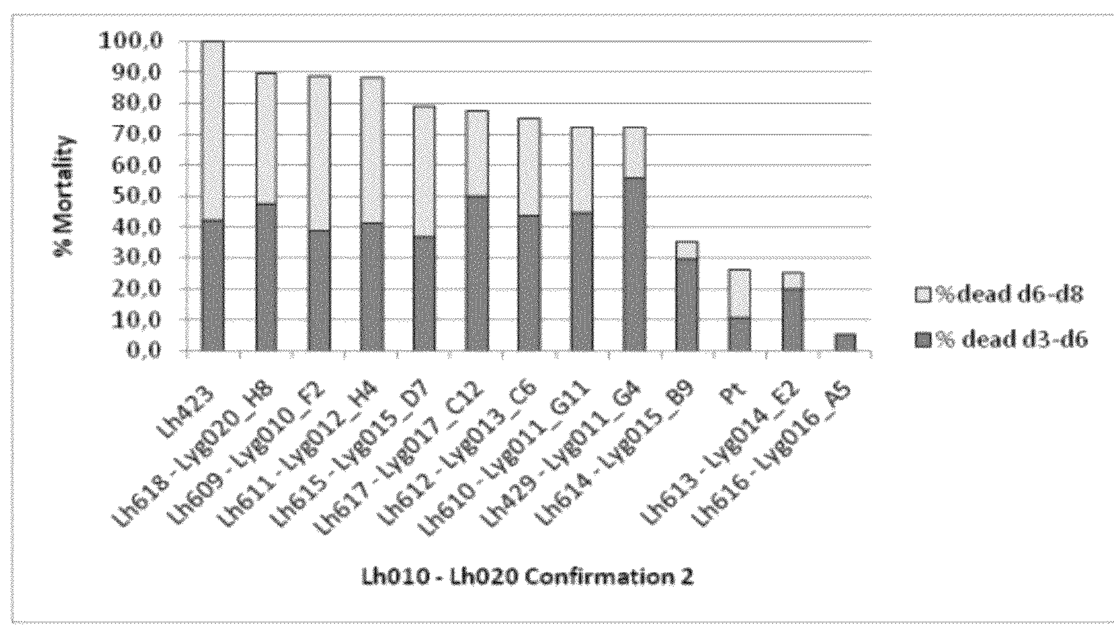

FIG. 2: Plates Lh010_020 second confirmation assay. Dark bars: mortality at day 3 to 6, light bars: mortality at day 6 to 8. Candidate clones are named using the "Lygxxx" screening codes and the "Lhxxx" target nomenclature codes.

Figure 3:
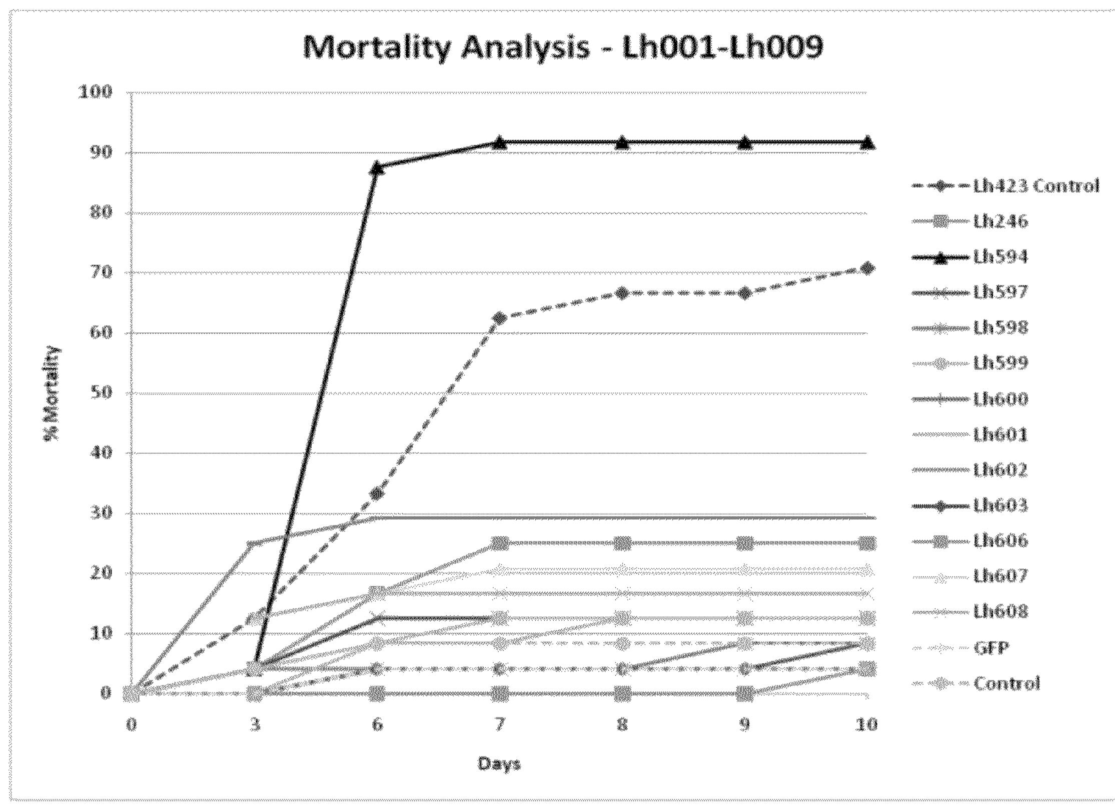

FIG. 3: Mortality analysis of *Lygus* novel targets from plates Lh001 to Lh009, expressed as % mortality over a 10 day period. Controls are indicated in dotted lines. Positive control: Lh423 dsRNA (RpL19). Negative controls: GFP dsRNA and diet only (Control).

Figure 4:
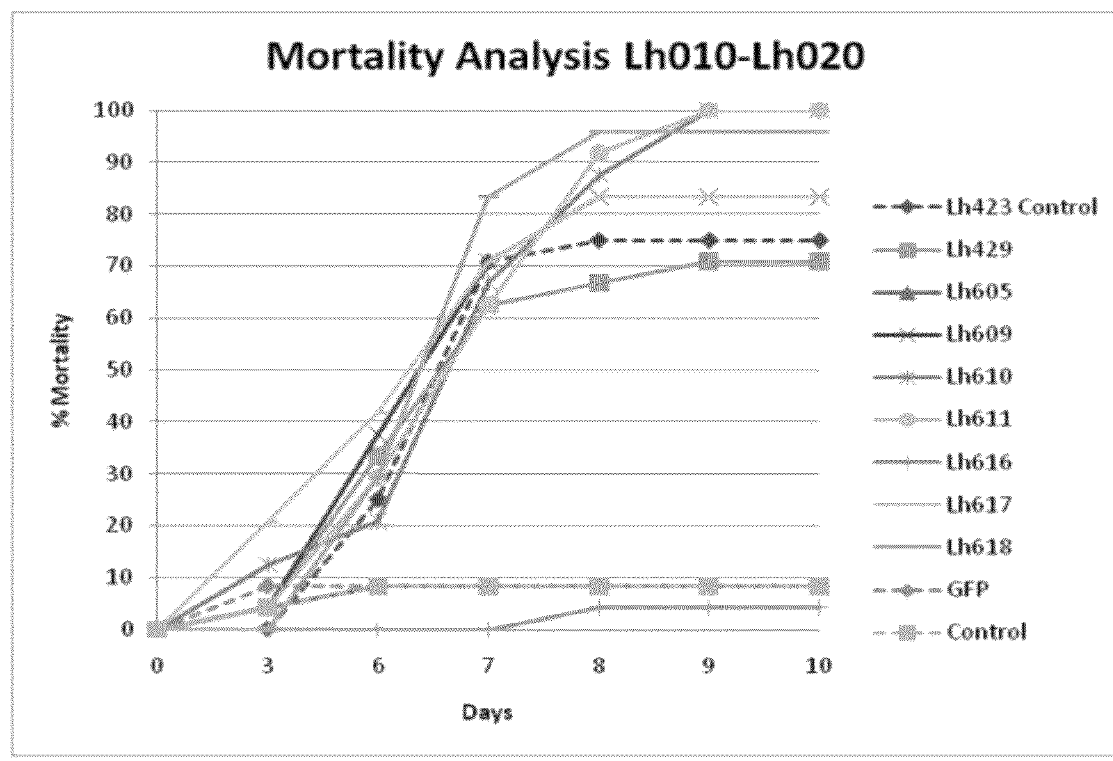
Figure 5:
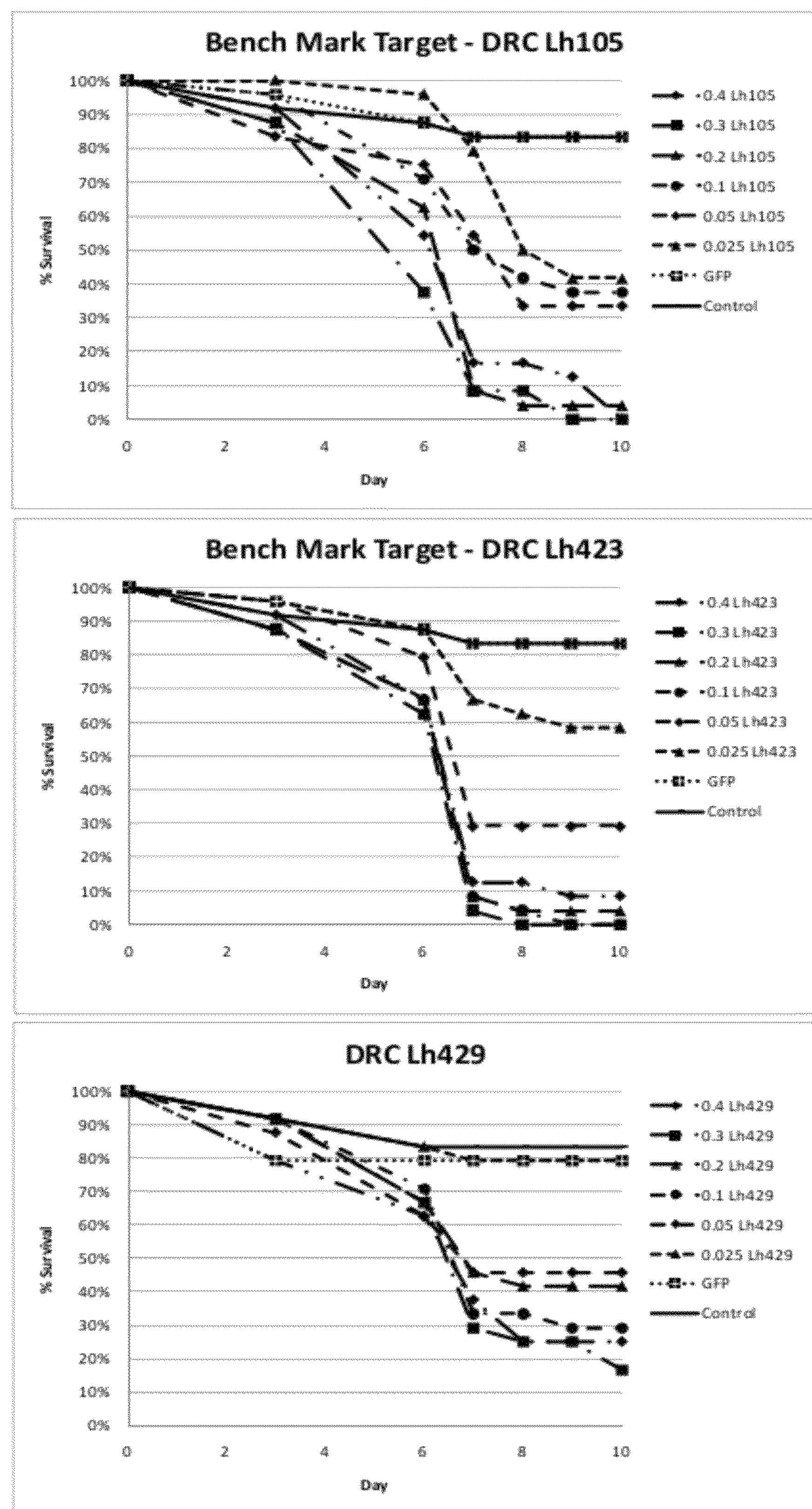
Figure 6:
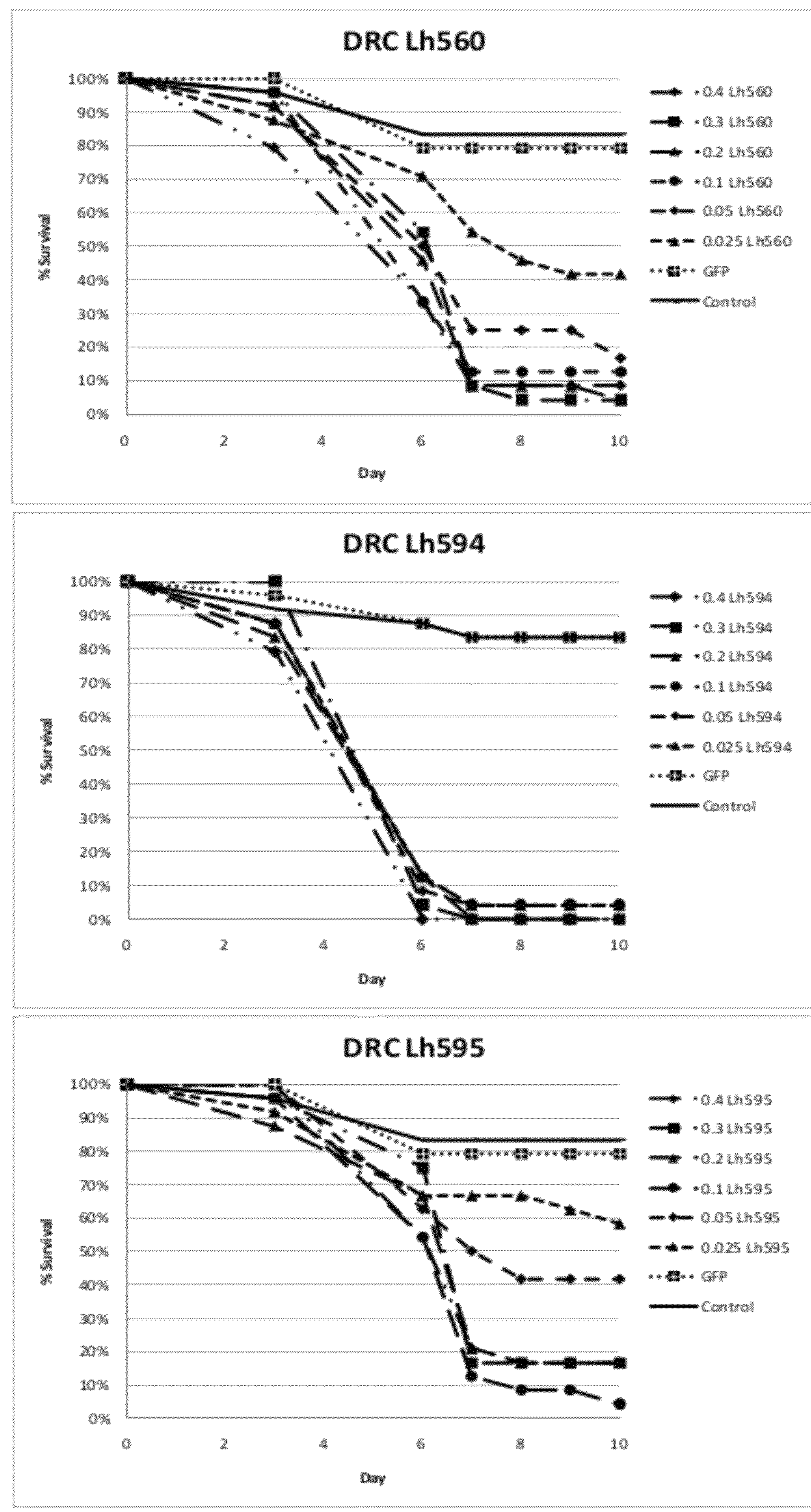
Figure 7:
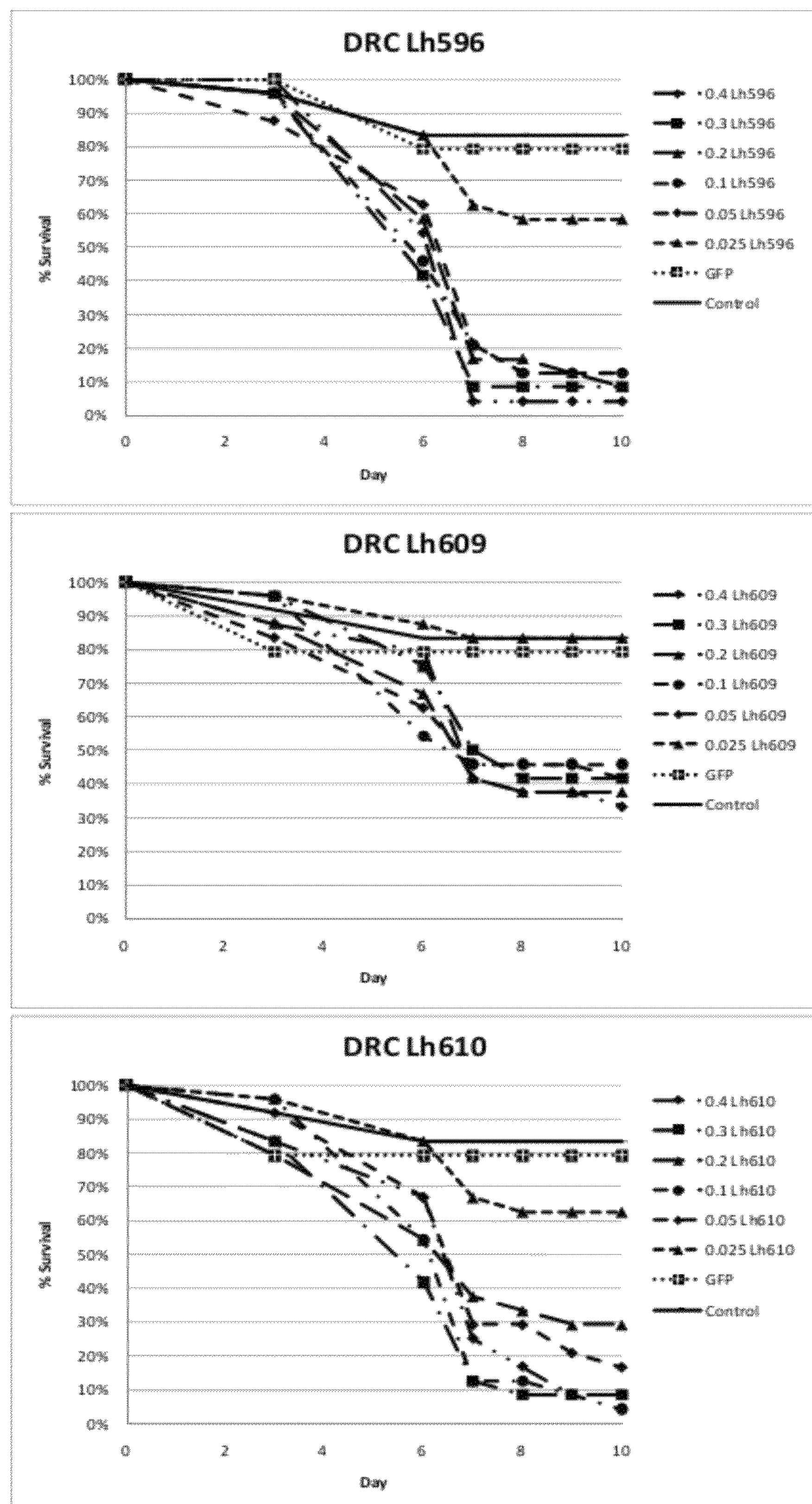
Figure 8:
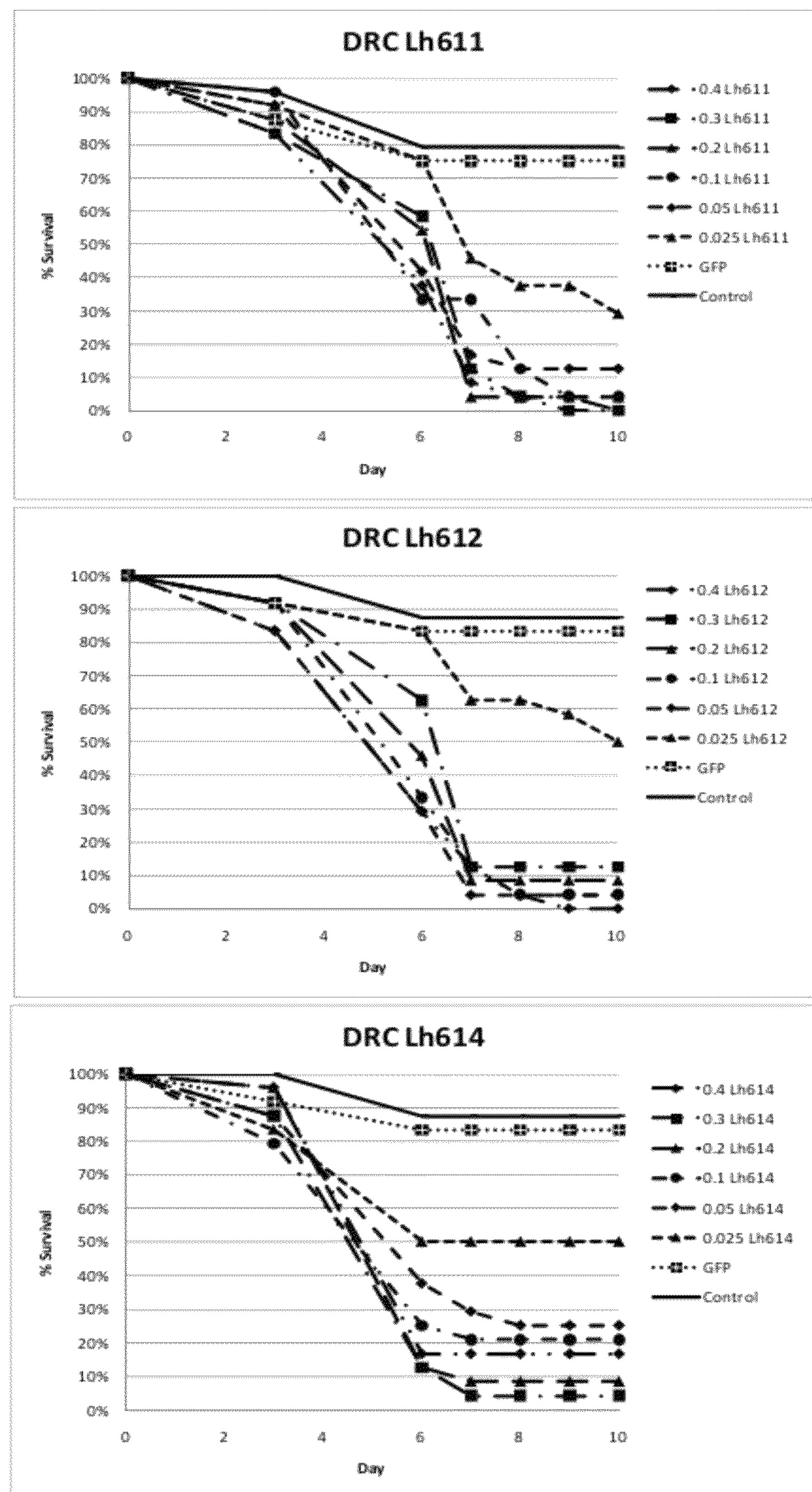
Figure 9:
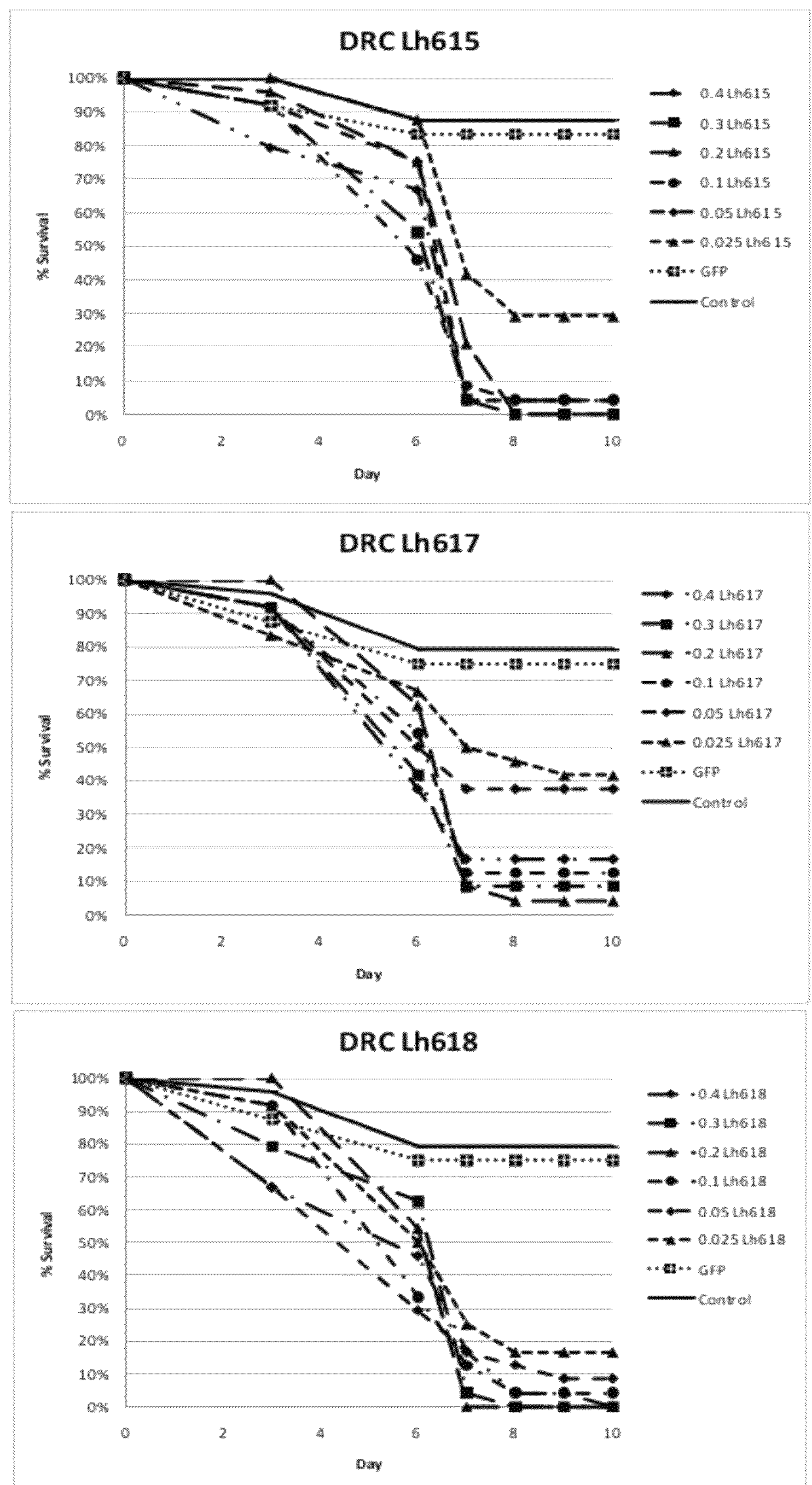

FIG. 4: Mortality analysis of *Lygus* novel targets from plates Lh010 to Lh020, expressed as % mortality over a 10 day period. Controls are indicated in dotted lines. Positive control: Lh423 (RpL19). Negative controls: GFP and diet only (Control).

FIGS. 5 to 9 *Lygus hesperus* novel targets—dose response curves at concentrations of purified synthetic dsRNA ranging from 0.4 to 0.025 μg/μl (in the figure, the unit "μg/μl" is not displayed). GFP dsRNA and milliQ water were used negative controls. dsRNA of targets were produced using the primers as described in the example section 1.1.

Figure 10:
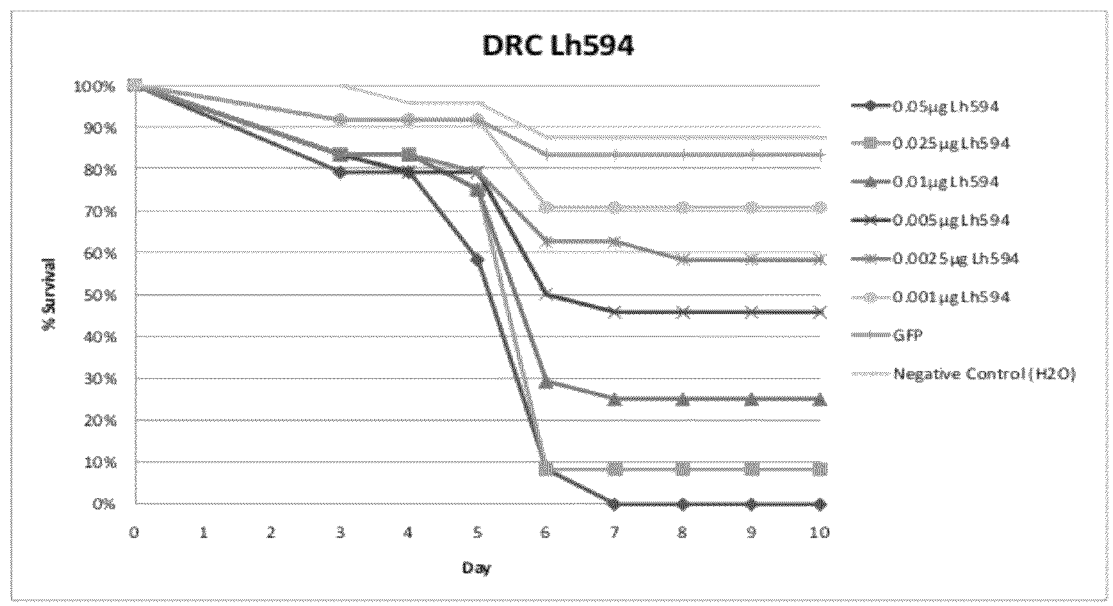

FIG. 10 Lh594 dose response curve, at dsRNA concentrations ranging from 0.05 to 0.001 μg/μl. GFP dsRNA and milliQ water were used negative controls.

Figure 11:
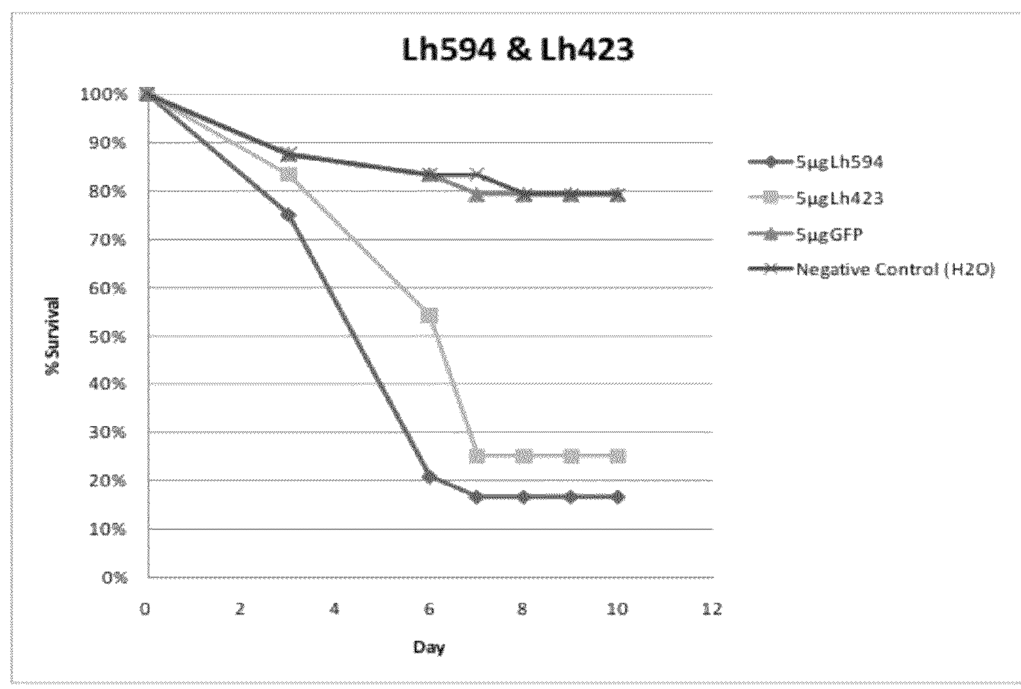
Figure 11:
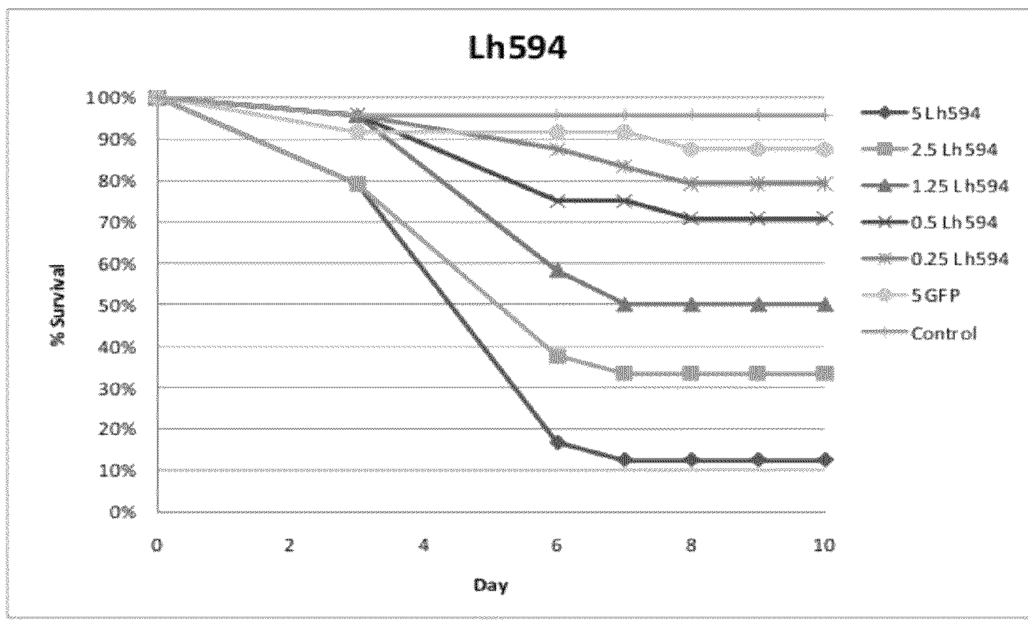

FIG. 11A dsRNA activity in *Lygus hesperus* bioassay in absence of tRNA. Lh594 (5 μg/μl); positive control: Lh423 (5 μg/μl); negative controls: GFP dsRNA (5 μg/μl) and milliQ water; B Identification of Lh594 limit of activity using decreasing concentration of dsRNA (from 5 μg to 0.25 μg). Negative controls: GFP dsRNA (5 μg/μl) and milliQ water.

Figure 12:
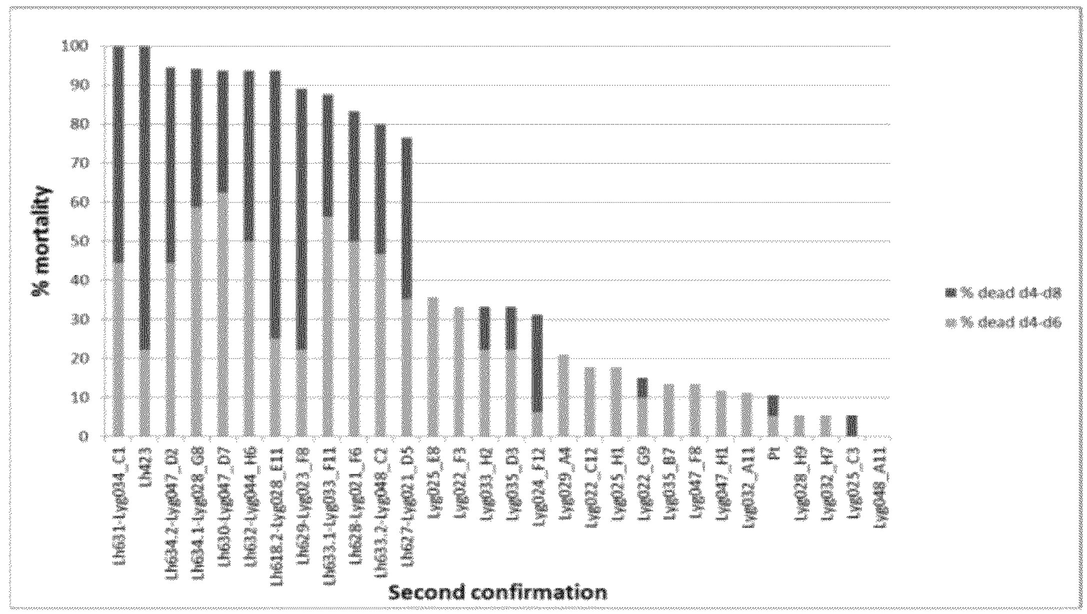

FIG. 12 Plates Lh010 to Lh020 second confirmation assay of second screen targets. Dark bars: mortality at day 4 to 8, light bars: mortality at day 4 to 6. Candidate clones are named using the "Lygxxx" screening codes and the "Lhxxx" target nomenclature codes.

Figure 13:
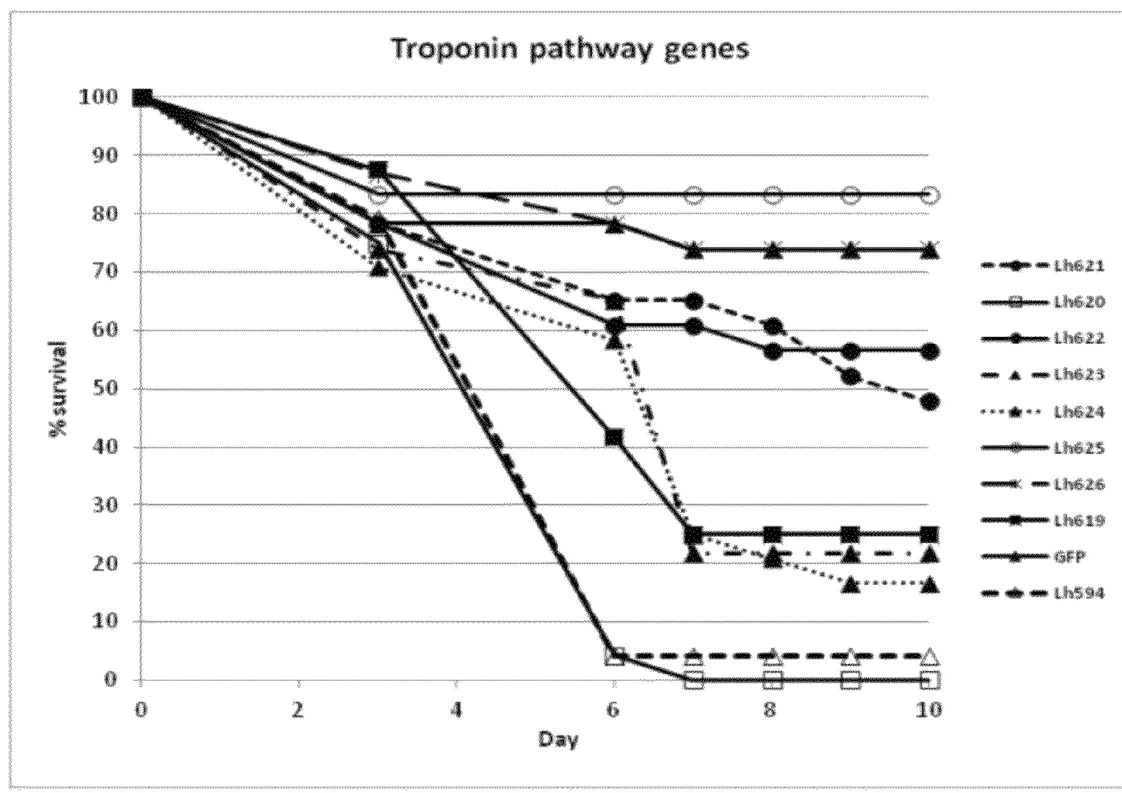

FIG. 13 Assay results for *Lygus* troponin pathway targets, tested at 0.5 μg/μl fixed.

Figure 14:
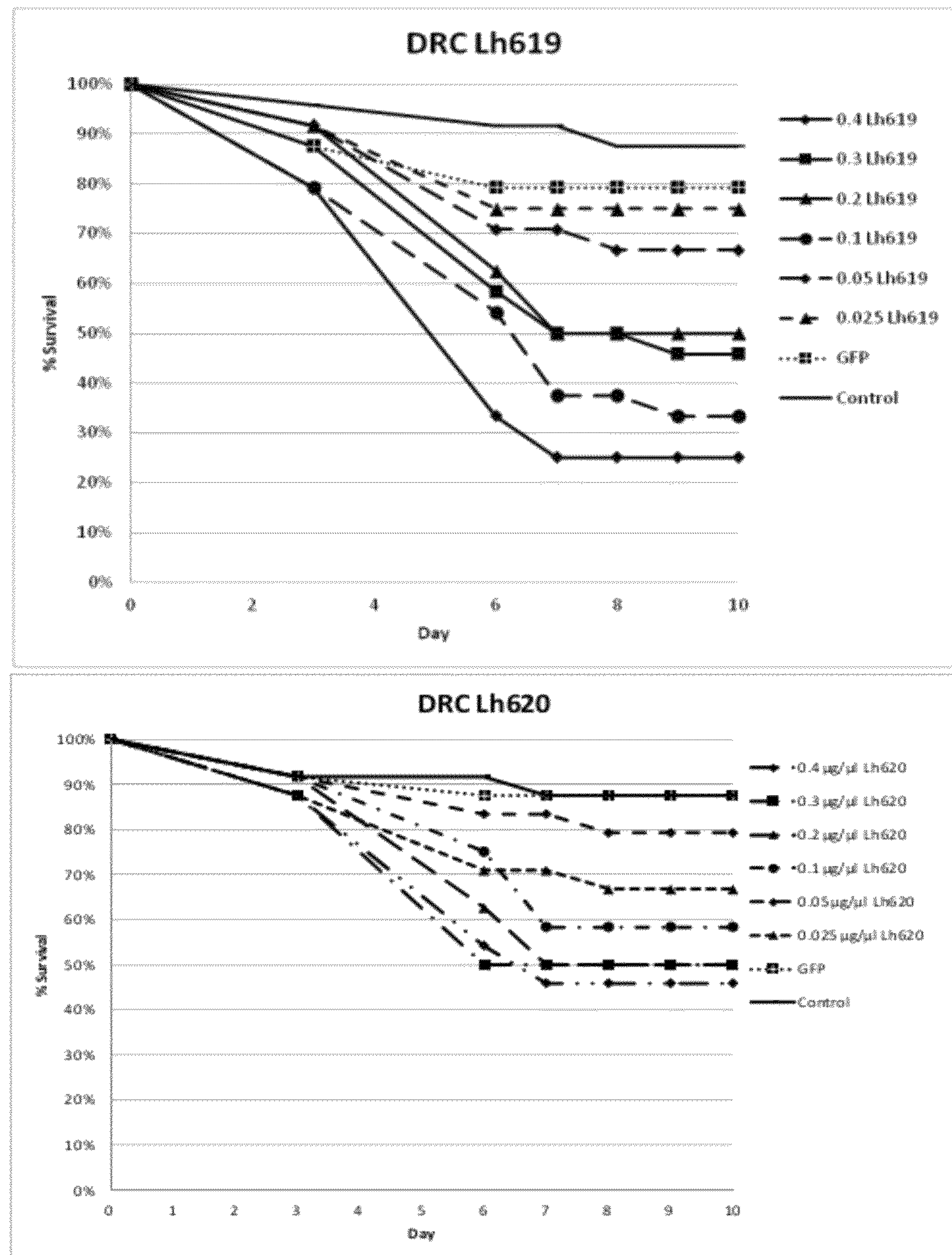
Figure 14:
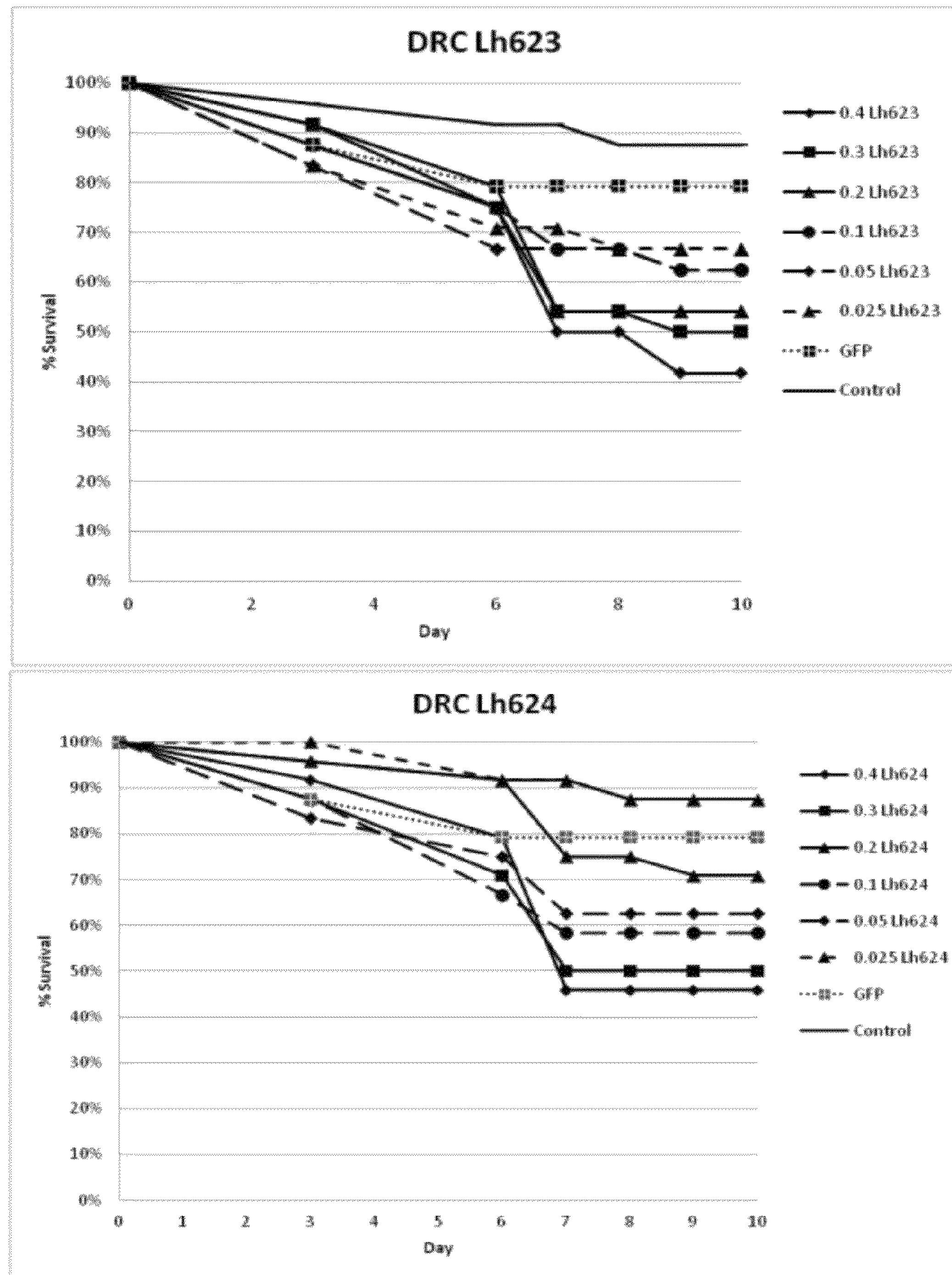

FIGS. 14 A-B *Lygus hesperus* novel targets from troponin pathway—dose response curves at concentrations of purified synthetic dsRNA ranging from 0.4 to 0.025 μg/μl (in the figure, the unit "μg/μl" is not always displayed). GFP dsRNA and milliQ water were used as negative controls.

Figure 15:
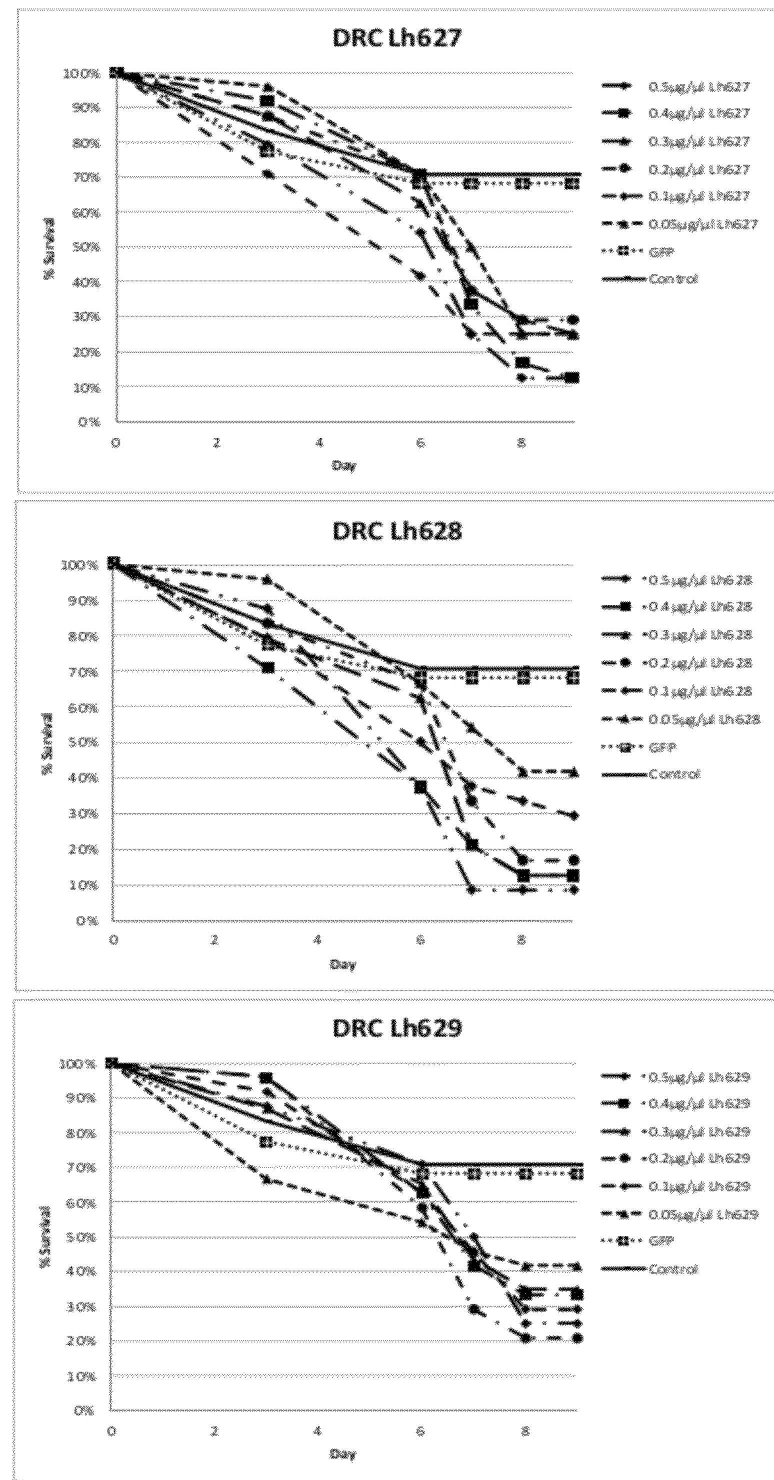
Figure 15:
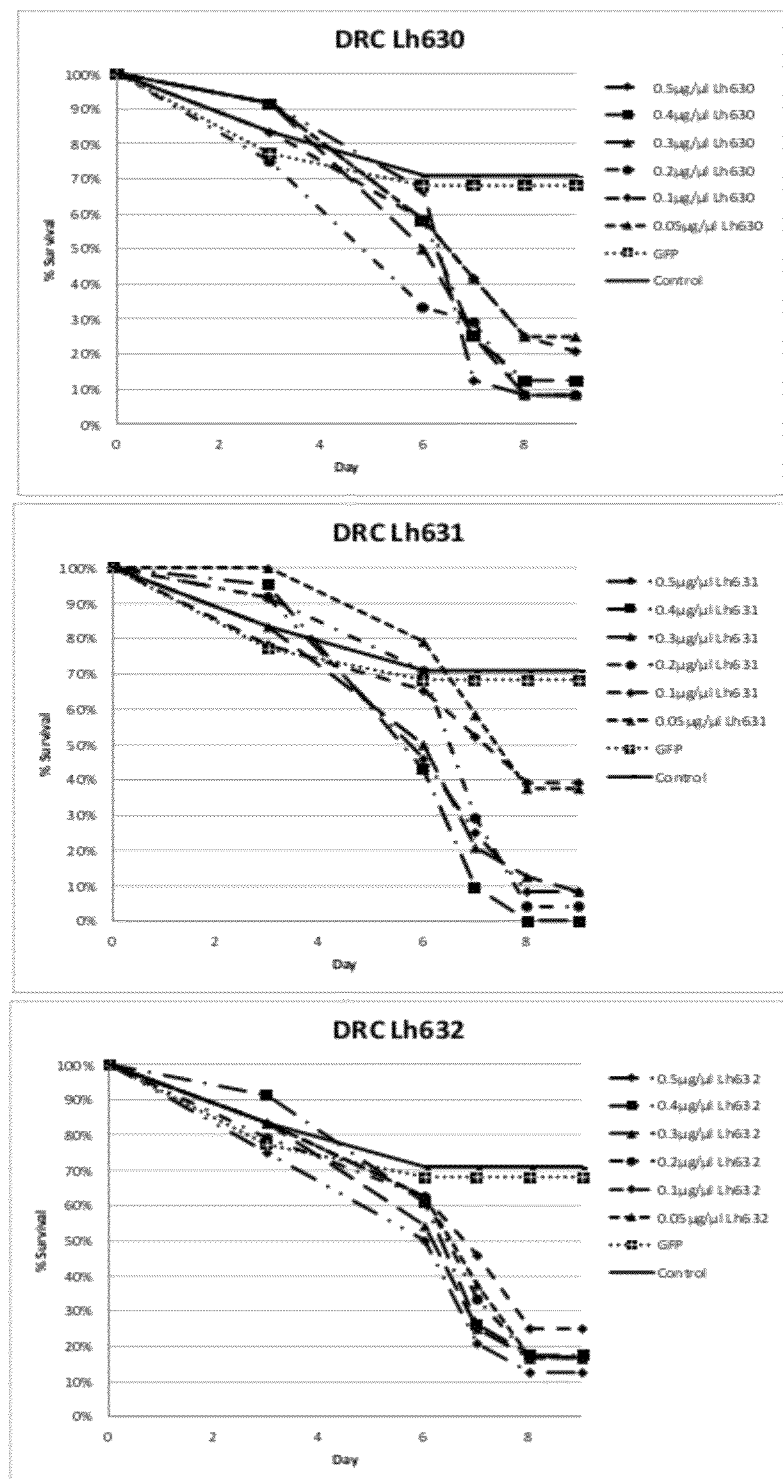
Figure 15:
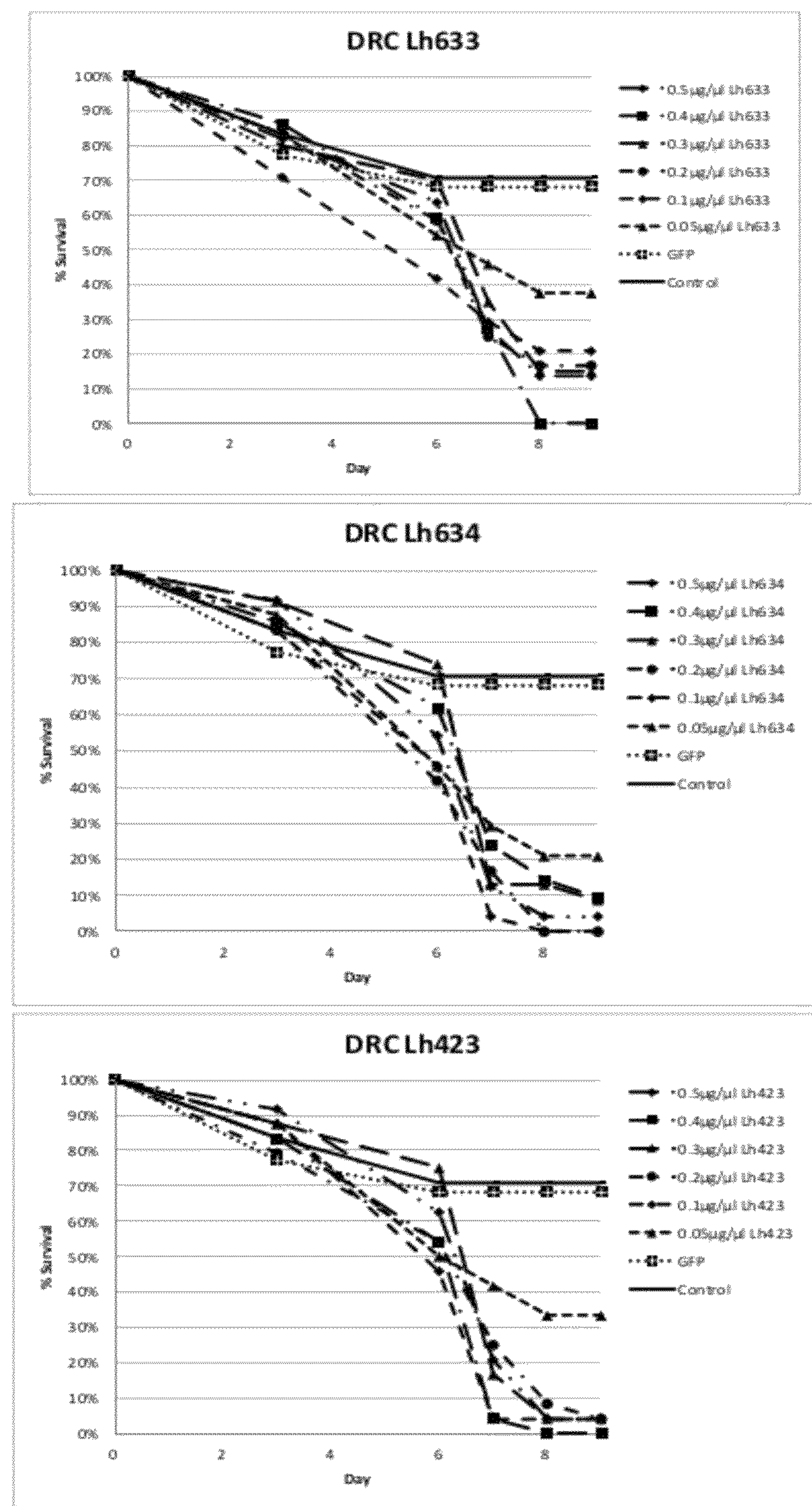
Figure 15:
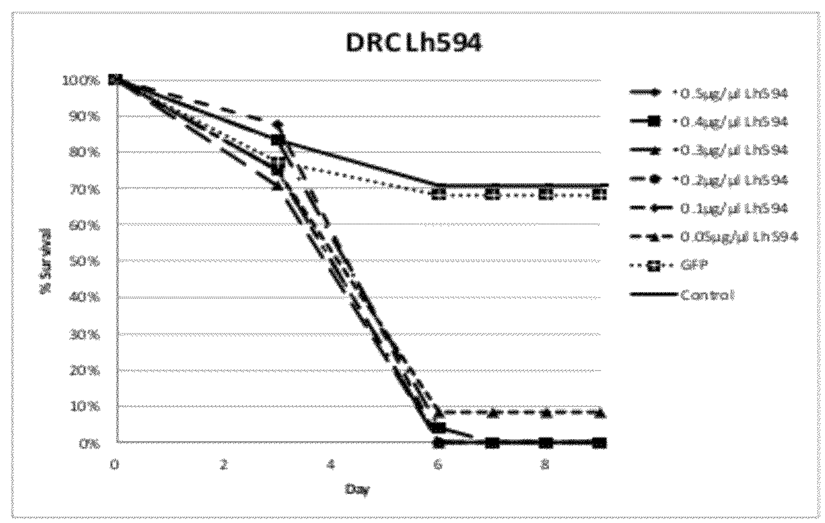

FIGS. 15 A-D *Lygus hesperus* novel targets of second screen targets—dose response curves at concentrations of purified synthetic dsRNA ranging from 0.5 to 0.05 μg/μl. GFP dsRNA and milliQ water were used as negative controls.

Figure 16:
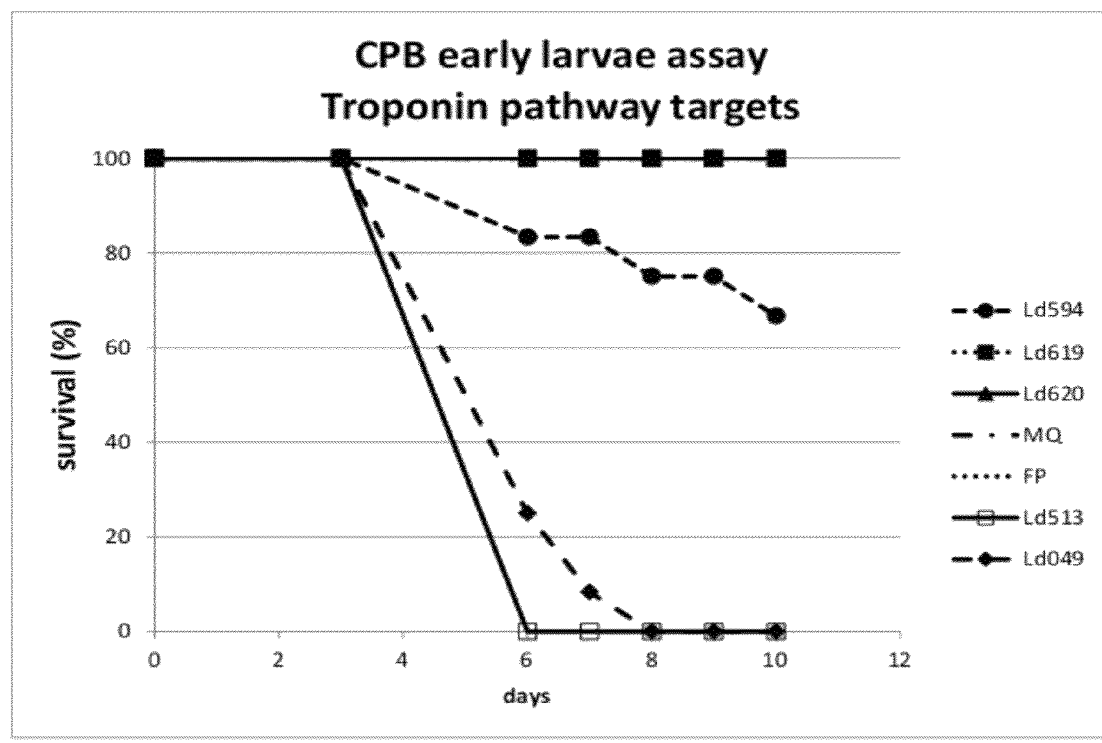

FIG. 16 Survival analysis of CPB larvae treated with 1 μg dsRNA Ld594, Ld619 and Ld620. Positive controls included 1 μg dsRNA of bench mark targets Ld513 and Ld049. Negative controls included milliQ water and FP.

Figure 17:
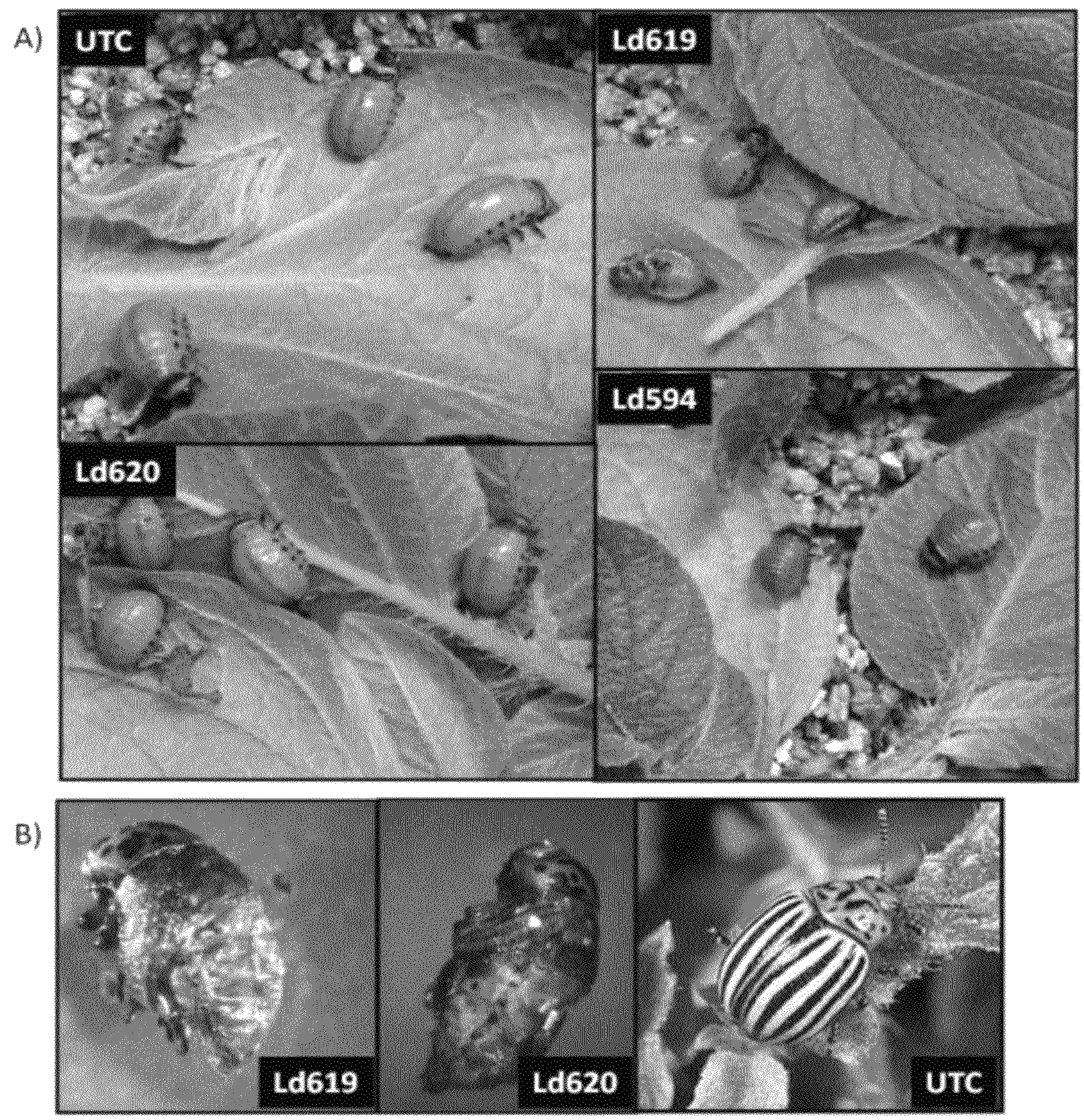

FIG. 17 Effects of Ld594, Ld619 and Ld620 dsRNAs on pupation of CPB 4$^{th}$ instar larvae, compared to untreated control (UTC). Bugs were fed 1 μg dsRNA dispensed in potato leaf disks, then were allowed to feed on untreated potato leaves (A) for 4 days before being placed on vermiculite. To assess the effect of the dsRNA, dead insects were excavated from the vermiculite (because of the strong effects induced by Ld594 dsRNA, no pupae could be recovered from the vermiculite and therefore, no image is available for this target dsRNA) (B).

Figure 18:
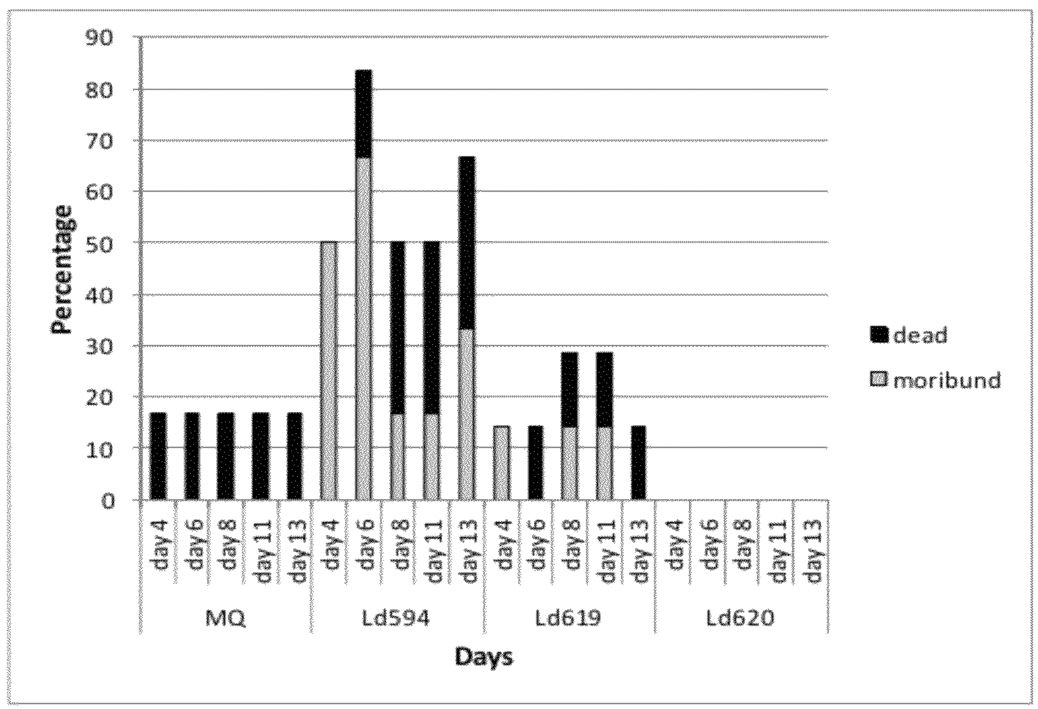

FIG. 18 Effect of CPB Ld594, 619 & 620 dsRNAs on survival and fitness of CPB adults. Assessments were performed on days 4, 6, 7, 8, 11 and 13. Control MQ: milliQ water.

Figure 19:
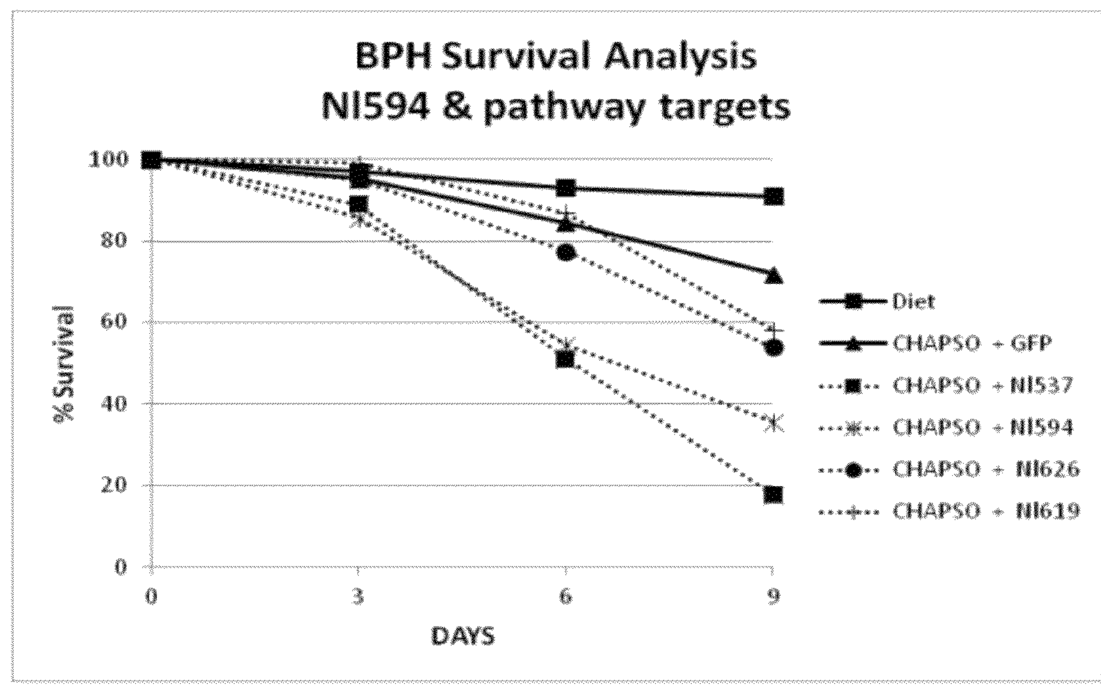

FIG. 19 Activity of dsRNA from N1594 pathway in brown plant hopper. DsRNAs were tested at 0.5 μg/μl in presence of 0.1% CHAPSO. Positive control: N1537 dsRNA (0.5 μg/μl), negative controls: GFP dsRNA (0.5 μg/μl) and diet alone.

Figure 20:
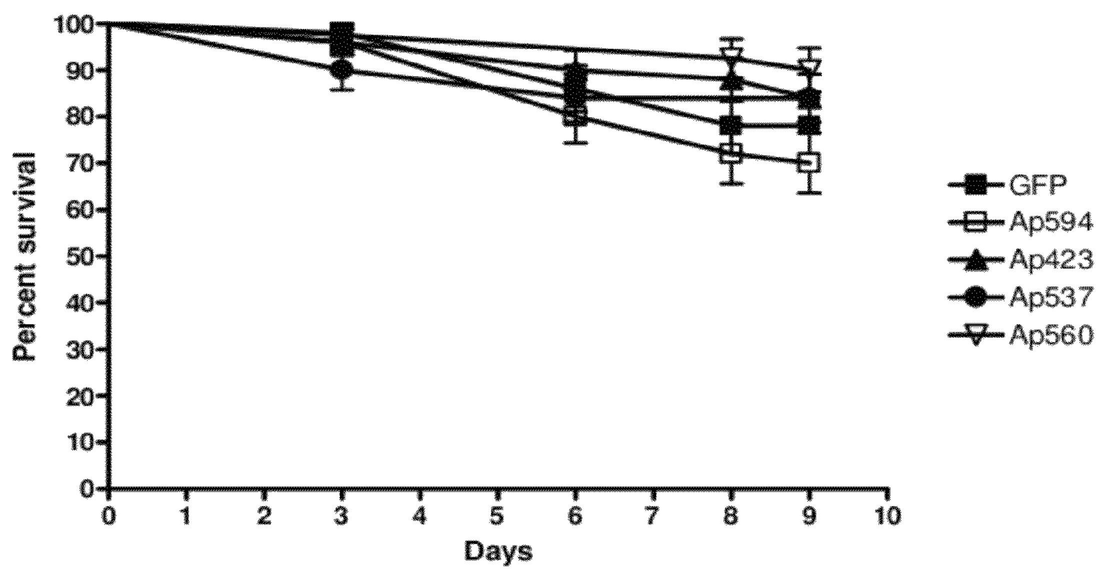

FIG. 20 Activity of dsRNA from Ap594, Ap423, Ap537 and Ap560 on *A. pisum*. DsRNAs were tested at 0.5 μg/μl in presence of 5 μg/μl tRNA. Negative control: GFP dsRNA (0.5 μg/μl).

Figure 21:
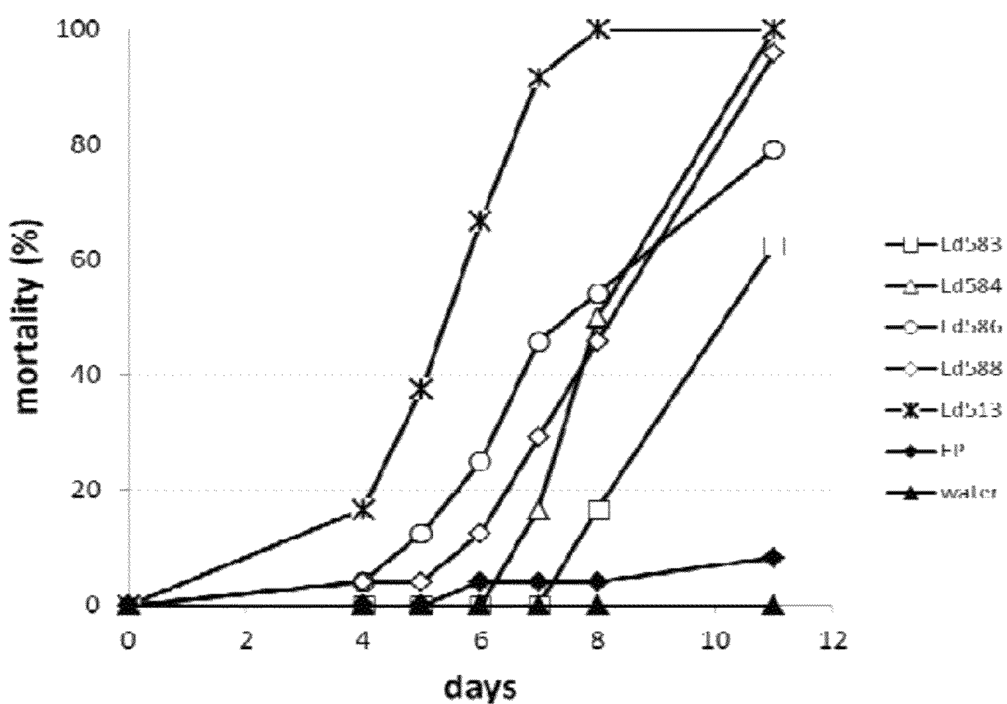

FIG. 21 Mortality percentages of *L. decemlineata* larvae on artificial diet treated with dsRNA. Ld583, Ld584, Ld586 & Ld588 represent target clones. Positive control: Ld513; negative control: FP.

DETAILED DESCRIPTION OF THE INVENTION

The present inventors have discovered that down-regulating the expression of particular target genes in insect pest species by RNAi can be used to effectively prevent and/or control infestation by said insect pest.

As used herein, the term "control" of pest infestation refers to any effect on a pest that serves to limit and/or reduce either the numbers of pest organisms and/or the damage caused by the pest.

Preferred target genes are therefore essential genes that control or regulate one or more essential biological functions within the insect pest, for example, cell division, reproduction, energy metabolism, digestion, neurological function and the like. Down-regulation of these essential genes by RNAi techniques can lead to death of the insect, or otherwise significantly retard growth and development or impair the ability of the pest to colonize an environment or infest host organisms.

The present inventors have now identified superior target genes of insect pest species belonging to the *Lygus, Leptinotarsa, Nilaparvata* and *Acyrthosiphum* genus, which targets are envisaged for use singly or in combination as an effective means for RNAi-mediated control of insect infestation, for example of agronomically important crops. Orthologues of these newly identified target genes can be used in other insect species to control pest infestation of the corresponding relevant crops. More specifically, the present inventors describe here that genes encoding for proteins of the troponin/myofilament complex form excellent target genes for suppression by the RNA inhibition machinery. One of these target genes encoded the insect troponin I protein (wings up A) which is an orthologue of the *Drosophila* CG7178 protein. This protein is involved in muscular contraction and belongs to a physiological pathway that was not yet fully explored for (insect) pest control through RNA inhibition. Moreover, since this protein complex is animal specific, no plant genes homologues or orthologues are known, reducing the risk of off-type plant phenotypes when expressing target dsRNA in plants. In addition, in *Drosophila*, troponin I is described as a haplo-insufficient gene, displaying a mutant phenotype in the heterozygote state. Such genes are particularly susceptible to reduced mRNA expression levels and as such can be considered as ideal RNAi targets. Further interesting target genes in this troponin/myofilament complex are listed below.

| Annotation ID | Cytology | Dm identifier |
|---|---|---|
| up | upheld | CG7107 |
| Tm1 | tropomyosin 1 | CG4898 |
| Tm2 | tropomyosin 2 | CG4843 |
| Mhc | myosin heavy chain | CG17927 |
| Mlc-c | myosin light chain cytoplasmic | CG3201 |
| sqh | spaghetti squash | CG3595 |
| zip | zipper | CG15792 |

Thus, according to one embodiment the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233 or the complement thereof, or having a nucleotide sequence so that, when the two sequences are optimally aligned and compared, is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233.

In a preferred embodiment, the target gene encodes an insect protein chosen from the troponin/myofilament complex chosen from the group comprising the troponin I (e.g. an insect orthologue of the CG7178 Dm protein), the upheld protein (e.g. an insect orthologue of the CG7107 Dm protein), the tropomyosin 1 protein (e.g. an insect orthologue of the CG4898 Dm protein), the tropomyosin 2 protein (e.g. an insect orthologue of the CG4843 Dm protein), the myosin heavy chain (e.g. an insect orthologue of the CG17927 Dm protein), the myosin light chain cytoplasmic protein (e.g. an insect orthologue of the CG3201 Dm protein), the spaghetti squash protein (e.g. an insect orthologue of the CG3595 Dm protein), the zipper protein (e.g. an insect orthologue of the CG15792 Dm protein), the troponin C (e.g. an insect orthologue of the CG2981, CG7930, CG9073, CG6514, CG12408, CG9073, CG7930, CG2981, CG12408 or CG6514 Dm protein)

In other embodiments, the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or having a nucleotide sequence so that, when the two sequences are optimally aligned and compared, is at least 75% preferably at least 80%, 85%, 90%, 95%, 98% or 99% identical to any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (ii) is selected from the group of genes having a nucleotide sequence comprising a fragment of at least 21 contiguous nucleotides of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or having a nucleotide sequence so that, when said gene comprising said fragment is optimally aligned and compared with any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, said nucleotide sequence is at least 75% preferably at least 80%, 85%, 90%, 95%, 98% or 99% identical to any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (iii) is selected from the group of genes having a nucleotide sequence comprising a fragment of at least 21 contiguous nucleotides of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, and wherein when said fragment is optimally aligned and compared with the corresponding fragment in any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, said nucleotide sequence of said fragment is at least 75% preferably at least 80%, 85%, 90%, 95%, 98% or 99% identical to said corresponding fragment of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (iv) is an insect pest orthologue of a gene having a nucleotide sequence comprising any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273.

In a preferred embodiment, the target gene encodes an insect ribosomal protein chosen from the group comprising the ribosomal protein S3A (e.g. an insect orthologue of the CG2168 Dm protein), the ribosomal protein LP1 (e.g. an insect orthologue of the CG4087 Dm protein), the ribosomal protein S3 (e.g. an insect orthologue of the CG6779 Dm protein), the ribosomal protein L10Ab (e.g. an insect orthologue of the CG7283 Dm protein), the ribosomal protein S18 (e.g. an insect orthologue of the CG8900 Dm protein), the ribosomal protein L4 (e.g. an insect orthologue of the CG5502 Dm protein), the ribosomal protein S27 (e.g. an insect orthologue of the CG10423 Dm protein), the ribosomal protein L6 (e.g. an insect orthologue of the CG11522 Dm protein), the ribosomal protein S13 (e.g. an insect orthologue of the CG13389 Dm protein), and the ribosomal protein L12 (e.g. an insect orthologue of the CG3195 Dm protein), the ribosomal protein L26 (e.g. an insect orthologue of the CG6846 Dm protein), the ribosomal protein L21 (e.g. an insect orthologue of the CG12775 Dm protein), the ribosomal protein S12 (e.g. an insect orthologue of the CG11271 Dm protein), the ribosomal protein S28b (e.g. an insect orthologue of the CG2998 Dm protein), the ribosomal protein L13 (e.g. an insect orthologue of the CG4651 Dm protein), the ribosomal protein L10 (e.g. an insect orthologue of the CG17521 Dm protein), the ribosomal protein L5 (e.g. an insect orthologue of the CG17489 Dm protein), the ribosomal protein S15Aa (e.g. an insect orthologue of the CG2033 Dm protein), the ribosomal protein L19 (e.g. an insect orthologue of the CG2746 Dm protein), the ribosomal protein L27 (e.g. an insect orthologue of the CG4759 Dm protein)

In one embodiment, the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, or the complement thereof, or having a nucleotide sequence so that, when the two sequences are optimally aligned and compared, is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313.

In one embodiment, the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 141, 11, 12, or the complement thereof, or having a nucleotide sequence so that, when the two sequences are optimally aligned and compared, is at least 75% preferably at least 80%, 85%, 90%, 95%, 98% or 99% identical to any of SEQ ID NOs 141, 11, 12, or the complement thereof, or (ii) is selected from the group of genes having a nucleotide sequence comprising a fragment of at least 21 contiguous nucleotides of any of SEQ ID NOs 141, 11, 12, or the complement thereof, or having a nucleotide sequence so that, when said gene comprising said fragment is optimally aligned and compared with any of SEQ ID NOs 141, 11, 12, said nucleotide sequence is at least 75% preferably at least 80%, 85%, 90%, 95%, 98% or 99% identical to any of SEQ ID NOs 141, 11, 12, or the complement thereof, or (iii) is selected from the group of genes having a nucleotide sequence comprising a fragment of at least 21 contiguous nucleotides of any of SEQ ID NOs 141, 11, 12, or the complement thereof, and wherein when said fragment is optimally aligned and compared with the corresponding fragment in any of SEQ ID NOs 141, 11, 12, said nucleotide sequence of said fragment is at least 75% preferably at least 80%, 85%, 90%, 95%, 98% or 99% identical to said corresponding fragment of any of SEQ ID NOs 141, 11, 12, or the complement thereof, or (iv) is an insect pest orthologue of a gene having a nucleotide sequence comprising any of SEQ ID NOs 141, 11, 12, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 141, 11, 12, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 141, 11, 12.

In one embodiment, the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 17, 18, or the complement thereof, or having a nucleotide sequence so that, when the two sequences are optimally aligned and compared, is at least 75% preferably at least 80%, 85%, 90%, 95%, 98% or 99% identical to any of SEQ ID NOs 17, 18, or the complement thereof, or (ii) is selected from the group of genes having a nucleotide sequence comprising a fragment of at least 21 contiguous nucleotides of any of SEQ ID NOs 17, 18, or the complement thereof, or having a nucleotide sequence so that, when said gene comprising said fragment is optimally aligned and compared with any of SEQ ID NOs 17, 18, said nucleotide sequence is at least 75% preferably at least 80%, 85%, 90%, 95%, 98% or 99% identical to any of SEQ ID NOs 17, 18, or the complement thereof, or (iii) is selected from the group of genes having a nucleotide sequence comprising a fragment of at least 21 contiguous nucleotides of any of SEQ ID NOs 17, 18, or the complement thereof, and wherein when said fragment is optimally aligned and compared with the corresponding fragment in any of SEQ ID NOs 17, 18, said nucleotide sequence of said fragment is at least 75% preferably at least 80%, 85%, 90%, 95%, 98% or 99% identical to said corresponding fragment of any of SEQ ID NOs 17, 18, or the complement thereof, or (iv) is an insect pest orthologue of a gene having a nucleotide sequence comprising any of SEQ ID NOs 17, 18, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 17, 18, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 17, 18.

In one embodiment, the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 19, 20, or the complement thereof, or having a nucleotide sequence so that, when the two sequences are optimally aligned and compared, is at least 75% preferably at least 80%, 85%, 90%, 95%, 98% or 99% identical to any of SEQ ID NOs 19, 20, or the complement thereof, or (ii) is selected from the group of genes having a nucleotide sequence comprising a fragment of at least 21 contiguous nucleotides of any of SEQ ID NOs 19, 20, or the complement thereof, or having a nucleotide sequence so that, when said gene comprising said fragment is optimally aligned and compared with any of SEQ ID NOs 19, 20, said nucleotide sequence is at least 75% preferably at least 80%, 85%, 90%, 95%, 98% or 99% identical to any of SEQ ID NOs 19, 20, or the complement thereof, or (iii) is selected from the group of genes having a nucleotide sequence comprising a fragment of at least 21 contiguous nucleotides of any of SEQ ID NOs 19, 20, or the complement thereof, and wherein when said fragment is optimally aligned and compared with the corresponding fragment in any of SEQ ID NOs 19, 20, said nucleotide sequence of said fragment is at least 75% preferably at least 80%, 85%, 90%, 95%, 98% or 99% identical to said corresponding fragment of any of SEQ ID NOs 19, 20, or the complement thereof, or (iv) is an insect pest orthologue of a gene having a nucleotide sequence comprising any of SEQ ID NOs 19, 20, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 19, 20, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 19, 20.

In one embodiment, the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 165, 166, 167, or the complement thereof, or having a nucleotide sequence so that, when the two sequences are optimally aligned and compared, is at least 75% preferably at least 80%, 85%, 90%, 95%, 98% or 99% identical to any of SEQ ID NOs 165, 166, 167, or the complement thereof, or (ii) is selected from the group of genes having a nucleotide sequence comprising a fragment of at least 21 contiguous nucleotides of any of SEQ ID NOs 165, 166, 167, or the complement thereof, or having a nucleotide sequence so that, when said gene comprising said fragment is optimally aligned and compared with any of SEQ ID NOs 165, 166, 167, said nucleotide sequence is at least 75% preferably at least 80%, 85%, 90%, 95%, 98% or 99% identical to any of SEQ ID NOs 165, 166, 167, or the complement thereof, or (iii) is selected from the group of genes having a nucleotide sequence comprising a fragment of at least 21 contiguous nucleotides of any of SEQ ID NOs 165, 166, 167, or the complement thereof, and wherein when said fragment is optimally aligned and compared with the corresponding fragment in any of SEQ ID NOs 17, 18, said nucleotide sequence of said fragment is at least 75% preferably at least 80%, 85%, 90%, 95%, 98% or 99% identical to said corresponding fragment of any of SEQ ID NOs 165, 166, 167, or the complement thereof, or (iv) is an insect pest orthologue of a gene having a nucleotide sequence comprising any of SEQ ID NOs 165, 166, 167, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 165, 166, 167, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 165, 166, 167.

In one embodiment, the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 143, 121, 142, 176, 182, 130, 177, 183, or the complement thereof, or having a nucleotide sequence so that, when the two sequences are optimally aligned and compared, is at least 75% preferably at least 80%, 85%, 90%, 95%, 98% or 99% identical to any of SEQ ID NOs 143, 121, 142, 176, 182, 130, 177, 183, or the complement thereof, or (ii) is selected from the group of genes having a nucleotide sequence comprising a fragment of at least 21 contiguous nucleotides of any of SEQ ID NOs 143, 121, 142, 176, 182, 130, 177, 183, or the complement thereof, or having a nucleotide sequence so that, when said gene comprising said fragment is optimally aligned and compared with any of SEQ ID NOs 143, 121, 142, 176, 182, 130, 177, 183, said nucleotide sequence is at least 75% preferably at least 80%, 85%, 90%, 95%, 98% or 99% identical to any of SEQ ID NOs 143, 121, 142, 176, 182, 130, 177, 183, or the complement thereof, or (iii) is selected from the group of genes having a nucleotide sequence comprising a fragment of at least 21 contiguous nucleotides of any of SEQ ID NOs 143, 121, 142, 176, 182, 130, 177, 183, or the complement thereof, and wherein when said fragment is optimally aligned and compared with the corresponding fragment in any of SEQ ID NOs 143, 121, 142, 176, 182, 130, 177, 183, said nucleotide sequence of said fragment is at least 75% preferably at least 80%, 85%, 90%, 95%, 98% or 99% identical to said corresponding fragment of any of SEQ ID NOs 143, 121, 142, 176, 182, 130, 177, 183, or the complement thereof, or (iv) is an insect pest orthologue of a gene having a nucleotide sequence comprising any of SEQ ID NOs 143, 121, 142, 176, 182, 130, 177, 183, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 143, 121, 142, 176, 182, 130, 177, 183, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 143, 121, 142, 176, 182, 130, 177, 183.

In one embodiment, the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 145, 122, 144, 178, 131, 179 or the complement thereof, or having a nucleotide sequence so that, when the two sequences are optimally aligned and compared, is at least 75% preferably at least 80%, 85%, 90%, 95%, 98% or 99% identical to any of SEQ ID NOs 145, 122, 144, 178, 131, 179, or the complement thereof, or (ii) is selected from the group of genes having a nucleotide sequence comprising a fragment of at least 21 contiguous nucleotides of any of SEQ ID NOs 145, 122, 144, 178, 131, 179, or the complement thereof, or having a nucleotide sequence so that, when said gene comprising said fragment is optimally aligned and compared with any of SEQ ID NOs 145, 122, 144, 178, 131, 179, said nucleotide sequence is at least 75% preferably at least 80%, 85%, 90%, 95%, 98% or 99% identical to any of SEQ ID NOs 145, 122, 144, 178, 131, 179, or the complement thereof, or (iii) is selected from the group of genes having a nucleotide sequence comprising a fragment of at least 21 contiguous nucleotides of any of SEQ ID NOs 145, 122, 144, 178, 131, 179, or the complement thereof, and wherein when said fragment is optimally aligned and compared with the corresponding fragment in any of SEQ ID NOs 145, 122, 144, 178, 131, 179, said nucleotide sequence of said fragment is at least 75% preferable at least 80%, 90%, 98%, 99% identical to said corresponding fragment of any of SEQ ID NOs 145, 122, 144, 178, 131, 179, or the complement thereof, or (iv) is an insect pest orthologue of a gene having a nucleotide sequence comprising any of SEQ ID NOs 145, 122, 144, 178, 131, 179, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 145, 122, 144, 178, 131, 179, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 145, 122, 144, 178, 131, 179.

In one embodiment, the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 128, 149, 184, 137, or the complement thereof, or having a nucleotide sequence so that, when the two sequences are optimally aligned and compared, is at least 75% preferably at least 80%, 85%, 90%, 95%, 98% or 99% identical to any of SEQ ID NOs 128, 149, 184, 137, or the complement thereof, or (ii) is selected from the group of genes having a nucleotide sequence comprising a fragment of at least 21 contiguous nucleotides of any of SEQ ID NOs 128, 149, 184, 137, or the complement thereof, or having a nucleotide sequence so that, when said gene comprising said fragment is optimally aligned and compared with any of SEQ ID NOs 128, 149, 184, 137, said nucleotide sequence is at least 75% preferably at least 80%, 85%, 90%, 95%, 98% or 99% identical to any of SEQ ID NOs 128, 149, 184, 137, or the complement thereof, or (iii) is selected from the group of genes having a nucleotide sequence comprising a fragment of at least 21 contiguous nucleotides of any of SEQ ID NOs 128, 149, 184, 137, or the complement thereof, and wherein when said fragment is optimally aligned and compared with the corresponding fragment in any of SEQ ID NOs 128, 149, 184, 137, said nucleotide sequence of said fragment is at least 75% preferably at least 80%, 85%, 90%, 95%, 98% or 99% identical to said corresponding fragment of any of SEQ ID NOs 128, 149, 184, 137, or the complement thereof, or (iv) is an insect pest orthologue of a gene having a nucleotide sequence comprising any of SEQ ID NOs 128, 149, 184, 137, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 128, 149, 184, 137, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 128, 149, 184, 137.

In yet other embodiments, the present invention relates to an interfering ribonucleic acid (RNA or double stranded RNA) that inhibits or downregulates the expression of a target gene that encodes a mitochondrial cytochrome c oxidase subunit II protein (e.g. an insect orthologue of the CG34069 Dm protein).

Thus, in one aspect, the invention provides an interfering ribonucleic acid (RNA) that functions upon uptake by an insect pest species to down-regulate expression of a target gene in said insect pest. As used herein, a “target gene” comprises any gene in the insect pest which one intends to down-regulate. In a preferred embodiment, the target gene is down-regulated so as to control pest infestation, for example by disrupting an essential biological process occurring in the pest, or by decreasing the pathogenicity of the pest. Preferred target genes therefore include but are not limited to those that play key roles in regulating feeding, survival, growth, development, reproduction, infestation and infectivity. According to one embodiment, the target gene is such that when its expression is down-regulated or inhibited, the insect pest is killed. According to another embodiment, the target gene is such that when its expression is down-regulated or inhibited, growth of the pest is prevented or retarded or stunted or delayed or impeded, pest reproduction is prevented, or transition through the life cycles of the pest is prevented. According to yet another embodiment of the invention, the target gene is such that when its expression is down-regulated or inhibited, the damage caused by the pest and/or the ability of the pest to infect or infest environments, surfaces and/or plant or crop species is reduced; or the pest stops feeding from its natural food resources such as plants and plant products. The terms “infest” and “infect” or “infestation” and “infection” are generally used interchangeably throughout.

The target genes may be expressed in all or some of the cells of the insect pest. Furthermore, the target genes may only be expressed by the insect pest at a particular stage of its life-cycle, for example, the mature adult phase, immature nymph or larval phase or egg phase. As used herein “pest” species are preferably insect species that cause infection or infestation, preferably of plants. The insect species may comprise and species belonging to the Orders Coleoptera, Lepidoptera, Diptera, Dichyoptera, Orthoptera, Hemiptera, or Siphonaptera. Preferred plant pathogenic insects according to the invention are plant pest are selected from the group consisting of *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); Laode/phax spp. (e.g. *L. striatellus* (small brown planthopper)); *Nephotettix* spp. (e.g. *N. virescens* or *N. cincticeps* (green leafhopper), or *N. nigropictus* (rice leafhopper)); *Sogatella* spp. (e.g. *S. furcifera* (white-backed planthopper)); *Chilo* spp. (e.g. *C. suppressalis* (rice striped stem borer), *C. auricilius* (gold-fringed stem borer), or *C. polychrysus* (dark-headed stem borer)); *Sesamia* spp. (e.g. *S. inferens* (pink rice borer)); *Tryporyza* spp. (e.g. *T. innotata* (white rice borer), or *T. incertulas* (yellow rice borer)); *Anthonomus* spp. (e.g. *A. grandis* (boll weevil)); *Phaedon* spp. (e.g. *P. cochleariae* (mustard leaf beetle)); *Epilachna* spp. (e.g. *E. varivetis* (mexican bean beetle)); *Tribolium* spp. (e.g. *T. castaneum* (red floor beetle)); *Diabrotica* spp. (e.g. *D. virgifera virgifera* (western corn rootworm), *D. barberi* (northern corn rootworm), *D. undecimpunctata howardi* (southern corn rootworm), *D. virgifera zeae* (Mexican corn rootworm); *Ostrinia* spp. (e.g. *O. nubilalis* (European corn borer)); *Anaphothrips* spp. (e.g. *A. obscrurus* (grass thrips)); *Pectinophora* spp. (e.g. *P. gossypiella* (pink bollworm)); *Heliothis* spp. (e.g. *H. virescens* (tobacco budworm)); *Trialeurodes* spp. (e.g. *T. abutiloneus* (banded-winged whitefly) *T. vaporariorum* (greenhouse whitefly)); *Bemisia* spp. (e.g. *B. argentifolii* (silverleaf whitefly)); *Aphis* spp. (e.g. *A. gossypii* (cotton aphid)); *Lygus* spp. (e.g. *L. lineolaris* (tarnished plant bug) or *L. hesperus* (western tarnished plant bug)); *Euschistus* spp. (e.g. *E. conspersus* (consperse stink bug)); *Chlorochroa* spp. (e.g. *C. sayi* (Say stinkbug)); *Nezara* spp. (e.g. *N. viridula* (southern green stinkbug)); *Thrips* spp. (e.g. *T. tabaci* (onion thrips)); *Frankliniella* spp. (e.g. *F. fusca* (tobacco thrips), or *F. occidentalis* (western flower thrips)); *Acheta* spp. (e.g. *A. domesticus* (house cricket)); *Myzus* spp. (e.g. *M. persicae* (green peach aphid)); *Macrosiphum* spp. (e.g. *M. euphorbiae* (potato aphid)); *Blissus* spp. (e.g. *B. leucopterus leucopterus* (chinch bug)); *Acrosternum* spp. (e.g. *A. hilare* (green stink bug)); *Chilotraea* spp. (e.g. *C. polychrysa* (rice stalk borer)); *Lissorhoptrus* spp. (e.g. *L. oryzophilus* (rice water weevil)); *Rhopalosiphum* spp. (e.g. *R. maidis* (corn leaf aphid)); and *Anuraphis* spp. (e.g. *A. maidiradicis* (corn root aphid)).

According to a more specific embodiment, the invention is applicable for species belonging to the family of Chrysomelidae or leaf beatles. Chrysomelid beetles such Colorado potato Beetles, Flea Beetles, Corn Rootworms and Curculionids such as Alfalfa Weevils are particularly important pests. Specific Leptinotarsa species to control according to the invention include Colorado Potato Beetle (Leptinotarsa decemlineata (Say) and False Potato Beetle (Leptinotarsa juncta (Say). CPB is a (serious) pest on our domestic potato, other cultivated and wild tuber bearing and non-tuber bearing potato species and other Solanaceous (nightshades) plant species incuding the crop species tomato, eggplant, peppers, tobacco (Nicotiana species including ornamentals), ground cherry, rice, corn or cotton; and the weed/herb species, horse nettle, common nightshade, thorn apple, henbane and buffalo burr. Corn rootworms include species found in the genus *Diabrotica* (e.g., *D. undecimpunctata* undecimpunctata, *D. undecimpunctata howardii, D. longicornis, D. virgifera* and *D. balteata*). Corn rootworms cause extensive damage to corn and curcubits.

According to a more specific embodiment, the invention is applicable for species belonging to the order of Hemipterans (family of Aphidoidea), such as *Myzus persicae* (green peach aphid, *Aphis fabae* (Black Bean Aphid), *Acyrthosiphum pisum* (Pea Aphid), *Brevicoryne brassicae* (Cabbage Aphid), *Sitobion avenae* (Grain Aphid), *Cavariella aegopodii* (Carrot Aphid), *Aphis* craccivora (Groundnut Aphid), *Aphis gossypii* (Cotton Aphid), *Toxoptera aurantii* (Black Citrus Aphid), *Cavariella* spp (Willow Aphid), *Chaitophorus* spp (Willow Leaf Aphids), *Cinara* spp. (Black Pine Aphids), *Drepanosiphum platanoides* (Sycamore Aphid) *Elatobium* spp (Spruce Aphids) which cause damage to plants such as *Prunus* trees, particularly peach, apricot and plum; trees that are mainly cultured for wood production such as willows and poplars, to row crops such as corn, cotton, soy, wheat and rice, to vegetable crops of the families Solanaceae, Chenopodiaceae, Compositae, Cruciferae, and Cucurbitaceae, including but not limited to, artichoke, asparagus, bean, beets, broccoli, Brussels sprouts, cabbage, carrot, cauliflower, cantaloupe, celery, corn, cucumber, fennel, kale, kohlrabi, turnip, eggplant, lettuce, mustard, okra, parsley, parsnip, pea, pepper, potato, radish, spinach, squash, tomato, turnip, watercress, and watermelon; or field crops such as, but not limited to, tobacco, sugar beet, and sunflower; a flower crop or other ornamental plant such as pine trees and conifers. Other Hemipterans belong to *Nilaparvata* ssp (eg. *N. lugens, Sogatella furcifera*) and cause damage to rice plants. Other Hemipterans belong to *Lygus* ssp (eg. *Lygus hesperus, Lygus rugulipennis, Lygus lineolaris, Lygus* sully) and other species of plant-feeding insects in the family of the Miridae, and cause damage to cotton, potato plants, strawberries, cotton, alfalfa, canola, peach, plums, grape, lettuce, eggplant, onion, green beans. As well as several Mediterranean trees and several ornamental trees such as elm tree (*Ulmus* spp.) pine nut (*Pinus Pinea*) London plane tree (*Platanus Acerifolia*), white redbud (*Malus alba*). Other Hemipterans belong to the family of the Pentatomoidea, they are commonly referred to as shield bugs, chust bugs, and stink bugs (eg; the brown marmorated stink bug (*Halyomorpha halys*), the Consperse stink bug (*Euschistus conspersus*), southern green stink bug (*Nezara viridula*), forest bug (*Pentatoma rufipes*), harlequin bug (*Murgantia histrionica*), rice stink bug (*Oebalus pugnax*)) and cause damage to fruits including apples, peaches, figs, mulberries, citrus fruits and persimmons, blackberry, and vegetables including sweetcorn, tomatoes, soy beans, lima beans and green peppers, cabbage, cauliflower, turnips, horseradish, collards, mustard, Brussels sprouts, potato, egg plant, okra, beans, asparagus, beets, weeds, fruit trees and field crops such as field corn and soy bean. Stink bugs are also a pest of grasses, sorghum and rice.

A plant to be used in the methods of the invention, or a transgenic plant according to the invention encompasses any plant, but is preferably a plant that is susceptible to infestation by a plant pathogenic insect.

Accordingly, the present invention extends to plants and to methods as described herein wherein the plant is chosen from the following group of plants (or crops): alfalfa, apple, apricot, artichoke, asparagus, avocado, banana, barley, beans, beet, blackberry, blueberry, broccoli, Brussels sprouts, cabbage, canola, carrot, cassaya, cauliflower, a cereal, celery, cherry, citrus, clementine, coffee, corn, cotton, cucumber, eggplant, endive, eucalyptus, figs, grape, grapefruit, groundnuts, ground cherry, kiwifruit, lettuce, leek, lemon, lime, pine, maize, mango, melon, millet, mushroom, nut oat, okra, onion, orange, an ornamental plant or flower or tree, papaya, parsley, pea, peach, peanut, peat, pepper, persimmon, pineapple, plantain, plum, pomegranate, potato, pumpkin, radicchio, radish, rapeseed, raspberry, rice, rye, sorghum, soy, soybean, spinach, strawberry, sugar beet, sugarcane, sunflower, sweet potato, tangerine, tea, tobacco, tomato, a vine, watermelon, wheat, yams and zucchini.

In specific embodiments, the present invention provides target genes which encode proteins involved in the function of a wings up A (troponin I), a mitochondrial cytochrome c oxidase subunit II protein, or one of the ribosomal proteins as specified in Table 1.

In preferred embodiments, the present invention provides target genes selected from the group of genes (i) having a nucleotide sequence comprising any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or having a nucleotide sequence so that, when the two sequences are optimally aligned and compared, is at least 75%, preferably at least 80%, 85%, 90%, 95%, 98% or 99% identical any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (ii) having a nucleotide sequence consisting of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iii) having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000, or 3000 contiguous nucleotides of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iv) having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000, or 3000 contiguous nucleotides of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (v) having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389 or (vi) which gene is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389;

and wherein the nucleotide sequence of said gene is no longer than 10000, 9000, 8000, 7000, 6000, 5000, 4000, 3000, 2000 or 1500 nucleotides.

The amino acid sequences encoded by the target genes of the present invention are represented by SEQ ID NOs. SEQ ID NOs 79, 349, 405, 352, 356, 80, 326, 81, 327, 82, 83, 328, 84, 329, 85, 86, 359, 87 to 91, 330, 350, 353, 331, 351, 332 to 336, 337, 354, 338 to 344, 346, 345, 347, 348, 357, 355, 358, 390 to 393.

As used herein, the term "having" has the same meaning as "comprising".

As used herein, the term "sequence identity" is used to describe the sequence relationship between two or more nucleotide or amino acid sequences. The percentage of "sequence identity" between two sequences is determined by comparing two optimally aligned sequences over a comparison window (a defined number of positions), wherein the portion of the sequence in the comparison window may comprise additions or deletions (i.e. gaps) as compared to the reference sequence in order to achieve optimal alignment. The percentage sequence identity is calculated by determining the number of positions at which the identical nucleotide base or amino acid residue occurs in both sequences to yield the number of 'matched' positions, dividing the number of matched positions by the total number of positions in the comparison window and multiplying the result by 100. Methods and software for determining sequence identity are available in the art and include the Blast software and GAP analysis. For nucleic acids, the percent identity is calculated preferably by the BlastN alignment tool whereby the percent identity is calculated over the entire length of the query nucleotide sequence. A person skilled in the art will recognise that homologues or orthologues (homologues existing in different species) of the target genes represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389 can be identified. These pest homologues and/or orthologues are also within the scope of the current invention. Preferred homologues and/or orthologues are genes similar in nucleotide sequence to such a degree that when the two genes are optimally aligned and compared, the homologue and/or orthologue has a sequence that is at least 75%, preferably at least 80% or 85%, more preferably at least 90% or 95%, and most preferably at least about 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389 or the complement thereof. Similarly, also preferred homologues and/or orthologues are proteins that are similar in amino acid sequence to such a degree that when the two amino acid sequences are optimally aligned and compared, the homologue and/or orthologue has a sequence that is at least 75%, preferably at least 80% or 85%, more preferably at least 90% or 95%, and most preferably at least about 99% identical to any of SEQ ID NOs 79, 349, 405, 352, 356, 80, 326, 81, 327, 82, 83, 328, 84, 329, 85, 86, 359, 87 to 91, 330, 350, 353, 331, 351, 332 to 336, 337, 354, 338 to 344, 346, 345, 347, 348, 357, 355, 358, 390 to 393.

Other homologues are genes which are alleles of a gene comprising a sequence as represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389. Further preferred homologues are genes comprising at least one single nucleotide polymorphism (SNP) compared to a gene comprising a sequence as represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389.

The 'interfering ribonucleic acid (RNA)' of the current invention encompasses any type of RNA molecule capable of down-regulating or 'silencing' expression of a target gene, including but not limited to sense RNA, antisense RNA, short interfering RNA (sRNA), microRNA (miRNA), double-stranded RNA (dsRNA), hairpin RNA (RNA) and the like. Methods to assay for functional interfering RNA molecules are well known in the art and are disclosed elsewhere herein.

The interfering RNA molecules of the current invention effect sequence-specific down-regulation of expression of a target gene by binding to a target nucleotide sequence within the target gene. Binding occurs as a result of base pairing between complementary regions of the interfering RNA and the target nucleotide sequence. As used herein, the term 'silencing element' refers to the portion or region of the interfering RNA comprising or consisting of a sequence of nucleotides which is complementary, or at least partially complementary, to a target nucleotide sequence within the target gene, and which functions as the active portion of the interfering RNA to direct down-regulation of expression of said target gene. In one embodiment of the invention, the silencing element comprises or consists of a sequence of at least 17 contiguous nucleotides, preferably at least 18 or 19 contiguous nucleotides, more preferably at least 21 contiguous nucleotides, even more preferably at least 22, 23, 24 or 25 contiguous nucleotides complementary to a target nucleotide sequence within the target gene.

As used herein, "expression of a target gene" refers to the transcription and accumulation of the RNA transcript encoded by a target gene and/or translation of the mRNA into protein. The term 'down-regulate' is intended to refer to any of the methods known in the art by which interfering RNA molecules reduce the level of primary RNA transcripts, mRNA or protein produced from a target gene. In certain embodiments, down-regulation refers to a situation whereby the level of RNA or protein produced from a gene is reduced by at least 10%, preferably by at least 33%, more preferably by at least 50%, yet more preferably by at least 80%. In particularly preferred embodiments, down-regulation refers to a reduction in the level of RNA or protein produced from a gene by at least 80%, preferably by at least 90%, more preferably by at least 95%, and most preferably by at least 99% within cells of the insect pest as compared with an appropriate control insect pest which has for example, not been exposed to an interfering RNA or has been exposed to a control interfering RNA molecule. Methods for detecting reductions in RNA or protein levels are well known in the art and include RNA solution hybridization, Northern hybridization, reverse transcription (e.g. quantitative RT-PCR analysis), microarray analysis, antibody binding, enzyme-linked immunosorbent assay (ELISA) and Western blotting. In another embodiment of the invention, down-regulation refers to a reduction in RNA or protein levels sufficient to result in a detectable change in a phenotype of the pest as compared with an appropriate pest control, for example, cell death, cessation of growth, or the like. Down-regulation can thus be measured by phenotypic analysis of the insect pest using techniques routine in the art.

In a preferred embodiment of the invention, the interfering RNA down-regulates gene expression by RNA interference or RNAi. RNAi is a process of sequence-specific gene regulation typically mediated by double-stranded RNA molecules such as short interfering RNAs (siRNAs). siRNAs comprise a sense RNA strand annealed by complementary basepairing to an antisense RNA strand. The sense strand or 'guide strand' of the siRNA molecule comprises a sequence of nucleotides complementary to a sequence of nucleotides located within the RNA transcript of the target gene. The sense strand of the siRNA is therefore able to anneal to the RNA transcript via Watson-Crick-type basepairing and target the RNA for degradation within a cellular complex known as the RNAi-induced silencing complex or RISC. Thus, in the context of preferred interfering RNA molecules of the current invention, the silencing element as referred to herein may be a double-stranded region comprising annealed complementary strands, at least one strand of which comprises or consists of a sequence of nucleotides which is complementary or at least partially complementary to a target nucleotide sequence within a target gene. In one embodiment the double-stranded region has a length of at least 21, 22, 23, 24, 25, 30, 35, 40, 50, 55, 60, 70, 80, 90, 100, 125, 150, 175, 200, 300, 400, 500, 600, 700, 800, 900, 1000, 1100, 1200, 1300, 1400, 1500, 2000 or 3000 base pairs.

Longer double-stranded RNA (dsRNA) molecules comprising one or more functional double-stranded silencing elements as described elsewhere herein, and capable of RNAi-mediated gene silencing are also contemplated within the scope of the current invention. Such longer dsRNA molecules comprise at least 80, 200, 300, 350, 400, 450, 500, 550, 600, 700, 800, 900, 1000, 1100, 1200, 1300, 1400, 1500, 2000 or 3000 base pairs. These dsRNA molecules may serve as precursors for the active siRNA molecules that direct the RNA transcript to the RISC complex for subsequent degradation. dsRNA molecules present in the environment surrounding an organism or the cells thereof may be taken up by the organism and processed by an enzyme called Dicer to yield siRNA molecules. Alternatively, the dsRNA may be produced in vivo i.e. transcribed from a polynucleotide or polynucleotides encoding the same present within a cell, for instance a bacterial cell or a plant cell, and subsequently processed by Dicer either within the host cell or preferably within the insect pest cells following uptake of the longer precursor dsRNA. The dsRNA may be formed from two separate (sense and antisense) RNA strands that anneal by virtue of complementary basepairing. Alternatively, the dsRNA may be a single strand that is capable of folding back on itself to form a hairpin RNA (RNA) or stem-loop structure. In the case of a RNA, the double-stranded region or 'stem' is formed from two regions or segments of the RNA that are essentially inverted repeats of one another and possess sufficient complementarity to allow the formation of a double-stranded region. One or more functional double-stranded silencing elements may be present in this 'stem region' of the molecule. The inverted repeat regions are typically separated by a region or segment of the RNA known as the 'loop' region. This region can comprise any nucleotide sequence conferring enough flexibility to allow self-pairing to occur between the flanking complementary regions of the RNA. In general, the loop region is substantially single-stranded and acts as a spacer element between the inverted repeats.

All the interfering RNA molecules of the invention effect sequence-specific down-regulation of expression of a target gene by binding to a target nucleotide sequence within the target gene. Binding occurs as a result of complementary base pairing between the silencing element of the interfering RNA and the target nucleotide sequence. The interfering RNA molecules of the invention comprise at least one or at least two silencing elements. In one embodiment of the current invention, the target nucleotide sequence comprises a sequence of nucleotides as represented by the RNA transcript of the target gene, or a fragment thereof wherein the fragment is preferably at least 17 nucleotides, more preferably at least 18, 19 or 20 nucleotides, or most preferably at least 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 nucleotides. In a preferred embodiment of the current invention, the target nucleotide sequence comprises a sequence of nucleotides equivalent to the RNA transcript encoded by any of the polynucleotides selected from the group consisting of (i) a polynucleotide which comprises at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (ii) a polynucleotide which consists of at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iii) a polynucleotide which comprises at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, so that, when the two sequences are optimally aligned and compared, said polynucleotide is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iv) a polynucleotide which comprises a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein said fragment or said complement has a nucleotide sequence so that, when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389 or the complement thereof, or (v) a polynucleotide which consists of a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein said fragment or said complement has a nucleotide sequence that, when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389 or the complement thereof, or (vi) a polynucleotide encoding an amino acid sequence that, when the two amino acid sequences are optimally aligned and compared, is at least 70% preferably at least 75%, 80%, 85%, 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389. In a more preferred embodiment of the above, said polynucleotide is no longer than 10000, 9000, 8000, 7000, 6000, 5000, 4000, 3000, 2000 or 1500 nucleotides.

Preferably, the interfering RNA molecules of the current invention comprise at least one double-stranded region, typically the silencing element of the interfering RNA, comprising a sense RNA strand annealed by complementary base-pairing to an antisense RNA strand wherein the sense strand of the dsRNA molecule comprises a sequence of nucleotides complementary to a sequence of nucleotides located within the RNA transcript of the target gene.

The silencing element, or at least one strand thereof wherein the silencing element is double-stranded, may be fully complementary or partially complementary to the target nucleotide sequence of the target gene. As used herein, the term "fully complementary" means that all the bases of the nucleotide sequence of the silencing element are complementary to or 'match' the bases of the target nucleotide sequence. The term "at least partially complementary" means that there is less than a 100% match between the bases of the silencing element and the bases of the target nucleotide sequence. The skilled person will understand that the silencing element need only be at least partially complementary to the target nucleotide sequence in order to mediate down-regulation of expression of the target gene. It is known in the art that RNA sequences with insertions, deletions and mismatches relative to the target sequence can still be effective at RNAi. According to the current invention, it is preferred that the silencing element and the target nucleotide sequence of the target gene share at least 80% or 85% sequence identity, preferably at least 90% or 95% sequence identity, or more preferably at least 97% or 98% sequence identity and still more preferably at least 99% sequence identity. Alternatively, the silencing element may comprise 1, 2 or 3 mismatches as compared with the target nucleotide sequence over every length of 24 partially complementary nucleotides.

It will be appreciated by the person skilled in the art that the degree of complementarity shared between the silencing element and the target nucleotide sequence may vary depending on the target gene to be down-regulated or depending on the insect pest species in which gene expression is to be controlled.

In another embodiment of the current invention, the silencing element comprises a sequence of nucleotides that is the RNA equivalent of any of the polynucleotides selected from the group consisting of a polynucleotide which comprises at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (ii) a polynucleotide which comprises at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, so that, when the two sequences are optimally aligned and compared, said polynucleotide is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iii) a polynucleotide which comprises a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein said fragment or said complement has a nucleotide sequence so that, when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, wherein said polynucleotide is no longer than 10000, 9000, 8000, 7000, 6000, 5000, 4000, 3000, 2000 or 1500 nucleotides. It will be appreciated that in such embodiments the silencing element may comprise or consist of a region of double-stranded RNA comprising annealed complementary strands, one strand of which, the sense strand, comprises a sequence of nucleotides at least partially complementary to a target nucleotide sequence within a target gene.

The target nucleotide sequence may be selected from any suitable region or nucleotide sequence of the target gene or RNA transcript thereof. For example, the target nucleotide sequence may be located within the 5'UTR or 3'UTR of the target gene or RNA transcript or within exonic or intronic regions of the gene.

The skilled person will be aware of methods of identifying the most suitable target nucleotide sequences within the context of the full-length target gene. For example, multiple silencing elements targeting different regions of the target gene can be synthesised and tested. Alternatively, digestion of the RNA transcript with enzymes such as RNAse H can be used to determine sites on the RNA that are in a conformation susceptible to gene silencing. Target sites may also be identified using in silico approaches, for example, the use of computer algorithms designed to predict the efficacy of gene silencing based on targeting different sites within the full-length gene.

The interfering RNAs of the current invention may comprise one silencing element or multiple silencing elements, wherein each silencing element comprises or consists of a sequence of nucleotides which is at least partially complementary to a target nucleotide sequence within a target gene and that functions upon uptake by an insect pest species to down-regulate expression of said target gene. Concatemeric RNA constructs of this type are described in WO2006/046148 as incorporated herein by reference. In the context of the present invention, the term 'multiple' means at least two, at least three, at least four, etc and up to at least 10, 15, 20 or at least 30. In one embodiment, the interfering RNA comprises multiple copies of a single silencing element i.e. repeats of a silencing element that binds to a particular target nucleotide sequence within a specific target gene. In another embodiment, the silencing elements within the interfering RNA comprise or consist of different sequences of nucleotides complementary to different target nucleotide sequences. It should be clear that combinations of multiple copies of the same silencing element combined with silencing elements binding to different target nucleotide sequences are within the scope of the current invention.

The different target nucleotide sequences may originate from a single target gene in an insect pest species in order to achieve improved down-regulation of a specific target gene in an insect pest species. In this case, the silencing elements may be combined in the interfering RNA in the original order in which the target nucleotide sequences occur in the target gene, or the silencing elements may be scrambled and combined randomly in any rank order in the context of the interfering RNA as compared with the order of the target nucleotide sequences in the target gene.

Alternatively, the different target nucleotide sequences are representing a single target gene but originating from different insect pest species.

Alternatively, the different target nucleotide sequences may originate from different target genes. If the interfering RNA is for use in preventing and/or controlling pest infestation, it is preferred that the different target genes are chosen from the group of genes regulating essential biological functions of insect pest species, including but not limited to survival, growth, development, reproduction and pathogenicity. The target genes may regulate the same or different biological pathways or processes. In one embodiment, at least one of the silencing elements comprises or consists of a sequence of nucleotides which is at least partially complementary to a target nucleotide sequence within a target gene wherein the target gene is selected from the group of genes as described earlier. In a further embodiment of the invention, the different genes targeted by the different silencing elements originate from the same insect pest species. This approach is designed to achieve enhanced attack against a single insect pest species. In particular, the different target genes may be expressed differentially in the different stages of the insect's life cycle, for example, the mature adult, immature larval and egg stages. The interfering RNA of the invention may thus be used to prevent and/or control insect pest infestation at more than one stage of the insect's life cycle.

In an alternative embodiment of the invention, the different genes targeted by the different silencing elements originate from different insect pest species. The interfering RNA of the invention can thus be used to prevent and/or control infestation by more than one insect pest species simultaneously. The silencing elements may be arranged as one contiguous region of the interfering RNA or may be separated by the presence of linker sequences. The linker sequence may comprise a short random nucleotide sequence that is not complementary to any target nucleotide sequences or target genes. In one embodiment, the linker is a conditionally self-cleaving RNA sequence, preferably a pH-sensitive linker or a hydrophobic-sensitive linker. In one embodiment, the linker comprises a sequence of nucleotides equivalent to an intronic sequence. Linker sequences of the current invention may range in length from about 1 base pair to about 10000 base pairs, provided that the linker does not impair the ability of the interfering RNA to down-regulate the expression of target gene(s).

In addition to the silencing element(s) and any linker sequences, the interfering RNA of the invention may comprise at least one additional polynucleotide sequence. In different embodiments of the invention, the additional sequence is chosen from (i) a sequence capable of protecting the interfering RNA against RNA processing, (ii) a sequence affecting the stability of the interfering RNA, (iii) a sequence allowing protein binding, for example to facilitate uptake of the interfering RNA by cells of the insect pest species, (iv) a sequence facilitating large-scale production of the interfering RNA, (v) a sequence which is an aptamer that binds to a receptor or to a molecule on the surface of the insect pest cells to facilitate uptake, or (v) a sequence that catalyses processing of the interfering RNA within the insect pest cells and thereby enhances the efficacy of the interfering RNA. Structures for enhancing the stability of RNA molecules are well known in the art and are described further in WO2006/046148 as incorporated herein by reference.

The length of the interfering RNA of the invention needs to be sufficient for uptake by the cells of an insect pest species and down-regulation of target genes within the pest as described elsewhere herein. However, the upper limit on length may be dependent on (i) the requirement for the interfering RNA to be taken up by cells of the pest and (ii) the requirement for the interfering RNA to be processed in the cells of the pest to mediate gene silencing via the RNAi pathway. The length may also be dictated by the method of production and the formulation for delivery of the interfering RNA to cells. Preferably, the interfering RNA of the current invention will be between 21 and 10000 nucleotides in length, preferably between 50 and 5000 nucleotides or between 100 and 2500 nucleotides, more preferably between 80 and 2000 nucleotides in length.

The interfering RNA may contain DNA bases, non-natural bases or non-natural backbone linkages or modifications of the sugar-phosphate backbone, for example to enhance stability during storage or enhance resistance to degradation by nucleases. Furthermore, the interfering RNA may be produced chemically or enzymatically by one skilled in the art through manual or automated reactions.

Alternatively, the interfering RNA may be transcribed from a polynucleotide encoding the same.

Thus, provided herein is an isolated polynucleotide encoding any of the interfering RNAs of the current invention.

Also provided herein is an isolated polynucleotide selected from the group consisting of (i) a polynucleotide which comprises at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (ii) a polynucleotide which consists of at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iii) a polynucleotide which comprises at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, so that, when the two sequences are optimally aligned and compared, said polynucleotide is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iv) a polynucleotide which comprises a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein said fragment or said complement has a nucleotide sequence so that, when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389 or the complement thereof, or (v) a polynucleotide which consists of a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein said fragment or said complement has a nucleotide sequence so that, when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389 or the complement thereof, or (vi) a polynucleotide encoding an amino acid sequence that, when the two amino acid sequences are optimally aligned and compared, is at least 70% preferably at least 75%, 80%, 85%, 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, and wherein said polynucleotide is no longer than 10000, 9000, 8000, 7000, 6000, 5000, 4000, 3000, 2000 or 1500 nucleotides.

In preferred embodiments, the isolated polynucleotide is part of an interfering RNA molecule, typically part of the silencing element, comprising at least one double-stranded region comprising a sense RNA strand annealed by complementary basepairing to an antisense RNA strand wherein the sense strand of the dsRNA molecule comprises a sequence of nucleotides complementary to a sequence of nucleotides located within the RNA transcript of the target gene. The sense strand of the dsRNA is therefore able to anneal to the RNA transcript and target the RNA for degradation within the RNAi-induced silencing complex or RISC.

The polynucleotides of the invention may be inserted via routine molecular cloning techniques into DNA constructs or vectors known in the art. Therefore, according to one embodiment, a DNA construct comprising any of the polynucleotides of the current invention is provided. Preferably, provided herein is a DNA construct comprising a polynucleotide encoding at least one of the interfering RNAs of the current invention. The DNA construct may be a recombinant DNA vector, for example a bacterial, viral or yeast vector. In a preferred embodiment of the invention, the DNA construct is an expression construct and the polynucleotide is operably linked to at least one regulatory sequence capable of driving expression of the polynucleotide sequence. The term 'regulatory sequence' is to be taken in a broad context and is intended to refer to any nucleotide sequence capable of effecting expression of polynucleotides to which it is operably linked including but not limited to promoters, enhancers and other naturally-occurring or synthetic transcriptional activator elements. The regulatory sequence may be located at the 5' or 3' end of the polynucleotide sequence. The term 'operably linked' refers to a functional linkage between the regulatory sequence and the polynucleotide sequence such that the regulatory sequence drives expression of the polynucleotide. Operably linked elements may be contiguous or non-contiguous.

Preferably, the regulatory sequence is a promoter selected from the group comprising but not limited to constitutive promoters, inducible promoters, tissue-specific promoters and growth/developmental stage-specific promoters. In one embodiment, the polynucleotide is placed under the control of a strong constitutive promoter such as any selected from the group comprising the CaMV35S promoter, doubled CaMV35S promoter, ubiquitin promoter, actin promoter, rubisco promoter, GOS2 promoter, Figwort mosaic virus 34S promoter.

Optionally, one or more transcription termination sequences may be incorporated in the expression construct of the invention. The term 'transcription termination sequence' encompasses a control sequence at the end of a transcriptional unit, which signals termination of transcription, 3' processing and poly-adenylation of a primary transcript. Additional regulatory sequences including but not limited to transcriptional or translational enhancers may be incorporated in the expression construct, for instance as with the double enhanced CaMV35S promoter.

The present invention also encompasses a method for generating any of the interfering RNAs of the invention comprising the steps of (i) contacting a polynucleotide encoding said interfering RNA or a DNA construct comprising the same with cell-free components; or (ii) introducing (e.g. by transformation, transfection or injection) a polynucleotide encoding said interfering RNA or a DNA construct comprising the same into a cell.

The invention thus also relates to any double stranded ribonucleotide produced from the expression of a polynucleotide described herein.

Accordingly, also provided herein is a host cell transformed with any of the polynucleotides described herein. Further encompassed by the present invention are host cells comprising any of the interfering RNA's of the current invention, any of the polynucleotides of the current invention or a DNA construct comprising the same. The host cell may be a prokaryotic cell including but not limited to gram-positive and gram-negative bacterial cells, or an eukaryotic cell including but not limited to yeast cells or plant cells. Preferably, said host cell is a bacterial cell or a plant cell. The bacterial cell can be chosen from the group comprising, but not limited to, Gram positive and Gram negative cells comprising *Escherichia* spp. (e.g. *E. coli*), *Bacillus* spp. (e.g. *B. thuringiensis*), *Rhizobium* spp., *Lactobacillus* spp., *Lactococcus* spp., *Pseudomonas* spp. and *Agrobacterium* spp. The polynucleotide or DNA construct of the invention may exist or be maintained in the host cell as an extra-chromosomal element or may be stably incorporated into the genome of the host cell.

Characteristics of particular interest in selecting a host cell for the purposes of the current invention include the ease with which the polynucleotide or DNA construct encoding the interfering RNA can be introduced into the host, the availability of compatible expression systems, the efficiency of expression, and the stability of the interfering RNA in the host.

Preferably, the interfering RNAs of the invention are expressed in a plant host cells. Preferred plants of interest include but are not limited to cotton, potato, rice, tomato, canola, soy, sunflower, sorghum, pearl millet, corn, alfalfa, strawberries, eggplant, pepper and tobacco.

In situations wherein the interfering RNA is expressed within a host cell and/or is used to prevent and/or control pest infestation of a host organism, it is preferred that the interfering RNA does not exhibit significant 'off-target' effects i.e. the interfering RNA does not affect expression of genes within the host. Preferably, the silencing element does not exhibit significant complementarity with nucleotide sequences other than the intended target nucleotide sequence of the target gene. In one embodiment of the invention, the silencing element shows less than 30%, more preferably less than 20%, more preferably less than 10% and even more preferably less than 5% sequence identity with any gene of the host cell or organism. If genomic sequence data is available for the host organism, one can cross-check identity with the silencing element using standard bioinformatics tools. In one embodiment, there is no sequence identity between the silencing element and a gene from the host cell or host organism over a region of 17, more preferably over a region of 18 or 19 and most preferably over a region of 20 or 21 contiguous nucleotides.

In the practical application of the invention, the interfering RNAs of the invention may be used for the prevention and/or control of any insect pest belonging to the Orders Coleoptera, Lepidoptera, Diptera, Dichyoptera, Orthoptera, Hemiptera and Siphonaptera.

Furthermore, in accordance with another aspect of the invention, there is provided herein a composition for preventing and/or controlling insect pest infestation comprising at least one interfering ribonucleic acid (RNA) and optionally at least one suitable carrier, excipient or diluent, wherein the interfering RNA functions upon uptake by the pest to down-regulate the expression of a target gene within said pest. The interfering RNA may be any of those as disclosed elsewhere herein. Preferably, the interfering RNA comprises or consists of at least one silencing element and said silencing element is a region of double-stranded RNA comprising annealed complementary strands, one strand of which (the sense strand) comprises a sequence of nucleotides which is at least partially complementary to a target nucleotide sequence within a target gene. The 'target gene' may be any of the pest target genes as disclosed elsewhere herein including but not limited to genes involved in regulating pest survival, growth, development, reproduction and pathogenicity. Alternatively, the composition comprises at least one host cell comprising at least one interfering RNA molecule or DNA construct encoding the same and optionally at least one suitable carrier, excipient or diluent, wherein the interfering RNA functions upon uptake of the host cell by the insect pest to down-regulate the expression of a target gene within said pest.

In the practical application of the invention, the composition may be used for the prevention and/or control of any insect pest belonging to the Orders Coleoptera, Lepidoptera, Diptera, Dichyoptera, Orthoptera, Hemiptera and Siphonaptera. The composition may therefore be in any suitable form for application to insect pests or for application to substrates and/or organisms, in particular plants, susceptible to infestation by said insect pest. In one embodiment, the composition is for use in preventing and/or controlling pest infestation of plants or propagation or reproductive material of plants and is thus directed towards insect pest species that infest plants. The composition of the present invention is particularly effective when the insect pest belongs to the category of 'chewing' insects that cause considerable damage to plants by eating plant tissues such as roots, leaves, flowers, buds, twigs and the like. Examples from this large insect category include beetles and their larvae.

The composition of the invention may be used to control insect pests at all stages of their life cycle, for example, the mature adult stage, the larval and egg stages.

In the context of the composition of the invention, the interfering RNA may be produced from a DNA construct, in particular an expression construct as described elsewhere herein, comprising a polynucleotide encoding the same. In preferred embodiments, the interfering RNA may be produced inside a host cell or organism engineered to express said interfering RNA from a polynucleotide encoding the same.

Suitable host organisms for use in the compositions of the current invention include but are not limited to microorganisms that are known to colonize the environment on and/or around plants or crops of interest i.e. plants or crops susceptible to infestation by insect pest species. Such microorganisms include but are not limited to those that occupy the phylloplane (the surface of plant leaves) and/or the rhizosphere (the soil surrounding plant roots). These microorganisms are selected so as to be capable of successfully competing with any wild-type organisms present in the plant environment. Suitable microorganisms for use as hosts include various species of bacteria, algae and fungi. It is clear that the chosen microorganisms must not be toxic to plants. Such compositions applied to plants susceptible of infestation by insect pest species will be ingested by the insect pests feeding on the treated plants.

Host organisms that do not naturally colonize plants and/or their environment are also within the scope of the current invention. Such organisms may serve only as a means to generate the interfering RNA of the composition. For example, in one embodiment, the interfering RNA is fermented/produced in a bacterial host and the bacteria are subsequently inactivated/killed. The resulting bacteria may be processed and used as an insecticidal spray in the same manner that *Bacillus thuringiensis* strains have been used as an insecticide for a spray application. In certain embodiments, a bacterial extract or lysate may be suitably purified to leave a substantially pure interfering RNA containing extract, which is subsequently formulated into one of the compositions of the invention. Standard extraction/purification techniques would be known by a person skilled in the art.

Compositions of the invention may be in any suitable physical form for application to insects. For example, the composition may be in solid form (powder, pellet or a bait), liquid form (including a form administered as a spray insecticide) or gel form. In a specific embodiment, the composition may be a coating, paste or powder that can be applied to a substrate in order to protect said substrate from infestation by insects. In this embodiment, the composition can be used to protect any substrate or material that is susceptible to infestation by or damage caused by an insect.

The nature of the excipients and the physical form of the composition may vary depending on the nature of the substrate that it is desired to treat. For example, the composition may be a liquid that is brushed or sprayed onto or imprinted into the material or substrate to be treated, or a coating or powder that is applied to the material or substrate to be treated.

In one embodiment, the composition is in the form of a bait. The bait is designed to lure the insect to come into contact with the composition. Upon coming into contact therewith, the composition is then internalised by the insect, by ingestion for example and mediates RNAi to thus kill the insect. Said bait may comprise a food substance, such as a protein based food, for example fish meal. Boric acid may also be used as a bait. The bait may depend on the species being targeted. An attractant may also be used. The attractant may be a pheromone, such as a male or female pheremone for example. As an example, the pheromones referred to in the book "Insect Pheremones and their use in Pest Management" (Howse et al, Chapman and Hall, 1998) may be used in the invention. The attractant acts to lure the insect to the bait, and may be targeted for a particular insect or may attract a whole range of insects. The bait may be in any suitable form, such as a solid, paste, pellet or powdered form.

The bait may also be carried away by the insect back to the colony. The bait may then act as a food source for other members of the colony, thus providing an effective control of a large number of insects and potentially an entire insect pest colony. This is an advantage associated with use of the double stranded RNA of the invention, because the delayed action of the RNAi mediated effects on the pests allows the bait to be carried back to the colony, thus delivering maximal impact in terms of exposure to the insects.

Additionally, compositions which come into contact with the insects may remain on the cuticle of the insect. When cleaning, either an individual insect cleaning itself or insects cleaning one another, the compositions may be ingested and can thus mediate their effects in the insect. This requires that the composition is sufficiently stable such that the interfering RNA remains intact and capable of mediating RNAi even when exposed to external environmental conditions for a length of time, which may be a period of days for example.

The baits may be provided in a suitable "housing" or "trap". Such housings and traps are commercially available and existing traps may be adapted to include the compositions of the invention. Any housing or trap which may attract an insect to enter it is included within the scope of the invention. The housing or trap may be box-shaped for example, and may be provided in pre-formed condition or may be formed of foldable cardboard for example. Suitable materials for a housing or trap include plastics and cardboard, particularly corrugated cardboard. Suitable dimensions for such a housing or trap are, for example, 7-15 cm wide, 15-20 cm long and 1-5 cm high. The inside surfaces of the traps may be lined with a sticky substance in order to restrict movement of the insect once inside the trap. The housing or trap may contain a suitable trough inside which can hold the bait in place. A trap is distinguished from a housing because the insect can not readily leave a trap following entry, whereas a housing acts as a "feeding station" which provides the insect with a preferred environment in which they can feed and feel safe from predators.

Accordingly, in a further aspect the invention provides a housing or trap for insects which contains a composition of the invention, which may incorporate any of the features of the composition described herein.

In a further alternative embodiment, the composition may be provided in the form of a spray. Thus, a human user can spray the pest directly with the composition. The composition is then internalized by the insect, from where it can mediate RNA interference, thus controlling the insect. The spray is preferably a pressurized/aerosolized spray or a pump spray. The particles may be of suitable size such that they adhere to the insect, for example to the exoskeleton, and may be absorbed therefrom. Particle size may be measured by known means, such as by use of a Mastersizer, which is a commercially available device.

In a still further embodiment, the carrier is an electrostatically charged powder or particle which adheres to the insect. Suitable powders and particles which are capable of adhering to an insect and thus delivering the RNA constructs of the invention are described in detail in WO 94/00980 and WO 97/33472, both of which are incorporated herein by reference.

Alternatively, the carrier may comprise magnetic particles which adhere to the insect cuticle. Suitable magnetic particles which are capable of adhering to an insect and thus delivering the RNA constructs of the invention are described in detail in WO 00/01236, which reference is incorporated herein.

In a still further embodiment, the carrier of the composition comprises metallic particles which are initially unmagnetised but which are capable of becoming magnetically polarised when subjected to the electrical field provided by the insect body. This mode of action is described in detail in WO 2004/049807 and is incorporated by reference herein.

Preferably, the composition incorporates a carrier which increases the uptake of the interfering RNA into the insect pest. Such a carrier may be a lipid-based carrier, preferably comprising one or more of, oil-in water emulsions, micelles, cholesterol, lipopolyamines and liposomes. Other agents which promote uptake of the constructs of the invention are well known to those of skill in the art and include polycations, dextrans and (tris) cationic lipids, such as CS096, CS102 etc. Commercially available liposomes include LIPOFECTIN® and CELLFECTIN® etc. A number of suitable carriers are listed under the heading "Transfection promoting agent" in WO 03/004644 and each of the examples provided is hereby incorporated by reference.

In a further preferred embodiment, the carrier is a nucleic acid condensing agent. Preferably, the nucleic acid condensing agent comprises spermidine or protamine sulphate or a derivative thereof. Wherein the composition of the invention is for use in preventing and/or controlling pest infestation of a plant, the composition can contain an agriculturally suitable carrier. Such a carrier may be any material that the plant to be treated can tolerate, which does not cause undue damage to the environment or other organisms therein and, which allows the interfering RNA to remain effective against the insect pest species. In particular, the compositions of the invention may be formulated for delivery to plants in accordance with routine agricultural practices used in the bioinsecticide industry. The composition may contain further components capable of performing other functions including but not limited to (i) enhancement or promotion of uptake of the interfering RNA by cells of the pest and (ii) stabilization of the active components of the composition. Specific examples of such further components contained in the composition comprising the interfering RNA, are yeast tRNA or yeast total RNA.

The compositions may be formulated for direct application or as a concentration of a primary composition that requires dilution prior to use. Alternatively, the composition may be supplied as kit comprising the interfering RNA or the host cell comprising or expressing the same in one container and the suitable diluent or carrier for the RNA or host cell in a separate container. In the practical application of the invention, the composition may be applied to a plant or any part of a plant at any stage of the plant's development. In one embodiment, the composition is applied to the aerial parts of a plant, for example during cultivation of plant crops in a field. In a further embodiment, the composition is applied to the seeds of a plant either while they are in storage or once they are planted in the soil. It is generally important to obtain good control of pests in the early stages of plant growth as this is the time when the plant can be most severely damaged by pest species.

The composition may be applied to the environment of an insect pest by various techniques including but not limited to spraying, atomizing, dusting, scattering, pouring, coating of seeds, seed treatment, introduction into the soil, and introduction into irrigation water. In the treatment of plants susceptible to pest infestation, the composition may be delivered to the plant or part of a plant before the appearance of the pest (for the purposes of prevention), or once signs of pest infestation begin to appear (for the purposes of pest control).

In a further embodiment of the invention, the compositions of the invention may be formulated so as to contain at least one further active agent. Thus, the composition may be provided as a "kit-of-parts" comprising the interfering RNA containing composition in one container and one or more suitable active ingredients, for example a chemical or biological pesticide, in a separate container. Alternatively, the compositions may be provided as a mixture which are stable and to be used in conjunction with one another.

Suitable active ingredients which may act in a complementary manner to the interfering RNA molecules of the present invention include, but are not limited to the following: Chlorpyrifos, Allethrin, Resmethrin, Tetrabromoethyl, Dimethol-cyclopropane carboxylic acid (which are generally included in liquid compostions); and Hydramethylnon, Avermectin, Chlorpyrifos, Sulfuramid, Hydroprene, Fipronil (GABA receptor), Isopropylphenyl methyl carbamate, lndoxacarb (PARA), Noviflumuron (Chitinsynthesis inhibitor), lmiprothrin (PARA), Abamectin (Glutamate-gated Chloride channel), Imidacloprid (Acethylcholin receptor) (which are generally included in bait compositions).

In a preferred embodiment, the active ingredient is known to be a preferred insecticide in terms of health and environmental considerations, such as for instance Hydramethylnon and Avermectin.

In a further embodiment of the invention, the composition is formulated so as to contain at least one further agronomical agent, for example a herbicide or an additional pesticide. As used herein, a 'second pesticide' or 'additional pesticide' refers to a pesticide other than the first or original interfering RNA molecule of the composition. Alternatively, the composition of the invention may be delivered in combination with at least one other agronomical agent, for a example a herbicide or a second pesticide. In one embodiment, the composition is provided in combination with a herbicide selected from any known in the art, for instance glyphosate, imidazolinone, sulphonylurea and bromoxynil. In a further embodiment, the composition is provided in combination with at least one additional pesticide. The additional pesticide may be selected from any pesticides known in the art and/or may comprise an interfering ribonucleic acid that functions upon uptake by a pest to down-regulate expression of a target gene in said pest species. In one embodiment, the target pest is an insect pest species and the interfering RNA is selected from any of the interfering RNAs as described herein. In a further embodiment, the additional pesticide comprises an interfering RNA that functions to down-regulate expression of a known gene in any target pest species, not limited to insect pests. The original interfering RNA molecule of the composition and the second or additional pesticide(s) may target the same insect pest species or may be intended to target different insect pest species. For example, the original interfering RNA and the second pesticide may target different species of insect pest or may target different families or classes of pest organisms, for example, fungi or nematodes or insects. It will be apparent to one skilled in the art how to test combinations of interfering RNA molecules and other agronomical agents for synergistic effects. In a preferred embodiment, the composition contains a first interfering RNA molecule described elsewhere herein and one or more additional pesticides, each toxic to the same insect pest, wherein the one or more additional pesticides are selected from a patatin, a *Bacillus thuringiensis* insecticidal protein, a *Xenorhabdus* insecticidal protein, a *Photorhabdus* insecticidal protein, a *Bacillus laterosporous* insecticidal protein, a *Bacillus spaericus* insecticidal protein, and a lignin, and wherein said *Bacillus thuringiensis* insecticidal protein is selected from the group consisting of a Cry1Ab, a Cry1C, a Cry2Aa, a Cry3, a TIC851, a CryET70, a Cry22, a VIP, a TIC901, a TIC1201, a TIC407, a TIC417, a binary insecticidal protein selected from CryET33 and CryET34, CryET80 and CryET76, TIC100 and TIC101, and PS149B1, and insecticidal chimeras of any of the preceding insecticidal proteins.

The different components of the combinations described herein may be administered, for example to a host organism susceptible to infestation by pest, in any order. The components may be delivered simultaneously or sequentially to the area or organism to be treated.

Also provided herein is a method for preventing and/or controlling pest infestation, comprising contacting an insect pest species with an effective amount of at least one interfering RNA wherein the RNA functions upon uptake by said pest to down-regulate expression of an essential pest target gene. The essential target gene may be any pest gene involved in the regulation of an essential biological process required by the pest to initiate or maintain infestation including but not limited to survival, growth, development, reproduction and pathogenicity. In particular, the target gene may be any of the pest genes as described elsewhere herein.

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides of any of SEQ ID NOs 1, 174, 404, 180, 188, 2, 175, 181, 189, 27 to 30, 282 to 285, 294 to 297 or 310 to 313, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), L. juncta (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm). In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 1, 174, 404, 180, 188, 2, 175, 181, 189, 27 to 30, 282 to 285, 294 to 297 or 310 to 313, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical the amino acid sequence as presented in any of SEQ ID NOs 79, 349, 405, 352 or 356 (when said encoded proteins are optimally aligned).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 141, 11, 12, 47 to 50, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 141, 11, 12, 47 to 50, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in any of SEQ ID NOs 328 or 84 (when said encoded proteins are optimally aligned).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 17, 18, 59 to 62, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 17, 18, 59 to 62, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae*

(Mexican corn rootworm), wherein the orthologous genes encode a protein having an amino acid sequence which is at least 85%, 90%, 92%, 94%, 96%, 98%, 99% identical to the amino acid sequence as presented in SEQ ID NOs 87 (when said encoded proteins are optimally aligned).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 19, 20, 63 to 66, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 19, 20, 63 to 66, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in SEQ ID NOs 88 (when said encoded proteins are optimally aligned). In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 165, 167, 166, 270 to 273, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm). In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 165, 167, 166, 270 to 273, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or L. texana (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae*

(green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in any of SEQ ID NOs 347 or 348 (when said encoded proteins are optimally aligned).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 143, 121, 142, 176, 182, 130, 177, 183, 206 to 209, 286 to 289, 298 to 301, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata* howardi (southern corn rootworm) or *D. virgifera zeae* (Mexican corn rootworm).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 143, 121, 142, 176, 182, 130, 177, 183, 206 to 209, 286 to 289, 298 to 301, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata* howardi (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in any of SEQ ID NOs 330, 350 or 353 (when said encoded proteins are optimally aligned).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 145, 122, 144, 178, 131, 179, 210 to 213, 290 to 293, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera* virgifera (western corn rootworm), *D. barberi* (northern corn rootworm), *D. undecimpunctata* howardi (southern corn rootworm) or *D. virgifera zeae* (Mexican corn rootworm).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 145, 122, 144, 178, 131, 179, 210 to 213, 290 to 293, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera* virgifera (western corn rootworm), *D. barberi* (northern corn rootworm), *D. undecimpunctata* howardi (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in any of SEQ ID NOs 331 or 351 (when said encoded proteins are optimally aligned).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 128, 149, 184, 137, 185, 234 to 237, 302 to 305, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera* virgifera (western corn rootworm), *D. barberi* (northern corn rootworm), *D. undecimpunctata* howardi (southern corn rootworm) or *D. virgifera zeae* (Mexican corn rootworm).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 128, 149, 184, 137, 185, 234 to 237, 302 to 305, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera* virgifera (western corn rootworm), *D. barberi* (northern corn rootworm), *D. undecimpunctata* howardi (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in any of SEQ ID NOs 337 or 354 (when said encoded proteins are optimally aligned).

Furthermore, there is provided herein a method for preventing and/or controlling insect pest infestation in a field of crop plants, said method comprising expressing in said plants an effective amount of an interfering RNA as described herein.

Wherein the method is for the control of pest infestation, the phrase 'effective amount' extends to the quantity or concentration of interfering RNA required to produce a phenotypic effect on the pest such that the numbers of pest organisms infesting a host organism are reduced and/or the amount of damage caused by the pest is reduced. In one embodiment, the phenotypic effect is death of the pest and the interfering RNA is used to achieve at least 20%, 30%, 40%, preferably at least 50%, 60%, 70%, more preferably at least 80% or 90% pest mortality as compared to control insect pests. In a further embodiment, the phenotypic effects include but are not limited to stunting of pest growth, cessation of feeding and reduced egg-laying. The total numbers of pest organisms infesting a host organism may thus be reduced by at least 20%, 30%, 40%, preferably at least 50%, 60%, 70%, more preferably at least 80% or 90% as compared with control pests. Alternatively, the damage caused by the insect pest may be reduced by at least 20%, 30%, 40%, preferably at least 50%, 60%, 70%, more preferably at least 80% or 90% as compared with control insect pests. Hence, the method of the invention can be used to achieve at least 20%, 30%, 40%, preferably at least 50%, 60%, 70%, more preferably at least 80% or 90% pest control.

As used herein, the term 'plant' may include any reproductive or propagation material for a plant. Reference to a plant may also include plant cells, plant protoplasts, plant tissue cultures, plant calli, plant clumps and plant cells that are intact in plants or parts of plants such as embryos, pollen, ovules, seeds, leaves, flowers, branches, fruit, kernels, ears, cobs, husks, stalks, roots, root tips and the like.

Also provided herein is the use of the interfering ribonucleic acid (RNA) as described herein or the DNA construct as described herein for preventing and/or controlling insect pest infestation, preferably insect pest infestation of plants.

The invention will be further understood with reference to the following non-limiting examples.

EXAMPLES

Example 1

Identification of target genes in insect pest species 1.1. *Lygus hesperus* Normalized cDNA Library and Preparation of dsRNAs in Multiwell Plates for the Screening Assays Nucleic acids were isolated from *Lygus hesperus* nymphs of different life stages, including freshly hatched nymphs 2, 4, 6 and 9 days old nymphs and adults. A cDNA library was prepared using the SMARTer™ PCR cDNA Synthesis Kit, following the manufacturer's instructions (Clontech Cat. No 634925). The cDNA library was normalized using the Trimmer kit (Evrogen Cat No NK001) and cloned in the PCR4-TOPO vector (Invitrogen). The normalization of the clones introduced M2 adapters (Trimmer Kit, Evrogen, SEQ ID NO 92: AAGCAGTGGTATCAACGCAG), oppositely oriented at each end of the clones. The recombinant vector constructs were transformed into cells of *Escherichia coli* strain TOP10 (Invitrogen). The transformed cells were subsequently diluted and plated so as to obtain single colonies or clones. The clones were checked to ensure that clone redundancy for the library did not exceed 5%. Single clones were picked in liquid LB (Luria-broth) media, in 96-deep-well plates, and grown overnight at 37° C. The plates also included positive (Lh423) and negative (FP) control clones.

To generate the dsRNA, sense and antisense DNA fragments, containing T7 promoter sequence, were generated by PCR. In brief, per clone, 1 μl of bacterial suspension was dispensed in multiwell PCR plates containing REDTaq® (Sigma Cat No D4309) and primers oGCC2738 (SEQ ID NO 93: AAGCAGTGGTATCAACGCAG) and oGCC2739 (SEQ ID NO 94: GCGTAATACGACTCACTATAGGAAGCAGTGGTATCAACGCAG) based on the M2 and the T7-M2 sequences respectively. The PCR reaction was followed by in vitro transcription, where per clone, 6 μl PCR product were added to 9 μl RiboMAXT™ Large Scale RNA Production System—T7 (Promega Cat No P1300) and incubated overnight at 37° C. The final dsRNA solution was diluted 2 times in *L. hesperus* sucrose diet, containing 15% sucrose and 5 μg/μl yeast tRNA (Invitrogen Cat No 15401-029) and used for screening. The dsRNA corresponding to the positive Lh423 control clone is SEQ ID NO 101 and to the negative FP control clone is SEQ ID NO 104 (see Table 4).

1.2. Screen for Novel and Potent *Lygus hesperus* Target Genes Using a dsRNA Expression cDNA Library A new screening assay for potent *Lygus hesperus* targets has been developed. The assay set-up was as follows: each well of a 96-well plate houses a one-day-old *L. hesperus* nymph exposed to a parafilm sachet containing sucrose diet which includes either test dsRNA or control dsRNA in the presence of tRNA. Each plate contained dsRNA from 90 different clones, 3×Lh423 (positive control) and 3×FP (fluorescent protein; negative control). Each clone (test dsRNA) was replicated over three plates. After three days exposure, the nymphal survival number was recorded and the diet replaced with fresh rearing (complex) diet in absence of dsRNA. The mortality was assessed at days 4, 6 and 8. An identical set up was used for the first and second round confirmation assays, with 8 and 20 insects respectively, with one nymph per well.

The assay system was validated using dsRNA corresponding to Lh423 target as the positive control and a fluorescent protein dsRNA as the negative control: over 90% were true positives and under 5% were false positives, respectively.

Twenty 96 well-plates, named Lh001 to Lh020 (see bottom line in FIGS. 1 & 2), containing 1800 individual clones have been tested. 205 candidates were identified and tested in a first confirmation assay. Setting the threshold at showing 50% mortality, 41 independent clones were identified and progressed to a second round of confirmation. In the assay, the clones were compared to the positive controls Lh423 (RpL19) and Lh105.2 (Sec23) and the negative control Pt (encoding a coral fluorescent protein). The dsRNA corresponding to the positive (Lh423) control clone is SEQ ID NO 101, to the positive Lh105.2 control clone is SEQ ID NO 102 and to the negative (Pt) control clone is SEQ ID NO 104 (see Table 4).

Second round confirmation assays, testing 20 insects/test dsRNA, were initiated for all the test dsRNAs displaying 50% mortality in the first confirmation (FIGS. 1 and 2). Candidate targets corresponding to the confirmed test dsRNAs were named with an "Lhxxx number" (see Table 1). Using the same cut-off at 50% mortality, 15 targets were confirmed in the first screen.

A second screen for identifying more *Lygus hesperus* targets was performed. The results of the second round confirmation assays are represented in FIG. 12. Using the same cut-off at 50% mortality, several targets were confirmed in the second screen (see Table 1C).

1.3. Identification of *Lygus* Targets

In parallel to the confirmation insect assays, the inserts corresponding to the positive clones were sequenced and BlastX searches against both *Drosophila* and *Tribolium* protein databases were used to confirm the identity of the targets. Table 1 provides a summary of the bio-informatics analysis and current annotation of the novel identified *L. hesperus* target sequences.

Fifteen novel *L. hesperus* targets were identified in the first screen and 11 novel *L. Hesperus* targets were identified in the second screen. All targets exhibit high potency against *L. hesperus* nymphs indicating that the cDNAs encoding double-stranded RNAs contained therein are essential for pest survival and thus represent target genes of interest for the purposes of pest control. The DNA sequences and deduced amino acid sequences of these target genes were therefore determined and are provided in Tables 2 and 3 respectively.

Lh594, the *Lygus hesperus* orthologue of *Drosophila* troponin I, involved in muscle contraction—and therefore absent in plants—, represents a novel class of target belonging to an animal specific physiological pathway not yet explored for GM-RNAi. In the fruit fly, troponin I is described as a haplo-insufficient gene, displaying a mutant phenotype in the heterozygote state. Such genes may be particularly susceptible to reduced mRNA expression levels and as such can be considered as ideal RNAi targets.

In this Lh594 pathway, eight targets were selected (see Table 1B). For each target, up to 4 pairs of degenerated PCR primers were designed based on the alignments of the sequences of various insects, including bee, *Tribolium* and aphid. The primers are being used to amplify fragments from *Lygus hesperus* targets. The DNA sequences and deduced amino acid sequences of these target genes were determined and are provided in Tables 2 and 3 respectively.

TABLE 1

*Lygus hesperus* novel targets ranked in % mortality according to the second confirmation assay results (first screen).

| Target ID | rank 2nd confirmation | Best *Drosophila* hit | NAME | SYMBOL |
|---|---|---|---|---|
| Lh594 | 1 | CG7178 | wings up A (troponin I) | wupA |
| Lh618 | 2 | CG2168 | ribosomal protein S3A | RpS3A |
| Lh609 | 3 | CG4087 | ribosomal protein LP1 | RpLP1 |
| Lh595 | 4 | — | no *Drosophila* hit found, *Lygus* specific target/sequence | |
| Lh611 | 5 | CG6779 | ribosomal protein S3 | RpS3 |
| Lh560 | 6 | CG10423 | ribosomal protein S27 | RpS27 |
| Lh596 | 7 | — | no *Drosophila* hit found, *Lygus* specific target/sequence | RpL34b |
| Lh615 | 8 | CG11522 | ribosomal protein L6 | RpL6 |
| Lh617 | 9 | CG7283 | ribosomal protein L10Ab | RpL10Ab |
| Lh612 | 10 | CG13389 | ribosomal protein S13 | RpS13 |
| Lh246 | 11 | CG3195 | ribosomal protein L12 | RpL12 |
| Lh429 | 12 | CG8900 | ribosomal protein S18 | RpS18 |
| Lh610 | 13 | CG5502 | ribosomal protein L4 | RpL4 |
| Lh597 | 14 | no hit found | | |
| Lh598 | 15 | CG34069 | mitochondrial cytochrome c oxidase subunit II | mt:CoII |
| Lh614 | — | CG7610 | ATP synthase-γ chain | ATPsyn-γ |

TABLE 1B

*Lygus hesperus* novel targets in Lh594 pathway

| Target ID | Best *Drosophila* hit(s) | NAME | SYMBOL |
|---|---|---|---|
| Lh619 | CG7107 | troponin T (upheld) | up |
| Lh620 | CG17927 | myosin heavy chain | Mhc |
| Lh621 | CG4843 | tropomyosin2 (Tm2) | Tm2 |
| Lh622 | CG3201 | myosin light chain cytoplasmic | Mlc-c |
| Lh623 | CG3595 | spaghetti squash | sqh |
| Lh624 | CG15792 | zipper | zip |
| Lh625 | *CG2981, CG7930, CG9073, CG6514, CG12408 | troponin C | |
| Lh626 | *CG9073, CG7930, CG2981, CG12408, CG6514 | troponin C | |

*unclear: multiple hits in family - ranked according e-value

TABLE 1C

*Lygus hesperus* novel targets ranked in % mortality according to the second confirmation assay results (second screen).

| Target ID | rank 2nd confirmation | Best *Drosophila* hit | NAME | SYMBOL |
|---|---|---|---|---|
| Lh631 | 1 | CG6846 | Ribosomal protein L26 | RpL26 |
| Lh634.2 | 2 | CG12775 | Ribosomal protein L21 | RpL21 |
| Lh634.1 | 3 | CG12775 | Ribosomal protein L21 | RpL21 |
| Lh630 | 4 | CG11271 | Ribosomal protein S12 | RpS12 |
| Lh632 | 5 | CG2998 S28b | Ribosomal protein | RpS28b |
| Lh618.2 | 6 | CG2168 S3A | Ribosomal protein | RpS3A |
| Lh629 | 7 | CG4651 | Ribosomal protein L13 | RpL13 |
| Lh633.2 | 8 | CG17521 | Ribosomal protein L10 | RpL10 |
| Lh628 | 9 | CG17489 | Ribosomal protein L5 | RpL5 |
| Lh633 | 10 | CG17521 | Ribosomal protein L10 | RpL10 |
| Lh627 | 11 | CG2033 S15Aa | Ribosomal protein | RpS15A |

1.4. Full Length cDNA Cloning by RACE (rapid Amplification of cDNA Ends)

In order to clone full length cDNA, starting from a known clone of internal fragment from the most potent targets, the 5'/3' RACE kit was used (Roche, Cat. No. 1 734 792; based on Sambrook, J. & Russell, D. M). The standard protocol, described in the Instruction Manual, was followed. Briefly, for a 5' RACE, a target sequence specific antisense primer was designed on the known sequence and used for a first strand cDNA synthesis, using *Lygus* RNA as template. A tail was added to the first strand cDNA and used as an anchor for the second strand synthesis and amplification of an unknown end portion of the transcript. For a 3' RACE, an oligo dT anchor primer was used for the first strand cDNA synthesis. For the 5' and 3' RACEs, nested primers, specific to the target sequence were used in a second PCR reaction. The PCR fragments were analysed on agarose gel, purified, cloned and sequenced for confirmation.

Full length cDNA sequences corresponding to the targets were assembled in Vector NTi, a fully integrated sequence analysis software package for DNA sequence analysis (Invitrogen).

Example 2

In Vitro Production of Double-stranded RNAs for Gene Silencing 2.2. Production of dsRNAs Corresponding to the Partial Sequences of the *Lygus hesperus* Target Genes Double-stranded RNA was synthesized in milligram quantities. First, two separate 5' T7 RNA polymerase promoter templates (a sense template and an antisense template) were generated by PCR. PCRs were designed and carried out so as to produce sense and antisense template polynucleotides, each having the T7 promoter in a different orientation relative to the target sequence to be transcribed.

For each of the target genes, the sense template was generated using a target-specific T7 forward primer and a target-specific reverse primer. The antisense templates were generated using target-specific forward primers and target-specific T7 reverse primers. The sequences of the respective primers for amplifying the sense and antisense templates via PCR for each of the target genes are provided in Table 4. The PCR products were analysed by agarose gel electrophoresis and purified. The resultant T7 sense and antisense templates were mixed and transcribed by the addition of T7 RNA polymerase. The single-stranded RNAs produced by transcription from the templates were allowed to anneal, were treated with DNase and RNase, and were purified by precipitation. The sense strand of the resulting dsRNA produced from each of the target genes is provided in Table 4.

2.2. Survival Analysis Assays for Novel *Lygus hesperus* Targets

To enable ranking according to potency, in vitro dsRNAs corresponding to the novel targets were synthesized and applied to *L. hesperus* in 10 days survival analysis bioassays. Briefly, one day old *L. hesperus* nymphs were placed in 96 well-plates with sucrose seals containing 0.5 μg/μl target dsRNA, supplemented with 5 μg/μl yeast tRNA. The plates were incubated for 3 days under standard *Lygus* rearing conditions. At day 3, 6 and 8, the diet seals were refreshed with seals containing *Lygus* diet only. Lh423 (RpL19) was used as positive control and GFP dsRNA and sucrose diet were used as negative controls.

The results from the survival analyses confirmed the data from the first and second confirmation assays. Lh594 was established as a highly potent target, with activity and speed-to-kill stronger than the strong control Lh423.

So far, the *Lygus* screen for novel targets identified new targets with activities higher or in the range of the positive control Lh423, these include Lh429, Lh594, Lh609, Lh610, Lh611, Lh617 and Lh618. The mortality induced by these targets is show in the FIGS. 3 and 4.

To allow a more precise ranking of the targets according to their activity, dose response concentration analyses were made. The novel targets were tested in in vitro assays, with concentrations ranging from 0.4 to 0.025 μg/μl. Per condition, 24 one day old nymphs were tested in the 96 well-plate set-up, in sucrose diet supplemented with dsRNA and tRNA carrier. The results are presented as % survival over a 10 day experiment (FIGS. 5 to 9) and are summarized in Table 5.

Based on the concentration curve analyses, the targets were ranked by comparison to the bench mark controls Lh423 and Lh105 (Table 5).

TABLE 5

*Lygus* novel targets ranking according to DRCs and compared to bench mark targets Lh423 & Lh105.

| Target ID | Potency expressed as μg/μl dsRNA needed to reach 90% kill at day 7 |
|---|---|
| Lh594 | 0.025 (at day 6) |
| Lh618 | 0.05-0.1 |
| Lh612 | 0.05 |
| Lh615 | 0.05 |
| Lh423 | 0.1 |
| Lh595 | 0.1 |
| Lh560 | 0.1 |
| Lh610 | 0.1 |
| Lh617 | 0.1 |
| Lh105 | 0.2 |
| Lh614 | 0.2 (at day 6) |
| Lh611 | 0.2 |
| Lh596 | 0.3 |
| Lh609 | ND |
| Lh429 | ND |

The potency of Lh594 was further confirmed. This target effect is clearly observed at least one day before the other targets and the bench mark positive control Lh105 and Lh423. Because Lh594 was highly potent, the LD50 was not reached in the standard DRC experiment, with concentration ranging from 0.4 to 0.025 μg/μl dsRNA (FIG. 6), the Lh594 experiment was therefore repeated, including lower concentrations ranging from 0.05 to 0.001 μg/μl dsRNA (FIG. 10). In conclusion, Lh594 activity was observed at concentration as low as 0.0025 μg/μl and about 90% kill (corresponding to about 10% survival) was obtained at day 6 with 0.025 μg dsRNA.

To further explore the potency of Lh594 and the role of tRNA carrier in the RNAi response in *Lygus hesperus*, additional in vitro feeding assays were set up in the absence of carrier tRNA. Lh594, Lh423 (bench mark control) and GFP (negative control) dsRNAs were produced in vitro, using the standard method. The dsRNAs were purified and tested at 5 μg/μl in the absence of tRNA (FIG. 11A).

In absence of tRNA, targets Lh594 and Lh423, induced high lethality in *Lygus* nymphs. The results from this experiment have been since reproduced. Target dsRNA was able to induce RNAi-by-feeding effects in *Lygus* nymphs in the absence of tRNA.

To investigate the activity of dsRNA at lower concentrations in the absence of carrier tRNA, additional experiments were set up, using decreasing amounts of dsRNA (FIG. 11B).

A similar approach was followed for the *Lygus* targets that were identified in the second screen. To allow a ranking of the targets according to their activity, dose response concentration analyses were made. The novel targets were tested in in vitro assays, with concentrations ranging from 0.5 to 0.05 μg/μl. Per condition, 24 one day old nymphs were tested in the 96 well-plate set-up, in sucrose diet supplemented with dsRNA and tRNA carrier. The results are presented as % survival over a 9 day experiment (FIGS. 15 A-D). Lh594 and Lh423 have been included in the assay as a reference targets. The results are summarized in Table 6. Based on the concentration curve analyses, the targets were ranked by comparison to the bench mark control Lh423.

TABLE 6

*Lygus* novel targets from second screen-ranking according to DRCs and compared to bench mark targets Lh423 & Lh594.

| Target ID | Potency expressed as μg/μl dsRNA needed to reach 90% kill at day 7 |
|---|---|
| Lh594 | 0.025 (at day 6) |
| Lh634 | 0.1 |
| Lh423 | 0.1 |
| Lh631 | 0.4 |
| Lh633 | 0.4 |
| Lh627 | 0.5 |
| Lh628 | 0.5 |
| Lh630 | 0.5 |
| Lh632 | 0.5 |
| Lh629 | ND |

Example 3

Troponin Pathway Screen

To enable testing of the Troponin pathway targets, in vitro produced dsRNAs corresponding to Lh619, Lh620, Lh621, Lh622, Lh622, Lh623, Lh624, Lh625 and Lh626 were synthesized and applied to *L. hesperus* in 10 days survival analysis bioassays. Briefly, one day old *L. hesperus* nymphs were placed in 96 well-plates with sucrose seals containing 0.54/μl target dsRNA, supplemented with 5 μg/μl yeast tRNA. The plates were incubated for 3 days under standard *Lygus* rearing conditions. At day 3, 6 and 8, the diet seals were refreshed with seals containing *Lygus* diet only. Lh594 (Troponin I) was used as positive control and GFP dsRNA and sucrose diet were used as negative controls (FIG. 13). Four targets were then included in dose response curve analyses in an in vitro assay, with concentrations ranging from 0.4 to 0.025 μg/μl. Per condition, 24 one day old nymphs were tested in the 96 well-plate set-up, in sucrose diet supplemented with dsRNA and tRNA carrier. The results are presented as % survival over a 10 day experiment (FIGS. 14 A-B).

Example 4

Identification of Target Genes in *Leptinotarsa decemlineata*

4.1. *Leptinotarsa Decemlineata* Normalized cDNA Library and Preparation of dsRNAs in multiwell plates for the screening assays Nucleic acids were isolated from *Leptinotarsa decemlineata* larvae of different stages. A cDNA library was prepared using the SMARTer™ PCR cDNA Synthesis Kit, following the manufacturer's instructions (Clontech Cat. No 634925). The cDNA library was normalized using the Trimmer kit (Evrogen Cat No NK001) and cloned in the PCR®-BLUNTII-TOPO® vector (Invitrogen). The normalization of the clones introduced M2 adapters (Trimmer Kit, Evrogen, SEQ ID NO 92: AAGCAGTGGTATCAACGCAG), oppositely oriented at each end of the clones. The recombinant vector constructs were transformed into cells of *Escherichia coli* strain TOP10 (Invitrogen). The transformed cells were subsequently diluted and plated so as to obtain single colonies or clones. The clones were checked to ensure that clone redundancy for the library did not exceed 5%. Single clones were inoculated into liquid LB (Luria-broth) media, in 96-well plates, and grown overnight at 37° C. The plates also included positive (Ld513) and negative (FP) control clones.

To generate the dsRNA, sense and antisense DNA fragments, containing T7 promoter sequence, were generated by PCR. In brief, per clone, 1 μl of bacterial suspension was dispensed in multiwell PCR plates containing REDTaq® (Sigma Cat No D4309) and primers oGCC2738 (SEQ ID NO 93: AAGCAGTGGTATCAACGCAG) and oGCC2739 (SEQ ID NO 94: GCGTAATACGACTCACTATAGGAAGCAGTGGTATCAACGCAG) based on the M2 and the T7-M2 sequences, respectively. The PCR reaction was followed by in vitro transcription, where, per clone, 6 μl PCR product was used in a 20 μl reaction volume containing the transcription reagents provided by the RiboMAXT™ Large Scale RNA Production System—T7 kit (Promega Cat No P1300) and incubated overnight at 37° C. The final dsRNA solution was diluted in sterile Milli-Q water and used for screening. The dsRNA corresponding to the positive Ld513 control clone is SEQ ID NO 400 (see Table 9) and to the negative FP control clone is SEQ ID NO 104 (see Table 4).

4.2. Screen for Novel and Potent *Leptinotarsa decemlineata* Target Genes Using a dsRNA Expression cDNA Library Each well of a 48-well plate contained 0.5 mL artificial diet pretreated with a topical overlay of 25 μl (or 1 μg) of the test or control dsRNA. One L2 larva was placed in each well and 3 larvae were tested per clone. CPB survival numbers were assessed at days 4, 7 and 10.

In a second bioassay, CPB larvae were fed on diet treated with topically applied test dsRNA generated from clones derived from a normalized cDNA library. One larva was placed in a well of a 48-well multiplate containing 0.5 mL diet pretreated with a topical overlay of 25 μL of a 40 ng/μL dsRNA solution. A total of twenty-four larvae were tested per treatment (clone). The number of surviving insects were assessed at days 4, 5, 6, 7, 8 & 11. The larval mortality percentage was calculated relative to day 0 (start of assay) (see FIG. 21).

4.3. Identification of *L. decemlineata* Beetle Targets

The new target sequences from the screen in 5.2. and the target sequences corresponding to the troponin pathway targets, orthologuous to the *Lygus* Lh594, Lh619 and Lh620 sequences, have been identified in *L. decemlineata*. The primers which provided relevant cDNA fragment for Ld594 are listed in Table 17. The cDNA sequences and deduced amino acid sequences of these target genes were determined and are provided in Tables 7 and 9 respectively.

4.4. Production of dsRNAs Corresponding to the Partial Sequences of the *L. Decemlineata* Target Genes dsRNA was synthesized using the primers as provided in Table 9. The sense strand of the resulting dsRNA produced from the target genes is provided in Table 9.

4.5. Survival Analysis Assays for Novel *L. Decemlineata* Targets

Early Larval Assay

Synthetic dsRNAs were produced for the 3 targets, Ld594, Ld619 and Ld620, and were tested in a feeding assay on CPB larvae (see FIG. 16). A 10 day assay was performed in 48 well plates, on artificial diet (based on et al, J Ins Sc, 1:7, 1-10: Artificial diets for rearing the Colorado Potato Beetle), supplemented with 1 μg dsRNA/well, with 12 larvae per condition.

A clear effect on the development of the larvae could be observed. A second assay was set up to investigate the effect of these dsRNAs during the course of pupation and metamorphosis (see pupation assay underneath).

Pupation Assay

A CPB pupation assay was set up to investigate the effect of RNAi knock-down of Ld594, Ld619 and Ld620 during pupation and metamorphosis. Fourth instar larvae were fed 1 μg in vitro synthesized dsRNA dispensed on a potato leaf disk and were then transferred to a box containing untreated fresh potato leaves. Four days later the surviving insects were placed on vermiculite to allow pupation. Lh594 treated insects were slow, smaller and mostly were unable to go through pupation. The hatching of the pupa was assessed at the end of the experiment. For the untreated control 24 larvae pupated and all hatched into healthy adults. For Ld620, a decrease in numbers of larvae progressing into pupation was observed. For the three targets tested, no larvae progressed into healthy pupae and none emerged into adult. Dead insects recovered from the vermiculite showed various degrees of malformations (FIG. 17).

Ld594, Ld619 and Ld620, first appeared as not lethal targets in the CPB larval assay, although a reduction of vitality was clearly observed in the dsRNA treated insects. On the other hand, in the pupation assay, all 3 targets induced strong effects and inhibited the entry in pupation and/or metamorphosis.

Adult Assay

To assess activity of Ld594, Ld619 and Ld620 in CPB adults, a leaf disc assay was set up. A potato leaf disc (1.7 cm diameter) was painted with dsRNA or controls and was placed in a 3.5 cm Petri dish with one adult beetle. The next day a fresh treated leaf disc was provided to the insects. On the third day, the adults were transferred to a box containing enough fresh, untreated potato leaves to sustain the survival of the untreated controls. Per treatment, 6 adults were tested and the numbers of survivors and moribund insects were counted at regular intervals from day 6 to day 13. The insects were considered moribund if they were unable to right themselves after being placed on their back. Despite the relatively high level of background in the negative control in this particular assay, clear effects were observed for the insects that had been exposed to Ld594 or Ld619 dsRNAs (FIG. 18).

Example 5

Identification of Target Genes in *Nilaparvata lugens*

5.1 Identification of *Nilaparvata lugens* Targets

New target sequences, corresponding to Troponin pathway targets and named N1594 (Troponin I), NI619 (Troponin T) and NI626 (Troponin C) have been identified in brown plant hopper, *Nilaparvata lugens*. Orthologous sequences of the *Lygus* genes, named NI594 (Troponin 1), NI619 (Troponin T) and NI625/626 (Troponin C), were cloned through degenerated primer PCR, using BPH cDNA as template. In addition, full length cDNA was identified for N1594, using RACE (see above for method). AmpliTaq Gold PCR system (Applied Biosystems) was used following the manufacters' instructions and with standard conditions for the degenerate primer PCR reactions, typically as follows: 1 cycle with 10 minutes at 95° C., followed by 40 cycles with 30 seconds at 95° C., 1 minute at 50° C. and 1 minute at 72° C., followed by 10 minutes at 72° C. To increase the rate of success, up to 10 different degenerated primers, forward and reverse, were designed, based on alignments of orthologous sequences in other species, and used in various combinations. PCR fragments obtained were purified from the gel by gel extraction kit (Qiagen Cat. No 28706) and cloned into a TOPO TA vector (Invitrogen). The clones were sequenced and the consensus sequences were used in Blast searches against various available insect sequence databases to confirm the relevance of the insert. The degenerated primers that resulted in successful amplification are listed in Table 18. The DNA sequences and deduced amino acid sequences of these target genes and one other target gene (N1537) were determined and are provided in Tables 10 and 11 respectively.

5.2 Production of dsRNAs Corresponding to the Partial Sequences of the *Nilaparvata lugens* Target Genes dsRNA was synthesized using the primers as provided in Table 12. The sense strand of the resulting dsRNA produced from each of the target genes is provided in Table 12.

5.3 Survival Analysis Assays for Novel *Nilaparvata lugens* Targets dsRNAs were synthesized and tested in the previously optimized BPH RNAi-by-feeding assays, in the presence of the zwitterionic detergent, CHAPSO, at 0.1% final concentration. The dsRNAs were tested at 0.5 μg/μl final concentration. N1537, a potent target in the BPH assays was used as bench mark target in the assay. The insect survival was assessed over the course of 9 days. The results of the bioassay showed that in BPH N1594, NI619 and N1626 were also potent RNAi targets in BPH (FIG. 19).

Example 6

Identification of target genes in *Acvrthosiphon pisum*

6.1 Identification of *Acyrthosiphon Pisum* Targets

New target sequences have been identified in aphids and were named Ap423, Ap537, Ap560 and Ap594, following the same nomenclature: "Apxxx", where "Ap" corresponds to *Acyrthosiphon pisum* and "xxx" to the ID of the target. Primers were designed based on public domain gene prediction in AphidBase, an on-line resource (Table 13).

The DNA sequences and deduced amino acid sequences of these target genes were determined and are provided in Tables 14 and 15 respectively.

6.2 Production of dsRNAs Corresponding to the Partial Sequences of the Aphid Target Genes dsRNA was synthesized using the primers as provided in Table 16. The sense strand of the resulting dsRNA produced from each of the target genes is provided in Table 16.

6.3 Survival Analysis Assays for Novel Aphid Targets

RNAi-by-feeding was tested in *Acyrthosiphon pisum* (pea aphid) with 4 targets Ap594, Ap423, Ap560, Ap537. The sequences were amplified by PCR using primers, designed on public domain sequence information found in AphidBase, an on-line resource, and cDNA prepared from aphids. The synthetic dsRNAs were prepared and tested at a final concentration of 0.5 μg/μl in presence of 5 μg/μl yeast tRNA in a sucrose diet. Ten neonate pea aphid nymphs were placed in a small Petri dish (32 mm). Fifty μl diet (with tRNA and dsRNA) was pipetted on top of the first layer of parafilm. A second layer of parafilm covered the diet and created a feeding sachet where the aphids could feed. Per target five replicates of 10 neonate nymphs were set-up. GFP dsRNA was used as a negative control. The diet was refreshed on day 4 and 7 of the assays and survival was assessed (FIG. 20).

TABLE 2

| Target ID | cDNA Sequence (sense strand) 5' → 3' |
|---|---|
| Lh594 | SEQ ID NO 1 |
| Lh609 | SEQ ID NO 3 |
| Lh610 | SEQ ID NO 5 |
| Lh610 (b) | SEQ ID NO 139 |
| Lh611 | SEQ ID NO 7 |
| Lh611 (b) | SEQ ID NO 140 |
| Lh617 | SEQ ID NO 9 |
| Lh618 | SEQ ID NO 11 |

TABLE 2-continued

| Target ID | cDNA Sequence (sense strand) 5' → 3' |
|---|---|
| Lh618 (b) | SEQ ID NO 141 |
| Lh429 | SEQ ID NO 13 |
| Lh423 | SEQ ID NO 95 |
| Lh105.2 | SEQ ID NO 96 |
| Lh560 | SEQ ID NO 15 |
| Lh615 | SEQ ID NO 17 |
| Lh612 | SEQ ID NO 19 |
| Lh246 | SEQ ID NO 21 |
| Lh597 | SEQ ID NO 23 |
| Lh598 | SEQ ID NO 25 |
| Lh619 | SEQ ID NO 121 |
| Lh619 (b) | SEQ ID NO 142 |
| Lh619 (c) | SEQ ID NO 143 |
| Lh620 | SEQ ID NO 122 |
| Lh620 (b) | SEQ ID NO 144 |
| Lh620 (c) | SEQ ID NO 145 |
| Lh621 | SEQ ID NO 123 |
| Lh622 | SEQ ID NO 124 |
| Lh623 | SEQ ID NO 125 |
| Lh623 (b) | SEQ ID NO 146 |
| Lh624 | SEQ ID NO 126 |
| Lh624 (b) | SEQ ID NO 147 |
| Lh625 | SEQ ID NO 127 |
| Lh625 (b) | SEQ ID NO 148 |
| Lh626 | SEQ ID NO 128 |
| Lh626 (b) | SEQ ID NO 149 |
| Lh614 | SEQ ID NO 129 |
| Lh627 | SEQ ID NO 150 |
| Lh628 | SEQ ID NO 152 |
| Lh629 | SEQ ID NO 154 |
| Lh630 | SEQ ID NO 156 |
| Lh631 | SEQ ID NO 158 |
| Lh632 | SEQ ID NO 160 |
| Lh633.1 | SEQ ID NO 162 |
| Lh633.2 | SEQ ID NO 163 |
| Lh634.1 | SEQ ID NO 165 |
| Lh634.2 | SEQ ID NO 167 |
| Lh595.1 | SEQ ID NO 168 |
| Lh595.2 | SEQ ID NO 170 |
| Lh596 | SEQ ID NO 172 |

TABLE 3

| Target ID | Corresponding amino acid sequence of cDNA clone as represented in Table 2 |
|---|---|
| Lh594 | SEQ ID NO 79 |
| Lh609 | SEQ ID NO 80 |
| Lh610 | SEQ ID NO 81 |
| Lh610 (b) | SEQ ID NO 326 |
| Lh611 | SEQ ID NO 82 |
| Lh611 (b) | SEQ ID NO 327 |
| Lh617 | SEQ ID NO 83 |
| Lh618 | SEQ ID NO 84 |
| Lh618 (b) | SEQ ID NO 328 |
| Lh429 | SEQ ID NO 85 |
| Lh429 (b) | SEQ ID NO 329 |
| Lh423 | SEQ ID NO 99 |
| Lh105.2 | SEQ ID NO 100 |
| Lh560 | SEQ ID NO 86 |
| Lh615 | SEQ ID NO 87 |
| Lh612 | SEQ ID NO 88 |
| Lh246 | SEQ ID NO 89 |
| Lh597 | SEQ ID NO 90 |
| Lh598 | SEQ ID NO 91 |
| Lh619 | SEQ ID NO 330 |
| Lh620 | SEQ ID NO 331 |
| Lh621 | SEQ ID NO 332 |
| Lh622 | SEQ ID NO 333 |
| Lh623 | SEQ ID NO 334 |
| Lh624 | SEQ ID NO 335 |
| Lh625 | SEQ ID NO 336 |
| Lh626 | SEQ ID NO 337 |
| Lh614 | SEQ ID NO 338 |

TABLE 3-continued

| Target ID | Corresponding amino acid sequence of cDNA clone as represented in Table 2 |
|---|---|
| Lh627 | SEQ ID NO 339 |
| Lh628 | SEQ ID NO 340 |
| Lh629 | SEQ ID NO 341 |
| Lh630 | SEQ ID NO 342 |
| Lh631 | SEQ ID NO 343 |
| Lh632 | SEQ ID NO 344 |
| Lh633.1 | SEQ ID NO 345 |
| Lh633.2 | SEQ ID NO 346 |
| Lh634.1 | SEQ ID NO 347 |
| Lh634.2 | SEQ ID NO 348 |

TABLE 4

| Target ID | Primers Forward 5' → 3' | Primers Reverse 5' → 3' | dsRNA: sense strand represented by equivalent DNA Sequence 5' → 3' |
|---|---|---|---|
| Lh594 | SEQ ID NO 27 | SEQ ID NO 28 | SEQ ID NO 2 |
| | SEQ ID NO 29 | SEQ ID NO 30 | |
| Lh609 | SEQ ID NO 31 | SEQ ID NO 32 | SEQ ID NO 4 |
| | SEQ ID NO 33 | SEQ ID NO 34 | |
| Lh610 | SEQ ID NO 35 | SEQ ID NO 36 | SEQ ID NO 6 |
| | SEQ ID NO 37 | SEQ ID NO 38 | |
| Lh611 | SEQ ID NO 39 | SEQ ID NO 40 | SEQ ID NO 8 |
| | SEQ ID NO 41 | SEQ ID NO 42 | |
| Lh617 | SEQ ID NO 43 | SEQ ID NO 44 | SEQ ID NO 10 |
| | SEQ ID NO 45 | SEQ ID NO 46 | |
| Lh618 | SEQ ID NO 47 | SEQ ID NO 48 | SEQ ID NO 12 |
| | SEQ ID NO 49 | SEQ ID NO 50 | |
| Lh429 | SEQ ID NO 51 | SEQ ID NO 52 | SEQ ID NO 14 |
| | SEQ ID NO 53 | SEQ ID NO 54 | |
| Lh423 | SEQ ID NO 105 | SEQ ID NO 106 | SEQ ID NO 101 |
| | SEQ ID NO 107 | SEQ ID NO 108 | |
| Lh105.2 | SEQ ID NO 109 | SEQ ID NO 110 | SEQ ID NO 102 |
| | SEQ ID NO 111 | SEQ ID NO 112 | |
| GFP | SEQ ID NO 113 | SEQ ID NO 114 | SEQ ID NO 103 |
| | SEQ ID NO 115 | SEQ ID NO 116 | |
| Pt | SEQ ID NO 117 | SEQ ID NO 118 | SEQ ID NO 104 |
| | SEQ ID NO 119 | SEQ ID NO 120 | |
| Lh560 | SEQ ID NO 55 | SEQ ID NO 56 | SEQ ID NO 16 |
| | SEQ ID NO 57 | SEQ ID NO 58 | |
| Lh615 | SEQ ID NO 59 | SEQ ID NO 60 | SEQ ID NO 18 |
| | SEQ ID NO 61 | SEQ ID NO 62 | |
| Lh612 | SEQ ID NO 63 | SEQ ID NO 64 | SEQ ID NO 20 |
| | SEQ ID NO 65 | SEQ ID NO 66 | |
| Lh246 | SEQ ID NO 67 | SEQ ID NO 68 | SEQ ID NO 22 |
| | SEQ ID NO 69 | SEQ ID NO 70 | |
| Lh597 | SEQ ID NO 71 | SEQ ID NO 72 | SEQ ID NO 24 |
| | SEQ ID NO 73 | SEQ ID NO 74 | |
| Lh598 | SEQ ID NO 75 | SEQ ID NO 76 | SEQ ID NO 26 |
| | SEQ ID NO 77 | SEQ ID NO 78 | |
| Lh619 | SEQ ID NO 206 | SEQ ID NO 207 | SEQ ID NO 130 |
| | SEQ ID NO 208 | SEQ ID NO 209 | |
| Lh620 | SEQ ID NO 210 | SEQ ID NO 211 | SEQ ID NO 131 |
| | SEQ ID NO 212 | SEQ ID NO 213 | |
| Lh621 | SEQ ID NO 214 | SEQ ID NO 215 | SEQ ID NO 132 |
| | SEQ ID NO 216 | SEQ ID NO 217 | |
| Lh622 | SEQ ID NO 218 | SEQ ID NO 219 | SEQ ID NO 133 |
| | SEQ ID NO 220 | SEQ ID NO 221 | |
| Lh623 | SEQ ID NO 222 | SEQ ID NO 223 | SEQ ID NO 134 |
| | SEQ ID NO 224 | SEQ ID NO 225 | |
| Lh624 | SEQ ID NO 226 | SEQ ID NO 227 | SEQ ID NO 135 |
| | SEQ ID NO 228 | SEQ ID NO 229 | |
| Lh625 | SEQ ID NO 230 | SEQ ID NO 231 | SEQ ID NO 136 |
| | SEQ ID NO 232 | SEQ ID NO 233 | |
| Lh626 | SEQ ID NO 234 | SEQ ID NO 235 | SEQ ID NO 137 |
| | SEQ ID NO 236 | SEQ ID NO 237 | |
| Lh614 | SEQ ID NO 238 | SEQ ID NO 239 | SEQ ID NO 138 |
| | SEQ ID NO 240 | SEQ ID NO 241 | |
| Lh627 | SEQ ID NO 242 | SEQ ID NO 243 | SEQ ID NO 151 |
| | SEQ ID NO 244 | SEQ ID NO 245 | |

TABLE 4-continued

| Target ID | Primers Forward 5' → 3' | Primers Reverse 5' → 3' | dsRNA: sense strand represented by equivalent DNA Sequence 5' → 3' |
|---|---|---|---|
| Lh628 | SEQ ID NO 246 | SEQ ID NO 247 | SEQ ID NO 153 |
| | SEQ ID NO 248 | SEQ ID NO 249 | |
| Lh629 | SEQ ID NO 250 | SEQ ID NO 251 | SEQ ID NO 155 |
| | SEQ ID NO 25 | SEQ ID NO 253 | |
| Lh630 | SEQ ID NO 254 | SEQ ID NO 255 | SEQ ID NO 157 |
| | SEQ ID NO 256 | SEQ ID NO 257 | |
| Lh631 | SEQ ID NO 258 | SEQ ID NO 259 | SEQ ID NO 159 |
| | SEQ ID NO 260 | SEQ ID NO 261 | |
| Lh632 | SEQ ID NO 262 | SEQ ID NO 263 | SEQ ID NO 161 |
| | SEQ ID NO 264 | SEQ ID NO 265 | |
| Lh633.2 | SEQ ID NO 266 | SEQ ID NO 267 | SEQ ID NO 164 |
| | SEQ ID NO 268 | SEQ ID NO 269 | |
| Lh634.1 | SEQ ID NO 270 | SEQ ID NO 271 | SEQ ID NO 166 |
| | SEQ ID NO 272 | SEQ ID NO 273 | |
| Lh595 | SEQ ID NO 274 | SEQ ID NO 275 | SEQ ID NO 169 |
| | SEQ ID NO 276 | SEQ ID NO 277 | |
| Lh596 | SEQ ID NO 278 | SEQ ID NO 279 | SEQ ID NO 173 |
| | SEQ ID NO 280 | SEQ ID NO 281 | |

TABLE 7

| Target ID | cDNA sequence (sense strand) 5' → 3' |
|---|---|
| Ld594 | SEQ ID NO 174 |
| Ld594(b) | SEQ ID NO 404 |
| Ld619 | SEQ ID NO 176 |
| Ld620 | SEQ ID NO 178 |
| Ld583 | SEQ ID NO 386 |
| Ld584 | SEQ ID NO 387 |
| Ld586 | SEQ ID NO 388 |
| Ld588 | SEQ ID NO 389 |
| Ld513 | SEQ ID NO 394 |

TABLE 8

| Target ID | Corresponding amino acid sequence of cDNA clone as represented in Table 9 |
|---|---|
| Ld594 | SEQ ID NO 349 |
| Ld594(b) | SEQ ID NO 405 |
| Ld619 | SEQ ID NO 350 |
| Ld620 | SEQ ID NO 351 |
| Ld583 | SEQ ID NO 390 |
| Ld584 | SEQ ID NO 391 |
| Ld586 | SEQ ID NO 392 |
| Ld588 | SEQ ID NO 393 |
| Ld513 | SEQ ID NO 395 |

TABLE 9

| Target ID | Primers Forward 5' → 3' | Primers Reverse 5' → 3' | dsRNA: sense strand represented by equivalent DNA Sequence 5' → 3' |
|---|---|---|---|
| Ld594 | SEQ ID NO 282 | SEQ ID NO 283 | SEQ ID NO 175 |
| | SEQ ID NO 284 | SEQ ID NO 285 | |
| Ld619 | SEQ ID NO 286 | SEQ ID NO 287 | SEQ ID NO 177 |
| | SEQ ID NO 288 | SEQ ID NO 289 | |
| Ld620 | SEQ ID NO 290 | SEQ ID NO 291 | SEQ ID NO 179 |
| | SEQ ID NO 292 | SEQ ID NO 293 | |
| Ld513 | SEQ ID NO 396 | SEQ ID NO 397 | SEQ ID NO 400 |
| | SEQ ID NO 398 | SEQ ID NO 399 | |

TABLE 10

| Target ID | cDNA Sequence (sense strand) 5' → 3' |
|---|---|
| Nl594 | SEQ ID NO 180 |
| Nl619 | SEQ ID NO 182 |
| Nl626 | SEQ ID NO 184 |
| Nl537 | SEQ ID NO 186 |

TABLE 11

| Target ID | Corresponding amino acid sequence of cDNA clone as represented in Table 12 |
|---|---|
| Nl594 | SEQ ID NO 352 |
| Nl619 | SEQ ID NO 353 |
| Nl626 | SEQ ID NO 354 |
| Nl537 | SEQ ID NO 355 |

TABLE 12

| Target ID | Primers Forward 5' → 3' | Primers Reverse 5' → 3' | dsRNA: sense strand represented by equivalent DNA Sequence 5' → 3' |
|---|---|---|---|
| Nl594 | SEQ ID NO 294 | SEQ ID NO 295 | SEQ ID NO 181 |
| | SEQ ID NO 296 | SEQ ID NO 297 | |
| Nl619 | SEQ ID NO 298 | SEQ ID NO 299 | SEQ ID NO 183 |
| | SEQ ID NO 300 | SEQ ID NO 301 | |
| Nl626 | SEQ ID NO 302 | SEQ ID NO 303 | SEQ ID NO 185 |
| | SEQ ID NO 304 | SEQ ID NO 305 | |
| Nl537 | SEQ ID NO 306 | SEQ ID NO 307 | SEQ ID NO 187 |
| | SEQ ID NO 308 | SEQ ID NO 309 | |

TABLE 13

| Target | Fw primer sequence | Reverse primer sequence |
|---|---|---|
| Ap594 | SEQ ID NO 369 | SEQ ID NO 370 |
| Ap423 | SEQ ID NO 371 | SEQ ID NO 372 |
| Ap537 | SEQ ID NO 373 | SEQ ID NO 374 |
| Ap560 | SEQ ID NO 375 | SEQ ID NO 376 |

TABLE 14

| Target ID | cDNA Sequence (sense strand) 5' → 3' |
|---|---|
| Ap594 | SEQ ID NO 188 |
| Ap423 | SEQ ID NO 200 |
| Ap537 | SEQ ID NO 202 |
| Ap560 | SEQ ID NO 204 |

TABLE 15

| Target ID | Corresponding amino acid sequence of cDNA clone as represented in Table 16 |
|---|---|
| Ap594 | SEQ ID NO 356 |
| Ap423 | SEQ ID NO 357 |
| Ap537 | SEQ ID NO 358 |
| Ap560 | SEQ ID NO 359 |

TABLE 16

| Target ID | Primers Forward 5' → 3' | Primers Reverse 5' → 3' | dsRNA: sense strand represented by equivalent DNA sequence 5' → 3' |
|---|---|---|---|
| Ap594 | SEQ ID NO 310 | SEQ ID NO 311 | SEQ ID NO 189 |
| | SEQ ID NO 312 | SEQ ID NO 313 | |
| Ap423 | SEQ ID NO 314 | SEQ ID NO 315 | SEQ ID NO 201 |
| | SEQ ID NO 316 | SEQ ID NO 317 | |
| Ap537 | SEQ ID NO 318 | SEQ ID NO 319 | SEQ ID NO 203 |
| | SEQ ID NO 320 | SEQ ID NO 321 | |
| Ap560 | SEQ ID NO 322 | SEQ ID NO 323 | SEQ ID NO 205 |
| | SEQ ID NO 324 | SEQ ID NO 325 | |

TABLE 17

| Target | Forward primer | Reverse primer |
|---|---|---|
| Ld594 | SEQ ID NO 377 | SEQ ID NO 378 |

TABLE 18

| Target | Forward primer | Reverse primer |
|---|---|---|
| Nl594 | seq id no 379 | seq id no 380 |
| Nl619 | seq id no 381 | seq id no 382 |
| Nl626 | seq id no 383 | seq id no 384 |

TABLE 19

| Target ID | Best *Drosophila* hit | NAME | SYMBOL |
|---|---|---|---|
| Ld583 | CG4759 | Ribosomal protein L27 | RpL27 |
| Ld584 | CG 17331 | Proteasome, beta-type subunit | |
| Ld586 | CG13704 | unknown | |
| Ld588 | CG4157 | Rpn12 | |

TABLE 20

| Target ID | Best *Drosophila* hit | NAME | SYMBOL |
|---|---|---|---|
| Nl594 | CG7178 | wings up A (troponin I) | wupA |
| Nl619 | CG7107 | troponin T (upheld) | up |
| Nl626 | *CG9073, CG7930, CG2981, CG12408, CG6514, CG2981, CG7930, CG9073, CG6514, CG12408 | troponin C | |
| Nl537 | CG32744 | Ubiquitin-5E; protein modification process | |

*unclear: multiple hits in family

TABLE 21

| Target ID | Best *Drosophila* hit | NAME | SYMBOL |
|---|---|---|---|
| Ap594 | CG7178 | wings up A (troponin I) | wupA |
| Ap423 | CG2746 | ribosomal protein L19 | RpL19 |
| Ap537 | CG32744 | Ubiquitin-5E; protein modification process | |
| Ap560 | CG10423 | ribosomal protein S27 | RpS27 |

It will be appreciated by persons skilled in the art that numerous variations and/or modifications may be made to the above mentioned assays without departing from the spirit or scope of this assay as generically described. Those skilled in the art will recognize, or be able to ascertain using no more than routine experimentation, many equivalents to the specific examples, and such equivalents are intended to be encompassed by the present invention. The present example, therefore, is to be considered in all respects as illustrative and not restrictive.

What is claimed is:

1. An interfering ribonucleic acid (RNA) wherein the RNA comprises at least one silencing element wherein the silencing element is a region of double-stranded RNA comprising annealed complementary strands, one strand of which comprises a sequence of at least 21 contiguous nucleotides which is at least partially complementary to a target nucleotide sequence within an insect troponin I target gene, and wherein the interfering RNA (i) is at least 85% identical to at a 21 contiguous nucleotide fragment of SEQ ID NO: 1, or the complement thereof; or (ii) comprises at least a 21 contiguous nucleotide fragment of SEQ ID NO: 1, or the complement thereof; or (iii) comprises at least a 21 contiguous fragment of a nucleotide sequence encoding an amino acid sequence encoded by SEQ ID NO: 1, or the complement thereof, wherein the inferring RNA down regulates the troponin I target gene in a target insect pest species.

2. The interfering RNA of claim 1 wherein the RNA comprises at least two silencing elements, wherein each silencing element comprises a sequence of nucleotides which is at least partially complementary to a target nucleotide sequence within the troponin I target gene.

3. The interfering RNA of claim 2 wherein each of the silencing elements comprises a different sequence of nucleotides which is complementary to a different target nucleotide sequence within the troponin I target gene.

4. The interfering RNA of claim 3 wherein the different target nucleotides sequences originate from a single troponin I target gene or from different target troponin I genes selected from *Lygus herperus, Leptinotarsa decemlineata, Nilaparvata lugens*, and *Acyrthosiphon pisum*.

5. The interfering RNA of claim 4 wherein the different target nucleotide sequences originate from the same insect pest species or different insect pest species.

6. The interfering RNA of claim 1 wherein the insect pest species is a plant pest.

7. The interfering RNA of claim 6 wherein the plant pest is selected from the orders *Coleoptera, Hemiptera, Lepidoptera, Diptera, Dichyoptera, Orthoptera*, and *Siphonaptera*.

8. The interfering RNA of claim 7 wherein the insect plant pest is selected from the group consisting of *Leptinotarsa* spp., optionally *L. decemlineata* (Colorado potato beetle), *L. juncta* (false potato beetle), and *L. texana* (Texan false potato beetle); *Nilaparvata* spp., optionally *N. lugens* (brown planthopper); *Lygus* spp., optionally *L. lineolaris* (tarnished plant bug) and *L. hesperus* (western tarnished plant bug); *Myzus* spp., optionally *M. persicae* (green peach aphid); *Diabrotica* spp., optionally *D. virgifera virgifera* (western corn rootworm), *D. barberi* (northern corn rootworm), *D. undecimpunctata howardi* (southern corn rootworm), and *D. virgifera zeae* (Mexican corn rootworm).

9. The interfering RNA of claim 1 wherein down-regulating expression of the troponin I target gene causes decreased growth, development, reproduction, or survival of the pest as compared with the pest species that is not exposed to said interfering RNA [ribonucleic acid targeting a non-essential gene or an interfering ribonucleic acidnthaqt does not down-regulate any genes within the pest species].

10. A polynucleotide comprising a sequence of nucleotides encoding the interfering RNA of claim 1.

11. A DNA construct comprising the polynucleotide of claim 10.

12. The DNA construct of claim 11 which is an expression construct, wherein the polynucleotide sequence encoding the interfering RNA is operably linked to at least one regulatory sequence capable of driving expression of the polynucleotide sequence.

13. A host cell comprising the RNA of claim 1.

14. The host cell of claim 13 wherein the host cell is a prokaryotic or a eukaryotic cell.

15. The host cell of claim 14 wherein the host cell is a bacterial cell.

16. A composition for preventing and/or controlling insect pest infestation comprising the interfering ribonucleic acid (RNA) according to claim 1 and at least one suitable carrier, excipient or diluent.

17. The composition of claim 16 wherein the interfering RNA is encoded by a polynucleotide comprising a sequence of nucleotides encoding the interfering RNA which is comprised in a DNA construct, which optionally is an expression construct wherein the polynucleotide sequence encoding the interfering RNA is operably linked to at least one regulatory sequence capable of driving expression of the polynucleotide sequence.

18. The composition of claim 16 comprising at least one host cell capable of expressing said interfering RNA [according to claim1].

19. The composition of claim 18 wherein the host cell is a bacterial cell.

20. The composition of claim 16 wherein the composition is in a form suitable for ingestion by an insect.

21. The composition of claim 16 wherein the composition is in solid, liquid or gel form.

22. The composition of claim 16 wherein the composition is formulated as an insecticidal spray.

23. The composition of claim 22 wherein the spray is a pressurized/aerosolized spray or a pump spray.

24. The composition of claim 16 wherein the composition further comprises at least one pesticidal agent selected from the group consisting of a *Bacillus thuringiensis* insecticidal protein.

25. The composition of claim 24 wherein said *Bacillus thuringiensis* insecticidal protein is a Cry3.

26. A combination for preventing and/or controlling pest infestation comprising the composition of claim 16 and at least one other active agent.

27. The combination of claim 26 wherein the combination is for preventing and/or controlling pest infestation of a plant and the other active agent is an agronomical agent.

28. The combination of claim 27 wherein the agronomical agent comprises a herbicide.

29. The combination of claim 27 wherein the agronomical agent comprises a pesticide.

30. The combination of claim 29 wherein the pesticide is a *Bacillus thuringiensis* insecticidal protein.

31. The combination of claim 30 wherein said *Bacillus thuringiensis* insecticidal protein is a Cry3.

32. A method for down-regulating expression of a troponin I target gene in an insect pest species in order to prevent and/or control pest infestation, comprising contacting said pest species with the interfering ribonucleic acid (RNA) according to claim 1.

33. The method of claim 32 wherein down-regulation of expression of the target gene in an insect pest species is used to obtain at least 20% pest control or at least 20% pest mortality as compared to said insect pests that are not contacted with said interfering ribonucleic acid (RNA) [targeting a non-essential pest gene or a target gene not expressed in said pest].

34. The method of claim 32 wherein the method is used to prevent or control pest infestation of a plant.

35. The method of claim 34 wherein the plant is chosen from the group comprising cotton, potato, rice, canola, sunflower, sorghum, pearl millet, corn, strawberries, soy, alfalfa, tomato, eggplant, pepper and tobacco.

* * * * *